(12) United States Patent
Basu et al.

(10) Patent No.: US 10,301,641 B2
(45) Date of Patent: May 28, 2019

(54) GENETIC MARKERS ASSOCIATED WITH DROUGHT TOLERANCE IN MAIZE

(71) Applicant: Syngenta Participations AG, Basel (CH)

(72) Inventors: Shib Sankar Basu, Research Triangle Park, NC (US); Michael Mahlon Magwire, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 129 days.

(21) Appl. No.: 15/172,614

(22) Filed: Jun. 3, 2016

(65) Prior Publication Data

US 2016/0348129 A1 Dec. 1, 2016

Related U.S. Application Data

(63) Continuation-in-part of application No. 14/967,593, filed on Dec. 14, 2015, now Pat. No. 10,047,373.

(60) Provisional application No. 62/093,055, filed on Dec. 17, 2014.

(51) Int. Cl.
*A01H 5/10* (2018.01)
*C12N 15/82* (2006.01)
*C12Q 1/6895* (2018.01)
*A01H 1/04* (2006.01)

(52) U.S. Cl.
CPC ........... *C12N 15/8273* (2013.01); *A01H 1/04* (2013.01); *A01H 5/10* (2013.01); *C12Q 1/6895* (2013.01); *C12Q 2600/13* (2013.01); *C12Q 2600/156* (2013.01); *Y02A 40/132* (2018.01)

(58) Field of Classification Search
None
See application file for complete search history.

(56) References Cited

U.S. PATENT DOCUMENTS

2011/0191892 A1 8/2011 Kishore et al.
2016/0355835 A1 12/2016 Frommer

OTHER PUBLICATIONS

*Zea mays* cultivar B73 chromosome 5 clone CH201-257F15, GenBank accession No. AC208973, published Sep. 23, 2013, selected pages only.*
*Zea mays* cultivar B73 chromosome 5 clone CH201-257F15, GenBank accession No. AC208973, published Sep. 23, 2013.

* cited by examiner

*Primary Examiner* — Bratislav Stankovic
(74) *Attorney, Agent, or Firm* — R. Kody Jones

(57) ABSTRACT

The present invention relates to methods and compositions for identifying, selecting and/or producing a maize plant or maize plant part having increased yield under non-drought conditions, increased yield stability under drought conditions, and/or increased drought tolerance. A maize plant or maize plant part, including any progeny and/or seeds derived from a maize plant or germplasm identified, selected and/or produced by any of the methods of the present invention is also provided.

8 Claims, 1 Drawing Sheet
Specification includes a Sequence Listing.

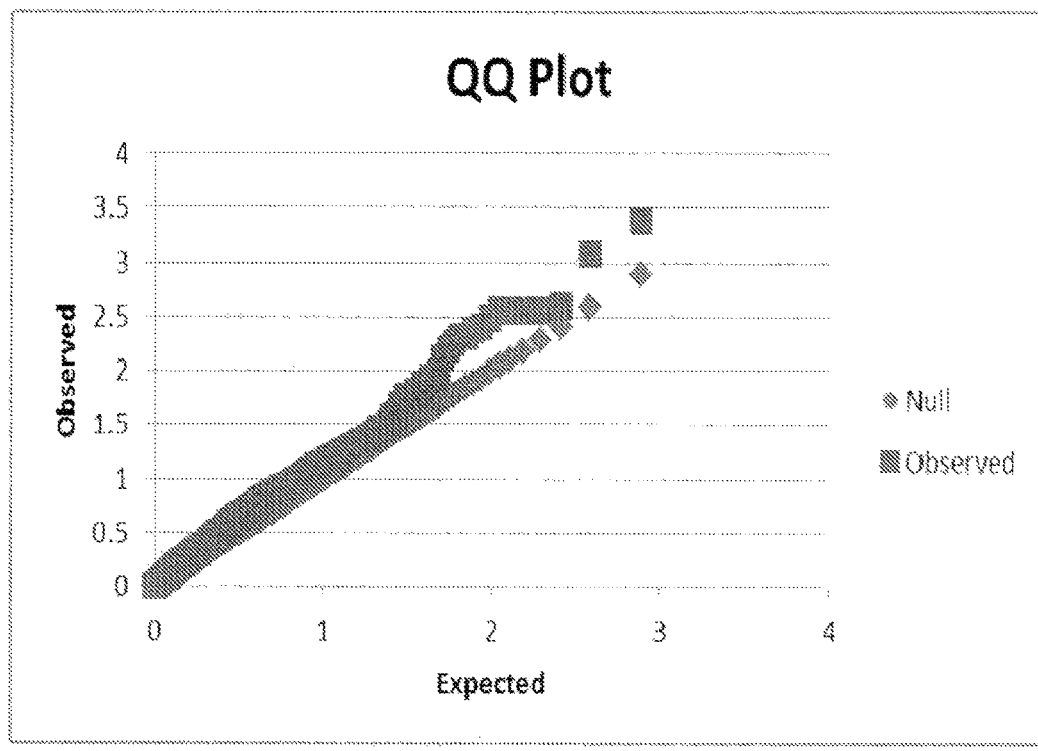

GENETIC MARKERS ASSOCIATED WITH DROUGHT TOLERANCE IN MAIZE

CROSS REFERENCES TO RELATED APPLICATIONS

This application is a continuation in part of pending U.S. application Ser. No. 14/967,593, which claims priority to U.S. application Ser. No. 62/093,055, filed Dec. 17, 2014, the disclosure of which is hereby incorporated by reference. The disclosures of all of the foregoing U.S. patent applications are herein incorporated by reference in their entirety.

FIELD OF THE INVENTION

The present invention relates to compositions and methods for identifying, selecting and/or producing maize plants having increased yield under non-drought conditions, increased yield stability under drought conditions, and/or increased drought tolerance.

STATEMENT REGARDING ELECTRONIC SUBMISSION OF A SEQUENCE LISTING

A Sequence Listing in ASCII text format, submitted under 37 C.F.R. § 1.821, entitled "80664-US-REG-P-NAT-1_ST25", 38 kilobytes. The Sequence Listing is attached and filed herewith and is incorporated herein by reference.

BACKGROUND

A goal of plant breeding is to combine various desirable traits in a single plant. For field crops such as corn, these traits can include greater yield and better agronomic quality. However, genetic loci that influence yield and agronomic quality are not always known, and even if known, their contributions to such traits are frequently unclear. Thus, new loci that can positively influence such desirable traits need to be identified and/or the abilities of known loci to do so need to be discovered.

Once discovered, these desirable loci can be selected for as part of a breeding program in order to generate plants that carry desirable traits. An exemplary method for generating such plants includes the transfer by introgression of nucleic acid sequences from plants that have desirable genetic information into plants that do not by crossing the plants using traditional breeding techniques.

Desirable loci can be introgressed into commercially available plant varieties using marker-assisted selection (MAS) or marker-assisted breeding (MAB). MAS and MAB involves the use of one or more of the molecular markers for the identification and selection of those progeny plants that contain one or more loci that encode the desired traits. Such identification and selection can be based on selection of informative markers that are associated with desired traits. MAB can also be used to develop near-isogenic lines (NIL) harboring loci of interest, allowing a more detailed study of the effect each locus can have on a desired trait, and is also an effective method for development of backcross inbred line (BIL) populations.

Drought is one of the major limitations to maize production worldwide. Identifying genes that enhance the drought tolerance of maize may lead to more efficient crop production by allowing for the identification, selection and production of maize plants with improved water optimization traits and enhanced drought tolerance.

SUMMARY OF THE INVENTION

Compositions and methods for identifying, selecting and/or producing maize plants having increased yield under non-drought conditions, increased yield stability under drought conditions, and/or increased drought tolerance are provided. As described herein, a marker associated with increased yield under non-drought conditions, increased yield stability under drought conditions, and/or increased drought tolerance may comprise, consist essentially of or consist of a single allele or a combination of alleles at one or more genetic loci.

Accordingly, in some embodiments, a method of identifying, selecting and/or producing a maize plant having increased yield under non-drought conditions, increased yield stability under drought conditions, and/or increased drought tolerance is provided, comprising: detecting, in a maize plant or maize plant part, an allele of at least one marker locus that is associated with increased yield under non-drought conditions, increased yield stability under drought conditions, and/or increased drought tolerance in a maize plant, wherein said at least one marker locus is located within a chromosomal interval comprising (a) a chromosome interval on chromosome 10 of the Maize B73 genome version 3 defined by and including base pair (bp) position 14765640 to base pair (bp) position 14772295 (SEQ ID NO. 22); (b) a chromosome interval on chromosome 3 of the Maize B73 genome version 3 defined by and including base pair (bp) position 171790082 to base pair (bp) position 171797701 (SEQ ID NO. 20); (c) a chromosome interval on chromosome 1 of the Maize B73 genome version 3 defined by and including base pair (bp) position 194963437 to base pair (bp) position 194970347 (SEQ ID NO. 21); (d) a chromosome interval on chromosome 5 of the Maize B73 genome version 3 defined by and including base pair (bp) position 164893210 to base pair (bp) position 164900398 (SEQ ID NO. 23); and (e) any combination of (a) to (d) above, thereby identifying, selecting and/or producing a maize plant having increased yield under non-drought conditions, increased yield stability under drought conditions.

In some embodiments, a method of identifying, selecting and/or producing a maize plant having increased yield under non-drought conditions, increased yield stability under drought conditions, and/or increased drought tolerance is provided, comprising: detecting, in a maize plant or maize plant part, the presence of an allele of at least one marker locus associated with increased yield under non-drought conditions, increased yield stability under drought conditions, and/or increased drought tolerance in a maize plant, wherein said allele of at least one marker locus comprises: chromosome 10 bp position 14770979 comprises a G allele (SEQ ID NO. 29); chromosome 10 bp position 14770796 comprises a C allele (SEQ ID NO. 30); chromosome 10 bp position 14769813 comprises a C allele (SEQ ID NO. 31); chromosome 10 bp position 14769855 comprises a G allele (SEQ ID NO. 32); chromosome 10 bp position 14770143 comprises a G allele (SEQ ID NO. 33); chromosome 3 bp position 171791580 comprises a G allele (SEQ ID NO. 39); chromosome 3 bp position 171795048 comprises a T allele (SEQ ID NO. 40); chromosome 3 bp position 171790578 comprises a G allele (SEQ ID NO. 41); chromosome 3 bp position 171791368 comprises a G allele (SEQ ID NO. 42); chromosome 3 bp position 171795101 comprises a C allele (SEQ ID NO. 43); chromosome 1 bp position 194967163 comprises a C allele (SEQ ID NO. 24); chromosome 1 bp position 194966087 comprises a C allele (SEQ ID NO. 25); chromosome 1 bp position 194966273 comprises a T allele (SEQ ID NO. 26); chromosome 1 bp position 194968091 comprises a G allele (SEQ ID NO. 27); chromosome 1 bp position 194967616 comprises a C allele (SEQ ID NO. 28); chromosome 5 bp position 164895193 comprises a C allele (SEQ ID NO. 34); chromosome 5 bp position 164896921 comprises a G allele (SEQ ID NO. 35); chromosome 5 bp position 164897496 comprises a G allele (SEQ ID NO. 36); chromosome 5 bp position 164897515 comprises a G allele (SEQ ID NO. 37); and chromosome 5 bp position 164897518 comprises a C allele (SEQ ID NO. 38); or any combination of the above, thereby identifying, selecting and/or producing a maize plant having increased yield under non-drought conditions, increased yield stability under drought conditions.

Accordingly, in some embodiments, a method of identifying, selecting and/or producing a maize plant having increased yield under non-drought conditions, increased yield stability under drought conditions, and/or increased drought tolerance is provided, comprising: detecting, in a maize plant or maize plant part, an allele of at least one marker locus that is associated with increased yield under non-drought conditions, increased yield stability under drought conditions, and/or increased drought tolerance in a maize plant, wherein said at least one marker comprises: "C" at a nucleotide position that corresponds to position 501 of SEQ ID NO: 24, "C" at a nucleotide position that corresponds to position 501 of SEQ ID NO: 25, "T" at a nucleotide position that corresponds to position 501 of SEQ ID NO: 26, "G" at a nucleotide position that corresponds to position 501 of SEQ ID NO: 27, "C" at a nucleotide position that corresponds to position 501 of SEQ ID NO: 28, "A" at a nucleotide position that corresponds to position 501 of SEQ ID NO: 29, "C" at a nucleotide position that corresponds to position 501 of SEQ ID NO: 30, "C" allele at a nucleotide position that corresponds to position 501 of SEQ ID NO: 31, "G" at a nucleotide position that corresponds to position 501 of SEQ ID NO: 32, "G" at a nucleotide position that corresponds to position 501 of SEQ ID NO: 33, "C" at a nucleotide position that corresponds to position 501 of SEQ ID NO: 34, "G" at a nucleotide position that corresponds to position 501 of SEQ ID NO: 35, "G" at a nucleotide position that corresponds to position 501 of SEQ ID NO: 36, "G" at a nucleotide position that corresponds to position 501 of SEQ ID NO: 37, "C" at a nucleotide position that corresponds to position 501 of SEQ ID NO: 38, "G" at a nucleotide position that corresponds to position 501 of SEQ ID NO: 39, "T" at a nucleotide position that corresponds to position 501 of SEQ ID NO: 40, "G" at a nucleotide position that corresponds to position 501 of SEQ ID NO: 41, "G" at a nucleotide position that corresponds to position 501 of SEQ ID NO: 42, and "C" at a nucleotide position that corresponds to position 501 of SEQ ID NO: 43.

In some embodiments, a method of selecting a maize plant or germplasm having increased yield under non-drought conditions, increased yield stability under drought conditions, and/or increased drought tolerance is provided, comprising crossing a first maize plant or germplasm with a second maize plant or germplasm, wherein said first miaze plant or germplasm comprises within its genome a genetic marker associated with increased yield under non-drought conditions, increased yield stability under drought conditions, and/or increased drought tolerance in a maize plant, wherein said genetic marker comprises any of (a) to (e), above.

In some embodiments, a plant can be regenerated from a plant part in which said genetic marker(s) is/are detected.

Also provided herein are maize plants and maize plant parts produced, selected and/or identified by the methods of the invention, as well as crops comprising said maize plants, harvested products produced from said plants and crops, and post-harvest products produced from the harvested products.

These and other aspects of the invention are set forth in more detail in the description of the invention below.

BRIEF DESCRIPTION OF THE DRAWINGS

FIG. 1 provides the QQ plot generated to look at the observed distribution of –log 10(P-values) of the data a shown in Tables 9.1-9.4.

BRIEF DESCRIPTION OF THE SEQUENCE LISTING

SEQ ID NO.: 1 ZmSWEET13a [GRMZM2G173669]
GRMZM2G173669 v2 coord=10:14762443 . . . 14765098:1
SEQ ID NO.: 2 ZmSWEET1a [GRMZM2G039365]
GRMZM2G039365 v2 coord=3:171748815 . . . 171752467:-1
SEQ ID NO.: 3 ZmSWEET11/MtN3 [GRMZM2G368827]
GRMZM2G368827 v2 coord=1:194932443 . . . 194935353:-1
SEQ ID NO.: 4 ZmSWEET16b [GRMZM2G111926]
GRMZM2G111926 v2 coord=8:33363546 . . . 33368983:-1
SEQ ID NO.: 5 ZmSWEET15b [GRMZM5G872392]
GRMZM5G872392 v2 coord=5:164854921 . . . 164858109:-1
SEQ ID NO.: 6 PZE1014822710
C/T SNP AT NUCLEOTIDE 401 identifies a favorable/unfavorable allele
SEQ ID NO.: 7 PZE1014822787
A/G SNP AT NUCLEOTIDE 401 identifies a favorable/unfavorable allele
SEQ ID NO.: 8 PZE1014822363
G/T SNP AT NUCLEOTIDE 401 identifies a favorable/unfavorable allele
SEQ ID NO.: 9 PZE1014822960
A/G SNP AT NUCLEOTIDE 401 identifies a favorable/unfavorable allele
SEQ ID NO.: 10 S_3355011
G/C SNP AT NUCLEOTIDE 251 identifies a favorable/unfavorable allele
SEQ ID NO.: 11 PZE1014822606
G/T SNP AT NUCLEOTIDE 401 identifies a favorable/unfavorable allele
SEQ ID NO.: 12 PZE03170079889
G/A SNP AT NUCLEOTIDE 401 identifies a favorable/unfavorable allele
SEQ ID NO.: 13 PZE03170077114
C/T SNP AT NUCLEOTIDE 401 identifies a favorable/unfavorable allele
SEQ ID NO.: 14 S_7767530
C/T SNP AT NUCLEOTIDE 251 identifies a favorable/unfavorable allele
SEQ ID NO.: 15 S_7767535
A/C SNP AT NUCLEOTIDE 251 identifies a favorable/unfavorable allele
SEQ ID NO.: 16 S_7767546
A/C SNP AT NUCLEOTIDE 251 identifies a favorable/unfavorable allele SEQ ID NO.: 17 PZE01194799632
A/T SNP AT NUCLEOTIDE 401 identifies a favorable/ unfavorable allele
SEQ ID NO.: 18 PZE0833363225
T/C SNP AT NUCLEOTIDE 401 identifies a favorable/ unfavorable allele
SEQ ID NO.: 19 S_25177407
A/C SNP AT NUCLEOTIDE 251 identifies a favorable/ unfavorable allele
SEQ ID NO.: 20 Sequenced region 2000 bp 5' and 3' of SWEET1a [GRMZM2G039365]
SEQ ID NO.: 21 Sequenced region 2000 bp 5' and 3' of SWEET11 [GRMZM2G368827]
SEQ ID NO.: 22 Sequenced region 2000 bp 5' and 3' of SWEET13a [GRMZM2G173669]
SEQ ID NO.: 23 Sequenced region 2000 bp 5' and 3' of SWEET15b [GRMZM5G872392]
SEQ ID NO.: 24 Maize B73 v3 Chr 1 fragment from 194966663 to 194967663
SEQ ID NO.: 25 Maize B73 v3 Chr 1 fragment from 194965587 to 194966587
SEQ ID NO.: 26 Maize B73 v3 Chr 1 fragment from 194965773 to 194966773
SEQ ID NO.: 27 Maize B73 v3 Chr 1 fragment from 194967591 to 194968591
SEQ ID NO.: 28 Maize B73 v3 Chr 1 fragment from 194968116 to 194969116
SEQ ID NO.: 29 Maize B73 v3 Chr 10 fragment from 14770479 to 14771479
SEQ ID NO.: 30 Maize B73 v3 Chr 10 fragment from Ser. No. 14/770,296 to Ser. No. 14/771,296
SEQ ID NO.: 31 Maize B73 v3 Chr 10 fragment from 14769313 to 14770313
SEQ ID NO.: 32 Maize B73 v3 Chr 10 fragment from 14769355 to 14770355
SEQ ID NO.: 33 Maize B73 v3 Chr 10 fragment from 14769643 to 14770643
SEQ ID NO.: 34 Maize B73 v3 Chr 5 fragment from 164894693 to 164895693
SEQ ID NO.: 35 Maize B73 v3 Chr 5 fragment from 164896421 to 164897421
SEQ ID NO.: 36 Maize B73 v3 Chr 5 fragment from 164896996 to 164897996
SEQ ID NO.: 37 Maize B73 v3 Chr 5 fragment from 164897015 to 164898015
SEQ ID NO.: 38 Maize B73 v3 Chr 5 fragment from 164897018 to 164898018
SEQ ID NO.: 39 Maize B73 v3 Chr 3 fragment from Ser. No. 17/791,080 to Ser. No. 17/792,080
SEQ ID NO.: 40 Maize B73 v3 Chr 3 fragment from 171794548 to 171795548
SEQ ID NO.: 41 Maize B73 v3 Chr 3 fragment from 171790078 to 171791078
SEQ ID NO.: 42 Maize B73 v3 Chr 3 fragment from 171790868 to 171791868
SEQ ID NO.: 43 Maize B73 v3 Chr 3 fragment from Ser. No. 17/794,601 to Ser. No. 17/795,601

DETAILED DESCRIPTION

The present invention provides compositions and methods for identifying, selecting and/or producing maize plants having increased yield under non-drought conditions, increased yield stability under drought conditions, and/or increased drought tolerance, as well as maize plants, parts thereof, including but not limited to seeds, and maize germplasm, that are identified, selected and/or produced by methods of this invention. The present invention further provides an assay for the detection of increased yield under non-drought conditions, increased yield stability under drought conditions, and/or increased drought tolerance in a maize plant, plant part and/or maize germplasm. In addition, the present invention provides maize plants, plant parts, and/or germplasm having within their genome one or more SNP or QTL markers associated with increased yield under non-drought conditions, increased yield stability under drought conditions, and/or increased drought tolerance.

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," an and the are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the term "allele" refers to one of two or more different nucleotides or nucleotide sequences that occur at a specific locus.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype. In some embodiments of this invention, the phrase "desired allele," "target allele" or "allele of interest" refers to an allele(s) that is associated with increased yield under non-drought conditions, increased yield stability under drought conditions, and/or increased drought tolerance in a maize plant relative to a control maize plant not having the target allele or alleles. Thus, for example, a maize plant comprising one or more of the markers associated with increased yield under non-drought conditions, increased yield stability under drought conditions, and/or increased drought tolerance in a maize plant as described herein (e.g., desired alleles) can have increased yield under non-drought conditions, increased yield stability under drought conditions, and/or increased drought tolerance as compared to a maize plant that does not comprise said one or more markers associated with increased yield under non-drought conditions, increased yield stability under drought conditions, and/or increased drought tolerance (e.g., desired alleles).

A marker is "associated with" a trait when said trait is linked to the marker and when the presence of the marker is an indicator of whether and/or to what extent the desired trait or trait form will occur in a plant/germplasm comprising the marker. Similarly, a marker is "associated with" an allele or chromosome interval when it is linked to said allele or said chromosome interval and when the presence of the marker is an indicator of whether the allele or chromosome interval is present in a plant/germplasm comprising the marker. For example, "a marker associated with a drought tolerance allele" refers to a marker whose presence or absence can be used to predict whether a plant will display drought tolerance.

As used herein, the terms "backcross" and "backcrossing" refer to the process whereby a progeny plant is crossed back to one of its parents one or more times (e.g., 1, 2, 3, 4, 5, 6, 7, 8, 9, 10, or more.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in Techniques et Utilisations des Marqueurs Moléculaires Les Colloques, Vol. 72, pp. 45-56 (1995); and Openshaw et al., *Marker-assisted Selection in Backcross Breeding*, in Proceedings of the Symposium "Analysis of Molecular Marker Data," pp. 41-43 (1994). The initial cross gives rise to the F1 generation. The term "BC1" refers to the second use of the recurrent parent, "BC2" refers to the third use of the recurrent parent, and so on. In some embodiments, the number of backcrosses can be about 1 to about 10 (e.g., 1, 2, 3, 4, 5, 6, 7, 8, 9, 10). In some embodiments, the number of backcrosses is about 7.

As used herein, a "control" maize plant means a maize plant which does not comprise said marker or markers of the invention, wherein said control maize plant is grown under the same environmental conditions as the identified, selected, produced, introgressed maize plant. In some embodiments, the control maize plant can have a substantially similar genetic background (e.g., 70%, 75%, 80%, 85%, 90%, 91%, 92%, 93%, 94%, 95%, 96%, 97%, 98%, 99%, or more) to the identified, selected, produced, introgressed plant. In some embodiments, the control plant is of the same elite line as that of the identified, selected, produced, introgressed plant but does not comprise said marker or markers of the invention.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of the gametes fusing via pollination to produce progeny.

As used herein, the terms "cultivar" and "variety" refer to a group of similar plants that by structural or genetic features and/or performance can be distinguished from other cultivars or varieties within the same species.

As used herein, the terms "drought tolerance" and "drought tolerant" refer to a plant's ability to endure and/or thrive under drought stress conditions. When used in reference to a plant part, the terms refer to the ability of a plant that arises from that plant part to endure and/or thrive under drought conditions. In general, a plant or plant part is designated as "drought tolerant" if it displays "increased drought tolerance." This can be measured in terms of a single plant or in terms of the results from a group of the drought tolerant plants of this invention. Thus, for example, when measuring yield, the measurements are made on a group of the plants of the invention, which is then compared to the yield of a group of appropriate control plants.

In some embodiments, as used herein, the term "increased drought tolerance" or "enhanced drought tolerance" refers to an improvement in one or more water optimization traits as compared to one or more controls (e.g., one or both parents, or a plant lacking a marker associated with drought tolerance when grown under the same environmental conditions). Exemplary water optimization traits include, but are not limited to, water loss, accumulation of reactive oxygen species, accumulation of dehydrins, root architecture, accumulation of late embryogenesis abundant proteins, grain yield at standard moisture percentage (YGSMN), grain moisture at harvest (GMSTP), grain weight per plot (GWTPN), percent yield recovery (PYREC), yield reduction (YRED), and percent barren (PB). Thus, a plant that exhibits decreased water loss, decreased accumulation of reactive oxygen species, increased accumulation of dehydrins, improved root architecture, increased accumulation of late embryogenesis abundant proteins, increased grain yield at standard moisture percentage (YGSMN), increased grain moisture at harvest (GMSTP), increased grain weight per plot (GWTPN), increased percent yield recovery (PYREC), decreased yield reduction (YRED), and/or decreased percent barren (PB) as compared to a control plant when each is grown under the same drought stress conditions displays enhanced or increased drought tolerance and may be designated as "drought tolerant."

As used herein, "increased yield" means increased grain yield at standard moisture percentage (YGSMN) in a plant or plants of this invention as compared to a control.

As used herein, "yield stability" refers to a difference in the relative rank of a plant line under well-watered versus drought conditions. "Increased yield stability" means that there is less change in rank for the plant line in the two conditions as compared to a control.

As used herein, "drought conditions" refers to water deprived conditions that result in a loss in yield of 30% or more versus well-watered conditions.

As used herein, "non-drought conditions" means that the plants are well watered.

As used herein, the terms "elite" and/or "elite line" refer to any line that is substantially homozygous and has resulted from breeding and selection for desirable agronomic performance As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make up for all the genes in its genome. Genotypes can be indirectly characterized, e.g., using markers and/or directly characterized by, e.g., nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.). In some embodiments, germplasm includes but is not limited to tissue culture.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" in the context of plant breeding refers to a plant that is the offspring of genetically dissimilar parents produced by crossing plants of different lines or breeds or species, including but not limited to a cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

The terms "increase," "increasing," "increased," "enhance," "enhanced," "enhancing," and "enhancement" (and grammatical variations thereof), as used herein, describe an elevation, for example, in yield, yield stability or the tolerance of a plant to drought by the introduction of a genetic marker(s) of the invention into the plant, thereby producing a plant having, for example, increased yield, yield stability, and/or drought tolerance (e.g., an elevation of at least about 20%, 25%, 30%, 35%, 40%, 45%, 50%, 75%, 100%, 125%, 150%, 175%, 200%, 350%, 300%, 350%, 400%, 450%, 500% or more). This increase can be observed by comparing the yield, yield stability, and/or drought tolerance of the plant comprising the genetic marker(s) of the invention to the yield, yield stability, and/or drought tolerance of a plant lacking said genetic marker(s) of the invention (i.e., a control).

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, 5, 6, 7, 8, 9, 10 or more times) to a line having a desired genetic background, selecting for the desired allele, with the result being that the desired allele becomes fixed in the desired genetic background. For example, a marker associated with increased yield under non-drought conditions, increased yield stability under drought conditions, and/or increased drought tolerance may be introgressed from a donor into a recurrent parent that is drought sensitive or does not comprise said marker(s) associated with increased yield under non-drought conditions, increased yield stability under drought conditions, and/or increased drought tolerance. The resulting offspring could then be backcrossed one or more times and selected until the progeny comprises the genetic marker(s) associated with increased yield under non-drought conditions, increased yield stability under drought conditions, and/or increased drought tolerance in the recurrent parent background.

As used herein, the term "linkage" refers to the degree with which one marker locus is associated with another marker locus or some other locus. The linkage relationship between a genetic marker and a phenotype may be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

A centimorgan ("cM") or a genetic map unit (m.u.) is a unit of measure of recombination frequency and is defined as the distance between genes for which one product of meiosis in 100 is recombinant One cM is equal to a 1% chance that a marker at one genetic locus will be separated from a marker at a second locus due to crossing over in a single generation. Thus, a recombinant frequency (RF) of 1% is equivalent to 1 map unit (m.u.).

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., increased yield under non-drought conditions, increased yield stability under drought conditions, and/or increased drought tolerance. The degree of linkage of a genetic marker to a phenotypic trait is measured, e.g., as a statistical probability of co-segregation of that marker with the phenotype.

Linkage disequilibrium is most commonly assessed using the measure $r^2$, which is calculated using the formula described by Hill and Robertson, Theor. Appl. Genet. 38:226 (1968). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al., Nature Reviews Genetics 3:299 (2002). Hence, alleles are in linkage disequilibrium when $r^2$ values between pairwise marker loci are greater than or equal to about 0.3, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

As used herein, the terms "marker" and "genetic marker" are used interchangeably to refer to a nucleotide and/or a nucleotide sequence that has been associated with a phenotype and/or trait. A marker may be, but is not limited to, an allele, a gene, a haplotype, a chromosome interval, a restriction fragment length polymorphism (RFLP), a simple sequence repeat (SSR), a random amplified polymorphic DNA (RAPD), a cleaved amplified polymorphic sequence (CAPS) (Rafalski and Tingey, Trends in Genetics 9:275 (1993)), an amplified fragment length polymorphism (AFLP) (Vos et al., Nucleic Acids Res. 23:4407 (1995)), a single nucleotide polymorphism (SNP) (Brookes, Gene 234: 177 (1993)), a sequence-characterized amplified region (SCAR) (Paran and Michelmore, Theor. Appl. Genet. 85:985 (1993)), a sequence-tagged site (STS) (Onozaki et al., Euphytica 138:255 (2004)), a single-stranded conformation polymorphism (SSCP) (Orita et al., Proc. Natl. Acad. Sci. USA 86:2766 (1989)), an inter-simple sequence repeat (ISSR) (Blair et al., Theor. Appl. Genet. 98:780 (1999)), an inter-retrotransposon amplified polymorphism (IRAP), a retrotransposon-microsatellite amplified polymorphism (REMAP) (Kalendar et al., Theor. Appl. Genet. 98:704 (1999)), an isozyme marker, an RNA cleavage product (such as a Lynx tag) or any combination of the markers described herein. A marker may be present in genomic or expressed nucleic acids (e.g., ESTs). A large number of maize genetic markers are known in the art, and are published or available from various sources, such as the MaizeGDB internet resource (maizegdb.org). In some embodiments, a genetic marker of this invention is a SNP allele, a SNP allele located in a chromosome interval and/or a haplotype (combination of SNP alleles), each of which is associated with increased yield under non-drought conditions, increased yield stability under drought conditions, and/or increased drought tolerance.

Markers corresponding to genetic polymorphisms between members of a population can be detected by methods well-established in the art. These include, but are not limited to, nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of randomly amplified polymorphic DNA (RAPD), detection of single nucleotide polymorphisms (SNPs), and/or detection of amplified fragment length polymorphisms (AFLPs). Thus, in some embodiments of this invention, such well known methods can be used to detect the SNP alleles as defined herein (See, e.g., Table 1).

Accordingly, in some embodiments of this invention, a marker is detected by amplifying a maize nucleic acid with two oligonucleotide primers by, for example, an amplification reaction such as the polymerase chain reaction (PCR).

A "marker allele," also described as an "allele of a marker locus," can refer to one of a plurality of polymorphic nucleotides found at a marker locus in a population that is polymorphic for the marker locus.

"Marker-assisted selection" (MAS) is a process by which phenotypes are selected based on marker genotypes. Marker assisted selection includes the use of marker genotypes for identifying plants for inclusion in and/or removal from a breeding program or planting.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the term "percent barren" (PB) refers to the percentage of plants in a given area (e.g., plot) with no grain. It is typically expressed in terms of the percentage of plants per plot and can be calculated as:

$$\frac{\text{number of plants in the plot with no grain}}{\text{total number of plants in the plot}} \times 100$$

As used herein, the term "percent yield recovery" (PYREC) refers to the effect an allele and/or combination of alleles has on the yield of a plant grown under stress conditions (e.g., drought conditions) as compared to that of a plant that is genetically identical except insofar as it lacks the allele and/or combination of alleles. PYREC is calculated as:

$$1 - \frac{\text{yield under full irrigation (w/allele(s) of interest)} - \text{yield under drought conditions (w/allele(s) of interest)}}{\text{yield under full irrigation (w/out allele(s) of interest)} - \text{yield under drought conditions (w/out allele(s) of interest)}} \times 100$$

By way of example and not limitation, if a control plant yields 200 bushels under full irrigation conditions, but yields only 100 bushels under drought stress conditions, then its percentage yield loss would be calculated at 50%. If an otherwise genetically identical hybrid that contains the allele(s) of interest yields 125 bushels under drought stress conditions and 200 bushels under full irrigation conditions, then the percentage yield loss would be calculated as 37.5% and the PYREC would be calculated as 25% [1.00−(200−125)/(200−100)×100)].

As used herein, the term "water optimization trait" refers to any trait that can be shown to influence the yield of a plant under different sets of growth conditions related to water availability.

As used herein, the term "yield reduction" (YD) refers to the degree to which yield is reduced in plants grown under stress conditions. YD is calculated as:

$$\frac{\text{yield under non-stress conditions} - \text{yield under stress conditions}}{\text{yield under non-stress conditions}} \times 100$$

As used herein, the term "probe" refers to a single-stranded oligonucleotide sequence that will form a hydrogen-bonded duplex with a complementary sequence in a target nucleic acid sequence analyte or its cDNA derivative. Thus, a "marker probe" and "probe" refers to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus. Based on the guidance provided herein, the nucleotide sequences of the genes (e.g., SEQ ID NO:1 (Gene Model ID No: GRMZM2G173669); SEQ ID NO:2 (Gene Model ID No: GRMZM2G039365); SEQ ID NO:3 (Gene Model ID No: GRMZM2G368827); SEQ ID NO:4 Gene Model ID No: GRMZM2G111926); SEQ ID NO:5 (Gene Model ID No: GRMZM5G872392), SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, and the location of the SNPs therein, probes can be readily developed for detecting the markers of this invention.

As used herein, the term "molecular marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum length of the primer can depend on many factors, including, but not limited to temperature and composition (A/T vs. G/C content) of the primer. In the context of amplification primers, these are typically provided as a pair of bi-directional primers consisting of one forward and one reverse primer or provided as a pair of forward primers as commonly used in the art of DNA amplification such as in PCR amplification. As such, it will be understood that the term "primer," as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

Based on the guidance provided herein, the nucleotide sequences of the genes (e.g., SEQ ID NO:1 (Gene Model ID No: GRMZM2G173669); SEQ ID NO:2 (Gene Model ID No: GRMZM2G039365); SEQ ID NO:3 (Gene Model ID No: GRMZM2G368827); SEQ ID NO:4 Gene Model ID No: GRMZM2G111926); SEQ ID NO:5 (Gene Model ID No: GRMZM5G872392) SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, and the location of the SNPs therein, probes can be readily developed for detecting the markers of this invention. Particular nucleotides that are present at particular locations in the markers and nucleic acids disclosed herein can be determined using standard molecular biology techniques including, but not limited to amplification of genomic DNA from plants and subsequent sequencing. Additionally, oligonucleotide primers can be designed that would be expected to specifically hybridize to particular sequences that include the polymorphisms disclosed herein. For example, oligonucleotides can be designed to distinguish between the "C" allele and the "T" allele at a nucleotide position that corresponds to position 401 of SEQ ID NO: 6 (PZE1014822710). For example, oligonucleotides can be designed to distinguish between the "A" allele and the "G" allele at a nucleotide position that corresponds to position 401 of SEQ ID NO: 7 (PZE1014822787). For example, oligonucleotides can be designed to distinguish between the "G" allele and the "T" allele at a nucleotide position that corresponds to position 401 of SEQ ID NO: 8 (PZE1014822363). For example, oligonucleotides can be designed to distinguish between the "A" allele and the "G" allele at a nucleotide position that corresponds to position 401 of SEQ ID NO: 9 (PZE1014822960). For example, oligonucleotides can be designed to distinguish between the "G" allele and the "C" allele at a nucleotide position that corresponds to position 251 of SEQ ID NO: 10 (S_3355011). For example, oligonucleotides can be designed to distinguish between the "G" allele and the "T" allele at a nucleotide position that corresponds to position 401 of SEQ ID NO: 11 (PZE1014822606). For example, oligonucleotides can be designed to distinguish between the "G" allele and the "A" allele at a nucleotide position that corresponds to position 401 of SEQ ID NO: 12 (PZE03170079889). For example, oligonucleotides can be designed to distinguish between the "C" allele and the "T" allele at a nucleotide position that corresponds to position 401 of SEQ ID NO: 13 (PZE03170077114). For example, oligonucleotides can be designed to distinguish between the "C" allele and the "T" allele at a nucleotide position that corresponds to position 251 of SEQ ID NO: 14 (S_7767530). For example, oligonucleotides can be designed to distinguish between the "A" allele and the "C" allele at a nucleotide position that corresponds to position 251 of SEQ ID NO: 15 (S_7767535). For example, oligonucleotides can be designed to distinguish between the "A" allele and the "C" allele at a nucleotide position that corresponds to position 251 of SEQ ID NO: 16 (S_7767546). For example, oligonucleotides can be designed to distinguish between the "A" allele and the "T" allele at a nucleotide position that corresponds to position 401 of SEQ ID NO: 17 (PZE01194799632). For example, oligonucleotides can be designed to distinguish between the "T" allele and the "C" allele at a nucleotide position that corresponds to position 401 of SEQ ID NO: 18 (PZE0833363225). For example, oligonucleotides can be designed to distinguish between the "A" allele and the "C" allele at a nucleotide position that corresponds to position 251 of SEQ ID NO: 19 (S_25177407).). For example, oligonucleotides can be designed to distinguish between the "C" allele and the "G" allele at a nucleotide position that corresponds to position 501 of SEQ ID NO. 24; For example, oligonucleotides can be designed to distinguish between the "C" allele and the "G" allele at a nucleotide position that corresponds to position 501 of SEQ ID NO. 25; For example, oligonucleotides can be designed to distinguish between the "T" allele and the "G" allele at a nucleotide position that corresponds to position 501 of SEQ ID NO. 26; For example, oligonucleotides can be designed to distinguish between the "G" allele and the "A" allele at a nucleotide position that corresponds to position 501 of SEQ ID NO. 27; For example, oligonucleotides can be designed to distinguish between the "C" allele and the "T" allele at a nucleotide position that corresponds to position 501 of SEQ ID NO. 28; For example, oligonucleotides can be designed to distinguish between the "A" allele and the "G" allele at a nucleotide position that corresponds to position 501 of SEQ ID NO. 29; For example, oligonucleotides can be designed to distinguish between the "C" allele and the "T" allele at a nucleotide position that corresponds to position 501 of SEQ ID NO. 30; For example, oligonucleotides can be designed to distinguish between the "C" allele and the "A" allele at a nucleotide position that corresponds to position 501 of SEQ ID NO. 31; For example, oligonucleotides can be designed to distinguish between the "G" allele and the "T" allele at a nucleotide position that corresponds to position 501 of SEQ ID NO. 32; For example, oligonucleotides can be designed to distinguish between the "G" allele and the "A" allele at a nucleotide position that corresponds to position 501 of SEQ ID NO. 33; For example, oligonucleotides can be designed to distinguish between the "C" allele and the "T" allele at a nucleotide position that corresponds to position 501 of SEQ ID NO. 34; For example, oligonucleotides can be designed to distinguish between the "G" allele and the "C" allele at a nucleotide position that corresponds to position 501 of SEQ ID NO. 35; For example, oligonucleotides can be designed to distinguish between the "G" allele and the "T" allele at a nucleotide position that corresponds to position 501 of SEQ ID NO. 36; For example, oligonucleotides can be designed to distinguish between the "G" allele and the "C" allele at a nucleotide position that corresponds to position 501 of SEQ ID NO. 37; For example, oligonucleotides can be designed to distinguish between the "C" allele and the "T" allele at a nucleotide position that corresponds to position 501 of SEQ ID NO. 38; For example, oligonucleotides can be designed to distinguish between the "G" allele and the "A" allele at a nucleotide position that corresponds to position 501 of SEQ ID NO. 39; For example, oligonucleotides can be designed to distinguish between the "T" allele and the "C" allele at a nucleotide position that corresponds to position 501 of SEQ ID NO. 40; For example, oligonucleotides can be designed to distinguish between the "G" allele and the "A" allele at a nucleotide position that corresponds to position 501 of SEQ ID NO. 41; For example, oligonucleotides can be designed to distinguish between the "G" allele and the "T" allele at a nucleotide position that corresponds to position 501 of SEQ ID NO. 42; and For example, oligonucleotides can be designed to distinguish between the "C" allele and the "T" allele at a nucleotide position that corresponds to position 501 of SEQ ID NO. 43;

The PCR method is well described in handbooks and known to the skilled person. After amplification by PCR, target polynucleotides can be detected by hybridization with a probe polynucleotide, which forms a stable hybrid with the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual, Third Edition*, Cold Spring Harbor Laboratory Press, Cold Spring Harbor, N.Y., United States of America. Generally, lower salt concentration and higher temperature hybridization and/or washes increase the stringency of hybridization conditions.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids, amino acids, and/or proteins.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 55, 60, 65, 70, 75, 80, 85, 90, 95, 96, 97, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST®; Altschul et al. (1990) *J Mol Biol* 215:403-10; Altschul et al. (1997) *Nucleic Acids Res* 25:3389-3402) and ClustalX (Chenna et al. (2003) *Nucleic Acids Res* 31:3497-3500) programs, both available on the Internet. Other suitable programs include, but are not limited to, GAP, BestFit, PlotSimilarity, and FASTA, which are part of the Accelrys GCG Package available from Accelrys Software, Inc. of San Diego, Calif., United States of America.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and Sequence Analysis Primer (Gribskov, M. and Devereux, J., eds.) Stockton Press, New York (1991).

As used herein, the term "substantially identical" or "corresponding to" with regard to the comparison of two (or more) nucleotide sequences means that the two nucleotide sequences have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity. In some embodiments, two nucleotide sequences can have at least about 75%, 80%, 85%, 90%, 95%, or 100% sequence identity, and any range or value therein. In representative embodiments, two nucleotide sequences can have at least about 95%, 96%, 97%, 98%, 99% or 100% sequence identity, and any range or value therein.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BEST-FIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.*, 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo et al. (*Applied Math* 48:1073(1988)). More particularly, preferred computer programs for determining sequence identity include but are not limited to the Basic Local Alignment Search Tool (BLAST®) programs, which are publicly available from National Center Biotechnology Information (NCBI) at the National Library of Medicine, National Institute of Health, Bethesda, Md. 20894; see BLAST® Manual, Altschul et al., NCBI, NLM, NIH; (Altschul et al., *J. Mol. Biol.* 215:403-410 (1990)); version 2.0 or higher of BLAST® programs allows the introduction of gaps (deletions and insertions) into alignments; for peptide sequence, BLASTX can be used to determine sequence identity; and for polynucleotide sequence, BLASTN can be used to determine sequence identity.

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, and/or an electromechanical assay. In some cases, a phenotype is directly controlled by a single gene or genetic locus, i.e., a "single gene trait." In other cases, a phenotype is the result of several genes.

As used herein, the term "polymorphism" refers to a variation in the nucleotide sequence at a locus, where said variation is too common to be due merely to a spontaneous mutation. A polymorphism must have a frequency of at least about 1% in a population. A polymorphism can be a single nucleotide polymorphism (SNP), or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the term "plant" can refer to a whole plant, a plant part or a plant organ (e.g., leaves, stems, roots, etc.), a plant tissue, a plant tissue culture, a seed, a plant cell and/or a plant germplasm. A plant cell is a cell of a plant, taken from a plant, or derived through culture from a cell taken from a plant.

As used herein, the term "plant part" includes but is not limited to embryos, pollen, seeds, leaves, flowers (including but not limited to anthers, ovules and the like), fruit, stems or branches, roots, root tips, cells including cells that are intact in plants and/or parts of plants, protoplasts, plant cell tissue cultures, plant calli, plant clumps, and the like. As used herein, "plant part" can also include germplasm. Thus, a plant part includes maize tissue culture from which soybmaizeean plants can be regenerated. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

As used herein, the term "population" refers to a genetically heterogeneous collection of plants sharing a common genetic derivation.

As used herein, the terms "progeny," "progeny plant," and/or "offspring" refer to a plant generated from a vegetative or sexual reproduction from one or more parent plants. A progeny plant may be obtained by cloning or selfing a single parent plant, or by crossing two parental plants and includes selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings or crossings of F1s, F2s and the like. An F1 can thus be (and in some embodiments is) a hybrid resulting from a cross between two true breeding parents (the phrase "true-breeding" refers to an individual that is homozygous for one or more traits), while an F2 can be an offspring resulting from self-pollination of the F1 hybrids.

As used herein, the term "maize" or "corn" refers to *Zea mays* plant(s).

As used herein, the term "reference sequence" refers to a defined nucleotide sequence used as a basis for nucleotide sequence comparison (e.g., Chromosome 10, Chromosome 3, Chromosome 1, Chromosome 5, and/or Chromosome 8 of *Zea mays* cultivar B73).

Genetic loci correlating with particular phenotypes, such as drought tolerance, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides markers associated with increased yield under non-drought conditions, increased yield stability under drought conditions, and/or increased drought tolerance in maize. Detection of these markers and/or other linked markers can be used to identify, select and/or produce maize plants having increased yield under non-drought conditions, increased yield stability under drought conditions, and/or increased drought tolerance and/or to eliminate maize plants from breeding programs or from planting that do not have increased yield under non-drought conditions, increased yield stability under drought conditions, and/or increased drought tolerance.

Molecular or gentic markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., SNP, STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson (1993) *Methods in Plant Molecular Biology and Biotechnology*, CRC Press, Boca Raton, Fla., United States of America; Zietkiewicz et al. (1994) Genomics 20:176-183.

Tables 1, 4, 5, 6, 7, and 8 provide the names of markers (SNPs) of this invention that are associated with increased yield under non-drought conditions, increased yield stability under drought conditions, and/or increased drought tolerance in maize, the physical genetic locations of each marker on the respective maize chromosome or linkage group, and the target allele that is associated with increased yield under non-drought conditions, increased yield stability under drought conditions, and/or increased drought tolerance.

Markers of the present invention are described herein with respect to the positions of marker loci in the genome of the maize B73 variety (version 2) at the Maize Genetics and Genomics Database internet resource (gbrowse.maizegdb.org/gb2/gbrowse/maize v2/) or maize B73 variety (version 3) at the Maize Genetics and Genomics Database internet resource (gbrowse.maizegdb.org/assembly/).

See Table 1, below.

Thus, in some embodiments of this invention, the marker alleles associated with increased yield under non-drought conditions, increased yield stability under drought conditions, and/or increased drought tolerance in maize are as set forth in Table 1.

In some embodiments of this invention, the marker allele(s) associated with increased yield under non-drought conditions, increased yield stability under drought conditions, and/or increased drought tolerance as set forth in Table 1 can be located in a chromosomal interval including, but not limited to (a) a chromosome interval on chromosome 10 defined by and including base pair (bp) position 14762443 to base pair (bp) position 14765098 (Gene Model ID No: GRMZM2G173669); (b) a chromosome interval on chromosome 10 defined by and including base pair (bp) position 14762443 to base pair (bp) position 14765012 (PZE10148229607.S_3355639); (c) a chromosome interval on chromosome 10 defined by and including base pair (bp) position 14762443 to base pair (bp) position 14764839 (PZE1014822787.S_3355210); (d) a chromosome interval on chromosome 10 defined by and including base pair (bp) position 14762443 to base pair (bp) position 14764763 (S_3355011); (e) a chromosome interval on chromosome 10 defined by and including base pair (bp) position 14762443 to base pair (bp) position 14764762 (PZE1014822710.S_3355009); (f) a chromosome interval on chromosome 10 defined by and including base pair (bp) position 14762443 to base pair (bp) position 14764658 (PZE101482206.S_3354710); (g) a chromosome interval on chromosome 10 defined by and including base pair (bp) position 14762443 to base pair (bp) position 14764415 (PZE1014822363.S_3353987); (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (l) a chromosome interval on chromosome 10 defined by and including base pair (bp) position

TABLE 1

The respective maize chromosome or linkage group of physical and genetic positions of the markers of the invention including allele associated with increased yield under non-drought conditions, increased yield stability under drought conditions, and/or increased drought tolerance (fav. allele).

| Gene Model ID | Gene name | Chrom. | Gene begin | Gene end | (SNP) name | Physical position in Maize B73 v2 | Fav. Allele/ Unfav. Allele |
|---|---|---|---|---|---|---|---|
| GRMZM2G173669 | SWEET-13a | chr10 | 14762443 | 14765098 | PZE1014822710 | 14764762 | C/T |
| GRMZM2G173669 | SWEET-13a | chr10 | 14762443 | 14765098 | PZE1014822787 | 14764839 | A/G |
| GRMZM2G173669 | SWEET-13a | chr10 | 14762443 | 14765098 | PZE1014822363 | 14764415 | G/T |
| GRMZM2G173669 | SWEET-13a | chr10 | 14762443 | 14765098 | PZE1014822960 | 14765012 | A/G |
| GRMZM2G173669 | SWEET-13a | chr10 | 14762443 | 14765098 | S_3355011 | 14764763 | G/C |
| GRMZM2G173669 | SWEET-13a | chr10 | 14762443 | 14765098 | PZE1014822606 | 14764658 | G/T |
| GRMZM2G039365 | SWEET-1a | chr3 | 171748815 | 171752467 | PZE03170079889 | 171752311 | G/A |
| GRMZM2G039365 | SWEET-1a | chr3 | 171748815 | 171752467 | PZE03170077114 | 171749536 | C/T |
| GRMZM2G039365 | SWEET-1a | chr3 | 171748815 | 171752467 | S_7767530 | 171749273 | C/T |
| GRMZM2G039365 | SWEET-1a | chr3 | 171748815 | 171752467 | S_7767535 | 171749283 | A/C |
| GRMZM2G039365 | SWEET-1a | chr3 | 171748815 | 171752467 | S_7767546 | 171749318 | A/C |
| GRMZM2G368827 | SWEET-11/MtN3 | chr1 | 194932443 | 194935353 | PZE01194799632 | 194932443 | A/T |
| GRMZM2G111926 | SWEET-16b | chr8 | 33363546 | 33368983 | PZE0833363225 | 33363625 | T/C |
| GRMZM5G872392 | SWEET-15b | chr5 | 164854921 | 164858109 | S_25177407 | 164855482 | A/C |

14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp) position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) position 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp) position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467 (Gene Model ID No: GRMZM2G039365); (cc) a chromosome interval on chromosome 3 defined by and including base pair (bp) position 171748815 to base pair (bp) position 171752311 (PZE03170079889.S_7768072); (dd) a chromosome interval on chromosome 3 defined by and including base pair (bp) position 171748815 to base pair (bp) position 171749536 (PZE03170077114.S_7767618); (ee) a chromosome interval on chromosome 3 defined by and including base pair (bp) position 171748815 to base pair (bp) position 171749318 (S_7767546); (ff) a chromosome interval on chromosome 3 defined by and including base pair (bp) position 171748815 to base pair (bp) position 171749283 (S_7767535); (gg) a chromosome interval on chromosome 3 defined by and including base pair (bp) position 171748815 to base pair (bp) position 171749273 (S_7767530); (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (ll) a chromosome interval on chromosome 3 defined by and including base pair (bp) position 171749273 to base pair (bp) position 171749283; (mm) a chromosome interval on chromosome 3 defined by and including base pair (bp) position 171749283 to base pair (bp) position 171752467; (nn) a chromosome interval on chromosome 3 defined by and including base pair (bp) position 171749283 to base pair (bp) position 171752311; (oo) a chromosome interval on chromosome 3 defined by and including base pair (bp) position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 (PZE01194799632) to base pair (bp) position 194935353 (Gene Model ID No: GRMZM2G368827); (ww) a chromosome interval on chromosome 8 defined by and including base pair (bp) position 33363546 to base pair (bp) position 33368983 (Gene Model ID No: GRMZM2G111926); (xx) a chromosome interval on chromosome 8 defined by and including base pair (bp) position 33363546 to base pair (bp) position 33363625 (PZE0833363225.S_16494088); (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109 (Gene Model ID No: GRMZM2G872392); (aaa) a chromosome interval on chromosome 5 defined by and including base pair (bp) position 164854921 to base pair (bp) position 164855482 (S_25177407); (bbb) a chromosome interval on chromosome 5 defined by and including base pair (bp) position 164855482 to base pair (bp) position 164858109; and (ccc) any combination of (a) to (bbb) above.

In some embodiments, by position 14762443 comprises a G allele; by position 14765098 comprises a C allele; by position 14765012 comprises an A allele; by position 14764839 comprises an A allele; by position 14764763 comprises a G allele; by position 14764762 comprises a C allele; by position 14764658 comprises a G allele; by position 14764415 comprises a G allele; by position 171748815 comprises a G allele; by position 171752467 comprises a C allele; by position 171752311 comprises a G allele; by position 171749536 comprises a C allele; by position 171749318 comprises an A allele; by position 171749283 comprises an A allele; by position 171749273 comprises a C allele; by position 194932443 comprises an A allele; by position 194935353 comprises a T allele; by position 33363546 comprises a C allele; by position 33368983 comprises an A allele; by position 33363625 comprises a T allele; by position 164854921 comprises a C allele; by position 164858109 comprises a G allele; and by position 164855482 comprises an A allele.

Thus, in some embodiments, the marker allele(s) associated with increased yield under non-drought conditions, increased yield stability under drought conditions, and/or increased drought tolerance as set forth in Table 1 can be located in a chromosomal interval defined by and including (a) a G allele at base pair (bp) position 14762443 and a C allele at base pair (bp) position 14765098; (b) a G allele at base pair (bp) position 14762443 and an A allele at base pair (bp) position 14765012; (c) a G allele at base pair (bp) position 14762443 and an A allele at base pair (bp) position 14764839; (d) a G allele at base pair (bp) position 14762443 and a G allele at base pair (bp) position 14764763; (e) a G allele at base pair (bp) position 14762443 and a C allele at base pair (bp) position 14764762; (f) a G allele at base pair (bp) position 14762443 and a G allele at base pair (bp) position 14764658; (g) a G allele at base pair (bp) position 14762443 and a G allele at base pair (bp) position 14764415; (h) a G allele at base pair (bp) position 14764415 and a C allele at base pair (bp) position 14765098; (i) a G allele at base pair (bp) position 14764415 and an A allele at base pair (bp) position 14765012; (j) a G allele at base pair (bp) position 14764415 and an A allele at base pair (bp) position 14764839; (k) a G allele at base pair (bp) position 14764415 and a G allele at base pair (bp) position 14764763; (1) a G allele at base pair (bp) position 14764415 and a C allele at base pair (bp) position 14764762; (m) a G allele at base pair (bp) position 14764415 and a G allele at base pair (bp) position 14764658; (n) a G allele at base pair (bp) position 14764658 and a C allele at base pair (bp) position 14765098; (o) a G allele at base pair (bp) position 14764658 and an A allele at base pair (bp) position 14765012; (p) a G allele at base pair (bp) position 14764658 and an A allele at base pair (bp) position 14764839; (q) a G allele at base pair (bp) position 14764658 and a G allele at base pair (bp) position 14764763; (r) a G allele at base pair (bp) position 14764658 and a C allele at base pair (bp) position 14764762; (s) a C allele at base pair (bp) position 14764762 and a C allele at base pair (bp) position 14765098; (t) a C allele at base pair (bp) position 14764762 and an A allele at base pair (bp) position 14765012; (u) a C allele at base pair (bp) position 14764762 and an A allele at base pair (bp) position 14764839; (v) a C allele at base pair (bp) position 14764762 and a G allele at base pair (bp) position 14764763; (w) a G allele at base pair (bp) position 14764763 and a C allele at base pair (bp) position 14765098; (x) a G allele at base pair (bp) position 14764763 and an A allele at base pair (bp) position 14765012; (y) a G allele at base pair (bp) 14764763 and an A allele at base pair (bp) position 14764839; (z) an A allele at base pair (bp) position 14764839 and a C allele at base pair (bp) position 14765098; (aa) an A allele at base pair (bp) position 14764839 and an A allele at base pair (bp) position 14765012; (bb) a G allele at base pair (bp) position 171748815 and a C allele at base pair (bp) position 171752467; (cc) a G allele at base pair (bp) position 171748815 and a G allele at base pair (bp) position 171752311; (dd) a G allele at base pair (bp) position 171748815 and a C allele at base pair (bp) position 171749536; (ee) a G allele at base pair (bp) position 171748815 and an A allele at base pair (bp) position 171749318; (ff) a G allele at base pair (bp) position 171748815 and an A allele at base pair (bp) position 171749283; (gg) a G allele at base pair (bp) position 171748815 and a C allele at base pair (bp) position 171749273; (hh) a C allele at base pair (bp) position 171749273 and a C allele at base pair (bp) position 171752467; (ii) a C allele at base pair (bp) position 171749273 and a G allele at base pair (bp) position 171752311; (jj) a C allele at base pair (bp) position 171749273 and a C allele at base pair (bp) position 171749536; (kk) a C allele at base pair (bp) position 171749273 and an A allele at base pair (bp) position 171749318; (11) a C allele at base pair (bp) position 171749273 and an A allele at base pair (bp) position 171749283; (mm) an A allele at base pair (bp) position 171749283 and a C allele at base pair (bp) position 171752467; (nn) an A allele at base pair (bp) position 171749283 a G allele at base pair (bp) position 171752311; (oo) an A allele at base pair (bp) position 171749283 and a C allele at base pair (bp) position 171749536; (pp) an A allele at base pair (bp) position 171749283 and an A allele at base pair (bp) position 171749318; (qq) an A allele at base pair (bp) position 171749318 and a C allele at base pair (bp) position 171752467; (rr) an A allele at base pair (bp) position 171749318 and a G allele at base pair (bp) position 171752311; (ss) an A allele at base pair (bp) position 171749318 and a C allele at base pair (bp) position 171749536; (tt) a C allele at base pair (bp) position 171749536 and a C allele at base pair (bp) position 171752467; (uu) a C allele at base pair (bp) position 171749536 and a G allele at base pair (bp) position 171752311; (vv) an A allele at base pair (bp) position 194932443 and a T allele at base pair (bp) position 194935353; (ww) a C allele at base pair (bp) position 33363546 and an A allele at base pair (bp) position 33368983; (xx) a C allele at base pair (bp) position 33363546 and a T allele at base pair (bp) position 33363625; (yy) a T allele at base pair (bp) position 33363625 and an A allele at base pair (bp) position 33368983; (zz) a C allele at base pair (bp) position 164854921 and a G allele at base pair (bp) position 164858109; (aaa) a C allele at base pair (bp) position 164854921 and an A allele at base pair (bp) position 164855482; (bbb) an A allele at base pair (bp) position 164855482 and a G allele at base pair (bp) position 164858109; and (ccc) any combination of (a) to (bbb) above. In some embodiments, the allele at each base pair position can be homozygous.

Thus, for example, in some embodiments, the marker allele(s) associated with increased yield under non-drought conditions, increased yield stability under drought conditions, and/or increased drought tolerance as set forth in Table 1 can be located in a chromosomal interval defined by and including (a) a GG allele at base pair (bp) position 14764415 and an AA allele at base pair (bp) position 14765012; (b) a GG allele at base pair (bp) position 14764415 and an AA allele at base pair (bp) position 14764839; (c) a GG allele at base pair (bp) position 14764415 and a GG allele at base pair (bp) position 14764763; (d) a GG allele at base pair (bp) position 14764415 and a CC allele at base pair (bp) position 14764762; (e) a GG allele at base pair (bp) position 14764415 and a GG allele at base pair (bp) position 14764658; (f) a GG allele at base pair (bp) position 14764658 and an AA allele at base pair (bp) position 14765012; (g) a GG allele at base pair (bp) position 14764658 and an AA allele at base pair (bp) position 14764839; (h) a GG allele at base pair (bp) position 14764658 and a GG allele at base pair (bp) position 14764763; (i) a GG allele at base pair (bp) position 14764658 and a CC allele at base pair (bp) position 14764762; (j) a CC allele at base pair (bp) position 14764762 and an AA allele at base pair (bp) position 14765012; (k) a CC allele at base pair (bp) position 14764762 and an AA allele at base pair (bp) position 14764839; (1) a CC allele at base pair (bp) position 14764762 and a GG allele at base pair (bp) position 14764763; (m) a GG allele at base pair (bp) position 14764763 and an AA allele at base pair (bp) position 14765012; (n) a GG allele at base pair (bp) position 14764763 and an AA allele at base pair (bp) position 14764839; (o) an AA allele at base pair (bp) position 14764839 and an AA allele at base pair (bp) position 14765012; (p) a CC allele at base pair (bp) position 171749273 and a GG allele at base pair (bp) position 171752311; (q) a CC allele at base pair (bp) position 171749273 and a CC allele at base pair (bp) position 171749536; (r) a CC allele at base pair (bp) position 171749273 and an AA allele at base pair (bp) position 171749318; (s) a CC allele at base pair (bp) position 171749273 and an AA allele at base pair (bp) position 171749283; (t) an AA allele at base pair (bp) position 171749283 a GG allele at base pair (bp) position 171752311; (u) an AA allele at base pair (bp) position 171749283 and a CC allele at base pair (bp) position 171749536; (v) an AA allele at base pair (bp) position 171749283 and an AA allele at base pair (bp) position 171749318; (w) an AA allele at base pair (bp) position 171749318 and a GG allele at base pair (bp) position 171752311; (x) an AA allele at base pair (bp) position 171749318 and a CC allele at base pair (bp) position 171749536; and/or (y) a CC allele at base pair (bp) position 171749536 and a GG allele at base pair position 171752311.

As would be understood by one of skill in the art, additional chromosomal intervals can be defined by the SNP markers provided herein in Table 1.

In some embodiments, a genetic marker of this invention as set forth in Table 1 is associated with increased yield under non-drought conditions, increased yield stability under drought conditions, and/or increased drought tolerance in maize, wherein the genetic marker includes but is not limited to: a G allele at base pair (bp) position 14762443; a C allele at base pair (bp) position 14765098; an A allele at base pair (bp) position 14765012; an A allele at base pair (bp) position 14764839; a G allele at base pair (bp) position 14764763; a C allele at base pair (bp) position 14764762; a G allele at base pair (bp) position 14764658; a G allele at base pair (bp) position 14764415; a G allele at base pair (bp) position 171748815; a C allele at base pair (bp) position 171752467; a G allele at base pair (bp) position 171752311; a C allele at base pair (bp) position 171749536; an A allele at base pair (bp) position 171749318; an A allele at base pair (bp) position 171749283; a C allele at base pair (bp) position 171749273; an A allele at base pair (bp) position 194932443; a T allele at base pair (bp) position 194935353; a C allele at base pair (bp) position 33363546; an A allele at base pair (bp) position 33368983; a T allele at base pair (bp) position 33363625; a C allele at base pair (bp) position 164854921; a G allele at base pair (bp) position 164858109; an A allele at base pair (bp) position 164855482; and/or any combination thereof. In some embodiments, the allele at each described base pair position can be independently homozygous or heterozygous. In some embodiments, the allele at each described base pair position can be homozygous.

In some embodiments, a combination of genetic markers of this invention as set forth in Table 1 is associated with increased yield under non-drought conditions, increased yield stability under drought conditions, and/or increased drought tolerance in maize, wherein the combination of genetic markers includes but is not limited to: (a) a G allele at base pair (bp) position 14762443 and a C allele at base pair (bp) position 14765098; (b) a G allele at base pair (bp) position 14762443 and an A allele at base pair (bp) position 14765012; (c) a G allele at base pair (bp) position 14762443 and an A allele at base pair (bp) position 14764839; (d) a G allele at base pair (bp) position 14762443 and a G allele at base pair (bp) position 14764763; (e) a G allele at base pair (bp) position 14762443 and a C allele at base pair (bp) position 14764762; (f) a G allele at base pair (bp) position 14762443 and a G allele at base pair (bp) position 14764658; (g) a G allele at base pair (bp) position 14762443 and a G allele at base pair (bp) position 14764415; (h) a G allele at base pair (bp) position 14764415 and a C allele at base pair (bp) position 14765098; (i) a G allele at base pair (bp) position 14764415 and an A allele at base pair (bp) position 14765012; (j) a G allele at base pair (bp) position 14764415 and an A allele at base pair (bp) position 14764839; (k) a G allele at base pair (bp) position 14764415 and a G allele at base pair (bp) position 14764763; (l) a G allele at base pair (bp) position 14764415 and a C allele at base pair (bp) position 14764762; (m) a G allele at base pair (bp) position 14764415 and a G allele at base pair (bp) position 14764658; (n) a G allele at base pair (bp) position 14764658 and a C allele at base pair (bp) position 14765098; (o) a G allele at base pair (bp) position 14764658 and an A allele at base pair (bp) position 14765012; (p) a G allele at base pair (bp) position 14764658 and an A allele at base pair (bp) position 14764839; (q) a G allele at base pair (bp) position 14764658 and a G allele at base pair (bp) position 14764763; (r) a G allele at base pair (bp) position 14764658 and a C allele at base pair (bp) position 14764762; (s) a C allele at base pair (bp) position 14764762 and a C allele at base pair (bp) position 14765098; (t) a C allele at base pair (bp) position 14764762 and an A allele at base pair (bp) position 14765012; (u) a C allele at base pair (bp) position 14764762 and an A allele at base pair (bp) position 14764839; (v) a C allele at base pair (bp) position 14764762 and a G allele at base pair (bp) position 14764763; (w) a G allele at base pair (bp) position 14764763 and a C allele at base pair (bp) position 14765098; (x) a G allele at base pair (bp) position 14764763 and an A allele at base pair (bp) position 14765012; (y) a G allele at base pair (bp) position 14764763 and an A allele at base pair (bp) position 14764839; (z) an A allele at base pair (bp) position 14764839 and a C allele at base pair (bp) position 14765098; (aa) an A allele at base pair (bp) position 14764839 and an A allele at base pair (bp) position 14765012; (bb) a G allele at base pair (bp) position 171748815 and a C allele at base pair (bp) position 171752467 (Gene Model ID No: GRMZM2G039365); (cc) a G allele at base pair (bp) position 171748815 and a G allele at base pair (bp) position 171752311; (dd) a G allele at base pair (bp) position 171748815 and a C allele at base pair (bp) position 171749536; (ee) a G allele at base pair (bp) position 171748815 and an A allele at base pair (bp) position 171749318; (ff) a G allele at base pair (bp) position 171748815 and an A allele at base pair (bp) position 171749283; (gg) a G allele at base pair (bp) position 171748815 and a C allele at base pair (bp) position 171749273; (hh) a C allele at base pair (bp) position 171749273 and a C allele at base pair (bp) position 171752467; (ii) a C allele at base pair (bp) position 171749273 and a G allele at base pair (bp) position 171752311; (jj) a C allele at base pair (bp) position 171749273 and a C allele at base pair (bp) position 171749536; (kk) a C allele at base pair (bp) position 171749273 and an A allele at base pair (bp) position 171749318; (ll) a C allele at base pair (bp) position 171749273 and an A allele at base pair (bp) position 171749283; (mm) an A allele at base pair (bp) position 171749283 and a C allele at base pair (bp) position 171752467; (nn) an A allele at base pair (bp) position 171749283 a G allele at base pair (bp) position 171752311;

(oo) an A allele at base pair (bp) position 171749283 and a C allele at base pair (bp) position 171749536; (pp) an A allele at base pair (bp) position 171749283 and an A allele at base pair (bp) position 171749318; (qq) an A allele at base pair (bp) position 171749318 and a C allele at base pair (bp) position 171752467; (rr) an A allele at base pair (bp) position 171749318 and a G allele at base pair (bp) position 171752311; (ss) an A allele at base pair (bp) position 171749318 and a C allele at base pair (bp) position 171749536; (tt) a C allele at base pair (bp) position 171749536 and a C allele at base pair (bp) position 171752467; (uu) a C allele at base pair (bp) position 171749536 and a G allele at base pair (bp) position 171752311; (vv) an A allele at base pair (bp) position 194932443 and a T allele at base pair (bp) position 194935353 (Gene Model ID No: GRMZM2G368827); (ww) a C allele at base pair (bp) position 33363546 and an A allele at base pair (bp) position 33368983 (Gene Model ID No: GRMZM2G111926); (xx) a C allele at base pair (bp) position 33363546 and a T allele at base pair (bp) position 33363625; (yy) a T allele at base pair (bp) position 33363625 and an A allele at base pair (bp) position 33368983; (zz) a C allele at base pair (bp) position 164854921 and a G allele at base pair (bp) position 164858109 (Gene Model ID No: GRMZM2G872392); (aaa) a C allele at base pair (bp) position 164854921 and an A allele at base pair (bp) position 164855482; (bbb) an A allele at base pair (bp) position 164855482 and a G allele at base pair (bp) position 164858109; and (ccc) any combination of (a) to (bbb) above. In some embodiments, the allele at each described base pair position can be independently homozygous or heterozygous. In some embodiments, the allele at each described base pair position can be homozygous.

In some embodiments, the combination of markers associated with increased yield under non-drought conditions, increased yield stability under drought conditions, and/or increased drought tolerance in maize, can be any combination of markers identified on chromosome 3, markers identified on chromosome 10, markers identified on chromosome 1, markers identified on chromosome 8, or markers identified on chromosome 5. Thus, in some embodiments, a combination of markers associated with increased yield under non-drought conditions, increased yield stability under drought conditions, and/or increased drought tolerance in maize can include, but are not limited to, all or any combination of a G allele at base pair (bp) position 14762443; a C allele at base pair (bp) position 14765098; an A allele at base pair (bp) position 14765012; an A allele at base pair (bp) position 14764839; a G allele at base pair (bp) position 14764763; a C allele at base pair (bp) position 14764762; a G allele at base pair (bp) position 14764658; and/or a G allele at base pair (bp) position 14764415 each of which are located on maize chromosome 10. In some embodiments, the combination of markers associated with increased yield under non-drought conditions, increased yield stability under drought conditions, and/or increased drought tolerance in maize can include, but are not limited to, all or any combination of a G allele at base pair (bp) position 171748815; a C allele at base pair (bp) position 171752467; a G allele at base pair (bp) position 171752311; a C allele at base pair (bp) position 171749536; an A allele at base pair (bp) position 171749318; an A allele at base pair (bp) position 171749283; and/or a C allele at base pair (bp) position 171749273 each of which are located on maize chromosome 3. In some embodiments, the combination of markers associated with increased yield under non-drought conditions, increased yield stability under drought conditions, and/or increased drought tolerance in maize can include, but are not limited to, an A allele at base pair (bp) position 194932443 and/or a T allele at base pair (bp) position 194935353, which are located on maize chromosome 1. In some embodiments, the combination of markers associated with increased yield under non-drought conditions, increased yield stability under drought conditions, and/or increased drought tolerance in maize can include, but are not limited to, all or any combination of a C allele at base pair (bp) position 33363546; an A allele at base pair (bp) position 33368983; and/or a T allele at base pair (bp) position 33363625 each of which are located on maize chromosome 8. In some embodiments, the combination of markers associated with increased yield under non-drought conditions, increased yield stability under drought conditions, and/or increased drought tolerance in maize can include, but are not limited to, all or any combination of a C allele at base pair (bp) position 164854921; a G allele at base pair (bp) position 164858109; and/or an A allele at base pair (bp) position 164855482 each of which are located on maize chromosome 5. In some embodiments, the allele at each described base pair position can be independently homozygous or heterozygous. In some embodiments, the allele at each described base pair position can be homozygous.

Accordingly, this invention further provides methods of identifying, selecting, and/or producing a maize plant or part thereof having increased yield under non-drought conditions, increased yield stability under drought conditions, and/or increased drought tolerance, said method comprising: detecting, in said maize plant or maize plant part, the presence of at least one genetic marker associated with increased yield under non-drought conditions, increased yield stability under drought conditions, and/or increased drought tolerance in a maize plant, as described herein. In further embodiments, said at least one marker can comprise, consist essentially of or consist of any marker linked to the aforementioned genetic markers. That is, any genetic marker that is in linkage disequilibrium with any of the aforementioned markers (SNPs, chromosome intervals and/or combinations of markers (haplotypes)) may also be used to identify, select and/or produce a maize plant having increased yield under non-drought conditions, increased yield stability under drought conditions, and/or increased drought tolerance. Linked markers may be determined, for example, by using resources available on the MaizeGDB website (maizegdb.org), Maize Sequence (ensembl.gramene.org), Phytozome v9.1: *Zea mays* (phytozome.net/maize.php).

The present invention further provides that the detecting of a genetic marker can comprise the use of a nucleic acid probe having a nucleotide base sequence that is substantially complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% complementary) to a nucleic acid sequence defining the molecular marker and which nucleic acid probe specifically hybridizes under stringent conditions with a nucleic acid sequence defining the molecular marker. A suitable nucleic acid probe can for instance be a single strand of the amplification product corresponding to the marker. In some embodiments, the detecting of a marker is designed to determine whether a particular allele of a SNP is present or absent in a particular plant.

Additionally, the methods of this invention include detecting an amplified DNA fragment associated with the presence of a particular allele of a SNP. In some embodiments, the amplified fragment associated with a particular allele of a SNP has a predicted length or nucleic acid sequence, and detecting an amplified DNA fragment having the predicted length or the predicted nucleic acid sequence is performed such that the amplified DNA fragment has a length that corresponds (plus or minus a few bases; e.g., a length of one, two or three bases more or less) to the expected length based on a similar reaction with the same primers with the DNA from the plant in which the marker was first detected or the nucleic acid sequence that corresponds (e.g., a homology of at least about 80%, 81%, 82%, 83%, 84%, 85%, 86%, 87%, 88%, 89%, 90%, 91%, 92%, 93%, 94%, 95%, 96%, 97%, 98%, 99% or more) to the expected sequence based on the sequence of the marker associated with that SNP in the plant in which the marker was first detected.

The detecting of an amplified DNA fragment having the predicted length or the predicted nucleic acid sequence can be performed by any of a number or techniques, including, but not limited to, standard gel-electrophoresis techniques or by using automated DNA sequencers. Such methods of detecting an amplified DNA fragment are not described here in detail as they are well known to those of ordinary skill in the art.

As shown in Table 1, the SNP markers of this invention are associated with increased yield under non-drought conditions, increased yield stability under drought conditions, and/or increased drought tolerance. In some embodiments, as described herein, one marker or a combination of markers can be used to detect the presence of a maize plant having increased yield under non-drought conditions, increased yield stability under drought conditions, and/or increased drought tolerance. In some embodiments, a marker can be located within a chromosomal interval (QTL) or be present in the genome of the plant as a haplotype as defined herein.

Thus, methods for identifying and/or selecting a maize plant or germplasm having increased yield under non-drought conditions, increased yield stability under drought conditions, and/or increased drought tolerance comprise detecting the presence of a genetic marker (e.g., SNP, SNP located in chromosomal interval (QTL) and/or combination of SNPs) associated with increased yield under non-drought conditions, increased yield stability under drought conditions, and/or increased drought tolerance in a maize plant or part thereof. The genetic marker can be detected in any sample taken from, for example, a maize plant or from a maize germplasm, including, but not limited to, the whole plant or germplasm or any part thereof (e.g., a seed, a leaf, a tissue culture, a cell, etc.).

Accordingly, in some aspects of the present invention, a method of identifying and/or selecting a maize plant or maize plant part having increased yield under non-drought conditions, increased yield stability under drought conditions, and/or increased drought tolerance is provided, the method comprising: detecting, in said maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of (a) a chromosome interval on chromosome 10 defined by and including base pair (bp) position 14762443 to base pair (bp) position 14765098; (b) a chromosome interval on chromosome 10 defined by and including base pair (bp) position 14762443 to base pair (bp) position 14765012; (c) a chromosome interval on chromosome 10 defined by and including base pair (bp) position 14762443 to base pair (bp) position 14764839; (d) a chromosome interval on chromosome 10 defined by and including base pair (bp) position 14762443 to base pair (bp) position 14764763; (e) a chromosome interval on chromosome 10 defined by and including base pair (bp) position 14762443 to base pair (bp) position 14764762; (f) a chromosome interval on chromosome 10 defined by and including base pair (bp) position 14762443 to base pair (bp) position 14764658; (g) a chromosome interval on chromosome 10 defined by and including base pair (bp) position 14762443 to base pair (bp) position 14764415; (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (l) a chromosome interval on chromosome 10 defined by and including base pair (bp) position 14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp) position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) position 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp) position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467; (cc) a chromosome interval on chromosome 3 defined by and including base pair (bp) position 171748815 to base pair (bp) position 171752311; (dd) a chromosome interval on chromosome 3 defined by and including base pair (bp) position 171748815 to base pair (bp) position 171749536; (ee) a chromosome interval on chromosome 3 defined by and including base pair (bp) position 171748815 to base pair (bp) position 171749318; (ff) a chromosome interval on chromosome 3 defined by and including base pair (bp) position 171748815 to base pair (bp) position 171749283; (gg) a chromosome interval on chromosome 3 defined by and including base pair (bp) position 171748815 to base pair (bp) position 171749273; (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (ll) a chromosome interval on chromosome 3 defined by and including base pair (bp) position 171749273 to base pair (bp) position 171749283; (mm) a chromosome interval on chromosome 3 defined by and including base pair (bp) position 171749283 to base pair (bp) position 171752467; (nn) a chromosome interval on chromosome 3 defined by and including base pair (bp) position 171749283 to base pair (bp) position 171752311; (oo) a chromosome interval on chromosome 3 defined by and including base pair (bp) position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 to base pair (bp) position 194935353; (ww) a chromosome interval on chromosome 8 defined by and including base pair (bp) position 33363546 to base pair (bp) position 33368983; (xx) a chromosome interval on chromosome 8 defined by and including base pair (bp) position 33363546 to base pair (bp) position 33363625; (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109; (aaa) a chromosome interval on chromosome 5 defined by and including base pair (bp) position 164854921 to base pair (bp) position 164855482; (bbb) a chromosome interval on chromosome 5 defined by and including base pair (bp) position 164855482 to base pair (bp) position 164858109; and (ccc) any combination of (a) to (bbb) above, thereby identifying and/or selecting a maize plant or maize plant part having increased yield under non-drought conditions, increased yield stability under drought conditions, and/or increased drought tolerance as compared to a control maize plant.

In some embodiments, an allele is detected at the base pair positions of the chromosome intervals described herein, wherein said allele comprises, consists essentially of, or consists of a G or GG at base pair (bp) position 14762443; a C or CC at base pair (bp) position 14765098; an A or AA at base pair (bp) position 14765012; an A or AA at base pair (bp) position 14764839; a G or GG at base pair (bp) position 14764763; a C or CC at base pair (bp) position 14764762; a G or GG at base pair (bp) position 14764658; a G or GG at base pair (bp) position 14764415; a G at base pair (bp) position 171748815; a C at base pair (bp) position 171752467; a G or GG at base pair (bp) position 171752311; a C or CC at base pair (bp) position 171749536; an A or AA at base pair (bp) position 171749318; an A or AA at base pair (bp) position 171749283; a C or CC at base pair (bp) position 171749273; an A or AA at base pair (bp) position 194932443; a T or TT at base pair (bp) position 194935353; a C or CC at base pair (bp) position 33363546; an A or AA at base pair (bp) position 33368983; a T or TT at base pair (bp) position 33363625; a C or CC at base pair (bp) position 164854921; a G or GG at base pair (bp) position 164858109; and/or an A or AA at base pair (bp) position 164855482. In some embodiments, the alleles defining the chromosome intervals can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in a maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 10 defined by and including a G or GG allele at base pair (bp) position 14762443 and a C or CC allele at base pair (bp) position 14765098; a G or GG allele at base pair (bp) position 14762443 and an A or AA allele at base pair (bp) position 14765012; a G or GG allele at base pair (bp) position 14762443 and an A or AA allele at base pair (bp) position 14764839; a G or GG allele at base pair (bp) position 14762443 and a G or GG allele at base pair (bp) position 14764763; a G or GG allele at base pair (bp) position 14762443 and a C or CC allele at base pair (bp) position 14764762; a G or GG allele at base pair (bp) position 14762443 and a G or GG allele at base pair (bp) position 14764658; a G or GG allele at base pair (bp) position 14762443 and a G or GG allele at base pair (bp) position 14764415; a G or GG allele at base pair (bp) position 14764415 and a C or CC allele at base pair (bp) position 14765098; a G or GG allele at base pair (bp) position 14764415 and an A or AA allele at base pair (bp) position 14765012; a G or GG allele at base pair (bp) position 14764415 and an A allele at base pair (bp) position 14764839; a G or GG allele at base pair (bp) position 14764415 and a G allele at base pair (bp) position 14764763; a G or GG allele at base pair (bp) position 14764415 and a C or CC allele at base pair (bp) position 14764762; a G or GG allele at base pair (bp) position 14764415 and a G or GG allele at base pair (bp) position 14764658; a G or GG allele at base pair (bp) position 14764658 and a C allele at base pair (bp) position 14765098; a G or GG allele at base pair (bp) position 14764658 and an A or AA allele at base pair (bp) position 14765012; a G or GG allele at base pair (bp) position 14764658 and an A or AA allele at base pair (bp)

position 14764839; a G or GG allele at base pair (bp) position 14764658 and a G or GG allele at base pair (bp) position 14764763; a G or GG allele at base pair (bp) position 14764658 and a C or CC allele at base pair (bp) position 14764762; a C or CC allele at base pair (bp) position 14764762 and a C or CC allele at base pair (bp) position 14765098; a C or CC allele at base pair (bp) position 14764762 and an A or AA allele at base pair (bp) position 14765012; a C or CC allele at base pair (bp) position 14764762 and an A or AA allele at base pair (bp) position 14764839; a C or CC allele at base pair (bp) position 14764762 and a G or GG allele at base pair (bp) position 14764763; a G or GG allele at base pair (bp) position 14764763 and a C or CC allele at base pair (bp) position 14765098; G or GG allele at base pair (bp) position 14764763 and an A or AA allele at base pair (bp) position 14765012; a G or GG allele at base pair (bp) position 14764763 and an A or AA allele at base pair (bp) position 14764839; an A or AA allele at base pair (bp) position 14764839 and a C or CC allele at base pair (bp) position 14765098; an A or AA allele at base pair (bp) position 14764839 and an A or AA allele at base pair (bp) position 14765012 or any combination thereof, thereby identifying and/or selecting a maize plant or maize plant part having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in said maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 3 defined by and including a G or GG allele at base pair (bp) position 171748815 and a C or CC allele at base pair (bp) position 171752467; a G or GG allele at base pair (bp) position 171748815 and a G or GG allele at base pair (bp) position 171752311; a G or GG allele at base pair (bp) position 171748815 and a C or CC allele at base pair (bp) position 171749536; a G or GG allele at base pair (bp) position 171748815 and an A or AA allele at base pair (bp) position 171749318; a G or GG allele at base pair (bp) position 171748815 and an A or AA allele at base pair (bp) position 171749283; a G or GG allele at base pair (bp) position 171748815 and a C or CC allele at base pair (bp) position 171749273; a C or CC allele at base pair (bp) position 171749273 and a C or CC allele at base pair (bp) position 171752467; a C or CC allele at base pair (bp) position 171749273 and a G or GG allele at base pair (bp) position 171752311; a C or CC allele at base pair (bp) position 171749273 and a C or CC allele at base pair (bp) position 171749536; a C or CC allele at base pair (bp) position 171749273 and an A or AA allele at base pair (bp) position 171749318; a C or CC allele at base pair (bp) position 171749273 and an A or AA allele at base pair (bp) position 171749283; an A or AA allele at base pair (bp) position 171749283 and a C or CC allele at base pair (bp) position 171752467; an A or AA allele at base pair (bp) position 171749283 a G or GG allele at base pair (bp) position 171752311; an A or AA allele at base pair (bp) position 171749283 and a C or CC allele at base pair (bp) position 171749536; an A or AA allele at base pair (bp) position 171749283 and an A or AA allele at base pair (bp) position 171749318; an A or AA allele at base pair (bp) position 171749318 and a C or CC allele at base pair (bp) position 171752467; an A or AA allele at base pair (bp) position 171749318 and a G or GG allele at base pair (bp) position 171752311; an A or AA allele at base pair (bp) position 171749318 and a C or CC allele at base pair (bp) position 171749536; a C or CC allele at base pair (bp) position 171749536 and a C or CC allele at base pair (bp) position 171752467; a C or CC allele at base pair (bp) position 171749536 and a G or GG allele at base pair (bp) position 171752311; or any combination thereof, thereby identifying and/or selecting a maize plant or maize plant part having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in said maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 1 defined by and including an A or an AA allele at base pair (bp) position 194932443 and a T or TT allele at base pair (bp) position 194935353, thereby identifying and/or selecting a maize plant or maize plant part having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in said maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 8 defined by and including a C or CC allele at base pair (bp) position 33363546 and an A or AA allele at base pair (bp) position 33368983;

a C or CC llele at base pair (bp) position 33363546 and a T or TT allele at base pair (bp) position 33363625; a T or TT allele at base pair (bp) position 33363625 and an A or AA allele at base pair (bp) position 33368983; or any combination thereof, thereby identifying and/or selecting a maize plant or maize plant part having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in said maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 5 defined by and including a C or CC allele at base pair (bp) position 164854921 and a G or GG allele at base pair (bp) position 164858109; a C or CC allele at base pair (bp) position 164854921 and an A or AA allele at base pair (bp) position 164855482; an A or AA allele at base pair (bp) position 164855482 and a G or GG allele at base pair (bp) position 164858109; or any combination thereof, thereby identifying and/or selecting a maize plant or maize plant part having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, detecting can comprise detecting any combination of markers associated with increased yield under non-drought conditions, increased yield stability under drought conditions, and/or increased drought tolerance in maize as defined herein. Thus, the combination of markers can be any combination of those identified on chromosome 3, those identified on chromosome 10, those identified on chromosome 1, those identified on chromosome 8, or those identified on chromosome 5. Thus, in some embodiments, a method of identifying and/or selecting a maize plant or maize plant part having increased yield under non-drought conditions, increased yield stability under drought conditions, and/or increased drought tolerance is provided, comprising: detecting, in a maize plant or maize plant part, the presence of a combination of markers associated with increased yield under non-drought conditions, increased yield stability under drought conditions, and/or increased drought tolerance in a maize plant, wherein said combination of markers comprises, consists essentially of, or consists of: (a) a G allele at base pair (bp) position 14762443 and a C allele at base pair (bp) position 14765098; (b) a G allele at base pair (bp) position 14762443 and an A allele at base pair (bp) position 14765012; (c) a G allele at base pair (bp) position 14762443 and an A allele at base pair (bp) position 14764839; (d) a G allele at base pair (bp) position 14762443 and a G allele at base pair (bp) position 14764763; (e) a G allele at base pair (bp) position 14762443 and a C allele at base pair (bp) position 14764762; (f) a G allele at base pair (bp) position 14762443 and a G allele at base pair (bp) position 14764658; (g) a G allele at base pair (bp) position 14762443 and a G allele at base pair (bp) position 14764415; (h) a G allele at base pair (bp) position 14764415 and a C allele at base pair (bp) position 14765098; (i) a G allele at base pair (bp) position 14764415 and an A allele at base pair (bp) position 14765012; (j) a G allele at base pair (bp) position 14764415 and an A allele at base pair (bp) position 14764839; (k) a G allele at base pair (bp) position 14764415 and a G allele at base pair (bp) position 14764763; (l) a G allele at base pair (bp) position 14764415 and a C allele at base pair (bp) position 14764762; (m) a G allele at base pair (bp) position 14764415 and a G allele at base pair (bp) position 14764658; (n) a G allele at base pair (bp) position 14764658 and a C allele at base pair (bp) position 14765098; (o) a G allele at base pair (bp) position 14764658 and an A allele at base pair (bp) position 14765012; (p) a G allele at base pair (bp) position 14764658 and an A allele at base pair (bp) position 14764839; (q) a G allele at base pair (bp) position 14764658 and a G allele at base pair (bp) position 14764763; (r) a G allele at base pair (bp) position 14764658 and a C allele at base pair (bp) position 14764762; (s) a C allele at base pair (bp) position 14764762 and a C allele at base pair (bp) position 14765098; (t) a C allele at base pair (bp) position 14764762 and an A allele at base pair (bp) position 14765012; (u) a C allele at base pair (bp) position 14764762 and an A allele at base pair (bp) position 14764839; (v) a C allele at base pair (bp) position 14764762 and a G allele at base pair (bp) position 14764763; (w) a G allele at base pair (bp) position 14764763 and a C allele at base pair (bp) position 14765098; (x) a G allele at base pair (bp) position 14764763 and an A allele at base pair (bp) position 14765012; (y) a G allele at base pair (bp) position 14764763 and an A allele at base pair (bp) position 14764839; (z) an A allele at base pair (bp) position 14764839 and a C allele at base pair (bp) position 14765098; (aa) an A allele at base pair (bp) position 14764839 and an A allele at base pair (bp) position 14765012; (bb) a G allele at base pair (bp) position 171748815 and a C allele at base pair (bp) position 171752467; (cc) a G allele at base pair (bp) position 171748815 and a G allele at base pair (bp) position 171752311; (dd) a G allele at base pair (bp) position 171748815 and a C allele at base pair (bp) position 171749536; (ee) a G allele at base pair (bp) position 171748815 and an A allele at base pair (bp) position 171749318; (ff) a G allele at base pair (bp) position 171748815 and an A allele at base pair (bp) position 171749283; (gg) a G allele at base pair (bp) position 171748815 and a C allele at base pair (bp) position 171749273; (hh) a C allele at base pair (bp) position 171749273 and a C allele at base pair (bp) position 171752467; (ii) a C allele at base pair (bp) position 171749273 and a G allele at base pair (bp) position 171752311; (jj) a C allele at base pair (bp) position 171749273 and a C allele at base pair (bp) position 171749536; (kk) a C allele at base pair (bp) position 171749273 and an A allele at base pair (bp) position 171749318; (ll) a C allele at base pair (bp) position 171749273 and an A allele at base pair (bp) position 171749283; (mm) an A allele at base pair (bp) position 171749283 and a C allele at base pair (bp) position 171752467; (nn) an A allele at base pair (bp) position 171749283 a G allele at base pair (bp) position 171752311; (oo) an A allele at base pair (bp) position 171749283 and a C allele at base pair (bp) position 171749536; (pp) an A allele at base pair (bp) position 171749283 and an A allele at base pair (bp) position 171749318; (qq) an A allele at base pair (bp) position 171749318 and a C allele at base pair (bp) position 171752467; (rr) an A allele at base pair (bp) position 171749318 and a G allele at base pair (bp) position 171752311; (ss) an A allele at base pair (bp) position 171749318 and a C allele at base pair (bp) position 171749536; (tt) a C allele at base pair (bp) position 171749536 and a C allele at base pair (bp) position 171752467; (uu) a C allele at base pair (bp) position 171749536 and a G allele at base pair (bp) position 171752311; (vv) an A allele at base pair (bp) position 194932443 and a T allele at base pair (bp) position 194935353; (ww) a C allele at base pair (bp) position 33363546 and an A allele at base pair (bp) position 33368983; (xx) a C allele at base pair (bp) position 33363546 and a T allele at base pair (bp) position 33363625; (yy) a T allele at base pair (bp) position 33363625 and an A allele at base pair (bp) position 33368983; (zz) a C allele at base pair (bp) position 164854921 and a G allele at base pair (bp) position 164858109; (aaa) a C allele at base pair (bp) position 164854921 and an A allele at base pair (bp) position 164855482; (bbb) an A allele at base pair (bp) position 164855482 and a G allele at base pair (bp) position 164858109; or (ccc) any combination of (a) to (bbb) above, thereby identifying and/or selecting a maize plant or maize plant part having increased yield under non-drought conditions, increased yield stability under drought conditions, and/or increased drought tolerance. In some embodiments, the alleles at the base pair positions defined herein can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in a maize plant or maize plant part, the presence of an allele of at least one marker locus associated with increased yield under non-drought conditions, increased yield stability under drought conditions and/or increased drought tolerance in a maize plant, wherein said allele of at least one marker locus comprises, consists essentially of, or consists of: a G allele at base pair (bp) position 14762443; a C allele at base pair (bp) position 14765098; an A allele at base pair (bp) position 14765012; an A allele at base pair (bp) position 14764839; a G allele at base pair (bp) position 14764763; a C allele at base pair (bp) position 14764762; a G allele at base pair (bp) position 14764658; a G allele at base pair (bp) position 14764415; a G allele at base pair (bp) position 171748815; a C allele at base pair (bp) position 171752467; a G allele at base pair (bp) position 171752311; a C allele at base pair (bp) position 171749536; an A allele at base pair (bp) position 171749318; an A allele at base pair (bp) position 171749283; a C allele at base pair (bp) position 171749273; an A allele at base pair (bp) position 194932443; a T allele at base pair (bp) position 194935353; a C allele at base pair (bp) position 33363546; an A allele at base pair (bp) position 33368983; a T allele at base pair (bp) position 33363625; a C allele at base pair (bp) position 164854921; a G allele at base pair (bp) position 164858109; an A allele at base pair (bp) position 164855482; or any combination thereof, thereby identifying and/or selecting a maize plant or maize plant part having increased yield under non-drought conditions, increased yield stability under drought conditions, and/or increased drought tolerance. In some embodiments, the marker alleles can be independently heterozygous or homozygous.

In representative embodiments, the detecting, in said maize plant or maize plant part, comprises, consists essentially of, or consists of detecting the presence of: a G or GG at base pair (bp) position 14762443; a C or CC at base pair (bp) position 14765098; an AA at base pair (bp) position 14765012; an AA at base pair (bp) position 14764839; a GG at base pair (bp) position 14764763; a CC at base pair (bp) position 14764762; a GG at base pair (bp) position 14764658; a GG at base pair (bp) position 14764415; a G or GG at base pair (bp) position 171748815; a C or CC at base pair (bp) position 171752467; a GG at base pair (bp) position 171752311; a CC at base pair (bp) position 171749536; an AA at base pair (bp) position 171749318; an AA at base pair (bp) position 171749283; a CC at base pair (bp) position 171749273; an AA at base pair (bp) position 194932443; a T or TT at base pair (bp) position 194935353; a C or CC at base pair (bp) position 33363546; an A or AA at base pair (bp) position 33368983; a TT at base pair (bp) position 33363625; a C or CC at base pair (bp) position 164854921; a G or CC at base pair (bp) position 164858109; an AA at base pair (bp) position 164855482, or any combination thereof.

Thus, in some embodiments, a method of producing a maize plant having increased yield under non-drought conditions, increased yield stability under drought conditions, and/or increased drought tolerance is provided, the method comprising: detecting, in a maize plant, at least one a marker locus that is associated with increased yield under non-drought conditions, increased yield stability under drought conditions, and/or increased drought tolerance, wherein said at least one marker locus is located within a chromosomal interval comprising, consisting essentially of, or consisting of: (a) a chromosome interval on chromosome 10 defined by and including base pair (bp) position 14762443 to base pair (bp) position 14765098; (b) a chromosome interval on chromosome 10 defined by and including base pair (bp) position 14762443 to base pair (bp) position 14765012; (c) a chromosome interval on chromosome 10 defined by and including base pair (bp) position 14762443 to base pair (bp) position 14764839; (d) a chromosome interval on chromosome 10 defined by and including base pair (bp) position 14762443 to base pair (bp) position 14764763; (e) a chromosome interval on chromosome 10 defined by and including base pair (bp) position 14762443 to base pair (bp) position 14764762; (f) a chromosome interval on chromosome 10 defined by and including base pair (bp) position 14762443 to base pair (bp) position 14764658; (g) a chromosome interval on chromosome 10 defined by and including base pair (bp) position 14762443 to base pair (bp) position 14764415; (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (l) a chromosome interval on chromosome 10 defined by and including base pair (bp) position 14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp) position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp) position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467; (cc) a chromosome interval on chromosome 3 defined by and including base pair (bp) position 171748815 to base pair (bp) position 171752311; (dd) a chromosome interval on chromosome 3 defined by and including base pair (bp) position 171748815 to base pair (bp) position 171749536; (ee) a chromosome interval on chromosome 3 defined by and including base pair (bp) position 171748815 to base pair (bp) position 171749318; (ff) a chromosome interval on chromosome 3 defined by and including base pair (bp) position 171748815 to base pair (bp) position 171749283; (gg) a chromosome interval on chromosome 3 defined by and including base pair (bp) position 171748815 to base pair (bp) position 171749273; (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (ll) a chromosome interval on chromosome 3 defined by and including base pair (bp) position 171749273 to base pair (bp) position 171749283; (mm) a chromosome interval on chromosome 3 defined by and including base pair (bp) position 171749283 to base pair (bp) position 171752467; (nn) a chromosome interval on chromosome 3 defined by and including base pair (bp) position 171749283 to base pair (bp) position 171752311; (oo) a chromosome interval on chromosome 3 defined by and including base pair (bp) position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 to base pair (bp) position 194935353; (ww) a chromosome interval on chromosome 8 defined by and including base pair (bp) position 33363546 to base pair (bp) position 33368983; (xx) a chromosome interval on chromosome 8 defined by and including base pair (bp) position 33363546 to base pair (bp) position 33363625; (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109; (aaa) a chromosome interval on chromosome 5 defined by and including base pair (bp) position 164854921 to base pair (bp) position 164855482; (bbb) a chromosome interval on chromosome 5 defined by and including base pair (bp) position 164855482 to base pair (bp) position 164858109; or (ccc) any combination of (a) to (bbb) above, thereby producing a plant having increased yield under non-drought conditions, increased yield stability under drought conditions, and/or increased drought tolerance as compared to a control maize plant.

In some embodiments, an allele is detected at the base pair positions of the chromosome intervals described herein, wherein said allele comprises, consists essentially of, or consists of: a G or GG at base pair (bp) position 14762443; a C or CC at base pair (bp) position 14765098; an A or AA at base pair (bp) position 14765012; an A or AA at base pair (bp) position 14764839; a G or GG at base pair (bp) position 14764763; a C or CC at base pair (bp) position 14764762; a G or GG at base pair (bp) position 14764658; a G or GG at base pair (bp) position 14764415; a G at base pair (bp) position 171748815; a C at base pair (bp) position 171752467; a G or GG at base pair (bp) position 171752311; a C or CC at base pair (bp) position 171749536; an A or AA at base pair (bp) position 171749318; an A or AA at base pair (bp) position 171749283; a C or CC at base pair (bp) position 171749273; an A or AA at base pair (bp) position 194932443; a T or TT at base pair (bp) position 194935353; a C or CC at base pair (bp) position 33363546; an A or AA at base pair (bp) position 33368983; a T or TT at base pair (bp) position 33363625; a C or CC at base pair (bp) position 164854921; a G or GG at base pair (bp) position 164858109; and/or an A or AA at base pair (bp) position 164855482. In some embodiments, the alleles defining the chromosome intervals can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 10 defined by and including a G or GG allele at base pair (bp) position 14762443 and a C or CC allele at base pair (bp) position 14765098; a G or GG allele at base pair (bp) position 14762443 and an A or AA allele at base pair (bp) position 14765012; a G or GG allele at base pair (bp) position 14762443 and an A or AA allele at base pair (bp) position 14764839; a G or GG allele at base pair (bp) position 14762443 and a G or GG allele at base pair (bp) position 14764763; a G or GG allele at base pair (bp) position 14762443 and a C or CC allele at base pair (bp) position 14764762; a G or GG allele at base pair (bp) position 14762443 and a G or GG allele at base pair (bp) position 14764658; a G or GG allele at base pair (bp) position 14762443 and a G or GG allele at base pair (bp) position 14764415; a G or GG allele at base pair (bp) position 14764415 and a C or CC allele at base pair (bp) position 14765098; a G or GG allele at base pair (bp) position 14764415 and an A or AA allele at base pair (bp) position 14765012; a G or GG allele at base pair (bp) position 14764415 and an A allele at base pair (bp) position 14764839; a G or GG allele at base pair (bp) position 14764415 and a G allele at base pair (bp) position 14764763; a G or GG allele at base pair (bp) position 14764415 and a C or CC allele at base pair (bp) position 14764762; a G or GG allele at base pair (bp) position 14764415 and a G or GG allele at base pair (bp) position 14764658; a G or GG allele at base pair (bp) position 14764658 and a C allele at base pair (bp) position 14765098; a G or GG allele at base pair (bp) position 14764658 and an A or AA allele at base pair (bp) position 14765012; a G or GG allele at base pair (bp) position 14764658 and an A or AA allele at base pair (bp) position 14764839; a G or GG allele at base pair (bp) position 14764658 and a G or GG allele at base pair (bp) position 14764763; a G or GG allele at base pair (bp) position 14764658 and a C or CC allele at base pair (bp) position 14764762; a C or CC allele at base pair (bp) position 14764762 and a C or CC allele at base pair (bp) position 14765098; a C or CC allele at base pair (bp) position 14764762 and an A or AA allele at base pair (bp) position 14765012; a C or CC allele at base pair (bp) position 14764762 and an A or AA allele at base pair (bp) position 14764839; a C or CC allele at base pair (bp) position 14764762 and a G or GG allele at base pair (bp) position 14764763; a G or GG allele at base pair (bp) position 14764763 and a C or CC allele at base pair (bp) position 14765098; G or GG allele at base pair (bp) position 14764763 and an A or AA allele at base pair (bp) position 14765012; a G or GG allele at base pair (bp) position 14764763 and an A or AA allele at base pair (bp) position 14764839; an A or AA allele at base pair (bp) position 14764839 and a C or CC allele at base pair (bp) position 14765098; an A or AA allele at base pair (bp) position 14764839 and an A or AA allele at base pair (bp) position 14765012, or any combination thereof, thereby producing a maize plant having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 3 defined by and including a G or GG allele at base pair (bp) position 171748815 and a C or CC allele at base pair (bp) position 171752467; a G or GG allele at base pair (bp) position 171748815 and a G or GG allele at base pair (bp) position 171752311; a G or GG allele at base pair (bp) position 171748815 and a C or CC allele at base pair (bp) position 171749536; a G or GG allele at base pair (bp) position 171748815 and an A or AA allele at base pair (bp) position 171749318; a G or GG allele at base pair (bp) position 171748815 and an A or AA allele at base pair (bp) position 171749283; a G or GG allele at base pair (bp) position 171748815 and a C or CC allele at base pair (bp) position 171749273; a C or CC allele at base pair (bp) position 171749273 and a C or CC allele at base pair (bp) position 171752467; a C or CC allele at base pair (bp) position 171749273 and a G or GG allele at base pair (bp) position 171752311; a C or CC allele at base pair (bp) position 171749273 and a C or CC allele at base pair (bp) position 171749536; a C or CC allele at base pair (bp) position 171749273 and an A or AA allele at base pair (bp) position 171749318; a C or CC allele at base pair (bp) position 171749273 and an A or AA allele at base pair (bp) position 171749283; an A or AA allele at base pair (bp) position 171749283 and a C or CC allele at base pair (bp) position 171752467; an A or AA allele at base pair (bp) position 171749283 a G or GG allele at base pair (bp) position 171752311; an A or AA allele at base pair (bp) position 171749283 and a C or CC allele at base pair (bp) position 171749536; an A or AA allele at base pair (bp) position 171749283 and an A or AA allele at base pair (bp) position 171749318; an A or AA allele at base pair (bp) position 171749318 and a C or CC allele at base pair (bp) position 171752467; an A or AA allele at base pair (bp) position 171749318 and a G or GG allele at base pair (bp) position 171752311; an A or AA allele at base pair (bp) position 171749318 and a C or CC allele at base pair (bp) position 171749536; a C or CC allele at base pair (bp) position 171749536 and a C or CC allele at base pair (bp) position 171752467; a C or CC allele at base pair (bp) position 171749536 and a G or GG allele at base pair (bp) position 171752311; or any combination thereof, thereby producing a maize plant having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 1 defined by and including an A or an AA allele at base pair (bp) position 194932443 and a T or TT allele at base pair (bp) position 194935353, thereby identifying and/or selecting a maize plant having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 8 defined by and including a C or CC allele at base pair (bp) position 33363546 and an A or AA allele at base pair (bp) position 33368983; a C or CC llele at base pair (bp) position 33363546 and a T or TT allele at base pair (bp) position 33363625; a T or TT allele at base pair (bp) position 33363625 and an A or AA allele at base pair (bp) position 33368983; or any combination thereof, thereby producing a maize plant having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 5 defined by and including a C or CC allele at base pair (bp) position 164854921 and a G or GG allele at base pair (bp) position 164858109; a C or CC allele at base pair (bp) position 164854921 and an A or AA allele at base pair (bp) position 164855482; an A or AA allele at base pair (bp) position 164855482 and a G or GG allele at base pair (bp) position 164858109; or any combination thereof, thereby providing a maize plant having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, detecting can comprise detecting one or more markers associated with increased yield under non-drought conditions, increased yield stability under drought conditions, and/or increased drought tolerance in maize as defined herein, in any combination. Thus, a combination of markers for detection can be any combination of markers identified on chromosome 3, markers identified on chromosome 10, markers identified on chromosome 1, markers identified on chromosome 8, and/or markers identified on chromosome 5. Thus, in some embodiments, a method of providing a maize plant having increased yield under non-drought conditions, increased yield stability under drought conditions, and/or increased drought tolerance is provided, comprising: detecting, in a maize plant, the presence of a combination of markers associated with increased yield under non-drought conditions, increased yield stability under drought conditions, and/or increased drought tolerance in a maize plant, wherein said combination of markers comprises, consists essentially of, or consists of: (a) a G allele at base pair (bp) position 14762443 and a C allele at base pair (bp) position 14765098; (b) a G allele at base pair (bp) position 14762443 and an A allele at base pair (bp) position 14765012; (c) a G allele at base pair (bp) position 14762443 and an A allele at base pair (bp) position 14764839; (d) a G allele at base pair (bp) position 14762443 and a G allele at base pair (bp) position 14764763; (e) a G allele at base pair (bp) position 14762443 and a C allele at base pair (bp) position 14764762; (f) a G allele at base pair (bp) position 14762443 and a G allele at base pair (bp) position 14764658; (g) a G allele at base pair (bp) position 14762443 and a G allele at base pair (bp) position 14764415; (h) a G allele at base pair (bp) position 14764415 and a C allele at base pair (bp) position 14765098; (i) a G allele at base pair (bp) position 14764415 and an A allele at base pair (bp) position 14765012; (j) a G allele at base pair (bp) position 14764415 and an A allele at base pair (bp) position 14764839; (k) a G allele at base pair (bp) position 14764415 and a G allele at base pair (bp) position 14764763; (1) a G allele at base pair (bp) position 14764415 and a C allele at base pair (bp) position 14764762; (m) a G allele at base pair (bp) position 14764415 and a G allele at base pair (bp) position 14764658; (n) a G allele at base pair (bp) position 14764658 and a C allele at base pair (bp) position 14765098; (o) a G allele at base pair (bp) position 14764658 and an A allele at base pair (bp) position 14765012; (p) a G allele at base pair (bp) position 14764658 and an A allele at base pair (bp) position 14764839; (q) a G allele at base pair (bp) position 14764658 and a G allele at base pair (bp) position 14764763; (r) a G allele at base pair (bp) position 14764658 and a C allele at base pair (bp) position 14764762; (s) a C allele at base pair (bp) position 14764762 and a C allele at base pair (bp) position 14765098; (t) a C allele at base pair (bp) position 14764762 and an A allele at base pair (bp) position 14765012; (u) a C allele at base pair (bp) position 14764762 and an A allele at base pair (bp) position 14764839; (v) a C allele at base pair (bp) position 14764762 and a G allele at base pair (bp) position 14764763; (w) a G allele at base pair (bp) position 14764763 and a C allele at base pair (bp) position 14765098; (x) a G allele at base pair (bp) position 14764763 and an A allele at base pair (bp) position 14765012; (y) a G allele at base pair (bp) position 14764763 and an A allele at base pair (bp) position 14764839; (z) an A allele at base pair (bp) position 14764839 and a C allele at base pair (bp) position 14765098; (aa) an A allele at base pair (bp) position 14764839 and an A allele at base pair (bp) position 14765012; (bb) a G allele at base pair (bp) position 171748815 and a C allele at base pair (bp) position 171752467; (cc) a G allele at base pair (bp) position 171748815 and a G allele at base pair (bp) position 171752311; (dd) a G allele at base pair (bp) position 171748815 and a C allele at base pair (bp) position 171749536; (ee) a G allele at base pair (bp) position 171748815 and an A allele at base pair (bp) position 171749318; (ff) a G allele at base pair (bp) position 171748815 and an A allele at base pair (bp) position 171749283; (gg) a G allele at base pair (bp) position 171748815 and a C allele at base pair (bp) position 171749273; (hh) a C allele at base pair (bp) position 171749273 and a C allele at base pair (bp) position 171752467; (ii) a C allele at base pair (bp) position 171749273 and a G allele at base pair (bp) position 171752311; (jj) a C allele at base pair (bp) position 171749273 and a C allele at base pair (bp) position 171749536; (kk) a C allele at base pair (bp) position 171749273 and an A allele at base pair (bp) position 171749318; (11) a C allele at base pair (bp) position 171749273 and an A allele at base pair (bp) position 171749283; (mm) an A allele at base pair (bp) position 171749283 and a C allele at base pair (bp) position 171752467; (nn) an A allele at base pair (bp) position 171749283 a G allele at base pair (bp) position 171752311;

(oo) an A allele at base pair (bp) position 171749283 and a C allele at base pair (bp) position 171749536; (pp) an A allele at base pair (bp) position 171749283 and an A allele at base pair (bp) position 171749318; (qq) an A allele at base pair (bp) position 171749318 and a C allele at base pair (bp) position 171752467; (rr) an A allele at base pair (bp) position 171749318 and a G allele at base pair (bp) position 171752311; (ss) an A allele at base pair (bp) position 171749318 and a C allele at base pair (bp) position 171749536; (tt) a C allele at base pair (bp) position 171749536 and a C allele at base pair (bp) position 171752467; (uu) a C allele at base pair (bp) position 171749536 and a G allele at base pair (bp) position 171752311; (vv) an A allele at base pair (bp) position 194932443 and a T allele at base pair (bp) position 194935353; (ww) a C allele at base pair (bp) position 33363546 and an A allele at base pair (bp) position 33368983; (xx) a C allele at base pair (bp) position 33363546 and a T allele at base pair (bp) position 33363625; (yy) a T allele at base pair (bp) position 33363625 and an A allele at base pair (bp) position 33368983; (zz) a C allele at base pair (bp) position 164854921 and a G allele at base pair (bp) position 164858109; (aaa) a C allele at base pair (bp) position 164854921 and an A allele at base pair (bp) position 164855482; (bbb) an A allele at base pair (bp) position 164855482 and a G allele at base pair (bp) position 164858109; or (ccc) any combination of (a) to (bbb) above, thereby producing a maize plant having increased yield under non-drought conditions, increased yield stability under drought conditions, and/or increased drought tolerance. In some embodiments, the alleles at the base pair positions defined herein can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of an allele of at least one marker locus associated with increased yield under non-drought conditions, increased yield stability under drought conditions and/or increased drought tolerance in a maize plant, wherein said allele of at least one marker locus comprises, consists essentially of, or consists of: a G allele at base pair (bp) position 14762443; a C allele at base pair (bp) position 14765098; an A allele at base pair (bp) position 14765012; an A allele at base pair (bp) position 14764839; a G allele at base pair (bp) position 14764763; a C allele at base pair (bp) position 14764762; a G allele at base pair (bp) position 14764658; a G allele at base pair (bp) position 14764415; a G allele at base pair (bp) position 171748815; a C allele at base pair (bp) position 171752467; a G allele at base pair (bp) position 171752311; a C allele at base pair (bp) position 171749536; an A allele at base pair (bp) position 171749318; an A allele at base pair (bp) position 171749283; a C allele at base pair (bp) position 171749273; an A allele at base pair (bp) position 194932443; a T allele at base pair (bp) position 194935353; a C allele at base pair (bp) position 33363546; an A allele at base pair (bp) position 33368983; a T allele at base pair (bp) position 33363625; a C allele at base pair (bp) position 164854921; a G allele at base pair (bp) position 164858109; an A allele at base pair (bp) position 164855482; or any combination thereof, thereby producing a maize plant having increased yield under non-drought conditions, increased yield stability under drought conditions, and/or increased drought tolerance. In some embodiments, the alleles of the markers can be independently heterozygous or homozygous.

In representative embodiments, the detecting, in said maize plant, comprises, consists essentially of, or consists of detecting the presence of: a G or GG at base pair (bp) position 14762443; a C or CC at base pair (bp) position 14765098; an AA at base pair (bp) position 14765012; an AA at base pair (bp) position 14764839; a GG at base pair (bp) position 14764763; a CC at base pair (bp) position 14764762; a GG at base pair (bp) position 14764658; a GG at base pair (bp) position 14764415; a G or GG at base pair (bp) position 171748815; a C or CC at base pair (bp) position 171752467; a GG at base pair (bp) position 171752311; a CC at base pair (bp) position 171749536; an AA at base pair (bp) position 171749318; an AA at base pair (bp) position 171749283; a CC at base pair (bp) position 171749273; an AA at base pair (bp) position 194932443; a T or TT at base pair (bp) position 194935353; a C or CC at base pair (bp) position 33363546; an A or AA at base pair (bp) position 33368983; a TT at base pair (bp) position 33363625; a C or CC at base pair (bp) position 164854921; a G or CC at base pair (bp) position 164858109; an AA at base pair (bp) position 164855482, or any combination thereof.

In some embodiments, in the methods of producing a maize plant having increased yield under non-drought conditions, increased yield stability under drought conditions, and/or increased drought tolerance, the detecting can comprise detecting markers in a maize plant part, plant cell or plant germplasm, wherein said maize plant part, plant cell or plant germplasm in which said marker(s) is/are detected can be regenerated into a maize plant, thereby producing a maize plant having increased yield under non-drought conditions, increased yield stability under drought conditions, and/or increased drought tolerance as compared to a control maize plant.

In some embodiments, a method of selecting a maize plant or germplasm having increased yield under non-drought conditions, increased yield stability under drought conditions, and/or increased drought tolerance is provided, comprising: crossing a first maize plant or germplasm with a second maize plant or germplasm, wherein said first maize plant or germplasm comprises within its genome at least one marker associated with increased yield under non-drought conditions, increased yield stability under drought conditions, and/or increased drought tolerance in a maize plant, wherein said marker is located within a chromosomal interval comprising, consisting essentially of, or consisting of: (a) a chromosome interval on chromosome 10 defined by and including base pair (bp) position 14762443 to base pair (bp) position 14765098; (b) a chromosome interval on chromosome 10 defined by and including base pair (bp) position 14762443 to base pair (bp) position 14765012; (c) a chromosome interval on chromosome 10 defined by and including base pair (bp) position 14762443 to base pair (bp) position 14764839; (d) a chromosome interval on chromosome 10 defined by and including base pair (bp) position 14762443 to base pair (bp) position 14764763; (e) a chromosome interval on chromosome 10 defined by and including base pair (bp) position 14762443 to base pair (bp) position 14764762; (f) a chromosome interval on chromosome 10 defined by and including base pair (bp) position 14762443 to base pair (bp) position 14764658; (g) a chromosome interval on chromosome 10 defined by and including base pair (bp) position 14762443 to base pair (bp) position 14764415; (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (l) a chromosome interval on chromosome 10 defined by and including base pair (bp) position 14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp) position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) position 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp) position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467; (cc) a chromosome interval on chromosome 3 defined by and including base pair (bp) position 171748815 to base pair (bp) position 171752311; (dd) a chromosome interval on chromosome 3 defined by and including base pair (bp) position 171748815 to base pair (bp) position 171749536; (ee) a chromosome interval on chromosome 3 defined by and including base pair (bp) position 171748815 to base pair (bp) position 171749318; (ff) a chromosome interval on chromosome 3 defined by and including base pair (bp) position 171748815 to base pair (bp) position 171749283; (gg) a chromosome interval on chromosome 3 defined by and including base pair (bp) position 171748815 to base pair (bp) position 171749273; (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (ll) a chromosome interval on chromosome 3 defined by and including base pair (bp) position 171749273 to base pair (bp) position 171749283; (mm) a chromosome interval on chromosome 3 defined by and including base pair (bp) position 171749283 to base pair (bp) position 171752467; (nn) a chromosome interval on chromosome 3 defined by and including base pair (bp) position 171749283 to base pair (bp) position 171752311; (oo) a chromosome interval on chromosome 3 defined by and including base pair (bp) position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 to base pair (bp) position 194935353; (ww) a chromosome interval on chromosome 8 defined by and including base pair (bp) position 33363546 to base pair (bp) position 33368983; (xx) a chromosome interval on chromosome 8 defined by and including base pair (bp) position 33363546 to base pair (bp) position 33363625; (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109; (aaa) a chromosome interval on chromosome 5 defined by and including base pair (bp) position 164854921 to base pair (bp) position 164855482; (bbb) a chromosome interval on chromosome 5 defined by and including base pair (bp) position 164855482 to base pair (bp) position 164858109; or (ccc) any combination of (a) to (bbb) above, and selecting a progeny maize plant or germplasm that comprises said at least one marker within its genome, thereby selecting a maize plant or germplasm having increased yield under non-drought conditions, increased yield stability under drought conditions, and/or increased drought tolerance.

In some embodiments, the allele at the base pair positions of said chromosome intervals comprises, consists essentially of, or consists of a G or GG at base pair (bp) position 14762443; a C or CC at base pair (bp) position 14765098; an A or AA at base pair (bp) position 14765012; an A or AA at base pair (bp) position 14764839; a G or GG at base pair (bp) position 14764763; a C or CC at base pair (bp) position 14764762; a G or GG at base pair (bp) position 14764658; a G or GG at base pair (bp) position 14764415; a G at base pair (bp) position 171748815; a C at base pair (bp) position 171752467; a G or GG at base pair (bp) position 171752311; a C or CC at base pair (bp) position 171749536; an A or AA at base pair (bp) position 171749318; an A or AA at base pair (bp) position 171749283; a C or CC at base pair (bp)

position 171749273; an A or AA at base pair (bp) position 194932443; a T or TT at base pair (bp) position 194935353; a C or CC at base pair (bp) position 33363546; an A or AA at base pair (bp) position 33368983; a T or TT at base pair (bp) position 33363625; a C or CC at base pair (bp) position 164854921; a G or GG at base pair (bp) position 164858109; and/or an A or AA at base pair (bp) position 164855482. In some embodiments, the alleles defining the chromosome intervals can be independently heterozygous or homozygous.

In some embodiments, a method of selecting a maize plant or germplasm having increased yield under non-drought conditions, increased yield stability under drought conditions, and/or increased drought tolerance is provided, comprising crossing a first maize plant or germplasm with a second maize plant or germplasm, wherein said first maize plant or germplasm comprises within its genome a combination of genetic markers associated with increased yield under non-drought conditions, increased yield stability under drought conditions, and/or increased drought tolerance in a maize plant, wherein said combination of genetic markers comprises, consists essentially of or consists of: (a) a G allele at base pair (bp) position 14762443 and a C allele at base pair (bp) position 14765098; (b) a G allele at base pair (bp) position 14762443 and an A allele at base pair (bp) position 14765012; (c) a G allele at base pair (bp) position 14762443 and an A allele at base pair (bp) position 14764839; (d) a G allele at base pair (bp) position 14762443 and a G allele at base pair (bp) position 14764763; (e) a G allele at base pair (bp) position 14762443 and a C allele at base pair (bp) position 14764762; (f) a G allele at base pair (bp) position 14762443 and a G allele at base pair (bp) position 14764658; (g) a G allele at base pair (bp) position 14762443 and a G allele at base pair (bp) position 14764415; (h) a G allele at base pair (bp) position 14764415 and a C allele at base pair (bp) position 14765098; (i) a G allele at base pair (bp) position 14764415 and an A allele at base pair (bp) position 14765012; (j) a G allele at base pair (bp) position 14764415 and an A allele at base pair (bp) position 14764839; (k) a G allele at base pair (bp) position 14764415 and a G allele at base pair (bp) position 14764763; (l) a G allele at base pair (bp) position 14764415 and a C allele at base pair (bp) position 14764762; (m) a G allele at base pair (bp) position 14764415 and a G allele at base pair (bp) position 14764658; (n) a G allele at base pair (bp) position 14764658 and a C allele at base pair (bp) position 14765098; (o) a G allele at base pair (bp) position 14764658 and an A allele at base pair (bp) position 14765012; (p) a G allele at base pair (bp) position 14764658 and an A allele at base pair (bp) position 14764839; (q) a G allele at base pair (bp) position 14764658 and a G allele at base pair (bp) position 14764763; (r) a G allele at base pair (bp) position 14764658 and a C allele at base pair (bp) position 14764762; (s) a C allele at base pair (bp) position 14764762 and a C allele at base pair (bp) position 14765098; (t) a C allele at base pair (bp) position 14764762 and an A allele at base pair (bp) position 14765012; (u) a C allele at base pair (bp) position 14764762 and an A allele at base pair (bp) position 14764839; (v) a C allele at base pair (bp) position 14764762 and a G allele at base pair (bp) position 14764763; (w) a G allele at base pair (bp) position 14764763 and a C allele at base pair (bp) position 14765098; (x) a G allele at base pair (bp) position 14764763 and an A allele at base pair (bp) position 14765012; (y) a G allele at base pair (bp) position 14764763 and an A allele at base pair (bp) position 14764839; (z) an A allele at base pair (bp) position 14764839 and a C allele at base pair (bp) position 14765098; (aa) an A allele at base pair (bp) position 14764839 and an A allele at base pair (bp) position 14765012; (bb) a G allele at base pair (bp) position 171748815 and a C allele at base pair (bp) position 171752467; (cc) a G allele at base pair (bp) position 171748815 and a G allele at base pair (bp) position 171752311; (dd) a G allele at base pair (bp) position 171748815 and a C allele at base pair (bp) position 171749536; (ee) a G allele at base pair (bp) position 171748815 and an A allele at base pair (bp) position 171749318; (ff) a G allele at base pair (bp) position 171748815 and an A allele at base pair (bp) position 171749283; (gg) a G allele at base pair (bp) position 171748815 and a C allele at base pair (bp) position 171749273; (hh) a C allele at base pair (bp) position 171749273 and a C allele at base pair (bp) position 171752467; (ii) a C allele at base pair (bp) position 171749273 and a G allele at base pair (bp) position 171752311; (jj) a C allele at base pair (bp) position 171749273 and a C allele at base pair (bp) position 171749536; (kk) a C allele at base pair (bp) position 171749273 and an A allele at base pair (bp) position 171749318; (ll) a C allele at base pair (bp) position 171749273 and an A allele at base pair (bp) position 171749283; (mm) an A allele at base pair (bp) position 171749283 and a C allele at base pair (bp) position 171752467; (nn) an A allele at base pair (bp) position 171749283 a G allele at base pair (bp) position 171752311; (oo) an A allele at base pair (bp) position 171749283 and a C allele at base pair (bp) position 171749536; (pp) an A allele at base pair (bp) position 171749283 and an A allele at base pair (bp) position 171749318; (qq) an A allele at base pair (bp) position 171749318 and a C allele at base pair (bp) position 171752467; (rr) an A allele at base pair (bp) position 171749318 and a G allele at base pair (bp) position 171752311; (ss) an A allele at base pair (bp) position 171749318 and a C allele at base pair (bp) position 171749536; (tt) a C allele at base pair (bp) position 171749536 and a C allele at base pair (bp) position 171752467; (uu) a C allele at base pair (bp) position 171749536 and a G allele at base pair (bp) position 171752311; (vv) an A allele at base pair (bp) position 194932443 and a T allele at base pair (bp) position 194935353; (ww) a C allele at base pair (bp) position 33363546 and an A allele at base pair (bp) position 33368983; (xx) a C allele at base pair (bp) position 33363546 and a T allele at base pair (bp) position 33363625; (yy) a T allele at base pair (bp) position 33363625 and an A allele at base pair (bp) position 33368983; (zz) a C allele at base pair (bp) position 164854921 and a G allele at base pair (bp) position 164858109; (aaa) a C allele at base pair (bp) position 164854921 and an A allele at base pair (bp) position 164855482; (bbb) an A allele at base pair (bp) position 164855482 and a G allele at base pair (bp) position 164858109; or (ccc) any combination of (a) to (bbb) above; and selecting a progeny maize plant or germplasm that comprises said marker within its genome, thereby selecting a maize plant or germplasm having increased yield under non-drought conditions, increased yield stability under drought conditions, and/or increased drought tolerance. In some embodiments, the alleles at the base pair positions defined herein can be independently heterozygous or homozygous.

In some embodiments, a method of selecting a maize plant or germplasm having increased yield under non-drought conditions, increased yield stability under drought conditions, and/or increased drought tolerance is provided, comprising: crossing a first maize plant or germplasm with a second maize plant or germplasm, wherein said first maize plant or germplasm comprises within its genome a genetic marker associated with increased yield under non-drought conditions, increased yield stability under drought conditions, and/or increased drought tolerance in a maize plant, wherein said genetic marker comprises, consists essentially of, or consists of a G or GG at base pair (bp) position 14762443; a C or CC at base pair (bp) position 14765098; an A or AA at base pair (bp) position 14765012; an A or AA at base pair (bp) position 14764839; a G or GG at base pair (bp) position 14764763; a C or CC at base pair (bp) position 14764762; a G or GG at base pair (bp) position 14764658; a G or GG at base pair (bp) position 14764415; a G at base pair (bp) position 171748815; a C at base pair (bp) position 171752467; a G or GG at base pair (bp) position 171752311; a C or CC at base pair (bp) position 171749536; an A or AA at base pair (bp) position 171749318; an A or AA at base pair (bp) position 171749283; a C or CC at base pair (bp) position 171749273; an A or AA at base pair (bp) position 194932443; a T or TT at base pair (bp) position 194935353; a C or CC at base pair (bp) position 33363546; an A or AA at base pair (bp) position 33368983; a T or TT at base pair (bp) position 33363625; a C or CC at base pair (bp) position 164854921; a G or GG at base pair (bp) position 164858109; an A or AA at base pair (bp) position 164855482; and/or any combination thereof; and selecting a progeny maize plant or germplasm that comprises said marker within its genome, thereby selecting a maize plant or germplasm having increased yield under non-drought conditions, increased yield stability under drought conditions, and/or increased drought tolerance. In some embodiments, the alleles at the base pair posisitons as defined herein can be independently heterozygous or homozygous.

In representative embodiments, said genetic marker comprises, consists essentially of, or consists of a G or GG at base pair (bp) position 14762443; a C or CC at base pair (bp) position 14765098; an AA at base pair (bp) position 14765012; an AA at base pair (bp) position 14764839; a GG at base pair (bp) position 14764763; a CC at base pair (bp) position 14764762; a GG at base pair (bp) position 14764658; a GG at base pair (bp) position 14764415; a G or GG at base pair (bp) position 171748815; a C or CC at base pair (bp) position 171752467; a GG at base pair (bp) position 171752311; a CC at base pair (bp) position 171749536; an AA at base pair (bp) position 171749318; an AA at base pair (bp) position 171749283; a CC at base pair (bp) position 171749273; an AA at base pair (bp) position 194932443; a T or TT at base pair (bp) position 194935353; a C or CC at base pair (bp) position 33363546; an A or AA at base pair (bp) position 33368983; a TT at base pair (bp) position 33363625; a C or CC at base pair (bp) position 164854921; a G or CC at base pair (bp) position 164858109; an AA at base pair (bp) position 164855482; or any combination thereof.

In some embodiments, the second maize plant or germplasm of this invention is of an elite variety of maize. In some embodiments, the genome of the second maize plant or germplasm is at least about 60%, 65%, 70%, 75%, 80%, 85%, 90%, 95%, 97%, 99% or 100% identical to that of an elite variety of maize.

In some embodiments of this invention, a method of introgressing a genetic marker associated with increased yield under non-drought conditions, increased yield stability under drought conditions, and/or increased drought tolerance in maize into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with increased yield under non-drought conditions, increased yield stability under drought conditions, and/or increased drought tolerance in a maize plant, wherein said marker is located within (a) a chromosome interval on chromosome 10 defined by and including base pair (bp) position 14762443 to base pair (bp) position 14765098; (b) a chromosome interval on chromosome 10 defined by and including base pair (bp) position 14762443 to base pair (bp) position 14765012; (c) a chromosome interval on chromosome 10 defined by and including base pair (bp) position 14762443 to base pair (bp) position 14764839; (d) a chromosome interval on chromosome 10 defined by and including base pair (bp) position 14762443 to base pair (bp) position 14764763; (e) a chromosome interval on chromosome 10 defined by and including base pair (bp) position 14762443 to base pair (bp) position 14764762; (f) a chromosome interval on chromosome 10 defined by and including base pair (bp) position 14762443 to base pair (bp) position 14764658; (g) a chromosome interval on chromosome 10 defined by and including base pair (bp) position 14762443 to base pair (bp) position 14764415; (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (1) a chromosome interval on chromosome 10 defined by and including base pair (bp) position 14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp) position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) position 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp) position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467; (cc) a chromosome interval on chromosome 3 defined by and including base pair (bp) position 171748815 to base pair (bp) position 171752311; (dd) a chromosome interval on chromosome 3 defined by and including base pair (bp) position 171748815 to base pair (bp) position 171749536; (ee) a chromosome interval on chromosome 3 defined by and including base pair (bp) position 171748815 to base pair (bp) position 171749318; (ff) a chromosome interval on chromosome 3 defined by and including base pair (bp) position 171748815 to base pair (bp) position 171749283; (gg) a chromosome interval on chromosome 3 defined by and including base pair (bp) position 171748815 to base pair (bp) position 171749273; (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (11) a chromosome interval on chromosome 3 defined by and including base pair (bp) position 171749273 to base pair (bp) position 171749283; (mm) a chromosome interval on chromosome 3 defined by and including base pair (bp) position 171749283 to base pair (bp) position 171752467; (nn) a chromosome interval on chromosome 3 defined by and including base pair (bp) position 171749283 to base pair (bp) position 171752311; (oo) a chromosome interval on chromosome 3 defined by and including base pair (bp) position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 to base pair (bp) position 194935353; (ww) a chromosome interval on chromosome 8 defined by and including base pair (bp) position 33363546 to base pair (bp) position 33368983; (xx) a chromosome interval on chromosome 8 defined by and including base pair (bp) position 33363546 to base pair (bp) position 33363625; (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109; (aaa) a chromosome interval on chromosome 5 defined by and including base pair (bp) position 164854921 to base pair (bp) position 164855482; (bbb) a chromosome interval on chromosome 5 defined by and including base pair (bp) position 164855482 to base pair (bp) position 164858109; or (ccc) any combination of (a) to (bbb) above; and producing a maize plant or germplasm having increased yield under non-drought conditions, increased yield stability under drought conditions, and/or increased drought tolerance and comprising said genetic marker associated with increased yield under non-drought conditions, increased yield stability under drought conditions, and/or increased drought tolerance in the genetic background of the recurrent parent, thereby introgressing the genetic marker associated with increased yield under non-drought conditions, increased yield stability under drought conditions, and/or increased drought tolerance into a genetic background lacking said marker. In some embodiments, the base pair positions defining the chromosomal intervals can comprise alleles, which can be heterozygous or homozygous, or any combination thereof.

In some embodiments of this invention, a method of introgressing a genetic marker associated with increased yield under non-drought conditions, increased yield stability under drought conditions, and/or increased drought tolerance in maize into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with increased yield under non-drought conditions, increased yield stability under drought conditions, and/or increased drought tolerance in a maize plant, wherein said marker comprises, consists essentially of, or consists of a G or GG at base pair (bp) position 14762443; a C or CC at base pair (bp) position 14765098; an A or AA at base pair (bp) position 14765012; an A or AA at base pair (bp) position 14764839; a G or GG at base pair (bp) position 14764763; a C or CC at base pair (bp) position 14764762; a G or GG at base pair (bp) position 14764658; a G or GG at base pair (bp) position 14764415; a G at base pair (bp) position 171748815; a C at base pair (bp) position 171752467; a G or GG at base pair (bp) position 171752311; a C or CC at base pair (bp) position 171749536; an A or AA at base pair (bp) position 171749318; an A or AA at base pair (bp) position 171749283; a C or CC at base pair (bp) position 171749273; an A or AA at base pair (bp) position 194932443; a T or TT at base pair (bp) position 194935353; a C or CC at base pair (bp) position 33363546; an A or AA at base pair (bp) position 33368983; a T or TT at base pair (bp) position 33363625; a C or CC at base pair (bp) position 164854921; a G or GG at base pair (bp) position 164858109; an A or AA at base pair (bp) position 164855482; or any combination thereof; and selecting a progeny maize plant or germplasm that comprises said marker within its genome, thereby selecting a maize plant or germplasm having increased yield under non-drought conditions, increased yield stability under drought conditions, and/or increased drought tolerance. In some embodiments, the alleles at the base pair positions as defined herein can be independently heterozygous or homozygous.

TABLE 2a

Significant Insertion/Deletion Markers from FBAM Study

| INDEL | Analysis_ID | Trait | Marker v2 | GeneModelID |
| --- | --- | --- | --- | --- |
| 1 | Sweet_SS_K_1PC | YGSMN_2008_irrigated | chr3_171748915_A_AGA | GRMZM2G039365 |
| 2 | Sweet_NSS_K_6PC | YGSMN_2009_irrigated | chr10_14764880_GCATG_G | GRMZM2G173669 |

TABLE 2b

Significant Insertion/Deletion Markers from FBAM Study

| INDEL | Chrom. | Site v2 | NegLogP | Num_Ind | Allele_1 | Allele1_effect | Allele_2 | Allele2_effect |
| --- | --- | --- | --- | --- | --- | --- | --- | --- |
| 1 | chr3 | 171748915 | 3.6662304 | 142 | D | 2.1373275 | I | −2.1373275 |
| 2 | chr10 | 14764880 | 3.5313721 | 229 | D | −2.11413 | I | 2.11413 |

In some embodiments, a method of identifying and/or selecting a maize plant or maize plant part having increased yield under non-drought conditions, increased yield stability under drought conditions, and/or increased drought tolerance is provided, the method comprising: detecting, in a maize plant or maize plant part, the presence of an allele of at least one marker locus associated with increased yield under non-drought conditions, increased yield stability under drought conditions and/or increased drought tolerance in a maize plant, wherein said allele of at least one marker locus is selected from the group comprised of INDEL 1 and INDEL2 found in Table 3.

ADDITIONAL SNPS IDENTIFIED IN THE SWEET11 LOCUS (GRMZM2G368827), SWEET1A LOCUS (GRMZM2G039365), SWEET15B LOCUS (GRMZM5G872392), AND SWEET13A LOCUS (GRMZM2G173669)

Additional sequencing was performed to identify additional SNPs at the SWEET11 locus, SWEET1a locus, SWEET15b locus and SWEET13a locus. These loci are described in table 3. Two thousand bases upstream and downstream of the gene were included in the sequencing.

TABLE 3

Regions sequenced with positions relative to the Maize B73 genome version 3.

| Name | Gene Model | Chromosome | Start V3 | End V3 | SEQ ID Number |
| --- | --- | --- | --- | --- | --- |
| SWEET11 | GRMZM2G368827 | 1 | 194970347 | 194963437 | 20 |
| SWEET1a | GRMZM2G039365 | 3 | 171797701 | 171790082 | 21 |
| SWEET15b | GRMZM5G872392 | 5 | 164900398 | 164893210 | 23 |
| SWEET 13a | GRMZM2G173669 | 10 | 14765640 | 14772295 | 22 |

Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., SNP, STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson (1993) Methods in Plant Molecular Biology and Biotechnology, CRC Press, Boca Raton, Fla., United States of America; Zietkiewicz et al. (1994) Genomics 20:176-183.

Tables 1, 4, 5, 6, 7, and 8 provide a summary of markers associated with having increased yield under non-drought conditions, increased yield stability under drought conditions, and/or increased drought tolerance in maize, their corresponding name, the physical location of the marker on the respective having increased yield under non-drought conditions, increased yield stability under drought conditions, and/or increased drought tolerance chromosome, and the target allele that is associated with having increased yield under non-drought conditions, increased yield stability under drought conditions, and/or increased drought tolerance.

TABLE 4

SNPs mapped on the Maize B73 genome version 3 with a significant association at NegLogP > 2.5 from SWEET11, gene model GRMZM2G368827, plus or minus 2 kb (SEQ ID NO. 21) with effect on yield measured in bushels per acre.

| Chr. | Site V3 | Analysis_ID | Trait | NegLogP | Favorable Allele | Unfavorable Allele | Yield Allele Effect Size in Bushels Per Acre |
|---|---|---|---|---|---|---|---|
| 1 | 194967163 | hybrid_2009_NSS | Drought Stress | 3.879887 | C | G | 4.10124 |
| 1 | 194966087 | hybrid_2009_NSS | Drought Stress | 3.53432 | C | G | 4.36633 |
| 1 | 194967163 | hybrid_2008_NSS | Well-Watered | 3.236527 | C | G | 5.76586 |
| 1 | 194965388 | hybrid_2008_SS | Well-Watered | 3.161964 | C | T | 12.3601 |
| 1 | 194966273 | inbred | Drought Stress | 3.057431 | T | G | 3.21065 |
| 1 | 194968091 | hybrid_2009_NSS | Drought Stress | 2.954677 | G | A | 3.6573 |
| 1 | 194967163 | hybrid_2009_NSS | Well-Watered | 2.636388 | C | G | 6.90804 |
| 1 | 194967616 | hybrid_2009_NSS | Drought Stress | 2.50724 | C | T | 3.04925 |

TABLE 5

SNPs mapped on the Maize B73 genome version 3 with a significant association at NegLogP > 2.5 from SWEET1a, gene model GRMZM2G039365, plus or minus 2 kb (SEQ ID NO. 20) with effect on yield measured in bushels per acre.

| Chr. | Site V3 | Analysis_ID | Trait | NegLogP | Favorable Allele | Unfavorable Allele | Yield Allele Effect Size in Bushels Per Acre |
|---|---|---|---|---|---|---|---|
| 3 | 171791580 | inbred | Well-Watered | 5.115613 | G | A | 9.3995 |
| 3 | 171795048 | inbred | Well-Watered | 5.073658 | T | C | 8.3205 |
| 3 | 171790578 | inbred | Well-Watered | 5.015725 | G | A | 9.0395 |
| 3 | 171791368 | inbred | Well-Watered | 4.678505 | G | T | 8.77563 |
| 3 | 171795101 | inbred | Well-Watered | 4.675944 | C | T | 8.203465 |
| 3 | 171791249 | inbred | Well-Watered | 4.522821 | G | A | 8.4165 |
| 3 | 171791181 | inbred | Well-Watered | 4.202802 | C | T | 8.073405 |
| 3 | 171793764 | inbred | Well-Watered | 4.169642 | C | G | 7.76601 |
| 3 | 171790729 | inbred | Well-Watered | 4.116594 | C | T | 7.924085 |
| 3 | 171790242 | inbred | Well-Watered | 4.048735 | C | T | 7.829055 |
| 3 | 171792281 | inbred | Well-Watered | 4.021792 | T | C | 7.869 |
| 3 | 171792609 | inbred | Well-Watered | 3.980884 | G | A | 7.6865 |
| 3 | 171792046 | inbred | Well-Watered | 3.978728 | G | T | 7.76005 |
| 3 | 171790356 | inbred | Well-Watered | 3.778508 | C | T | 7.49401 |
| 3 | 171791877 | inbred | Well-Watered | 3.689604 | C | G | 7.40435 |
| 3 | 171790863 | hybrid_2009_SS | Well-Watered | 3.34879 | T | G | 10.279 |
| 3 | 171792700 | inbred | Drought Stress | 3.32457 | G | C | 1.9658 |
| 3 | 171790860 | hybrid_2009_SS | Well-Watered | 3.304063 | A | G | 9.36786 |
| 3 | 171794113 | inbred | Well-Watered | 3.263476 | C | T | 6.99644 |
| 3 | 171790097 | inbred | Well-Watered | 3.22253 | G | A | 7.2515 |
| 3 | 171792700 | inbred | Well-Watered | 3.138579 | G | C | 1.9658 |
| 3 | 171791279 | hybrid_2009_NSS | Well-Watered | 3.131855 | C | T | 9.29628 |
| 3 | 171790833 | hybrid_2009_SS | Well-Watered | 3.129549 | G | A | 9.4833 |
| 3 | 171793764 | hybrid_2008_SS | Well-Watered | 3.078256 | C | G | 12.33725 |
| 3 | 171794699 | hybrid_2009_SS | Well-Watered | 2.924453 | A | G | 9.52317 |
| 3 | 171790889 | hybrid_2009_SS | Well-Watered | 2.869666 | G | A | 7.2645 |
| 3 | 171794646 | hybrid_2009_SS | Well-Watered | 2.863279 | G | C | 4.241 |
| 3 | 171790428 | hybrid_2009_NSS | Well-Watered | 2.730487 | C | G | 7.72251 |
| 3 | 171791351 | hybrid_2009_NSS | Well-Watered | 2.718967 | T | C | 8.6827 |
| 3 | 171791465 | inbred | Well-Watered | 2.712198 | C | A | 3.44395 |
| 3 | 171791187 | hybrid_2009_NSS | Well-Watered | 2.707744 | A | G | 7.17022 |
| 3 | 171794646 | hybrid_2008_SS | Well-Watered | 2.645892 | G | C | 4.2361 |
| 3 | 171791552 | hybrid_2009_NSS | Well-Watered | 2.634512 | T | C | 9.6936 |
| 3 | 171791214 | hybrid_2009_NSS | Well-Watered | 2.527244 | G | C | 7.3121 |
| 3 | 171795034 | hybrid_2009_SS | Well-Watered | 2.517126 | C | T | 4.01167 |
| 3 | 171791216 | hybrid_2009_NSS | Well-Watered | 2.512862 | G | C | 8.3756 |

TABLE 6

SNPs mapped on the Maize B73 genome version 3 with a significant association at NegLogP > 2.5 from SWEET15b, gene model GRMZM5G872392, plus or minus 2 kb (SEQ ID NO. 23) with effect on yield measured in bushels per acre.

| Chr. | Site V3 | Analysis_ID | Trait | NegLogP | Favorable Allele | Unfavorable Allele | Yield Allele Effect Size in Bushels Per Acre |
|---|---|---|---|---|---|---|---|
| 5 | 164895193 | hybrid_2008_SS | Well-Watered | 6.700166 | C | T | 15.59343 |
| 5 | 164896921 | hybrid_2008_SS | Well-Watered | 6.106771 | G | C | 14.823 |
| 5 | 164897496 | hybrid_2008_SS | Well-Watered | 5.781018 | G | T | 13.20848 |
| 5 | 164897515 | hybrid_2008_SS | Well-Watered | 5.711974 | G | C | 13.108 |
| 5 | 164897518 | hybrid_2008_SS | Well-Watered | 5.711974 | C | T | 13.10835 |
| 5 | 164896797 | hybrid_2008_SS | Well-Watered | 5.648822 | G | A | 13.231 |
| 5 | 164897574 | hybrid_2008_SS | Well-Watered | 5.608924 | C | T | 12.95274 |
| 5 | 164896808 | hybrid_2008_SS | Well-Watered | 5.603034 | C | A | 13.153 |
| 5 | 164897386 | hybrid_2008_SS | Well-Watered | 5.194594 | G | C | 11.791 |
| 5 | 164895831 | hybrid_2008_SS | Well-Watered | 5.139237 | A | C | 12.03305 |
| 5 | 164897335 | hybrid_2008_SS | Well-Watered | 5.112293 | A | G | 11.66738 |
| 5 | 164895604 | hybrid_2008_SS | Well-Watered | 5.01941 | C | T | 11.83812 |
| 5 | 164898796 | hybrid_2009_SS | Well-Watered | 4.863819 | A | C | 13.12005 |
| 5 | 164895579 | hybrid_2008_SS | Well-Watered | 4.601314 | A | G | 11.1 |
| 5 | 164895754 | hybrid_2008_SS | Well-Watered | 4.508064 | G | T | 10.37686 |
| 5 | 164898809 | hybrid_2009_SS | Well-Watered | 4.113058 | A | G | 10.74552 |
| 5 | 164895521 | hybrid_2009_SS | Drought Stress | 3.230623 | A | G | 3.88969 |
| 5 | 164895523 | hybrid_2009_SS | Drought Stress | 3.230623 | C | T | 3.88969 |
| 5 | 164897630 | hybrid_2008_SS | Well-Watered | 3.187214 | G | T | 8.22958 |
| 5 | 164896918 | hybrid_2009_NSS | Drought Stress | 3.115907 | G | C | 3.5324 |
| 5 | 164895193 | hybrid_2009_SS | Drought Stress | 3.077503 | C | T | 3.3913 |
| 5 | 164895831 | hybrid_2009_SS | Drought Stress | 3.030738 | A | C | 3.06066 |
| 5 | 164897500 | hybrid_2009_NSS | Drought Stress | 3.025106 | T | C | 4.1897 |
| 5 | 164896550 | hybrid_2009_NSS | Drought Stress | 3.005309 | G | C | 3.2431 |
| 5 | 164894861 | hybrid_2008_SS | Well-Watered | 3.004575 | A | G | 10.97907 |
| 5 | 164895604 | hybrid_2009_SS | Drought Stress | 2.8041 | C | T | 2.91219 |
| 5 | 164894762 | hybrid_2008_NSS | Well-Watered | 2.747147 | C | G | 7.08521 |
| 5 | 164897496 | hybrid_2009_SS | Drought Stress | 2.703335 | G | T | 2.8445 |
| 5 | 164897515 | hybrid_2009_SS | Drought Stress | 2.69897 | G | C | 2.84 |
| 5 | 164897518 | hybrid_2009_SS | Drought Stress | 2.69897 | C | T | 2.84002 |
| 5 | 164895579 | hybrid_2008_SS | Drought Stress | 2.688246 | A | G | 8.47162 |
| 5 | 164896921 | hybrid_2009_SS | Drought Stress | 2.677781 | G | C | 3.14 |
| 5 | 164897574 | hybrid_2009_SS | Drought Stress | 2.673664 | C | T | 2.82233 |
| 5 | 164897479 | hybrid_2009_NSS | Drought Stress | 2.67162 | A | C | 4.20778 |
| 5 | 164895754 | hybrid_2009_SS | Drought Stress | 2.645892 | G | T | 2.58891 |
| 5 | 164898870 | hybrid_2008_SS | Well-Watered | 2.643974 | A | G | 4.35255 |
| 5 | 164895604 | hybrid_2008_SS | Drought Stress | 2.625252 | C | T | 8.42928 |
| 5 | 164895579 | hybrid_2009_SS | Drought Stress | 2.623423 | A | G | 2.77526 |
| 5 | 164897511 | hybrid_2009_NSS | Drought Stress | 2.598599 | G | C | 3.7672 |
| 5 | 164898869 | hybrid_2008_SS | Well-Watered | 2.598599 | C | T | 4.33053 |
| 5 | 164896808 | hybrid_2009_SS | Drought Stress | 2.568636 | C | A | 2.7898 |
| 5 | 164899821 | hybrid_2009_SS | Drought Stress | 2.568636 | C | G | 3.57609 |
| 5 | 164896797 | hybrid_2009_SS | Drought Stress | 2.548214 | G | A | 2.7783 |
| 5 | 164897523 | hybrid_2009_NSS | Drought Stress | 2.528708 | G | T | 3.62675 |
| 5 | 164896550 | hybrid_2008_SS | Well-Watered | 2.508638 | G | C | 3.4862 |

TABLE 7

SNPs mapped on the Maize B73 genome version 3 with a significant association at NegLogP > 2.5 from SWEET13a, gene model GRMZM2G173669, plus or minus 2 kb (SEQ ID NO. 22) with effect on yield measured in bushels per acre.

| Chr. | Site V3 | Analysis_ID | Trait | NegLogP | Favorable Allele | Unfavorable Allele | Yield Allele Effect Size in Bushels Per Acre |
|---|---|---|---|---|---|---|---|
| 10 | 14770979 | hybrid_2008_SS | Drought Stress | 5.123909 | A | G | 7.27563 |
| 10 | 14770796 | hybrid_2008_SS | Drought Stress | 4.767436 | C | T | 6.90935 |
| 10 | 14769813 | hybrid_2008_SS | Drought Stress | 4.558069 | C | A | 6.8344 |
| 10 | 14769855 | hybrid_2008_SS | Drought Stress | 4.540502 | G | T | 6.82154 |
| 10 | 14770143 | inbred | Well-Watered | 4.438684 | G | A | 2.65785 |
| 10 | 14770146 | inbred | Well-Watered | 4.407191 | T | C | 2.6854 |
| 10 | 14771337 | hybrid_2008_SS | Drought Stress | 4.301212 | C | A | 6.635 |
| 10 | 14770566 | hybrid_2008_SS | Drought Stress | 4.257581 | G | A | 6.5973 |
| 10 | 14771209 | hybrid_2008_SS | Drought Stress | 4.25265 | G | T | 6.60749 |
| 10 | 14771216 | hybrid_2008_SS | Drought Stress | 4.208843 | C | T | 6.37728 |
| 10 | 14768884 | hybrid_2008_SS | Well-Watered | 4.096986 | A | T | 5.57298 |

TABLE 7-continued

SNPs mapped on the Maize B73 genome version 3 with a significant association at NegLogP > 2.5 from SWEET13a, gene model GRMZM2G173669, plus or minus 2 kb (SEQ ID NO. 22) with effect on yield measured in bushels per acre.

| Chr. | Site V3 | Analysis_ID | Trait | NegLogP | Favorable Allele | Unfavorable Allele | Yield Allele Effect Size in Bushels Per Acre |
|---|---|---|---|---|---|---|---|
| 10 | 14770999 | hybrid_2008_SS | Drought Stress | 4.055128 | G | C | 6.5291 |
| 10 | 14771012 | hybrid_2008_SS | Drought Stress | 4.024003 | A | T | 6.45204 |
| 10 | 14770497 | hybrid_2008_SS | Drought Stress | 3.995808 | C | T | 6.4249 |
| 10 | 14770658 | hybrid_2008_SS | Drought Stress | 3.915674 | G | A | 6.2481 |
| 10 | 14770602 | hybrid_2008_SS | Drought Stress | 3.90879 | T | C | 6.102 |
| 10 | 14770036 | hybrid_2008_SS | Drought Stress | 3.86544 | A | G | 6.35061 |
| 10 | 14766703 | inbred | Well-Watered | 3.859209 | C | T | 10.23589 |
| 10 | 14770375 | hybrid_2008_SS | Drought Stress | 3.77692 | G | A | 6.23 |
| 10 | 14770181 | inbred | Well-Watered | 3.691222 | C | A | 10.1755 |
| 10 | 14769893 | hybrid_2008_SS | Drought Stress | 3.685648 | G | C | 5.9502 |
| 10 | 14769292 | hybrid_2009_NSS | Drought Stress | 3.67391 | T | C | 4.5426 |
| 10 | 14770520 | hybrid_2008_SS | Drought Stress | 3.669667 | A | G | 6.17721 |
| 10 | 14771349 | hybrid_2008_SS | Drought Stress | 3.607901 | G | A | 6.0306 |
| 10 | 14770915 | hybrid_2008_SS | Drought Stress | 3.487289 | A | T | 5.40066 |
| 10 | 14766789 | hybrid_2008_SS | Drought Stress | 3.413536 | A | T | 6.06067 |
| 10 | 14770439 | hybrid_2008_SS | Drought Stress | 3.367725 | G | A | 5.6522 |
| 10 | 14769364 | hybrid_2009_NSS | Well-Watered | 3.346353 | A | G | 8.76778 |
| 10 | 14771231 | hybrid_2008_SS | Drought Stress | 3.291537 | C | T | 5.35392 |
| 10 | 14770722 | inbred | Well-Watered | 3.176037 | C | T | 7.201815 |
| 10 | 14770955 | hybrid_2008_SS | Drought Stress | 3.158071 | A | T | 5.0687 |
| 10 | 14770663 | hybrid_2008_SS | Drought Stress | 3.150421 | G | A | 5.4719 |
| 10 | 14769612 | hybrid_2008_SS | Drought Stress | 3.131426 | G | T | 5.29014 |
| 10 | 14768375 | hybrid_2009_NSS | Well-Watered | 3.10716 | T | C | 8.2261 |
| 10 | 14768039 | hybrid_2008_SS | Drought Stress | 3.106105 | G | T | 4.50777 |
| 10 | 14768028 | hybrid_2008_SS | Drought Stress | 3.055596 | A | G | 4.4608 |
| 10 | 14766537 | inbred | Well-Watered | 3.035604 | A | C | 0.026745 |
| 10 | 14771072 | inbred | Well-Watered | 3.021176 | C | T | 2.423595 |
| 10 | 14771255 | hybrid_2008_SS | Drought Stress | 3.013757 | C | T | 5.01477 |
| 10 | 14770696 | hybrid_2008_SS | Drought Stress | 2.939302 | G | A | 4.8283 |
| 10 | 14771388 | hybrid_2008_SS | Drought Stress | 2.924453 | G | A | 4.8294 |
| 10 | 14770791 | hybrid_2008_SS | Drought Stress | 2.886057 | A | G | 4.63432 |
| 10 | 14771179 | hybrid_2008_SS | Drought Stress | 2.876148 | C | T | 4.80964 |
| 10 | 14769364 | inbred | Drought Stress | 2.872895 | A | G | 2.042005 |
| 10 | 14768027 | hybrid_2008_SS | Drought Stress | 2.844664 | G | C | 4.3108 |
| 10 | 14770870 | hybrid_2008_SS | Well-Watered | 2.841638 | A | G | 5.24988 |
| 10 | 14770526 | hybrid_2008_SS | Drought Stress | 2.829738 | C | G | 4.75951 |
| 10 | 14768024 | hybrid_2008_SS | Drought Stress | 2.826814 | T | C | 4.1932 |
| 10 | 14770571 | hybrid_2008_SS | Drought Stress | 2.826814 | T | C | 4.7235 |
| 10 | 14771007 | inbred | Well-Watered | 2.809668 | C | T | 2.511865 |
| 10 | 14768061 | hybrid_2008_SS | Drought Stress | 2.779892 | T | A | 4.5162 |
| 10 | 14770143 | inbred | Drought Stress | 2.767004 | G | A | 11.545 |
| 10 | 14771317 | hybrid_2008_SS | Drought Stress | 2.747147 | C | T | 4.59649 |
| 10 | 14770146 | inbred | Drought Stress | 2.723538 | T | C | 11.489 |
| 10 | 14771591 | hybrid_2008_SS | Well-Watered | 2.723538 | C | T | 6.84992 |
| 10 | 14770760 | hybrid_2008_SS | Drought Stress | 2.718967 | T | C | 4.5738 |
| 10 | 14767614 | hybrid_2008_SS | Drought Stress | 2.694649 | T | G | 3.8415 |
| 10 | 14770955 | hybrid_2008_SS | Well-Watered | 2.694649 | A | T | 4.42008 |
| 10 | 14770897 | hybrid_2008_SS | Well-Watered | 2.679854 | C | T | 4.43727 |
| 10 | 14770915 | hybrid_2008_SS | Well-Watered | 2.675718 | A | T | 4.40605 |
| 10 | 14770475 | hybrid_2008_SS | Drought Stress | 2.667562 | A | C | 4.4881 |
| 10 | 14770897 | hybrid_2008_SS | Drought Stress | 2.638272 | C | T | 4.5712 |
| 10 | 14770601 | hybrid_2008_SS | Drought Stress | 2.632644 | T | C | 4.4399 |
| 10 | 14768381 | hybrid_2008_SS | Drought Stress | 2.614394 | C | A | 4.1702 |
| 10 | 14768228 | hybrid_2008_SS | Drought Stress | 2.610834 | T | G | 3.9441 |
| 10 | 14770571 | hybrid_2008_SS | Well-Watered | 2.598599 | T | C | 4.3173 |
| 10 | 14768027 | hybrid_2009_NSS | Well-Watered | 2.5867 | C | G | 7.79839 |
| 10 | 14771045 | hybrid_2008_SS | Drought Stress | 2.583359 | G | A | 4.4191 |
| 10 | 14771315 | hybrid_2008_SS | Drought Stress | 2.573489 | T | C | 4.4924 |
| 10 | 14770686 | inbred | Well-Watered | 2.539102 | T | C | 5.837 |
| 10 | 14768375 | hybrid_2009_NSS | Drought Stress | 2.531653 | T | C | 3.4185 |
| 10 | 14770377 | hybrid_2008_SS | Drought Stress | 2.517126 | T | C | 4.4073 |
| 10 | 14768024 | hybrid_2009_NSS | Drought Stress | 2.50724 | C | T | 3.59744 |
| 10 | 14768293 | hybrid_2008_NSS | Well-Watered | 2.500313 | C | T | 8.58562 |

TABLE 8

Sequences are provided with the SNP Position at nucleotide 501.

| Name | Chromosome | Site Maize B73 genome version 3 | Favorable Allele | Unfavorable Allele | SEQ ID NO. |
|---|---|---|---|---|---|
| SWEET11 | 1 | 194967163 | C | G | 24 |
| SWEET11 | 1 | 194966087 | C | G | 25 |
| SWEET11 | 1 | 194966273 | T | G | 26 |
| SWEET11 | 1 | 194968091 | G | A | 27 |
| SWEET11 | 1 | 194967616 | C | T | 28 |
| SWEET13a | 10 | 14770979 | A | G | 29 |
| SWEET13a | 10 | 14770796 | C | T | 30 |
| SWEET13a | 10 | 14769813 | C | A | 31 |
| SWEET13a | 10 | 14769855 | G | T | 32 |
| SWEET13a | 10 | 14770143 | G | A | 33 |
| SWEET15b | 5 | 164895193 | C | T | 34 |
| SWEET15b | 5 | 164896921 | G | C | 35 |
| SWEET15b | 5 | 164897496 | G | T | 36 |
| SWEET15b | 5 | 164897515 | G | C | 37 |
| SWEET15b | 5 | 164897518 | C | T | 38 |
| SWEET1a | 3 | 171791580 | G | A | 39 |
| SWEET1a | 3 | 171795048 | T | C | 40 |
| SWEET1a | 3 | 171790578 | G | A | 41 |
| SWEET1a | 3 | 171791368 | G | T | 42 |
| SWEET1a | 3 | 171795101 | C | T | 43 |

Compositions and methods for identifying, selecting and/or producing maize plants having increased yield under non-drought conditions, increased yield stability under drought conditions, and/or increased drought tolerance are provided. As described herein, a marker associated with increased yield under non-drought conditions, increased yield stability under drought conditions, and/or increased drought tolerance may comprise, consist essentially of or consist of a single allele or a combination of alleles at one or more genetic loci.

Accordingly, in some embodiments, a method of identifying, selecting and/or producing a maize plant having increased yield under non-drought conditions, increased yield stability under drought conditions, and/or increased drought tolerance is provided, comprising: detecting, in a maize plant or maize plant part, an allele of at least one marker locus that is associated with increased yield under non-drought conditions, increased yield stability under drought conditions, and/or increased drought tolerance in a maize plant as set forth in Tables 4, 5, 6, 7, and 8, wherein said at least one marker locus is located within a chromosomal interval comprising (a) a chromosome interval on chromosome 10 of the Maize B73 genome version 3 defined by and including base pair (bp) position 14765640 to base pair (bp) position 14772295 (SEQ ID NO. 22); (b) a chromosome interval on chromosome 3 of the Maize B73 genome version 3 defined by and including base pair (bp) position 171790082 to base pair (bp) position 171797701 (SEQ ID NO. 20); (c) a chromosome interval on chromosome 1 of the Maize B73 genome version 3 defined by and including base pair (bp) position 194963437 to base pair (bp) position 194970347 (SEQ ID NO. 21); (d) a chromosome interval on chromosome 5 of the Maize B73 genome version 3 defined by and including base pair (bp) position 164893210 to base pair (bp) position 164900398 (SEQ ID NO. 23); and (e) any combination of (a) to (d) above, thereby identifying, selecting and/or producing a maize plant having increased yield under non-drought conditions, increased yield stability under drought conditions.

In some embodiments, a method of identifying, selecting and/or producing a maize plant having increased yield under non-drought conditions, increased yield stability under drought conditions, and/or increased drought tolerance is provided, comprising: detecting, in a maize plant or maize plant part, the presence of an allele of at least one marker locus associated with increased yield under non-drought conditions, increased yield stability under drought conditions, and/or increased drought tolerance in a maize plant as set forth in Tables 4, 5, 6, 7, and 8, wherein said allele of at least one marker locus comprises: chromosome 10 bp position 14770979 comprises a A allele (SEQ ID NO. 29); chromosome 10 bp position 14770796 comprises a C allele (SEQ ID NO. 30); chromosome 10 bp position 14769813 comprises a C allele (SEQ ID NO. 31); chromosome 10 bp position 14769855 comprises a G allele (SEQ ID NO. 32); chromosome 10 bp position 14770143 comprises a G allele (SEQ ID NO. 33); chromosome 3 bp position 171791580 comprises a G allele (SEQ ID NO. 39); chromosome 3 bp position 171795048 comprises a T allele (SEQ ID NO. 40); chromosome 3 bp position 171790578 comprises a G allele (SEQ ID NO. 41); chromosome 3 bp position 171791368 comprises a G allele (SEQ ID NO. 42); chromosome 3 bp position 171795101 comprises a C allele (SEQ ID NO. 43); chromosome 1 bp position 194967163 comprises a C allele (SEQ ID NO. 24); chromosome 1 bp position 194966087 comprises a C allele (SEQ ID NO. 25); chromosome 1 bp position 194966273 comprises a T allele (SEQ ID NO.26); chromosome 1 bp position 194968091 comprises a G allele (SEQ ID NO. 27); chromosome 1 bp position 194967616 comprises a C allele (SEQ ID NO. 28); chromosome 5 bp position 164895193 comprises a C allele (SEQ ID NO. 34); chromosome 5 bp position 164896921 comprises a G allele (SEQ ID NO. 35); chromosome 5 bp position 164897496 comprises a G allele (SEQ ID NO. 36); chromosome 5 bp position 164897515 comprises a G allele (SEQ ID NO. 37); and chromosome 5 bp position 164897518 comprises a C allele (SEQ ID NO. 38); or any combination of the above, thereby identifying, selecting and/or producing a maize plant having increased yield under non-drought conditions, increased yield stability under drought conditions.

Accordingly, in some embodiments, a method of identifying, selecting and/or producing a maize plant having increased yield under non-drought conditions, increased yield stability under drought conditions, and/or increased drought tolerance is provided, comprising: detecting, in a maize plant or maize plant part, an allele of at least one marker locus that is associated with increased yield under non-drought conditions, increased yield stability under drought conditions, and/or increased drought tolerance in a maize plant as set forth in Tables 4, 5, 6, 7, and 8, wherein said at least one marker comprises: "C" at a nucleotide position that corresponds to position 501 of SEQ ID NO: 24, "C" at a nucleotide position that corresponds to position 501 of SEQ ID NO: 25, "T" at a nucleotide position that corresponds to position 501 of SEQ ID NO: 26, "G" at a nucleotide position that corresponds to position 501 of SEQ ID NO: 27, "C" at a nucleotide position that corresponds to position 501 of SEQ ID NO: 28, "A" at a nucleotide position that corresponds to position 501 of SEQ ID NO: 29, "C" at a nucleotide position that corresponds to position 501 of SEQ ID NO: 30, "C" allele at a nucleotide position that corresponds to position 501 of SEQ ID NO: 31, "G" at a nucleotide position that corresponds to position 501 of SEQ ID NO: 32, "G" at a nucleotide position that corresponds to position 501 of SEQ ID NO: 33, "C" at a nucleotide position that corresponds to position 501 of SEQ ID NO: 34, "G" at a nucleotide position that corresponds to position 501 of SEQ ID NO: 35, "G" at a nucleotide position that corresponds to position 501 of SEQ ID NO: 36, "G" at a nucleotide position that corresponds to position 501 of SEQ ID NO: 37, "C" at a nucleotide position that corresponds to position 501 of SEQ ID NO: 38, "G" at a nucleotide position that corresponds to position 501 of SEQ ID NO: 39, "T" at a nucleotide position that corresponds to position 501 of SEQ ID NO: 40, "G" at a nucleotide position that corresponds to position 501 of SEQ ID NO: 41, "G" at a nucleotide position that corresponds to position 501 of SEQ ID NO: 42, and "C" at a nucleotide position that corresponds to position 501 of SEQ ID NO: 43.

In some embodiments, a method of identifying, selecting and/or producing a maize plant having increased yield under non-drought conditions, increased yield stability under drought conditions, and/or increased drought tolerance is provided, comprising: detecting, in a maize plant or maize plant part, the presence of an allele of at least one marker locus associated with increased yield under non-drought conditions, increased yield stability under drought conditions, and/or increased drought tolerance in a maize plant as set forth in Tables 4, 5, 6, 7, and 8, wherein said allele of at least one marker locus comprises: chromosome 10 bp position 14770979 comprises a A allele (SEQ ID NO. 29); chromosome 1 bp position 194967163 comprises a C allele; chromosome 1 bp position 194966087 comprises a C allele; chromosome 1bp position 194967163 comprises a C allele; chromosome 1 bp position 194965388 comprises a T allele; chromosome 1 bp position 194966273 comprises a T allele; chromosome 1 bp position 194968091 comprises a G allele; chromosome 1 bp position 194967163 comprises a C allele; chromosome 1 bp position 194967616 comprises a C allele; chromosome 10 bp position 14770979 comprises a A allele; chromosome 10 bp position 14770796 comprises a C allele; chromosome 10 bp position 14769813 comprises a C allele; chromosome 10 bp position 14769855 comprises a G allele; chromosome 10 bp position 14770143 comprises a G allele; chromosome 10 bp position 14770146 comprises a T allele; chromosome 10 bp position 14771337 comprises a C allele; chromosome 10 bp position 14770566 comprises a G allele; chromosome 10 bp position 14771209 comprises a G allele; chromosome 10 bp position 14771216 comprises a C allele; chromosome 10 bp position 14768884 comprises a A allele; chromosome 10 bp position 14770999 comprises a G allele; chromosome 10 bp position 14770999 comprises a G allele; chromosome 10 bp position 14771012 comprises a A allele; chromosome 10 bp position 14770497 comprises a C allele; chromosome 10 bp position 14770658 comprises a G allele; chromosome 10 bp position 14770602 comprises a T allele; chromosome 10 bp position 14770036 comprises a A allele; chromosome 10 bp position 14766703 comprises a C allele; chromosome 10 bp position 14770375 comprises a G allele; chromosome 10 bp position 14770181 comprises a C allele; chromosome 10 bp position 14770181 comprises a C allele; chromosome 10 bp position 14769893 comprises a G allele; chromosome 10 bp position 14769292 comprises a T allele; chromosome 10 bp position 14770520 comprises a A allele; chromosome 10 bp position 14770520 comprises a A allele; chromosome 10 bp position 14771349 comprises a G allele; chromosome 10 bp position 14770915 comprises a A allele; chromosome 10 bp position 14766789 comprises a A allele; chromosome 10 bp position 14770439 comprises a G allele; chromosome 10 bp position 14769364 comprises a A allele; chromosome 10 bp position 14771231 comprises a C allele; chromosome 10 bp position 14770722 comprises a C allele; chromosome 10 bp position 14770955 comprises a A allele; chromosome 10 bp position 14770663 comprises a G allele; chromosome 10 bp position 14769612 comprises a G allele; chromosome 10 bp position 14768375 comprises a T allele; chromosome 10 bp position 14768039 comprises a G allele; chromosome 10 bp position 14768028 comprises a A allele; chromosome 10 bp position 14766537 comprises a A allele; chromosome 10 bp position 14771072 comprises a C allele; chromosome 10 bp position 14771255 comprises a C allele; chromosome 10 bp position 14770696 comprises a G allele; chromosome 10 bp position 14771388 comprises a G allele; chromosome 10 bp position 14770791 comprises a A allele; chromosome 10 bp position 14771179 comprises a C allele; chromosome 10 bp position 14769364 comprises a A allele; chromosome 10 bp position 14768027 comprises a G allele; chromosome 10 bp position 14770870 comprises a A allele; chromosome 10 bp position 14770526 comprises a C allele; chromosome 10 bp position 14768024 comprises a T allele; chromosome 10 bp position 14770571 comprises a T allele; chromosome 10 bp position 14771007 comprises a C allele; chromosome 10 bp position 14768061 comprises a T allele; chromosome 10 bp position 14770143 comprises a G allele; chromosome 10 bp position 14771317 comprises a C allele; chromosome 10 bp position 14770146 comprises a T allele; chromosome 10 bp position 14771591 comprises a C allele; chromosome 10 bp position 14770760 comprises a T allele; chromosome 10 bp position 14767614 comprises a T allele; chromosome 10 bp position 14770955 comprises a A allele; chromosome 10 bp position 14770897 comprises a C allele; chromosome 10 bp position 14770915 comprises a A allele; chromosome 10 bp position 14770475 comprises a A allele; chromosome 10 bp position 14770897 comprises a C allele; chromosome 10 bp position 14770601 comprises a T allele; chromosome 10 bp position 14768381 comprises a C allele; chromosome 10 bp position 14768228 comprises a T allele; chromosome 10 bp position 14770571 comprises a T allele; chromosome 10 bp position 14768027 comprises a C allele; chromosome 10 bp position 14771045 comprises a G allele; chromosome 10 bp position 14771315 comprises a T allele; chromosome 10 bp position 14770686 comprises a T allele; chromosome 10 bp position 14768375 comprises a T allele; chromosome 10 bp position 14770377 comprises a T allele; chromosome 10 bp position 14768024 comprises a C allele; chromosome 10 bp position 14768293 comprises a C allele;

chromosome 5 bp position 164895193 comprises a C allele;
chromosome 5 bp position 164896921 comprises a G allele;
chromosome 5 bp position 164897496 comprises a G allele;
chromosome 5 bp position 164897515 comprises a G allele;
chromosome 5 bp position 164897518 comprises a C allele;
chromosome 5 bp position 164896797 comprises a G allele;
chromosome 5 bp position 164897574 comprises a C allele;
chromosome 5 bp position 164896808 comprises a C allele;
chromosome 5 bp position 164897386 comprises a G allele;
chromosome 5 bp position 164895831 comprises a A allele;
chromosome 5 bp position 164897335 comprises a A allele;
chromosome 5 bp position 164895604 comprises a C allele;
chromosome 5 bp position 164898796 comprises a A allele;
chromosome 5 bp position 164895579 comprises a A allele;
chromosome 5 bp position 164895754 comprises a G allele;
chromosome 5 bp position 164898809 comprises a A allele;
chromosome 5 bp position 164895521 comprises a A allele;
chromosome 5 bp position 164895523 comprises a C allele;
chromosome 5 bp position 164897630 comprises a G allele;
chromosome 5 bp position 164896918 comprises a G allele;
chromosome 5 bp position 164895193 comprises a C allele;
chromosome 5 bp position 164895831 comprises a A allele;
chromosome 5 bp position 164897500 comprises a T allele;
chromosome 5 bp position 164896550 comprises a C allele;
chromosome 5 bp position 164894861 comprises a A allele;
chromosome 5 bp position 164895604 comprises a C allele;
chromosome 5 bp position 164894762 comprises a C allele;
chromosome 5 bp position 164897496 comprises a G allele;
chromosome 5 bp position 164897515 comprises a G allele;
chromosome 5 bp position 164897518 comprises a C allele;
chromosome 5 bp position 164895579 comprises a A allele;
chromosome 5 bp position 164896921 comprises a G allele;
chromosome 5 bp position 164897574 comprises a C allele;
chromosome 5 bp position 164897479 comprises a A allele;
chromosome 5 bp position 164895754 comprises a G allele;
chromosome 5 bp position 164898870 comprises a A allele;
chromosome 5 bp position 164895604 comprises a C allele;
chromosome 5 bp position 164895579 comprises a A allele;
chromosome 5 bp position 164897511 comprises a G allele;
chromosome 5 bp position 164898869 comprises a C allele;
chromosome 5 bp position 164896808 comprises a C allele;
chromosome 5 bp position 164899821 comprises a C allele;
chromosome 5 bp position 164896797 comprises a G allele;
chromosome 5 bp position 164897523 comprises a G allele;
chromosome 5 bp position 164896550 comprises a G allele;
chromosome 3 bp position 171791580 comprises a G allele;
chromosome 3 bp position 171795048 comprises a T allele;
chromosome 3 bp position 171790578 comprises a G allele;
chromosome 3 bp position 171791368 comprises a G allele;
chromosome 3 bp position 171795101 comprises a C allele;
chromosome 3 bp position 171791249 comprises a G allele;
chromosome 3 bp position 171791181 comprises a C allele;
chromosome 3 bp position 171793764 comprises a C allele;
chromosome 3 bp position 171790729 comprises a C allele;
chromosome 3 bp position 171790242 comprises a C allele;
chromosome 3 bp position 171792281 comprises a T allele;
chromosome 3 bp position 171792609 comprises a G allele;
chromosome 3 bp position 171792046 comprises a G allele;
chromosome 3 bp position 171790356 comprises a C allele;
chromosome 3 bp position 171791877 comprises a C allele;
chromosome 3 bp position 171790863 comprises a T allele;
chromosome 3 bp position 171792700 comprises a G allele;
chromosome 3 bp position 171790860 comprises a A allele;
chromosome 3 bp position 171794113 comprises a C allele;
chromosome 3 bp position 171790097 comprises a G allele;
chromosome 3 bp position 171792700 comprises a G allele;
chromosome 3 bp position 171791279 comprises a C allele;
chromosome 3 bp position 171790833 comprises a G allele;
chromosome 3 bp position 171793764 comprises a C allele;
chromosome 3 bp position 171794699 comprises a A allele;
chromosome 3 bp position 171790889 comprises a G allele;
chromosome 3 bp position 171794646 comprises a G allele;
chromosome 3 bp position 171790428 comprises a C allele;
chromosome 3 bp position 171791351 comprises a T allele;
chromosome 3 bp position 171791465 comprises a C allele;
chromosome 3 bp position 171791187 comprises a A allele;
chromosome 3 bp position 171794646 comprises a G allele;
chromosome 3 bp position 171791552 comprises a T allele;
chromosome 3 bp position 171791214 comprises a G allele;
chromosome 3 bp position 171795034 comprises a C allele;
and chromosome 3 bp position 171791216 comprises a G allele; or any combination of the above, thereby identifying, selecting and/or producing a maize plant having increased yield under non-drought conditions, increased yield stability under drought conditions.

In some embodiments, a method of selecting a maize plant or germplasm having increased yield under non-drought conditions, increased yield stability under drought conditions, and/or increased drought tolerance is provided, comprising crossing a first maize plant or germplasm with a second maize plant or germplasm, wherein said first maize plant or germplasm comprises within its genome a genetic marker associated with increased yield under non-drought conditions, increased yield stability under drought conditions, and/or increased drought tolerance in a maize plant, wherein said genetic marker comprises any of (a) to (e), above.

In some embodiments, a plant can be regenerated from a plant part in which said genetic marker(s) is/are detected.

Also provided herein are maize plants and maize plant parts produced, selected and/or identified by the methods of the invention, as well as crops comprising said maize plants, harvested products produced from said plants and crops, and post-harvest products produced from the harvested products.

These and other aspects of the invention are set forth in more detail in the description of the invention below.

Thus, as described herein, methods for identifying and/or selecting a maize plant or maize plant part having increased yield under non-drought conditions, increased yield stability under drought conditions, and/or increased drought tolerance can comprise detecting the presence of a marker or a combination of markers associated with increased yield under non-drought conditions, increased yield stability under drought conditions, and/or increased drought tolerance in a maize plant as defined herein. Any combination of genetic markers of this invention can be used to identify and/or select a maize plant or germplasm having increased yield under non-drought conditions, increased yield stability under drought conditions, and/or increased drought tolerance.

The subject matter disclosed herein also relates to methods for producing maize plants comprising detecting the presence of a marker allele or a locus associated with increased yield under non-drought conditions, increased yield stability under drought conditions, and/or increased drought tolerance in a donor maize plant according to the methods described herein and transferring a nucleic acid sequence comprising at least one allele thus detected from the donor plant to a maize plant not having increased yield under non-drought conditions, increased yield stability under drought conditions, and/or increased drought tolerance. The transfer of the nucleic acid sequence can be performed by any known or later developed methods for transferring genetic material between plants.

Thus, the present invention encompasses methods of plant breeding and methods of selecting/identifying plants, in particular maize plants, particularly cultivated maize plants as breeder plants for use in breeding programs or cultivated maize plants having desired genotypic or potential phenotypic properties, in particular related to producing valuable maize plants, also referred to herein as commercially valuable plants. Herein, a cultivated plant is defined as a plant being purposely selected or having been derived from a plant having been purposely selected in agricultural or horticultural practice for having desired genotypic or potential phenotypic properties, for example, a plant obtained by inbreeding.

The presently disclosed subject matter thus also provides methods for selecting a plant of the species Zea mays exhibiting increased yield under non-drought conditions, increased yield stability under drought conditions, and/or increased drought tolerance, the methods comprising detecting in the plant the presence of one or more genetic markers associated with increased yield under non-drought conditions, increased yield stability under drought conditions, and/or increased drought tolerance as defined herein. In an exemplary embodiment, a method for selecting such a plant comprises providing a sample of genomic DNA from a maize plant or maize plant part; and detecting in the sample of genomic DNA at least one genetic marker associated with increased yield under non-drought conditions, increased yield stability under drought conditions, and/or increased drought tolerance as described herein. In some embodiments, the detecting can comprise detecting one or more SNPs, a combination of SNPs (haplotype), and/or SNPs located in chromosomal intervals that are associated with increased yield under non-drought conditions, increased yield stability under drought conditions, and/or increased drought tolerance in a maize plant.

The providing of a sample of genomic DNA from a maize plant can be performed by standard DNA isolation methods well known in the art.

As is well known in the art, the detecting of a genetic marker can in some embodiments comprise the use of one or more sets of primer pairs that can be used to produce one or more amplification products that are suitable for identifying, for example, a SNP. Primer pairs can be readily prepared using the nucleotide sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, and/or SEQ ID NO:43, and the positions and alleles of the markers as provided herein.

In some embodiments of this invention, a method is provided, said method comprising transfer by introgression of the nucleic acid sequence conferring increased yield under non-drought conditions, increased yield stability under drought conditions, and/or increased drought tolerance from a donor maize plant into a recipient maize plant by crossing the plants. This transfer can be accomplished by using traditional breeding techniques. Loci associated with increased yield under non-drought conditions, increased yield stability under drought conditions, and/or increased drought tolerance in maize plants are introgressed in some embodiments into commercial corn varieties using marker-assisted selection (MAS) or marker-assisted breeding (MAB). MAS and MAB involves the use of one or more of the molecular markers, identified as having a significant likelihood of co-segregation with a desired trait, and used for the identification and selection of those offspring plants that contain one or more of the genes that encode the desired trait. As disclosed herein, such identification and selection is based on selection of one or more SNP alleles of this invention or markers associated therewith. MAB can also be used to develop near-isogenic lines (NIL) harboring one or more alleles of interest associated with increased yield under non-drought conditions, increased yield stability under drought conditions, and/or increased drought tolerance in a maize plant, allowing a more detailed study of an effect of such allele(s), and is also an effective method for development of backcross inbred line (BIL) populations. Maize plants developed according to these embodiments can in some embodiments derive a majority of their traits from the recipient plant and derive increased yield under non-drought conditions, increased yield stability under drought conditions, and/or increased drought tolerance from the donor plant. MAB/MAS techniques increase the efficiency of backcrossing and introgressing genes using marker-assisted selection (MAS) or marker-assisted breeding (MAB).

Thus, traditional breeding techniques can be used to introgress a nucleic acid sequence associated with increased yield under non-drought conditions, increased yield stability under drought conditions, and/or increased drought tolerance into a recipient maize plant not having increased yield under non-drought conditions, increased yield stability under drought conditions, and/or increased drought tolerance. For example, inbred maize lines having increased yield under non-drought conditions, increased yield stability under drought conditions, and/or increased drought tolerance can be developed using the techniques of recurrent selection and backcrossing, selfing, and/or dihaploids, or any other technique used to make parental lines. In a method of recurrent selection and backcrossing, increased yield under non-drought conditions, increased yield stability under drought conditions, and/or increased drought tolerance can be introgressed into a target recipient plant (the recurrent parent) by crossing the recurrent parent with a first donor plant, which differs from the recurrent parent and is referred to herein as the "non-recurrent parent." The recurrent parent can be a plant that does not exhibit or exhibits a low level of increased yield under non-drought conditions, increased yield stability under drought conditions, and/or increased drought toleranc, but which, in some embodiments, comprises commercially desirable characteristics, such as, but not limited to disease and/or insect resistance, valuable nutritional characteristics, valuable additional abiotic stress tolerance (including, but not limited to, additional drought tolerance, salt tolerance), and the like. In some embodiments, the non-recurrent parent exhibits increased yield under non-drought conditions, increased yield stability under drought conditions, and/or increased drought tolerance and comprises a nucleic acid sequence that is associated with increased yield under non-drought conditions, increased yield stability under drought conditions, and/or increased drought tolerance. The non-recurrent parent can be any maize variety or inbred line that is cross-fertile with the recurrent parent. In some embodiments, a recurrent parent plant can be the control plant against which increased yield under non-drought conditions, increased yield stability under drought conditions, and/or increased drought tolerance can be measured.

In some embodiments, the progeny resulting from a cross between the recurrent parent and non-recurrent parent are backcrossed to the recurrent parent. The resulting plant population is then screened for the desired characteristics, which screening can occur in a number of different ways. For instance, the population can be screened using phenotypic pathology screens or quantitative bioassays as are known in the art. Alternatively, instead of using bioassays, MAB can be performed using one or more of the hereinbefore described molecular markers, hybridization probes, or polynucleotides to identify those progeny that comprise a nucleic acid sequence associated with increased yield under non-drought conditions, increased yield stability under drought conditions, and/or increased drought tolerance. Also, MAB can be used to confirm the results obtained from the quantitative bioassays. In some embodiments, the markers defined herein are suitable to select proper offspring plants by genotypic screening.

Following screening, the F1 hybrid plants that exhibit a phenotype of increased yield under non-drought conditions, increased yield stability under drought conditions, and/or increased drought tolerance or, in some embodiments, the genotype, and thus comprise the requisite nucleic acid sequence associated with increased yield under non-drought conditions, increased yield stability under drought conditions, and/or increased drought tolerance, can then be selected and backcrossed to the recurrent parent for one or more generations in order to allow for the maize plant to become increasingly inbred. This process can be performed for one, two, three, four, five, six, seven, eight, or more generations.

Thus, a marker that demonstrates linkage with a locus affecting a desired phenotypic trait provides a useful tool for selection of the trait in a plant population. This is particularly true where the phenotype may be difficult to assay or occurs at a late stage in plant development. Since DNA marker assays are less laborious and take up less physical space than field phenotyping, much larger populations can be assayed, increasing the chances of finding a recombinant plant with the target segment from the donor line moved to the recipient line. The closer the linkage, the more useful the marker, as recombination is less likely to occur between the marker and the gene that causes or imparts the trait. In addition, having flanking markers can decrease the chance that false positive selection will occur. Ideally, a marker is in the gene itself, so that recombination cannot occur between the marker and the gene. Such a marker is called a "perfect marker."

The availability of integrated linkage maps of the maize genome containing increasing densities of public maize markers has facilitated maize genetic mapping and MAS. See, e.g. MaizeGDB (maizegdb.org/map.php).

Of all the molecular marker types, SNPs are the most abundant and have the potential to provide the highest genetic map resolution (Bhattramakki et al., Plant Molec. Biol. 48:539 (2002)). SNPs can be assayed in a so-called "ultra-high-throughput" fashion because they do not require large amounts of nucleic acid and automation of the assay is straight-forward. SNPs also have the benefit of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in various publications: Gut, *Hum. Mutat.* 17:475 (2001); Shi, *Clin. Chem.* 47:164 (2001); Kwok, *Pharmacogenomics* 1:95 (2000); Bhattramakki and Rafalski, *Discovery and application of single nucleotide polymorphism markers in plants*, in PLANT GENOTYPING: THE DNA FINGERPRINTING OF PLANTS, CABI Publishing, Wallingford (2001). A wide range of commercially available technologies utilize these and other methods to interrogate SNPs, including Masscode™ (Qiagen, Germantown, Md.), Invader® (Hologic, Madison, Wis.), SnapShot® (Applied Biosystems, Foster City, Calif.), Taqman® (Applied Biosystems, Foster City, Calif.) and Beadarrays™ (Illumina, San Diego, Calif.).

Accordingly, the markers of the present invention can be used in marker-assisted selection methods to identify and/or select and/or produce progeny having a genetic marker associated with increased yield under non-drought conditions, increased yield stability under drought conditions, and/or increased drought tolerance in maize. Thus, in some embodiments, the present invention relates to methods for producing maize plants comprising an allele associated with increased yield under non-drought conditions, increased yield stability under drought conditions, and/or increased drought tolerance, comprising detecting the presence of at least one allele associated with increased yield under non-drought conditions, increased yield stability under drought conditions, and/or increased drought tolerance in a donor maize plant as described herein, crossing the donor maize plant with a second maize plant or germplasm, and detecting in the progeny plant(s) the presence of said at least one allele associated with increased yield under non-drought conditions, increased yield stability under drought conditions, and/or increased drought tolerance, thereby transferring the at least one allele associated with increased yield under non-drought conditions, increased yield stability under drought conditions, and/or increased drought tolerance thus detected from the donor maize plant to the second maize plant and producing a maize plant (e.g., progeny plant) having increased yield under non-drought conditions, increased yield stability under drought conditions, and/or increased drought tolerance. In some embodiments, the second maize plant does not comprise increased yield under non-drought conditions, increased yield stability under drought conditions, and/or increased drought tolerance. The transfer of the allele associated with increased yield under non-drought conditions, increased yield stability under drought conditions, and/or increased drought tolerance can be performed by any of the methods described herein.

The present invention provides maize plants and germplasms having increased yield under non-drought conditions, increased yield stability under drought conditions, and/or increased drought tolerance as compared to a control. As discussed above, the methods of the present invention can be utilized to identify, produce and/or select a maize plant or germplasm having increased yield under non-drought conditions, increased yield stability under drought conditions, and/or increased drought tolerance. In addition to the methods described above, a maize plant or germplasm having increased yield under non-drought conditions, increased yield stability under drought conditions, and/or increased drought tolerance may be produced by any method whereby a marker associated with increased yield under non-drought conditions, increased yield stability under drought conditions, and/or increased drought tolerance in a maize plant is introduced into the maize plant or germplasm. Such methods include, but are not limited to, transformation (including, but not limited to, bacterial-mediated nucleic acid delivery (e.g., via *Agrobacteria*)), viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, or any combination thereof, protoplast transformation or fusion, a double haploid technique, embryo rescue, or by any other nucleic acid transfer system.

"Introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced, these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell.

Thus, a maize plant or maize plant part having a genetic marker associated with increased yield under non-drought conditions, increased yield stability under drought conditions, and/or increased drought tolerance, obtainable by the methods of the presently disclosed subject matter, are aspects of the presently disclosed subject matter. The maize plant, or maize plant parts, or maize germplasm of this invention having at least one genetic marker associated with increased yield under non-drought conditions, increased yield stability under drought conditions, and/or increased drought tolerance can be heterozygous or homozygous for the genetic marker.

In some embodiments, the maize plant or germplasm may be the progeny of a cross between an elite maize variety and a variety of maize that comprises an allele associated with increased yield under non-drought conditions, increased yield stability under drought conditions, and/or increased drought tolerance. In some embodiments, the maize plant or germplasm is at least about 60%, 65%, 70%, 75%, 80%, 85%, 90%, 95%, 97%, 99% or 100% identical to that of an elite variety of maize.

The maize plant or germplasm may be the progeny of an introgression wherein the recurrent parent is an elite variety of maize and the donor comprises a genetic marker associated (e.g., SNP, combination of SNPs, SNP located in a chromosome interval) with increased yield under non-drought conditions, increased yield stability under drought conditions, and/or increased drought tolerance in a maize plant as described herein.

The maize plant or germplasm may be the progeny of a cross between a first elite variety of maize (e.g., a tester line) and the progeny of a cross between a second elite variety of maize (e.g., a recurrent parent) and a variety of maize that comprises a genetic marker associated with increased yield under non-drought conditions, increased yield stability under drought conditions, and/or increased drought tolerance in a maize plant as described herein (e.g., a donor).

Another aspect of the presently disclosed subject matter relates to a method of producing seeds that can be grown into maize plants comprising increased yield under non-drought conditions, increased yield stability under drought conditions, and/or increased drought tolerance. In some embodiments, the method comprises providing a maize plant of this invention having increased yield under non-drought conditions, increased yield stability under drought conditions, and/or increased drought tolerance, crossing said maize plant with another maize plant, and collecting seeds resulting from the cross, which when planted, produce maize plants having increased yield under non-drought conditions, increased yield stability under drought conditions, and/or increased drought tolerance as compared to a control (e.g., the "another maize plant").

Accordingly, the present invention provides improved maize plants, seeds, and/or maize tissue culture produced by the methods described herein.

In some embodiments, the presently disclosed subject matter provides methods for analyzing the genomes of maize plants/germplasms to identify those that include desired markers associated with increased yield under non-drought conditions, increased yield stability under drought conditions, and/or increased drought tolerance. In some embodiments, the methods of analysis comprise amplifying subsequences of the genomes of the maize plants/germplasms and determining the nucleotides present in one, some, or all positions of the amplified subsequences.

Additional aspects of the invention include a harvested product produced from the plants and/or parts thereof of the invention, as well as a post-harvest product produced from said harvested product. A harvested product can be a whole plant or any plant part, as described herein, wherein said harvested product comprises a recombinant nucleic acid molecule/nucleotide sequence of the invention. Thus, in some embodiments, non-limiting examples of a harvested product include a seed, a fruit, a flower or part thereof (e.g., an anther, a stigma, and the like), a leaf, a stem, and the like. In other embodiments, a post-harvested product includes, but is not limited to, a flour, meal, oil, starch, cereal, and the like produced from a harvested seed of the invention, wherein said seed comprises in its genome a recombinant nucleic acid molecule/nucleotide sequence of the invention.

In some embodiments, the invention further provides a maizr crop comprising a plurality of maize plants of the invention planted together in, for example, an agricultural field, a golf course, a residential lawn, a road side, an athletic field, and/or a recreational field.

In some embodiments, a method of improving the yield of a maize crop when said maize crop is exposed to drought conditions is provided, the method comprising cultivating a plurality of plants of the invention as the plant crop, wherein the plurality of plants of said maizer crop have increased yield under non-drought conditions, increased yield stability under drought conditions, and/or increased drought tolerance, thereby improving the yield of said maize crop as compared to a control maize crop, wherein the control plant crop is produced from a plurality of maize plants lacking said genetic marker grown under the same environmental conditions.

The following examples are included to demonstrate various embodiments of the invention and are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

EXAMPLES

Example 1. Identification of Markers Associated with Increased Yield Under Non-Drought Conditions, Increased Yield Stability Under Drought Conditions, and/or Increased Drought Tolerance Several genome-wide association studies (GWAS) were performed to identify markers associated with three yield traits (yield under irrigation, yield under drought stress and the difference between them) using diverse inbred and hybrid panels of maize. The inbred panel consisted of 262,224 genic SNPs across 478 inbred lines. The hybrid panel was split between the two heterotic groups (294 non-stiff stalk lines crossed to a single tester and 210 stiff stalk lines crossed to a different single tester) and between two years. The first year (2008) consisted primarily of locations used for flowering-time drought stress and the second year (2009) consisted primarily of locations used for season-long drought stress. The non-stiff stalk panels consisted of approximately 230,000 SNPs and the stiff stalk panels consisted of approximately 150,000 SNPs. At least 4 lines contained the minor allele (less common allele) in the case of all the SNPs.

Best linear unbiased predictors (BLUPs) were calculated for yield under irrigation and yield under drought stress for each line in each panel according to the model: Trait=Line+Trial+Line x Trial+error. The BLUPs for yield under irrigation and yield under drought stress were then standardized and these values were used to calculate the difference between the two traits (standardized yield under irrigation—standardized yield under drought stress). Associations were conducted using the model: $y=Pv+S\alpha+Iu+e$. Where y is a vector of phenotypic values (BLUPs), v is a vector of fixed effects regarding population structure, $\alpha$ is the fixed effect for the candidate marker, u is a vector of the random effects pertaining to recent co-ancestry, and e is a vector of residuals. P is a matrix of principal component (PC) vectors defining population structure, S is the vector of genotypes at the candidate marker, and I is an identity matrix. The variances of the random effects are assumed to be $Var(u)=2 KV_g$ and $Var(e)=IV_R$, where K is the kinship matrix consisting of the proportion of shared allele values.

All markers were extracted that fell within a set of 23 putative SWEET genes from maize in order to take a candidate gene-based approach for identifying potential associations. This resulted in 113 markers examined for yield under irrigation and yield under drought stress in the five testing panels described above (results attached below in Tables 9.1-9.4). In some cases a particular marker may not have been tested in a specific panel due to too few lines with the minor genotype which varied from panel to panel. A QQ-Plot was generated to look at the observed distribution of –log 10(P-values) (FIG. 1). Based on the QQ-Plot a –log 10(P-value) threshold of 2 was used to select marker-trait associations (MTAs) to be used to help prioritize construct leads. Those markers showing a significant association are provided in Table 1.

TABLE 9.1

Data for the 113 markers examined for yield under irrigation and yield under drought stress in the five testing panels described in Example 1.

| SNP | GeneModelID | Description | Chr | Gene begin v2 | Gene end v2 |
| --- | --- | --- | --- | --- | --- |
| 1 | GRMZM2G173669 | SWEET-13a | chr10 | 14762443 | 14765098 |
| 2 | GRMZM2G039365 | SWEET-1a | chr3 | 171748815 | 171752467 |
| 3 | GRMZM2G039365 | SWEET-1a | chr3 | 171748815 | 171752467 |
| 4 | GRMZM2G368827 | SWEET-11/MtN3 | chr1 | 194932443 | 194935353 |
| 5 | GRMZM2G039365 | SWEET-1a | chr3 | 171748815 | 171752467 |
| 6 | GRMZM2G039365 | SWEET-1a | chr3 | 171748815 | 171752467 |
| 7 | GRMZM2G039365 | SWEET-1a | chr3 | 171748815 | 171752467 |
| 8 | GRMZM2G173669 | SWEET-13a | chr10 | 14762443 | 14765098 |
| 9 | GRMZM2G173669 | SWEET-13a | chr10 | 14762443 | 14765098 |
| 10 | GRMZM2G111926 | SWEET-16b | chr8 | 33363546 | 33368983 |
| 11 | GRMZM2G173669 | SWEET-13a | chr10 | 14762443 | 14765098 |
| 12 | GRMZM5G872392 | SWEET-15b | chr5 | 164854921 | 164858109 |
| 13 | GRMZM2G173669 | SWEET-13a | chr10 | 14762443 | 14765098 |
| 14 | GRMZM2G173669 | SWEET-13a | chr10 | 14762443 | 14765098 |
| 15 | GRMZM2G173669 | SWEET-13a | chr10 | 14762443 | 14765098 |
| 16 | GRMZM2G173669 | SWEET-13a | chr10 | 14762443 | 14765098 |
| 17 | GRMZM2G173669 | SWEET-13a | chr10 | 14762443 | 14765098 |
| 18 | GRMZM2G173669 | SWEET-13a | chr10 | 14762443 | 14765098 |
| 19 | GRMZM2G173669 | SWEET-13a | chr10 | 14762443 | 14765098 |
| 20 | GRMZM2G039365 | SWEET-1a | chr3 | 171748815 | 171752467 |
| 21 | GRMZM2G000812 | Sweet-4a | chr5 | 126816126 | 126819003 |
| 22 | GRMZM2G000812 | Sweet-4a | chr5 | 126816126 | 126819003 |
| 23 | GRMZM2G144581 | Sweet-4b | chr5 | 127602043 | 127605592 |
| 24 | GRMZM2G144581 | Sweet-4b | chr5 | 127602043 | 127605592 |
| 25 | GRMZM2G173669 | SWEET-13a | chr10 | 14762443 | 14765098 |
| 26 | GRMZM2G153358 | SWEET-1b | chr6 | 147913391 | 147916344 |
| 27 | GRMZM2G179349 | SWEET-13c | chr3 | 108706693 | 108708062 |
| 28 | GRMZM5G872392 | SWEET-15b | chr5 | 164854921 | 164858109 |
| 29 | GRMZM2G111926 | SWEET-16b | chr8 | 33363546 | 33368983 |
| 30 | GRMZM2G111926 | SWEET-16b | chr8 | 33363546 | 33368983 |
| 31 | GRMZM2G173669 | SWEET-13a | chr10 | 14762443 | 14765098 |
| 32 | GRMZM2G039365 | SWEET-1a | chr3 | 171748815 | 171752467 |
| 33 | GRMZM5G872392 | SWEET-15b | chr5 | 164854921 | 164858109 |
| 34 | GRMZM2G106462 | SWEET-16a | chr3 | 56812209 | 56820107 |

TABLE 9.1-continued

Data for the 113 markers examined for yield under irrigation and yield under drought stress in the five testing panels described in Example 1.

| SNP | GeneModelID | Description | Chr | Gene begin v2 | Gene end v2 |
|---|---|---|---|---|---|
| 35 | GRMZM2G039365 | SWEET-1a | chr3 | 171748815 | 171752467 |
| 36 | GRMZM2G021706 | SWEET-13b | chr10 | 14642867 | 14645735 |
| 37 | GRMZM2G021706 | SWEET-13b | chr10 | 14642867 | 14645735 |
| 38 | GRMZM2G039365 | SWEET-1a | chr3 | 171748815 | 171752467 |
| 39 | GRMZM2G039365 | SWEET-1a | chr3 | 171748815 | 171752467 |
| 40 | GRMZM2G039365 | SWEET-1a | chr3 | 171748815 | 171752467 |
| 41 | GRMZM2G368827 | SWEET-11/MtN3 | chr1 | 194932443 | 194935353 |
| 42 | GRMZM2G173669 | SWEET-13a | chr10 | 14762443 | 14765098 |
| 43 | GRMZM2G173669 | SWEET-13a | chr10 | 14762443 | 14765098 |
| 44 | GRMZM2G173669 | SWEET-13a | chr10 | 14762443 | 14765098 |
| 45 | GRMZM2G039365 | SWEET-1a | chr3 | 171748815 | 171752467 |
| 46 | GRMZM2G106462 | SWEET-16a | chr3 | 56812209 | 56820107 |
| 47 | GRMZM2G021706 | SWEET-13b | chr10 | 14642867 | 14645735 |
| 48 | GRMZM2G021706 | SWEET-13b | chr10 | 14642867 | 14645735 |
| 49 | GRMZM2G039365 | SWEET-1a | chr3 | 171748815 | 171752467 |
| 50 | GRMZM2G153358 | SWEET-1b | chr6 | 147913391 | 147916344 |
| 51 | GRMZM5G872392 | SWEET-15b | chr5 | 164854921 | 164858109 |
| 52 | GRMZM2G111926 | SWEET-16b | chr8 | 33363546 | 33368983 |
| 53 | GRMZM2G153358 | SWEET-1b | chr6 | 147913391 | 147916344 |
| 54 | GRMZM2G039365 | SWEET-1a | chr3 | 171748815 | 171752467 |
| 55 | GRMZM2G173669 | SWEET-13a | chr10 | 14762443 | 14765098 |
| 56 | GRMZM2G111926 | SWEET-16b | chr8 | 33363546 | 33368983 |
| 57 | GRMZM2G039365 | SWEET-1a | chr3 | 171748815 | 171752467 |
| 58 | GRMZM2G000812 | Sweet-4a | chr5 | 126816126 | 126819003 |
| 59 | GRMZM2G153358 | SWEET-1b | chr6 | 147913391 | 147916344 |
| 60 | GRMZM2G111926 | SWEET-16b | chr8 | 33363546 | 33368983 |
| 61 | GRMZM5G872392 | SWEET-15b | chr5 | 164854921 | 164858109 |
| 62 | GRMZM2G021706 | SWEET-13b | chr10 | 14642867 | 14645735 |
| 63 | GRMZM2G173669 | SWEET-13a | chr10 | 14762443 | 14765098 |
| 64 | GRMZM2G173669 | SWEET-13a | chr10 | 14762443 | 14765098 |
| 65 | GRMZM2G144581 | Sweet-4b | chr5 | 127602043 | 127605592 |
| 66 | GRMZM2G144581 | Sweet-4b | chr5 | 127602043 | 127605592 |
| 67 | GRMZM2G153358 | SWEET-1b | chr6 | 147913391 | 147916344 |
| 68 | GRMZM2G173669 | SWEET-13a | chr10 | 14762443 | 14765098 |
| 69 | GRMZM2G173669 | SWEET-13a | chr10 | 14762443 | 14765098 |
| 70 | GRMZM2G368827 | SWEET-11/MtN3 | chr1 | 194932443 | 194935353 |
| 71 | GRMZM2G000812 | Sweet-4a | chr5 | 126816126 | 126819003 |
| 72 | GRMZM2G000812 | Sweet-4a | chr5 | 126816126 | 126819003 |
| 73 | GRMZM2G144581 | Sweet-4b | chr5 | 127602043 | 127605592 |
| 74 | GRMZM2G144581 | Sweet-4b | chr5 | 127602043 | 127605592 |
| 75 | GRMZM2G153358 | SWEET-1b | chr6 | 147913391 | 147916344 |
| 76 | GRMZM2G153358 | SWEET-1b | chr6 | 147913391 | 147916344 |
| 77 | GRMZM5G872392 | SWEET-15b | chr5 | 164854921 | 164858109 |
| 78 | GRMZM2G039365 | SWEET-1a | chr3 | 171748815 | 171752467 |
| 79 | GRMZM2G039365 | SWEET-1a | chr3 | 171748815 | 171752467 |
| 80 | GRMZM5G872392 | SWEET-15b | chr5 | 164854921 | 164858109 |
| 81 | GRMZM5G872392 | SWEET-15b | chr5 | 164854921 | 164858109 |
| 82 | GRMZM2G039365 | SWEET-1a | chr3 | 171748815 | 171752467 |
| 83 | GRMZM2G039365 | SWEET-1a | chr3 | 171748815 | 171752467 |
| 84 | GRMZM2G021706 | SWEET-13b | chr10 | 14642867 | 14645735 |
| 85 | GRMZM2G021706 | SWEET-13b | chr10 | 14642867 | 14645735 |
| 86 | GRMZM2G179679 | SWEET-3a | chr8 | 112530662 | 112532375 |
| 87 | GRMZM2G000812 | Sweet-4a | chr5 | 126816126 | 126819003 |
| 88 | GRMZM2G153358 | SWEET-1b | chr6 | 147913391 | 147916344 |
| 89 | GRMZM2G153358 | SWEET-1b | chr6 | 147913391 | 147916344 |
| 90 | GRMZM2G368827 | SWEET-11/MtN3 | chr1 | 194932443 | 194935353 |
| 91 | GRMZM2G021706 | SWEET-13b | chr10 | 14642867 | 14645735 |
| 92 | GRMZM2G039365 | SWEET-1a | chr3 | 171748815 | 171752467 |
| 93 | GRMZM2G039365 | SWEET-1a | chr3 | 171748815 | 171752467 |
| 94 | GRMZM2G153358 | SWEET-1b | chr6 | 147913391 | 147916344 |
| 95 | GRMZM2G021706 | SWEET-13b | chr10 | 14642867 | 14645735 |
| 96 | GRMZM2G168365 | SWEET-15a | chr4 | 96310951 | 96312854 |
| 97 | GRMZM5G872392 | SWEET-15b | chr5 | 164854921 | 164858109 |
| 98 | GRMZM2G021706 | SWEET-13b | chr10 | 14642867 | 14645735 |
| 99 | GRMZM2G368827 | SWEET-11/MtN3 | chr1 | 194932443 | 194935353 |
| 100 | GRMZM2G021706 | SWEET-13b | chr10 | 14642867 | 14645735 |
| 101 | GRMZM2G106462 | SWEET-16a | chr3 | 56812209 | 56820107 |
| 102 | GRMZM2G173669 | SWEET-13a | chr10 | 14762443 | 14765098 |
| 103 | GRMZM2G173669 | SWEET-13a | chr10 | 14762443 | 14765098 |
| 104 | GRMZM2G144581 | Sweet-4b | chr5 | 127602043 | 127605592 |
| 105 | GRMZM2G173669 | SWEET-13a | chr10 | 14762443 | 14765098 |
| 106 | GRMZM2G368827 | SWEET-11/MtN3 | chr1 | 194932443 | 194935353 |
| 107 | GRMZM2G039365 | SWEET-1a | chr3 | 171748815 | 171752467 |
| 108 | GRMZM2G021706 | SWEET-13b | chr10 | 14642867 | 14645735 |
| 109 | GRMZM2G153358 | SWEET-1b | chr6 | 147913391 | 147916344 |

TABLE 9.1-continued

Data for the 113 markers examined for yield under irrigation and yield under drought stress in the five testing panels described in Example 1.

| SNP | GeneModelID | Description | Chr | Gene begin v2 | Gene end v2 |
|---|---|---|---|---|---|
| 110 | GRMZM2G173669 | SWEET-13a | chr10 | 14762443 | 14765098 |
| 111 | GRMZM2G021706 | SWEET-13b | chr10 | 14642867 | 14645735 |
| 112 | GRMZM2G368827 | SWEET-11/MtN3 | chr1 | 194932443 | 194935353 |
| 113 | GRMZM2G106462 | SWEET-16a | chr3 | 56812209 | 56820107 |

TABLE 9.2

Data for the 113 markers examined for yield under irrigation and yield under drought stress in the five testing panels described in Example 1, continued.

| SNP | Marker | Site v2 | hyb_irr_nss_2008_NegLogP | hyb_irr_nss_2009_NegLogP |
|---|---|---|---|---|
| 1 | PZE1014822710 | 14764762 | 2.48339402 | 1.93998254 |
| 2 | PZE03170079889 | 171752311 | 0.80951454 | 3.08080659 |
| 3 | PZE03170077114 | 171749536 | 0.01915102 | 0.37952685 |
| 4 | PZE01194799632 | 194932443 | 0.85943617 | 1.17238029 |
| 5 | S_7767530 | 171749273 | 1.29880915 | 2.55131038 |
| 6 | S_7767535 | 171749283 | 1.29880915 | 2.55131038 |
| 7 | S_7767546 | 171749318 | 1.29880915 | 2.55131038 |
| 8 | PZE1014822787 | 14764839 | 0.42135623 | 0.26547596 |
| 9 | PZE1014822363 | 14764415 | 0.17635983 | 0.18174604 |
| 10 | PZE0833363225 | 33363625 | 0.06956905 | 1.13162812 |
| 11 | PZE1014822960 | 14765012 | 0.85169843 | 0.91924154 |
| 12 | S_25177407 | 164855482 | 0.69820466 | 0.67099443 |
| 13 | S_3355011 | 14764763 | 1.1780373 | 1.57865605 |
| 14 | PZE1014822606 | 14764658 | 0.56943117 | 0.08699943 |
| 15 | PZE1014822564 | 14764616 | 0.49697049 | 0.33590677 |
| 16 | S_3354810 | 14764696 | 0.44083186 | 0.38491027 |
| 17 | PZE1014822691.S_3354951 | 14764743 | 0.99690825 | 1.20836387 |
| 18 | PZE1014822841.S_3355363 | 14764893 | 0.79186145 | 0.91622315 |
| 19 | PZE1014822866.S_3355438 | 14764918 | 0.79186145 | 0.91622315 |
| 20 | PZE03170076681.S_7767421 | 171749103 | 0.11900814 | 0.00865314 |
| 21 | PZE05126115268.S_11834715 | 126816519 | 0.2079189 | 0.13401627 |
| 22 | S_11834745 | 126816572 | 0.2079189 | 0.13401627 |
| 23 | PZE05126891291 | 127605008 | 0.83345758 | 1.6839096 |
| 24 | PZE05126891427.S_11835752 | 127605144 | 0.83345758 | 1.6839096 |
| 25 | PZE1014822809.S_3355271 | 14764861 | 0.01245327 | 0.74596913 |
| 26 | S_14101102 | 147913800 | 0.32257144 | 0.13757348 |
| 27 | PZE0386521032.S_7281790 | 108707214 | 1.5683837 | 1.31891826 |
| 28 | S_12049233 | 164855895 | | |
| 29 | PZE0833363158.S_16494064 | 33363558 | 0.08469174 | 0.86221774 |
| 30 | PZE0833363197.S_16494076 | 33363597 | 0.08469174 | 0.86221774 |
| 31 | S_3354602 | 14764622 | 0.65441341 | 0.16214315 |
| 32 | PZE03170079878.S_7768070 | 171752300 | 1.35406698 | 0.1877092 |
| 33 | S_25177376 | 164855387 | 0.2351574 | 0.29429341 |
| 34 | PZE0356470659.S_7124418 | 56812375 | | |
| 35 | PZE03170077201.S_7767630 | 171749623 | 0.38453167 | 0.28107766 |
| 36 | PZE1014702229 | 14644281 | 1.13164967 | 0.51957672 |
| 37 | S_3349719 | 14644977 | 1.14601099 | 1.25251975 |
| 38 | PZE03170076798 | 171749220 | 0.78567606 | 0.82631165 |
| 39 | PZE03170078108.S_7767931 | 171750530 | 0.23477054 | 1.23784226 |
| 40 | S_55135874 | 171749906 | | 0.14198191 |
| 41 | PZE01194801358 | 194934169 | | 0.79314162 |
| 42 | PZE1014822786.S_3355207 | 14764838 | 0.24523972 | 1.1831317 |
| 43 | PZE1014822819.S_3355299 | 14764871 | 0.24523972 | 1.1831317 |
| 44 | PZE1014822928 | 14764980 | 0.24523972 | 1.1831317 |
| 45 | PZE03170076953.S_7767584 | 171749375 | 0.12667685 | 1.18035898 |
| 46 | PZE0356471257 | 56812973 | | |
| 47 | PZE1014702037 | 14644089 | 0.38125336 | 0.28426884 |
| 48 | S_3348847 | 14643477 | 0.16215297 | 0.6734687 |
| 49 | PZE03170077026 | 171749448 | 0.2181933 | 0.07603965 |
| 50 | PZE06148080134 | 147915823 | 0.06038515 | 0.54062193 |
| 51 | S_25177378 | 164855388 | 0.23544921 | 0.2283158 |
| 52 | PZE0833363578 | 33363978 | 0.23143252 | 1.07639439 |
| 53 | PZE06148080313 | 147916002 | 0.61740718 | 0.46596029 |
| 54 | S_23029935 | 171752133 | 1.06640515 | 0.51746593 |
| 55 | PZE1014821787.S_3353035 | 14763839 | 1.05948751 | 0.2107891 |
| 56 | S_16494954 | 33368521 | 0.38046935 | 1.02758367 |
| 57 | PZE03170076625.S_7767384 | 171749047 | 0.38453167 | 0.46470533 |
| 58 | PZE05126115149.S_25071732 | 126816400 | 0.41281548 | 0.28286337 |
| 59 | PZE06148078578 | 147914267 | 0.32958285 | 1.04140018 |

TABLE 9.2-continued

Data for the 113 markers examined for yield under irrigation and yield under drought stress in the five testing panels described in Example 1, continued.

| SNP | Marker | Site v2 | hyb_irr_nss_2008_NegLogP | hyb_irr_nss_2009_NegLogP |
|---|---|---|---|---|
| 60 | S_16494695 | 33367991 | 1.0281558 | 0.64993946 |
| 61 | S_33794968 | 164856230 | 1.01816406 | 0.35236426 |
| 62 | PZE1014701114 | 14643166 | 0.08155626 | 0.43892973 |
| 63 | PZE1014822003.S_3353589 | 14764055 | 0.03416064 | 0.53398819 |
| 64 | S_3353692 | 14764202 | | |
| 65 | PZE05126891289 | 127605006 | 0.36125549 | 0.24063273 |
| 66 | PZE05126891675 | 127605392 | 0.36125549 | 0.20252672 |
| 67 | PZE06148077991.S_14100829 | 147913680 | 0.09065364 | 0.02898161 |
| 68 | S_3355358 | 14764891 | | |
| 69 | S_3355625 | 14765003 | | |
| 70 | PZE01194801561 | 194934372 | 0.94554625 | 0.84000889 |
| 71 | PZE05126116874 | 126818125 | | |
| 72 | PZE05126117144 | 126818395 | | |
| 73 | PZE05126889656.S_11835494 | 127603373 | 0.71174015 | 0.44459382 |
| 74 | PZE05126889836.S_11835524 | 127603553 | 0.71174015 | 0.44459382 |
| 75 | S_14100779 | 147913649 | 0.07955528 | 0.15616572 |
| 76 | S_14101249 | 147913892 | 0.00902683 | 0.34687826 |
| 77 | S_12049219 | 164855078 | 0.91412257 | 0.61446207 |
| 78 | PZE03170076986.S_7767599 | 171749408 | 0.30600068 | 0.03369069 |
| 79 | PZE03170076676.S_7767416 | 171749098 | 0.4951291 | 0.32049511 |
| 80 | S_25177445 | 164855596 | 0.30128326 | 0.133377 |
| 81 | S_33794965 | 164856183 | 0.22150278 | 0.48601471 |
| 82 | PZE03170076989.S_7767600 | 171749411 | 0.82255903 | 0.0083933 |
| 83 | PZE03170077032 | 171749454 | 0.82255903 | 0.0083933 |
| 84 | PZE1014702682.S_3349436 | 14644734 | 0.86440975 | 0.22637006 |
| 85 | PZE1014702775.S_3349611 | 14644827 | 0.86440975 | 0.22637006 |
| 86 | PZE08111162512 | 112532312 | | |
| 87 | PZE05126115152.S_11834667 | 126816403 | 0.0251784 | 0.81197321 |
| 88 | S_14101038 | 147913767 | 0.21532276 | 0.20231402 |
| 89 | S_14101413 | 147914335 | 0.07852808 | 0.16386486 |
| 90 | S_49741167 | 194933875 | | 0.21886861 |
| 91 | PZE1014702114 | 14644166 | | |
| 92 | PZE03170078386 | 171750808 | | |
| 93 | PZE03170078405 | 171750827 | | |
| 94 | PZE06148079640 | 147915329 | 0.10227987 | 0.00545827 |
| 95 | PZE1014703058.S_3349905 | 14645110 | 0.72205718 | 0.05191929 |
| 96 | PZE04103664044 | 96311232 | 0.16240214 | 0.0892337 |
| 97 | S_33794964 | 164856180 | 0.01683392 | 0.07885298 |
| 98 | PZE1014703254.S_3350242 | 14645306 | 0.32558755 | 0.51510299 |
| 99 | PZE01194799750.S_20076659 | 194932561 | 0.29531278 | 0.00565575 |
| 100 | PZE1014701102 | 14643154 | 0.37088935 | 0.62915452 |
| 101 | S_7124415 | 56812284 | | |
| 102 | S_3354083 | 14764448 | | |
| 103 | S_3354105 | 14764455 | | |
| 104 | PZE05126889689 | 127603406 | | |
| 105 | PZE1014821892.S_3353328 | 14763944 | | |
| 106 | PZE01194800515.S_20076953 | 194933326 | 0.48477092 | 0.03444593 |
| 107 | PZE03170079877.S_7768069 | 171752299 | 0.37278741 | 0.45828978 |
| 108 | S_3350152 | 14645275 | | |
| 109 | PZE06148077958.S_14100776 | 147913647 | 0.21745347 | 0.23155189 |
| 110 | S_3353995 | 14764418 | | |
| 111 | PZE1014700929 | 14642981 | | |
| 112 | S_20077149 | 194935223 | | |
| 113 | PZE0356471931 | 56813647 | | |

TABLE 9.3

Data for the 113 markers examined for yield under irrigation and yield under drought stress in the five testing panels described in Example 1, continued.

| SNP | hyb_irr_ss_2008_NegLogP | hyb_irr_ss_2009_NegLogP | hyb_str_nss_2008_NegLogP | hyb_str_nss_2009_NegLogP |
|---|---|---|---|---|
| 1 | | | 3.39143188 | 1.4803721 |
| 2 | 0.17035041 | 0.15083801 | 0.04265472 | 1.38336068 |
| 3 | 2.60149002 | 0.46241344 | 0.10046913 | 0.45416226 |
| 4 | 0.24142934 | 0.37040433 | 0.42821394 | 0.28761583 |
| 5 | 1.24732304 | 1.34656524 | 0.47643233 | 1.12107774 |
| 6 | 1.24732304 | 1.34656524 | 0.47643233 | 1.12107774 |
| 7 | 1.24732304 | 1.34656524 | 0.47643233 | 1.12107774 |
| 8 | 0.08226949 | 0.69270568 | 0.76344493 | 0.20260388 |

TABLE 9.3-continued

Data for the 113 markers examined for yield under irrigation and yield under drought stress in the five testing panels described in Example 1, continued.

| SNP | hyb_irr_ss_2008_NegLogP | hyb_irr_ss_2009_NegLogP | hyb_str_nss_2008_NegLogP | hyb_str_nss_2009_NegLogP |
|---|---|---|---|---|
| 9 | 0.0394166 | 0.6487939 | 0.0324467 | 0.17463126 |
| 10 | 0.66515757 | 0.33654449 | 0.69628303 | 2.31572792 |
| 11 | | | 2.31533522 | 1.01516461 |
| 12 | 0.89221201 | 1.41575634 | 0.00794551 | 0.26033852 |
| 13 | | | 2.20181199 | 1.86373415 |
| 14 | 0.01009048 | 0.5880692 | 0.66912419 | 0.6967561 |
| 15 | 0.03978049 | 0.66876859 | 0.68017307 | 0.28246053 |
| 16 | 0.11586244 | 0.56134977 | 0.52037422 | 0.33815468 |
| 17 | | | 1.87979971 | 0.94138623 |
| 18 | | | 1.80179111 | 0.9850086 |
| 19 | | | 1.80179111 | 0.9850086 |
| 20 | 0.90166818 | 0.14862839 | 0.42571055 | 0.16682025 |
| 21 | 0.07171003 | 0.2249717 | 0.11157745 | 1.75450587 |
| 22 | 0.07171003 | 0.2249717 | 0.11157745 | 1.75450587 |
| 23 | | | 0.1680075 | 0.3179246 |
| 24 | | | 0.1680075 | 0.3179246 |
| 25 | 0.21064378 | 0.55333316 | 0.38183604 | 0.7257265 |
| 26 | | | 0.27214435 | 0.01218352 |
| 27 | | | 0.36668521 | 1.0273156 |
| 28 | 0.06916874 | 0.92722315 | | |
| 29 | 0.54143235 | 0.62092881 | 0.24379132 | 1.46841459 |
| 30 | 0.47882086 | 0.72908185 | 0.24379132 | 1.46841459 |
| 31 | 1.40942615 | 0.2525479 | 0.33747166 | 0.17561225 |
| 32 | | | 0.22775511 | 0.20636099 |
| 33 | | | 0.16613632 | 0.07044957 |
| 34 | | | | |
| 35 | | | 0.00674386 | 0.21213239 |
| 36 | | | 1.27178032 | 0.52889891 |
| 37 | | | 0.70339154 | 0.67286045 |
| 38 | 0.00880482 | 0.37389168 | 0.98180881 | 1.23848499 |
| 39 | | | 0.27464134 | 0.1701788 |
| 40 | 0.60955534 | 0.10276846 | | 0.13080242 |
| 41 | | | | 0.14467926 |
| 42 | | | 0.58093681 | 0.49845824 |
| 43 | | | 0.58093681 | 0.49845824 |
| 44 | | | 0.58093681 | 0.49845824 |
| 45 | | | 0.02818854 | 0.11809184 |
| 46 | 0.2603309 | 0.54498871 | | |
| 47 | 0.07871399 | 0.15019633 | 0.84039179 | 1.16318697 |
| 48 | 0.21488713 | 0.00364405 | 0.6531258 | 1.16156555 |
| 49 | 0.32048789 | 0.03471632 | 0.09529312 | 0.01989565 |
| 50 | | | 0.17180631 | 0.01684251 |
| 51 | | | 0.372673 | 0.15935658 |
| 52 | 0.18352772 | 0.60785611 | 0.17161956 | 0.78005224 |
| 53 | 0.09885423 | 0.70315714 | 0.85810591 | 0.09850591 |
| 54 | | | 0.14280239 | 1.0603578 |
| 55 | | | 0.00214107 | 0.26888295 |
| 56 | | | 0.11795649 | 0.304178 |
| 57 | | | 0.00674386 | 0.09139199 |
| 58 | | | 0.20615436 | 1.04273075 |
| 59 | | | 0.07559816 | 0.41486199 |
| 60 | | | 0.50471775 | 0.31009355 |
| 61 | | | 0.32385166 | 0.43967138 |
| 62 | 0.10343422 | 0.19339268 | 0.16128381 | 0.24096409 |
| 63 | | | 0.08954728 | 0.4201517 |
| 64 | | | | |
| 65 | 0.39490445 | 0.86126817 | 0.06464071 | 0.54750432 |
| 66 | 0.39490445 | 0.86126817 | 0.06464071 | 0.64083061 |
| 67 | | | 0.1292642 | 0.08327594 |
| 68 | 0.70286357 | 0.01891023 | | |
| 69 | 0.70286357 | 0.01891023 | | |
| 70 | | | 0.30345124 | 0.89740677 |
| 71 | | | | |
| 72 | | | | |
| 73 | | | 0.70017186 | 0.24389019 |
| 74 | | | 0.70017186 | 0.24389019 |
| 75 | 0.8337981 | 0.32359724 | 0.20778395 | 0.74528403 |
| 76 | 0.8337981 | 0.32359724 | 0.14437167 | 0.6873758 |
| 77 | 0.60321326 | 0.01628966 | 0.23165403 | 0.22630309 |
| 78 | 0.17164071 | 0.64915989 | 0.15059474 | 0.51382078 |
| 79 | | | 0.09857463 | 0.05819587 |
| 80 | 0.76351467 | 0.18058756 | 0.11714046 | 0.32463538 |
| 81 | 0.25865768 | 0.25946203 | 0.18284056 | 0.08950717 |
| 82 | 0.29490762 | 0.33754669 | 0.33860049 | 0.34734388 |

TABLE 9.3-continued

Data for the 113 markers examined for yield under irrigation and yield under drought stress in the five testing panels described in Example 1, continued.

| SNP | hyb_irr_ss_2008_ NegLogP | hyb_irr_ss_2009_ NegLogP | hyb_str_nss_2008_ NegLogP | hyb_str_nss_2009_ NegLogP |
|---|---|---|---|---|
| 83 | 0.29490762 | 0.33754669 | 0.33860049 | 0.34734388 |
| 84 |  |  | 0.72135738 | 0.34154198 |
| 85 |  |  | 0.72135738 | 0.34154198 |
| 86 |  |  |  |  |
| 87 |  |  | 0.10947197 | 0.56609322 |
| 88 |  |  | 0.20347512 | 0.80043395 |
| 89 |  |  | 0.19501085 | 0.79763293 |
| 90 |  |  |  | 0.21436624 |
| 91 | 0.36200708 | 0.61187712 |  |  |
| 92 |  |  |  |  |
| 93 |  |  |  |  |
| 94 |  |  | 0.18954134 | 0.74141519 |
| 95 |  |  | 0.66093211 | 0.12520398 |
| 96 | 0.23307677 | 0.67286986 | 0.25142866 | 0.03662018 |
| 97 | 0.43441612 | 0.34207415 | 0.00147716 | 0.57908725 |
| 98 | 0.0146588 | 0.28840556 | 0.12406035 | 0.63250236 |
| 99 |  |  | 0.14284817 | 0.63099133 |
| 100 | 0.56137911 | 0.27352189 | 0.07446952 | 0.19202566 |
| 101 |  |  |  |  |
| 102 |  |  |  |  |
| 103 |  |  |  |  |
| 104 |  |  |  |  |
| 105 |  |  |  |  |
| 106 |  |  | 0.03055306 | 0.2105521 |
| 107 |  |  | 0.07977212 | 0.18803518 |
| 108 | 0.42740335 | 0.03697505 |  |  |
| 109 |  |  | 0.14762923 | 0.30591534 |
| 110 |  |  |  |  |
| 111 | 0.05763862 |  |  |  |
| 112 |  |  |  |  |
| 113 | 0.14662528 |  |  |  |

TABLE 9.4

Data for the 113 markers examined for yield under irrigation and yield under drought stress in the five testing panels described in Example 1, continued.

| SNP | hyb_str_ss_2008_ NegLogP | hyb_str_ss_2009_ NegLogP | inb_irr_NegLogP | inb_str_NegLogP |
|---|---|---|---|---|
| 1 |  |  | 0.373054399 | 0.076996764 |
| 2 | 0.20384843 | 0.279931 | 1.500484195 | 0.670790029 |
| 3 | 0.4399636 | 0.59132297 | 0.62228643 | 0.656175758 |
| 4 | 0.31037268 | 2.55740394 | 0.120744517 | 0.986680896 |
| 5 | 0.80420835 | 0.491335 | 0.499833323 | 0.636127781 |
| 6 | 0.80420835 | 0.491335 | 0.499833323 | 0.636127781 |
| 7 | 0.80420835 | 0.491335 | 0.499833323 | 0.636127781 |
| 8 | 2.40231752 | 1.26800461 | 0.295774098 | 0.009709508 |
| 9 | 2.37737739 | 0.56688203 | 0.43065048 | 0.452683321 |
| 10 | 0.59938658 | 0.66878475 | 0.114010795 | 0.005951511 |
| 11 |  |  | 0.221808508 | 1.379449511 |
| 12 | 0.12046294 | 2.25430347 | 0.50578442 | 0.043683773 |
| 13 |  |  | 0.285182163 | 0.355048953 |
| 14 | 2.12591997 | 0.82126335 | 0.220915086 | 0.062437492 |
| 15 | 1.99301641 | 1.0064282 | 0.266411049 | 0.165332726 |
| 16 | 1.9395473 | 0.41006296 | 0.534310238 | 0.03807785 |
| 17 |  |  | 0.079928948 | 0.817674324 |
| 18 |  |  | 0.088895297 | 1.373614984 |
| 19 |  |  | 0.088895297 | 1.373614984 |
| 20 | 0.92387922 | 1.75651396 | 0.324044082 | 0.093021432 |
| 21 | 0.46952224 | 0.18876057 | 0.114311589 | 0.013256512 |
| 22 | 0.46952224 | 0.18876057 | 0.114311589 | 0.013256512 |
| 23 |  |  | 0.836334763 | 0.087089228 |
| 24 |  |  | 0.539590869 | 0.084772044 |
| 25 | 1.61522161 | 1.1499741 | 0.571634535 | 0.507395516 |
| 26 |  |  | 0.329899175 | 1.569756551 |
| 27 |  |  | 0.03812525 | 0.004129948 |
| 28 | 0.39220084 | 0.00338498 | 1.48318061 | 0.732881644 |
| 29 | 0.55694877 | 0.37947032 | 0.567011759 | 0.08501641 |
| 30 | 0.6647357 | 0.37074831 | 0.306606148 | 0.014619638 |
| 31 | 1.21178291 | 0.08659301 | 0.661369831 | 1.128088593 |

TABLE 9.4-continued

Data for the 113 markers examined for yield under irrigation and yield under drought stress in the five testing panels described in Example 1, continued.

| SNP | hyb_str_ss_2008_NegLogP | hyb_str_ss_2009_NegLogP | inb_irr_NegLogP | inb_str_NegLogP |
|---|---|---|---|---|
| 32 | | | 0.196916201 | 0.318886372 |
| 33 | | | 1.123148402 | 1.339399124 |
| 34 | | | 0.435339592 | 1.304043311 |
| 35 | | | 1.275031713 | 1.000595196 |
| 36 | | | 0.053296334 | 0.366012088 |
| 37 | | | 0.111741885 | 1.035595681 |
| 38 | 0.05943094 | 0.34197826 | 0.244403507 | 0.394698158 |
| 39 | | | 0.614657472 | 0.828193448 |
| 40 | 0.57384751 | 1.22686808 | 0.617441001 | 0.369195761 |
| 41 | | | 0.898600064 | 1.192877118 |
| 42 | | | 0.635189751 | 0.031774589 |
| 43 | | | 0.462109042 | 0.215332784 |
| 44 | | | 0.462109042 | 0.215332784 |
| 45 | | | 0.75070662 | 0.884372283 |
| 46 | 1.17308179 | 0.34275546 | 0.07392808 | 0.084881527 |
| 47 | 0.09087783 | 0.38867158 | 0.500719704 | 0.329135138 |
| 48 | 1.0650841 | 0.40541214 | 0.498098923 | 0.667240935 |
| 49 | 0.31924899 | 1.13040968 | 0.740420949 | 0.049688845 |
| 50 | | | 0.280607024 | 1.119239292 |
| 51 | | | 0.880406377 | 1.08889322 |
| 52 | 0.11788978 | 0.47142233 | 0.991926824 | 0.759895665 |
| 53 | 0.54691989 | 0.64743411 | 1.069873955 | 0.093545818 |
| 54 | | | 0.099635146 | 0.046375319 |
| 55 | | | 0.054219933 | 0.02205439 |
| 56 | | | 1.058658119 | 0.439031785 |
| 57 | | | 0.923674412 | 1.046945321 |
| 58 | | | 0.601254631 | 0.497986267 |
| 59 | | | 0.923313767 | 0.949017422 |
| 60 | | | 0.106412931 | 0.31940991 |
| 61 | | | 0.118543162 | 0.035742647 |
| 62 | 1.01322275 | 0.20034712 | 0.574197909 | 0.317530916 |
| 63 | | | 0.315598219 | 1.007936407 |
| 64 | | | 0.902677655 | 0.978997285 |
| 65 | 0.976811 | 0.81332864 | 0.751278108 | 0.029576463 |
| 66 | 0.976811 | 0.81332864 | 0.813942695 | 0.150877497 |
| 67 | | | 0.530561112 | 0.965785588 |
| 68 | 0.95496493 | 0.24304959 | 0.031225577 | 0.139501054 |
| 69 | 0.95496493 | 0.24304959 | 0.005118358 | 0.126327378 |
| 70 | | | 0.13507934 | 0.300988246 |
| 71 | | | 0.381404942 | 0.941261233 |
| 72 | | | 0.381404942 | 0.941261233 |
| 73 | | | 0.367861331 | 0.928155204 |
| 74 | | | 0.367861331 | 0.928155204 |
| 75 | 0.91902831 | 0.3474665 | 0.321751596 | 0.238776131 |
| 76 | 0.91902831 | 0.3474665 | 0.328244125 | 0.006892388 |
| 77 | 0.26628927 | 0.30360471 | 0.172661772 | 0.094141347 |
| 78 | 0.08720609 | 0.90116286 | 0.363779149 | 0.260174022 |
| 79 | | | 0.754839994 | 0.889639553 |
| 80 | 0.55842804 | 0.88741576 | 0.189868222 | 0.442479239 |
| 81 | 0.43630846 | 0.88582055 | 0.738200969 | 0.103855159 |
| 82 | 0.53951015 | 0.87508174 | 0.419856631 | 0.025420967 |
| 83 | 0.53951015 | 0.87508174 | 0.419856631 | 0.025420967 |
| 84 | | | | |
| 85 | | | | |
| 86 | | | 0.839293909 | 0.196563596 |
| 87 | | | 0.216988836 | 0.022491942 |
| 88 | | | 0.321896287 | 0.323990061 |
| 89 | | | 0.141113753 | 0.344734649 |
| 90 | | | 0.782004637 | 0.403715325 |
| 91 | 0.42557976 | 0.16817132 | 0.694102707 | 0.754336779 |
| 92 | | | 0.313314916 | 0.747050149 |
| 93 | | | 0.313314916 | 0.747050149 |
| 94 | | | 0.106311353 | 0.053774493 |
| 95 | | | 0.595745125 | 0.652391602 |
| 96 | 0.33750562 | 0.35698415 | 0.080388865 | 0.02798058 |
| 97 | 0.26156448 | 0.60952707 | 0.637038663 | 0.157100172 |
| 98 | 0.15963718 | 0.28587802 | 0.361150032 | 0.061883957 |
| 99 | | | 0.334722878 | 0.415136614 |
| 100 | 0.04369916 | 0.07755263 | 0.213980447 | 0.053872558 |
| 101 | | | 0.428339218 | 0.610827375 |
| 102 | | | 0.537479086 | 0.609312506 |
| 103 | | | 0.537479086 | 0.609312506 |
| 104 | | | 0.186312847 | 0.579248188 |
| 105 | | | 0.267221962 | 0.509327867 |

TABLE 9.4-continued

Data for the 113 markers examined for yield under irrigation and yield under drought stress in the five testing panels described in Example 1, continued.

| SNP | hyb_str_ss_2008_NegLogP | hyb_str_ss_2009_NegLogP | inb_irr_NegLogP | inb_str_NegLogP |
|---|---|---|---|---|
| 106 | | | 0.023529605 | 0.046735768 |
| 107 | | | 0.04557972 | 0.078764555 |
| 108 | 0.15789273 | 0.02014709 | 0.073885391 | 0.260104342 |
| 109 | | | 0.074211147 | 0.360438138 |
| 110 | | | 0.202889986 | 0.005580223 |
| 111 | 0.19986353 | | | |
| 112 | | | 0.097822876 | 0.194000286 |
| 113 | 0.16996956 | | 0.07392808 | 0.084881527 |

Example 2. Identification of Markers Associated with Increased Yield Under Non-Drought Conditions, Increased Yield Stability Under Drought Conditions, and/or Increased Drought Tolerance Several family based association studies (FBAM) were performed to identify markers associated with three yield traits (yield under irrigation, yield under drought stress and the difference between them) using diverse inbred and hybrid panels of maize. Populations from 24 parental lines were used to generate the families (progeny lines) used in the NSS analyses. In total these parents had 167,854 variants segregating among them. The 24 parental lines were sequenced using a reduced genomic next generation sequencing approach and used to project the next generation sequencing variants onto the families within each population (or cross). Merging the genotypic and phenotypic data from the NSS-MSE analysis resulted in 24 parental lines crossed to generate 45 populations which had a grand total of 1040 families. These families were then crossed to two testers. Populations with less than 10 families were excluded from the analysis since they would provide little additional value.

Twenty parental lines were used to generate the populations and families for the SS datasets. Across these twenty parents 112,466 variants were segregating. Similar to the NSS datasets, parental lines were sequenced using a reduced genomic next generation sequencing approach and used to project the next generation sequencing variants onto the families within each population (or cross). Upon merging this genotypic data with the phenotypic data there were 23 populations and a grand total of 553 families that had genotypic and phenotypic data available. Replicates from these families were then crossed to two testers to generate the hybrids that were phenotyped.

The two initial models tested were the fixed effect model with interaction term (1) tested using PROC GLM in SAS and a random effect model with interaction term (2) tested using PROC Mixed REML in SAS.

$$y=\text{Population(fixed)}+\text{SNP(fixed)}+\text{Population}\times\text{SNP(fixed)}+\varepsilon \quad (1)$$

$$y=\text{Population(random)}+\text{SNP(fixed)}+\text{Population}\times\text{SNP(random)}+\varepsilon \quad (2)$$

Those markers showing a significant association with yield (YGSMN) when grown under irrigated conditions (non-drought) are provided in Table 3.

Example 3—Sequencing a Maize Germplasm Panel to Identify Native Variability within SWEET1a, SWEET11, SWEET13a, and SWEET15b To map the natural variability in the sequences of SWEET1a, SWEET11, SWEET13a, and SWEET15b and identify genetic variants that would be expected to have functional consequences at the transcript and/or protein level, the SWEET1a, SWEET11, SWEET13a, and SWEET15b sequence was submitted for target capture sequencing across a diverse panel of public and private maize lines, representing all major breeding groups and including materials ranging from elite pure inbred lines to open pollenated ancestral Zea mays varieties.

Diversity Panel Selection

A collection of 994 Unique maize lines was chosen for study with the goals of maximizing genetic breadth, capturing the range of genetic diversity from conventional inbreds to ancestral landraces, and providing sufficient power to enable future association mapping analyses. The panel of maize lines utilized for this study combines components of several different diversity panels. It includes a subset of unique conventional and elite inbred lines, along with a series of exotic and tropical varieties. Out of this panel, approximately 919 maize lines were grown and sampled for subsequent sequencing efforts.

Sample Collection

Each line was planted and grown under standard greenhouse conditions to approximately the V3 stage, at which point leaf tissue was collected. Samples were stored at −80 C until processed. Samples were lyophilized and subsequently ground using a Genogrinder (Spex).

For each line, an approximately 30 mg (dry weight) aliquot of the ground material was submitted for analysis.

Target-Capture Sequencing

All steps in the target-capture sequencing (Target-seq) process were the same as that for the Sequence-Capture method outlined in Gnirke A, et. al. (2009) Nature Biotechnology 27, 182-189.

For Target-seq, a series of biotinylated 120-mer probes were designed to complement each sequence. The probes were designed against a maize B73 reference genome. To capture regulatory sequences flanking the protein-encoding region that might influence transcription and/or translation, the 5' and 3' UTRs (2 kb on each end of the gene model) were included in the sequencing effort. To ensure sufficient saturation of the target locus, the probes were designed at ~60 bp intervals. The probes covered the majority of the SWEET1a (SEQ ID NO. 21), SWEET11 (SEQ ID NO. 20), SWEET13a (SEQ ID NO. 23), and SWEET15b (SEQ ID NO. 22) sequence. The regions sequenced can be found in table 2.

Genomic DNA extraction was carried out using a semi-automated bead-based method utilizing standard protocols. Samples were quantified and normalized to the same concentration before progressing to the next step. The gDNA is then sheared and fragments are ligated to barcoded adapters.

Samples were PCR-amplified prior to hybridization in solution against the probes. DNA that does not hybridize against the target probe is washed away. This results in a highly enriched solution for the target regions. Each enriched sample is then sequenced and analyzed to identify sequence polymorphisms.

Identification of Markers Associated with Increased Yield Under Non-Drought Conditions, Increased Yield Stability Under Drought Conditions, and/or Increased Drought Tolerance Several genome-wide association studies (GWAS) were performed to identify markers associated with three yield traits (yield under irrigation, yield under drought stress and the difference between them) using diverse inbred and hybrid panels of maize. The inbred panel consisted of 478 inbred lines. The hybrid panel was split between the two heterotic groups (294 non-stiff stalk lines crossed to a single tester and 210 stiff stalk lines crossed to a different single tester) and between two years. The first year (2008) consisted primarily of locations used for flowering-time drought stress and the second year (2009) consisted primarily of locations used for season-long drought stress. At least 4 lines contained the minor allele (less common allele) in the case of all the SNPs.

Best linear unbiased predictors (BLUPs) were calculated for yield under irrigation and yield under drought stress for each line in each panel according to the model: Trait=Line+Trial+Line×Trial+error. The BLUPs for yield under irrigation and yield under drought stress were then standardized and these values were used to calculate the difference between the two traits (standardized yield under irrigation—standardized yield under drought stress). Associations were conducted using the model: y=Pv+Sα+Iu+e. Where y is a vector of phenotypic values (BLUPs), v is a vector of fixed effects regarding population structure, α is the fixed effect for the candidate marker, u is a vector of the random effects pertaining to recent co-ancestry, and e is a vector of residuals. P is a matrix of principal component (PC) vectors defining population structure, S is the vector of genotypes at the candidate marker, and I is an identity matrix. The variances of the random effects are assumed to be Var(u)=2$KV_g$ and Var(e)=$IV_R$, where K is the kinship matrix consisting of the proportion of shared allele values.

As is well known in the art, the detecting of a genetic marker can in some embodiments comprise the use of one or more sets of primer pairs that can be used to produce one or more amplification products that are suitable for identifying, for example, a SNP. Primer pairs can be readily prepared using the nucleotide sequences of SEQ ID NO: 24, 25, 26, 27, 28, 29, 30, 31, 32, 33, 34, 35, 36, 37, 38, 39, 40, 41, 42, and 43, and the positions and alleles of the markers as provided herein.

```
Nucleotide Sequences
Genomic sequences B73 maize
ZmSWEET13a [GRMZM2G173669]
Genomic sequence/Gene region->lcl|GRMZM2G173669 seq = gene;
coord = 10:14762443 . . . 14765098:1
```
SEQ ID NO: 1

GCCTATATAAAGCCACCCACAGCCCTGCCTATCATTGCAAGAGTTTGAGCCAACACACACAGAGAGAGGACAACTCCTCA

CAACTCTCCCTTCCCTCCTGTAGGGGCCAAAAGGGTTAGAGAGTAGGAGAAGTAGTTCCCTAGCCCAACACAAGAAAAAC

AAGCTCGATCTCCTCATCACCCTAATCCAAGCAACTGCTTTGTGTGTTGGGAAATTCTTGTGACCCCTGTTATATTATTA

TCCGTGTAGCTACTAGCTTCATTCCCCCCTTTGTACCCATCAAATGGCTGGCATGTCTCTGCAACACCCCTGGGCGTTTG

CTTTCGGTCTACTAGGTACATACTACACCTTCACTAATAGCTAAACAAGCGCCCGCCGCAAAGCTATGAATTAAGGGCAG

GCATGTTTGGTTTGCTACCTATTTTACCATACTTTGTCTAACTTTTCTGTCTAAGGTTATAGTTCTTCAATTCGAACGAT

TAATCTTAGCCAAAGTGTGACATGGTTAGCCACGAACTAAGCAGGCCCTTAATTATTGCGCATGTATATATTATATATTT

ATCTTTCTATTCTGTTTAATTTGTTTTCTCTTTACATATATATACTACTATGTAAGTATATATTATATGCACAACAAGCA

GGCCTCCTTCGTGCACATATGCATAGAATCAATCTATACCCTTCATAGAAGCCACTTTGAGATATACCTTCCAAAACAAT

CCCAAAAACAAGACGCTCGATCTTGCGCTCACAATCACTTAGTTTTGCACCAGATTAAGCATGCACCACTAGATTTTATG

TACTGTATTACCTCTGCCATCCATGGTCGATCCTTTAGTTTATCCTATTCATTTCCGTCATGAACTACCTGTCGAGCTAG

CAATCGGTCCTTTATTTAGAGTGTTCAGATAGGCATCTGTCTTTATACAAACAATAAAGCCTCACGAATCTTTAGTCACA

AAACAAGGCAAATTAGACAGGCCACGGAGGTGTAAAGTGTCAGCTCTGCTTATCACAACTTATCTCTGCTTTATTTGGGC

ACACTTTTGCCATACAAATGGCTGATCTTGGCGCCTTTTTTTTCTCCTTGCTTTGCAGGTAACGTCATCTCCTTCATGAC

CTTCCTGGCCCCGATGTAAGTGACATATATATATATATATTGCTTAATTAATTATCACTGCTTCTTCAGATATATATT

CATCGGTTATTTTAATTAATTATGTGGATATGTATGCATCGTATAACAGACCGACGTTCTACCGCATCTACAAGAGCAAG

TCGACGGAAGGCTTCCAGTCGGTTCCCTACGTGGTTGCCCTGTTCAGCGCCATGCTGTGGATCTTCTACGCACTGATCAA

GTCCAACGAGACCTTCCTCATCACCATCAACGCCGCCGGCTGCGTCATCGAGACCATCTACGTCGTCATGTACTTCGTCT

ACGCGCCCAAGAAAGCCAAGCTGTTCACGGCCAAGATCATGGTCCTCCTCAATGGCGGCGTCTTTGGGGTCATCCTCCTG

CTCACCCTTCTCCTCTTCAAGGGCAGTAAGCGCGTTGTGCTGCTTGGCTGGATCTGCGTCGGCTTCTCCGTCAGTGTCTT

CGTCGCGCCACTCAGCATCATGGTGAGCCCTGAGCACGCGTATAAAACTGTGCCAAGATGCATGGACGACAGATCGATCA

-continued

ACCCAATCAGTTTTGATCCATGTGTATCGTTTCTAATGCACCGTGTTTATATATGTGTGCAGAGACGAGTGATCCAGACG

AAGAGCGTGGAGTACATGCCCTTCTCCCTCTCCCTCTCGCTCACCCTCAGCGCCGTCGTCTGGTTCCTCTACGGCCTCCT

CATCAAGGACAAATACGTCGCGGTAATTGTTTCATCTAATCTGCTGCAACCGCCATGGTATTGGTATCTCTCACTGGTCT

TTACTGATAAACTACATACGATCTCTGTACGTATGCAGCTTCCAAACATCCTGGGGTTCACCTTCGGCGTGGTCCAGATG

GTGCTCTACGTGTTGTACATGAACAAGACGCCGGTGGCGGCGACTGCCGAGGGCAAGGATGCCGGCAAGCTTTCCTCAGC

TGCAGACGAGCACGTCCTCGTCAACATCGCCAAGCTCAGCCCAGCCCTCCCGGAGAGGAGCTCCGGGGTGCACCCAGTCA

CCCAGATGGCGGGCGTTCCTGTCAGGAGCTGCGCTGCTGAAGCAACCGCGCCGGCGATGCTGCCCAACAGGGACGTGGTC

GACGTCTTCGTCAGCCGACACAGCCCCGCCGTCCACGTGGCATAGATTCTCGATCGATCGCGTGCATGGCCCATGCATGC

GCCCGCCACACGTACGCTAGCTTTTATATATTCGAAGGACGACTTGCTGCTGGTCGTGAGCATATATATGATGGAGAAAA

TGATTAAGTAGTATATATAAGTAATTAACTGCCATGCATGGAAGCTAGCTAATGGATGGAGGCAGAGGCCAGAACGAT

GAAGGGGGAAGCTATACATATATGTGTGTAATTAATATAGATATATGGGCTTTGTGTTCATCTTTGCAGCTATGTATTAA

TTTGCATGGATATCTGTTATTCCTTTTTATGTGTAACGTCTTCTAATAAAATGTAATTGAACCCACACTACTGTTGTTAG

CTACCACAAGTTTCCC

ZmSWEET1a [GRMZM2G039365]
>lcl|GRMZM2G039365 seq = gene; coord = 3:171748815 . . . 171752467:-1
SEQ ID NO: 2
GGCTCTCTTCTCCACCGGTCCTACCCCTTACCTCCCAAGATCACAATCCTCTGCTCCTTATATATTAGCCACACCGCTCG

TTCCCTGCTGCACCGGGTGACACACAGGCACAAAGACACCGCCCGTACACAGGCTCGTTGGCTTGGCTGCTGTGTGTTGC

GCTCAGCCATTCAGACTTGAGAGCTACTAGCTAACTGCTCGTTGGGTGTGGGTGCGCTCCCGGCCTAGACCGTGGAGGAA

AGGAGTCCAGTCCACTCACTACCCCCTCTGCTCCGTTCGGGTTCCAGGCCAGCACAGCCGAGGGTTCCGCACAGCGATAA

GCGCGAAGCGGAAGAGATGGAGCATATCGCCAGGTTCTTCTTCGGAGTTTCTGGTCAGTATCACCATGCCATTCCTGCCT

CTGCTGCATGCCTACCTGATGGTCTTCTTCTTGCCTCGCCTAATCTCTGTTAGATCTGTCTCCCCAGGGAATGTCATTGC

GCTCTTCCTCTTCCTGTCGCCTGTGTAAGTTTTTGATTCCACGTACCTGAATCCTTCTGTTCCTCACTGCCCGCGTCCAT

GCTTTAAAAAAAAATCGAAAACAGAGAAGCAATGATATAGTACTTACTTCTACTATATGACAAAGACTAGAACATGGGG

AGAATCAGTGTGGAGAGAAAGGCTATAGCATCTTTTAGGTTCAATCCTTTCCAGCGAAACACTGAAATTTCATACATATA

TAATTTTTTCTAAAAAAAGCAAGTAGCTTTTCCCCATCCGAAATGCTTCTTCTTCCCAACCACGCCGCACCTTTTTTCT

TGCGTCTTGCCTCAGCAGCCTTCAGGGGCAGCAGCGCAGTGCGTGTGTTCCTCTGACGGGTGAGAAATCTCTTTGCAGTG

TCACCTTCTGGAGGGTCATCAGGAAGCGGTCGACGGAGGACTTCTCCGGCGTGCCCTACAACATGACGCTGCTCAACTGC

CTCCTATCGGCTTGGTAACGAACCGCTCTCTCTCTCTCTCTCCCTGAGAGACACGGCCTTTTGATGAGCACTCCACAC

CATTTCTGTTTCTGTCTCTTCAGAAAATTAAATCGCATCGCAGATTTATGGAGTGGCCGTAAAGCAGTAAAACCGGCGTG

GTGGTGTAGTTTGTTTTACTTAGATTTCGGAAATGCTGCATGGTTTGCTGGCCTGGGTGAAGCAAACGCTTGGCTCCTAG

CGTAGCCTCTGCCCAACCCGGCCTGTCCTGTAGATAGAGTACTACCCGTGGACCCACTCGCTAGACGCTAGCACTGTAAG

TCTGTGACAACGACTGCAATGAAGGGGAAAAGCTTATTGCACTGCACCACTGCCCGTGGGAGCAGAGCCTACCTGTTGG

CATTGCCAGGACGGAGATGACGACCTGTGGGCCTCGCGGCCCTTGAGCCCGCACATGCAGCGTCACGTTCAAGTGTTCGT

ACCTCCAAACAAAAAAAGTCTTGACGCTTTTTTTTTTCTTTTTGGTTATTATGATGACGGACGATTCTGGTCAGGGCATC

CACATAAATATCTTAAAAGGTATTAACGACGTAAGTGCAAAAAAAAGACAGTCTCTAGCACTACCACGGTTTTATCCAT

ACAACTCACGTACATGAATCATATCATGAGATCTTCTAGTGGAATAAGATATAAAACTTAAATATATTGGGCTATATGAA

AGAGTTTTTTAGATGTATTTAGTGCTTAAAGAACTGAAACGTAGTATCTAGATTGTACATGTCTTTATGACTATATGGAT

GAGTTGGTGTCCCGTTTGATTTTTCACGCGCCTTTGAATCCATGTGAAGATCGATGTGCTAGCTAGCTAGCTCGCTCTTC

ATGCGTTCGTCTGGATTTTGTTTGAAATTCACGCAGCATATATGTGTGGAATATAATCTGTATGCACATACAGGTACGGC

CTGCCGTTCGTGTCCCCGAACAACATCCTGGTGTCGACGATCAACGGGACGGGGTCGGTGATCGAGGCCATCTACGTGGT

GATCTTCCTCATCTTCGCGGTGGACCGGCGGGCCAGGCTCAGCATGCTGGGCCTCCTGGGCATCGTCGCCTCCATCTTCA

-continued

```
CCACCGTGGTGCTCGTCTCGCTGCTGGCCCTCCACGGCAACGCCCGCAAGGTCTTCTGCGGCCTCGCCGCCACCATCTTC
TCCATCTGCATGTACGCCTCGCCGCTCTCCATCATGGTACGTGAGCGATGATGATTGGTTGTTGCTGCCTTGCTGGGTAG
CTAGCTCCAGCGGGTCCCCTTCTGGGCGTGTACGTGCGTCCTTGCTGTCAACGTACGGCATCAGTTAACAAGCTAAGCGT
GTGCTTGGTGTGTGCAGAGGCTGGTGATCAAGACGAAGAGCGTGGAGTTCATGCCGTTCCTGCTCTCCCTGGCCGTGTTC
CTGTGCGGCACCTCCTGGTTCATCTACGGCCTCCTCGGCCGCGACCCCTTCATTATTGTACGCACACGGTTCTCTCTCTA
GTCTAGATCCTGAGCCGCACTCACCGCCCGGCCGTACGCACGTGCTATCCGCGCATGTTGTCCGATTGGCACTCGGAAAC
CACTGTAGCAGCACTGTATCACTAGCTGTTGGGACTGGACGTAACTGCATCTGATCTGGCCAGCACAGTACCCCCGGGCT
GGGCGTCGGTTGCCCTTTCGATGTCCCGCCCAAGCCCAACCAGGCGCACATGCCTGCCGCTGCCGCAGCCGATGCACGGG
CATGGGCGCCGGTAGCGTCTAGCAGCGTGGGCGTGGCCACCCACAGGCAGCGCACGCCGGTGCTAGCTGCCGATGGGCCG
CCGTGCCCATGTCCATGCAGCTGGATTGGACCCGGCACAGGCAGAAGCAACAGCGCCCGCGCTCTTTCTTGTCGCAATGC
TAGTTAGCAAACTGCACGGTGCACTCCACTTCAGTACACACCAACGCGACAGACTGCGATGAAATATCTAAGGCCGAGTT
TTTTTTTTTGCAAATCTCATCATGTCGGAATGATTCATGCGGTCCAAACTTCAGCACACCCCCACTGTCGCTAAACCCG
CGCTGTCTGTGCATGCGTGCAGATCCCGAACGGGTGCGGGAGCTTCCTGGGCCTGATGCAGCTCATCCTGTACGCCATCT
ACCGGAAAAACAAGGGCCCCGCCGCGCCGGCCGGCAAGGGAGAGGCCGCCGCCGCCGCCGCGGAGGTGGAGGACACCAAG
AAGGTGGCCGCTGCCGTGGAGCTGGCCGATGCCACGACCAACAAGGCAGCGGACGCCGTCGGCGGCGACGGCAAGGTCGC
CAGCCAGGTGTAGGCGGGCAAGGCTTATTTGCTGTCTGGGACTGGGAGGAACATCCTAAACGAGGCTGCCTTAGTTTGTC
GGTGGAGCAGATTGGTGTTGGTTTCTGTGGGCTTTTACGGTTGTTGTTACTCTCATCTCCATCTCTCCCAGGAGGCTACC
CCAAGCATGTAGTAGCTTCCATTCTGATTCTGGGACGGTGTTGCACGTTACAGTGCTCTCAAGCTGTCTCTGCAAAGTGT
GTTTTTTATTCCATTTCCCTCCTGCTCTTGTTCTCCAACTGCGCTTACCTGCCCCCGATTTCTCTAAAAAATGTATTAA
ACTATCTGAGAAATTCATCCAACTGCGAGTACTGTGCTGTGCGTGAGCAATGC

ZmSWEET11/MtN3 [GRMZM2G368827]
>lcl|GRMZM2G368827 seq = gene; coord = 1:194932443 . . . 194935353:-1
                                                                   SEQ ID NO: 3
ACACACAAACACATCAGCATTCAGCAATAGCTAATCGAGCATCGTCGCCTTAGCTCCTCTCCTCTCCTCTCCGTCGTCGT
GGAACTTCTCTCCGCCGGCTGTCATATATATAAAGGAGAAGAAGAGAACAGCAACTCTAGCTAGCCGGCCGGCCTCCGTC
GTCGCCGGCGTCGTCGACTAGCTAGCTAACTCTCGATCTCCAGTTCCTGCCCCCGCGCCCCACGCCCGGCCGTCGTCGTC
AGCAATGGCAGGAGGCTTCTTCTCCATGGCTCACCCGGCCGTCACCCTCTCCGGCATCGCAGGTACGTACGCGCCAATGA
AACAACAACGTCGTCTCGAGCTAGATCGATCCATGCATGACGCCGGCCGGGACCGGCCGGATAGATAGGCGGAGATCGAC
TTGCATAATGCTTCGCGTGTTTGGCCTTTTCCTGGTGCTTCTTTTTTTTTTTAAAAAAAATCTTATGGGACCTTGATGAC
ATGCTTTTCATGTGGTTTTCATTCATTCTGTTGCCGTACTACGTTCTTCTAGATTTTGTTTATTCCGACATGACGACTGT
CTTGTCCATCCTTGTATCATCGATCCGTCCTTTGCATGCATGCATCCACCAGTCGTCAGCCTTCCTTTTTGCCGTTTGTG
CCATTGCACTGTAGAGCACGCACGCACTCTCTAGCTGTAGAGAGGCGCGGCAGTAGGCATGCATGCAGCAGCTAGTCACA
CTGGACAACCAACTGTCTTGTCCATCATCTATCAACAATACTTGCATATCAGAATACGTAGTATGTAGCTTTAGCATTTT
TTTTTCTTCACCTATACTACTGCTAGCTGCATCTTCTTGAACTTTCTCTGATGCTCCCCGCGGCCCATTGAGACGACGAT
GCACTCTTTCTCCAATTCGTTAGCTGCGATCATGGCACAGGCCTTTAATTTGTTGCTAGCTAGAACACACATGCATGCAT
CGCCGAGGTATAGCAACTTTTCCACTCAAGAATAATGGTAATAAGCAGTGCAGATCAGATCCACATATTGGGCATTAGAT
CACGAAATACAGTTGCAAATAGCTGCTCACAACGTAACGCACTATCTAAGAATCATTTCTATATACGTGTATTTTTGCT
GGAATGGTTATGATCGATCGGTTGGGCATGCAGCAGGGAAGGCGTGTGCGTGTGCATGCAGCTACCTAGCTTTTTGCCAT
ATCAGCGTTTCCTTAACCTAATCACCACGCTTCTCTCTGTTAGTGGACGCACACGCATTGTACATATATATGTGTATAGT
ATTGTACTCCTACCACTTTTACTGAAAATGACGACACTGACGCGTAGTTACCCTCTTCTCTCTTGTTTCTTCGATTTGGA
TTGTGCAGGAAACATCATCTCCTTCCTGGTGTTCCTTGCACCAGTGTAAGTAGCTAGCTATAGCCACCTTTCTTCGTTCC
CTTACTGTCTCAATTTCAGACCGACTCGGATTCATGCGTGAATCGATGGATGATCCAAGACTGACATGGCATGCCTCTTG
```

```
TACGCACCGTACCAAAAACAGGGCGACGTTCCTGCAGGTGTACCGGAAGAAGTCGACGGGCGGGTTCAGCTCGGTGCCGT

ACGTGGTGGCGCTCTTCAGCTCGGTGCTGTGGATCTTCTACGCGCTGGTGAAGACCAACTCGAGGCCGCTGCTGACCATC

AACGCCTTCGGCTGCGGCGTGGAGGCGGCCTACATAGTCCTCTACCTGGCGTACGCGCCGCGGCGGGCGCGCCTGCGGAC

TCTGGCCTACTTCTTCCTGCTGGACGTGGCGGCCTTCGCGCTCGTCGTCGCCGTCACGCTCTTCGCCGTCCGCGAGCCCC

ACCGCGTCAAGTTCCTCGGCAGCGTCTGCCTCGCCTTCTCCATGGCCGTCTTCGTCGCGCCGCTCAGCATCATCGTCAAG

GTGGTCAAGACCAAGAGCGTCGAGTTCCTGCCCATCAGCCTCTCCTTCTGCCTCACGCTCAGCGCCGTCGCCTGGTTCTG

CTACGGCCTCTTCACCAAGGACCCCTTTGTCATGGTAACGACTGATCAATAATGTAATATATGGTTAACTGATCCATATA

TATATATAAAATGGTAACTGAATAATGCTGGGGATGTTTCTCGATTATATATATCTATTCAGTACCCCAACGTCGGCGGC

TTCTTCTTCAGCTGCGTCCAGATGGGCCTCTACTTCTGGTACCGCAAGCCCCGCCCGGCGGCCAAGAACAACGCCGTGCT

GCCGACGACCACGGACGGCGCCAACGCGGTGCAGGTGCAGGGGCAGGTCATCGAGCTGGCGCCCAACACGGTGGCCATCC

TGTCGGTGAGCCCCATCCCCATCGTGGGCGTGCACAAGATCGAGGTGGTGGAGCAGCAGCACAAGGAGGCCGCCGTGGCC

GCCGAGACCCGCCGGATGGCCGCCGCAAACCCGGACGGCGCCATGCCGGAGGTCATCGAGATCGTCCCCGCCGCCGCCGC

GGTGTGACCCAACGCCAATCACCATGCACCGTACACACCCTGCTAGCTTCTTATTAGCTAGCTCGGATGACGTACGACAG

TTTGGTGGCAAGTGGCTGGCAGCTCAAGCATGCAGATGCAGGCATCGTCGTCTGCTAGTTGATCGTTTAGTTGGTTAATT

GTTGGATTATTATTGCGTGTCTCTCTCGTGTGCGTAGTCTTGTCAGTTCAGTTCAGTTCAGTGTCGAATCAAGTAGTAGT

AGCTGTTGTTTGCATTGGATCTGACAATGCATGCTAATAATTATGGTGGTGTGATGGTCTTGGTCGGTACGTGCGTAGTC

GTCTACGTACGCCGTGTCAACGTCGTAGATCTCTACGGGAAGATGATAAGACTGTAACATGCAGGGCATGCATCTATTTA

TACTTAACATATTCTTTGTGTGCTTAATTTT
```

ZmSWEET16b [GRMZM2G111926]
>lcl|GRMZM2G111926 seq = gene; coord = 8:33363546 . . . 33368983:-1

SEQ ID NO: 4

```
CTGAGCTGACTGTGGATCTCATCCGTATCGTATATACGTCGTCCTGTTTGGATCCACCGCGTTTTGCTAATTCCCTTCGA

ACCGGCCGGTGGCCTTCGTTCTCCCACCAGGCCTGTCGTCTGCTGTATCCGCCAGAGCTTCCATGGATTCCACCCTCTT

CATCATCGGCGTCATAGGTAAGCTTGTGTATCATTCTGAACTGCTTTGTTATTATTATTAGTCTTCATTCGTCCAGCTTT

CCTTATCTTCTTCTTCTACATTGAAATAGGCAACATCATCTCAGTTCTCGTCTTCATATCGCCTATGTAAGTGTCTTTCT

CCATATATATGGTTTCCCTGTCGTCGCTGTTGCTAGCTAGCTTTCTTTCTGAACACCACCACGGGCACCAATCCATGCAT

GGATACAGCAAGACGTTCTGGAGGATCGTGCGGGCGGGACGACGGAGGAGTTCGAGCCGGCGCCGTACGTGTTGACGCT

GCTCAACGCGCTGCTGTGGCTCTACTACGGCCTCACCAAGCCTGACGGCTTCCTCGTCGCCACCGTCAATGGCTTTGGGG

CTGTCATGGAGGCCATCTACGTCGTCCTCTTCATCGTCTACGCCGCCAACCATGCCACAAGGGTGAGGGGTCGGAGCAGC

TGGGGCCAGTATATATAGTTCACTCACACAATCCGTTGCTTAATTCTGCATAATTCTTTCTTCAAGCACTTGAGTCTTAG

GAATTACGGAGTATATAGTTAAAGAAAAGCACAACCACCATTCGTTTATTAAAGAAAAGCATGTGTTGCCTTATATTATA

GTTTGTTCCTTTATCGCAATTATGATTATGCAGGTTAAGACCGCGAAGCTGGCAGCAGCGTTGGACATCGGTGGCTTCGG

AGTCGTGTTGCGGCCACCACATTCGCCATCAGTGAATTTGAATTGAGAATTATGGTGATAGGAATGATATGTGCCTGCC

TCAATGTGCTCATGTACGGGTCACCCCTTGCTTCTATGGTAAGTTTTTTTCCTCACATGCATATTTATACACTATTCCT

CTTTTCTTTCCTTTTTTGGTTATTTTAGAAACTTAAATCCCCTCTGGTATTAATTCCCGAGAATTTCACTTAATTCCCAA

GAATCCCAAAAAAAATTAAGTTTCTAAACTAGCCCTTAGTGAGACTTAATTTATTTGTTCGCCGTAAGTCGATTTTGAGA

TGCACATTTCTCCTTAATTTTCCTTTTATAGCTGACCGTGCACGGCCTTGAAACATCACGATCTTTTCAGTTAAATTTAA

TTAGCACGGGCTAAATTTTACATTGCAAAGAAAATAAACTAATTTCACACACACATATATAGTATATAGCTAGCAAAC

TGCTAATGGGCCAGCAAAACTTATGGATGATAACATTGAGCAATGAAATTATTGTCATGTAACGGTAACTATATTATAAT

AGTGAGTTTCGATCCATGATCTAATATATACCATATAATAATATTGATGCCACTTGGCCCCACAGACAAAGTAGAGTATA

GTTCAAGTTTGGAGATATATAAATGATAATAATAATAATAAAGCTGCTCAAGATATTTTCATTCTGGCGATCCATGTCTG

TCCACGATGGATCGACGATAAAATACTCGGTGTTTATTATAATGGACAGGGCGCTTTGTGGGGCGATTATTTTATGTTGT
```

-continued

```
GTTGTCCCTTTCATGATTATTTATTAAATATAAGGACAGAAGTCCAAGCAAAACACATGTGCCCCAAGCAATAGGGATAT

ATAGTGACATATTGTGGAAATAGTTATATATTTTGGGGGAGAATCATGTGTCAGGGATATTGTACAATAGAAAAACATTT

CTTAGTATGTAGGTCCTCAACTGCCCCTGTTTTTTCTCTTATTTTTAGCAGATGTTCGATCCACTTCCACAATTCCACTT

GCAGGAATAATATAATAAATATAGATATATATGGTACATAAGCTGTATGTAAAATCCATATAATAATATTAATATTACAT

TATATACCTCAACGAATCATTTCTAAAGCTTTTATTAGGTATAATAAAAAGTAAATTTATATTTTGGTGCTTGTAGCTAG

GTGTGGCCGTGTGGGGCACGTGCAAGCAACCTTACTCGTTCCACCTCCTATCTTTTGCTCCACTTTGTAAATAATACATA

TTACAGCGTAAAACTGTGTAGAAAGTATGATTTTACGGCTATATACACGGTGTGCTACGACTAAAAGTTAGGGACGACCT

CACGCCGATAATTGGATGACAGATTTTTTTCCTTTGATATCTTTCTTCTCTGGCATGCCAAATCGAATTCCTCCCTCTGC

CTTTAATTTCTATTTGTTAGGATTATATGAAACTATTTCCACAAGTATAGTTAGAGACTCAAATTCAGATACTAGAAATT

AATGATGGTTTACAAGCCATAAATAAATAAATTAAAAATAAACATATTTAGATTTTAATTTGAATGAAAAGAGAACATTG

CTTCGGTTTGATGCAGATTAACTTATACAGAAATCATATATTATGTCATGAGAGACAAGCAAAGATTGGTCAACTTATTA

CCATTTCTTGCAAAATCAAGTTTGCCGTATTATTATTTTGTCCTTTTCTTTTTTAAAAGATTATTAGCTGGTTATTGGTT

CTCTGGGCAGTTAACGGGGTAGAGTATTCCACAGAATTAAATAATCACCATGCAAGGAACACGCGTTGTCCTCTACATAC

GATTCTTTATTTACTTAATTCTACATCACACATTTTGTGCAAGAACAGTAGCTATTAGAAAAAAAATGTGAGCATCGGTT

CACAACCGGCTATAGTACTGGATTATCAACTGATATTAGACAATCGAAATTAAAGACCTTATTTTTGAAGGACCGGTGAA

ATGACCAGAAGGGGTGAATTAGAGCCAATCAAATTTTATTGTTAAAAACTTAAATTTAGACCTTATTTGTGAAGGACCAG

AAGAGGTGAATGAGAGCCAATCAAATTTTATTACAAAAAACTAAAATTTAGCACTTAACTTCAATTGAGATGAAGAAATC

GTTCAAACCAGAAGCACATCGGCCAAATAGTAATCTTACGATTTCAAAATGGTACCCCTAGATACATTTGGTTTTTTGTT

TAGAATACCGGTATTCTTTGGCTAAGTTCATTTGGTTTATTGGTTTTTGTTTAGAATATGGGTATTCTAAACAAAAACCA

AATGAATTTTGCCAAAAGAGATGGATGTCAATAAAAGCCCACATATCTATTTATAGAGGTGATGGATACATCATATCCAC

TTAGCCGGGGCAAAATGGATCAACTCCTAGGATTTTGATCAGACGACCACGCGCTCTACACAAAGTTGCTTCGCCTCGAC

ACACCCTTTGTGATGATGTCATGTGCCACCTCTGATTCCTGCCGAAACCGCCACCGTCAAGTTTTGAGGCCCAAACTCAG

CAAAACCAGCAGATGGGTGGTTTTGAGGCTCAACCACAAAACCACCGCGAGTAGTGCATCGCATGCGCGTCCCCACGTCC

TGGACACATGTCCCATTAGTCCTTGACCGCATCGGCGACAGTGCGACACAAGCCACTCTGTCATGTCCTCGCGCTAGTGC

GTGTCCTAGGTGTGAGCCACCACAACTTGTCAACCGGCTCCTCCGACCCCTTGGTCAAGTCCTAGTGCTCGTCTTTCATC

ACTCTCCGTCTATCGGCATAAACCCTCGTGTGACCTTCACATTCGCCATTGAACAACATACATGTACTTCACACCTGCAC

ACCATAAGCCGAGAGACATGGTTGCACAATACATAACTCATACTCTGGTCAGTCCACCGACTACATCAAAATACTATCCG

TTGACAATCACTTATCATCAACTCGAACCACAAGGGACAAATCAACTTGTGTTCACAATTGTTTGCCATAGAGAGAAAGA

AAGCGTACTCCGTGTGTTGCTTGGGTTTACCGAGAAGCACGTGTGTAAAATGGGTAGCATACTCTAGTAGTACTACGAGT

GCACGACGTGACTCCTACAGATTCCAAACTCTTGGCAAAATTAATATCGCGACATGTCATCATGTCCATGCCATTACCTT

AGCTGTATTGACAGGCCGGACCTGCTATTTGTGTCGGCCGTACGTGTTCTTGCGGTCCTCGTCGGGTGGGTTTCGCTCT

CTGAATTTTCTGATTGGTTCCATCGATATTTTCTGATTGGTTCCATCGAAAGCGAAACCAGGACCGTACGTGGCGCCAAA

TTCAACCAGACCACCCATCCCTTCCCGGGGTCATGTCACATCCCTGTTGCTTCACGTTTTCTTACAAAATTACCCGCTCC

GTCCGTGAAGCAAATATAACTATGATATCCCTATCTGTCAGAGTAGTTTAAATTTAACTAAATTTATAATAAACAATACT

CGCTTTGGTCCTAAATCTAGACACATATATATATATATATATATATAACACATACATCAAGTATTGTATAAATTCACA

AAATACCACTATATGAACGCCCTTAAATTTTAAATTAAAAAATTATCTAAGAAAACATAAGCAATAATTAACCCATGCCA

ATGCAAGTTGAATACTTGAATTGAAAAAGTTGATTCCAGCTCAGGGAACCTATAACCATGGCTTCGCATGAGTTGGCGA

TTGCCTGAACAGGCCCATGCAGAGCAACTAACCATAGAATAGAACAATACGCGATGAAATTCACCGTACCCTGCAACGTA

ATGGATGTGTGATTAGTATCACCGGCACCTCATTTTTACCCGTCATCTCGTTGTACCTACATTTTCAGAAAACGGTGATC

ACGACAAAGAGCGTGGAGTTCATGCCATTCTTCCTGTCCTTCTTCCTCTTCCTCAACGGAGGCGTCTGGGCAACGTACGC

GGTGCTTGACCGCGACATCTTCCTCGGGGTAATGTTTAAAGCCTCTCTGTTCTTCTCGATCTTCTTCCCCAACCTCTGTC
```

-continued

TTTTCCGCTACCCATACTAAACAGAACCTCTCGATCGCTCTCTGCATGCAGATCCCCAATGGGATAGGCTTCGTGCTTGG

CACCATCCAGCTGATCGTCTACGCGATCTACATGAACAGCAAGGCCTCCCAATGCAGCAAAGAAACAGCGTCCTCGCCTC

TTCTGGCCTCCGACCGGGGAGAAGCATCTAGCCATGTCTGATGATGAGCTTCGATCAGTGCGCGCGCTGGAGTATAGCAT

AGAAGTCTCTTGCTGTCAAAAACTTCCAAGACCAACGGTACCTACCAGCATGCATGCATGCAAGAGGTTACCAATTTTTA

TTGTTTGAAAATTCATGTAAACTTGTGACCTCCATGGATTGTTTCTTTCTTTGGTATAAGCTTCGAAGATGTTAGATTGT

TAGCACGGTAGTTTTGCCAGAGAAGGGTGTTGTCAATATAATGAAGAAATGGTGAAAATCCATACATTTGATTATCGA

ZmSWEET15b [GRMZM5G872392]
>lcl|GRMZM5G872392 seq = gene; coord = 5:164854921 . . . 164858109:-1

SEQ ID NO: 5

CTCAGGAGCTAATGACTCACCTCTCCGTGCTCACCTCCTCTTCTTGGAGGCTTGAGCTCTCTCTTCCTCTCTCCCCTCAGC

TCATCTCCACCGTCTCCCTATATATAGGATGCTCTGCCGGCTCCAAGGTTCCCAAGCGCCCAAGGCAGCGGAGAGAGCTA

GCTCCCTCCTCCTCCTCAGGTAGCGAGCGAGCGAGCTCCTCTGCCCCTCTGCACACCTGGCCTCCCCTTCTCCGCTGCAG

GACCGCCGTTGACGACTGCTCCACCAGTACTGCGCGCGCCCGCGCTGCCTACCCTTACCTAGCCAGAGCGCGGCGCGCGA

GAGGGAGAACGACCAGGAGGGGAGGAGATCGATCGATCGATCGATCGAGATAGATGGCTTTCCTCAACATGGAGCAGCAG

ACCTGGGCCTTCACCTTCGGTATCCTAGGTACATATATACTGTCAGTCTGTCACTCGTAGCTACTAATTAACCGCATCAA

CGGAGCCGCCCTGCCGTCTTCGTCCTCGTCAGTGTTTCTGCATTGTTTTCCTTCCTTGTCCCAAGTCCTTTGAGACGCAC

GCATACATGATACATGCATGGCATCATCGTCTCCCAAGTCCTAGGTACAGTTTCATCACCGCGCGCCTCTCTCAGATATG

TGTCGTCGTACAGGACAACACAACACGTCCTCGTCAATCTACTAGCTATATGCGCTAATAACCACCTCTTCCTTTCCGAG

CCACGGCACAGTATAGCCTGCCATCCGAACGAACGGAACCGCCCAAAACCCAACTTTTTTTGGGCCTAACTAATGCGGTG

GTTAGCCCAAACAAAGAAACCAGGGCAGTCATACATTTTACATGTAGTACCTGCTTGACGACGGGAACCAACACAACGGC

GCGCCGCGAGGAGAGTTTGTTCCATTTCCTCCGCCTGCAGGCTAGCTGCAGCTAATAACCCCGGCCGCCGGATGTTCTCC

TTCTCGCATGCTTTTTTTTGGGGGGTTCTTTCTCCGCCTCCTGCTCTTCGTCTGTTCTACCATCGTCGATCACACAGCA

ATTTGACTGACCGCGTCTGTCCTTCCGACCTTGCCGTTTTGCTTTGCAGGTAACATAATCTCGCTGATGGTGTTCCTTTC

GCCGCTGTAAGTAACTCTCTGCTTTAATTTATTTAACCTAGCCGTGAACTTTTCATATTTACGTTTACAGTATCCAGTAC

CATGCATAATATACTACCAATATGTTTCTATGTATATTCAGTAAAGGGAAGCGTCCAAAATATATACTGCCATCAGGTAT

GATGAGAACATATATATAAAGAACATGGCACGCACGCATGCGTATCTCACTGTTGAATGAATGACGTGCCATCATCGTCC

ATGCTCTTCTAGATCCTTTTCCTTTAATTTATGCGTGGTTCTAGATCCCCCTATATATATATATATATATATATATATAT

ATATATATACGTACACCTGAAGACAACATAGCTAGCTAGGAAATAAACTCGTTGGGAATTGAATTGTCGCATTAATAA

CGTCACTTTAATCAGTTGCGAGCCAGTACGTGTCACTGTTCGGTGGTTGCGTTGCACATGCTTTTAGTATGGAACAGCGC

ACGCAATCTAGTAATAATTAATCTAAAAAATCACACGGTAAAAAATATTCGTTCCCGCTGATCCCGCGCAGGCCGACGTT

CTACCGCGTGTACCGCAAGAAGTCGACGGAGGGGTTCCAGTCGACCCCGTACGTGGTGACGCTGTTCAGCTGCATGCTGT

GGATCTTCTACGCGCTGCTCAAGTCCGGCGCCGAGCTGCTGGTGACCATCAACGGCGTCGGGTGCGTGATCGAGGCGGCG

TACCTGGCCGCGTACCTGGTGTACGCGCCCAAGGCCGCCAGGGCGCTGACGGCCAAGATGCTGCTGGGGCTCAACGTCGG

CGTCTTTGGACTCGCCGCGCTCGCCACCATGGTGGTCTCCAGCGCCGGCCTCCGCGTGCGCGTGCTCGGCTGGATCTGCG

TCAGCGTCGCGCTCAGCGTATTCGCCGCGCCGCTCAGCATCATGGCACGTATCTAATTTAATCTCTCTCTCTCTCTCT

CTCTCTCTCTCTCTCTCTCTCTGAAGAGGGATGTGAATTGTTGGAACCGCCATTAATTCGCTGACTGCCCTATCTACA

TCTACTTTCCTGCAGCGGCAGGTGGTCCGGACCAAGAGCGTGGAGTTCATGCCCATCTCGCTCTCCTTCTTCCTGGTGCT

GAGCGCCGTGATCTGGTTCGCGTACGCGCGCTGAAGAGGGACGTGTTCGTGGCGTTCCCCAACGTGCTGGGCTTCGTCT

TCGGCGTCGCGCAGATAGCGCTGTACATGGCGTACAGGAACAAGGAGCCCGCGGCGGTGACGGTGGAGGAGGCGAAGCTG

CCGGAGCACGCCAAGGAGGTGGTGGTGGCCGGCGGCGGCCGAGGCCAGGGCGAGCTGCGGTGCTGAGGTGCACCCCAT

CGACATCGACATCGAAGCTACGCCGACGCCGGTGGAGGAGGTGCACGAGCCGCAGGTGGTCGTGGTCGTCGACGTGGACG

TGGAGCCTGTCACCTGCGCCGGCGCCGCCGAGGCAGCTGCGGGAGCAGGGGCAGATGCGTCCGGCGTGGCCGACGGCGGC

-continued

```
GTCCCTGGACCCATGGCGCCGCCGGAGCAGCTGGCGATCAAGCCCGACATGGCCATTTCCGTGGAGGCGTAGGTTGGTTA

AAGTGTAATAGCAGAGTGAGTCGATATCGATCAGTAGTAGATTTGTCGAGTCAAGGAAGGGGCCTGCTGCTGCTGCTACG

CGACAGCAGCGGCCAGATGTACTGCCTGCATGCATGCAGTCCCTCCCGTTGACTCGACCCGTAGAGAAGGGATGGGATGG

AAGTAGCCGGGTCCTTGGGCGAGTAGCGGCGCCTTGGCACCCACGGGCCAGCCGTACTGGCCTGTGTGATGAACCGGCGA

GAGAGATGAGATAATGTGCGAGCGAGAGAGGGTTGGTTGGGTTGTGGTAGTTGAAGAAGACGGCTAGCTAGCTGCTGCTG

CTGGGCTCTCTATCTGTCTCTAGATCTGTGTATGTCTGTGTAATCGAGGATTCCCTCACCTTGCATGCCGCCTCCCTTTT

GTGTCCTTCTAGTCTGATGATTGTTTTCATTCCATCCATGCCGGCGTCGCAGTAATAAAATTTTTTGG
```

---

That which is claimed:

1. A method of identifying and/or selecting a maize plant or maize plant part having increased yield under non-drought conditions, increased yield stability under drought conditions, and/or increased drought tolerance, said method comprising:
   (a) detecting, in a maize plant or plant part, an allele of at least one marker locus that is associated with increased yield under non-drought conditions, increased yield stability under drought conditions, and/or increased drought tolerance in a plant, wherein said at least one marker locus is located within a chromosomal interval on chromosome 5 of the Maize B73 genome version 3 defined by and including base pair (bp) position 164893210 to base pair (bp) position 164900398 (SEQ ID NO: 23), wherein the chromosome interval comprises a haplotype selected from the group consisting of at least one of a C allele corresponding to position 164895193, a G allele corresponding to position 164896921, a G allele corresponding to position 164897496, a G allele corresponding to position 164897515, and a C allele corresponding to position 164897518,
   (b) selecting a maize plant or maize part on the basis of the presence of the at least one allele of a marker locus in (a);
   (c) crossing the plant of (b) with a maize plant not comprising said at least one allele of marker locus; and
   (d) growing progeny from the cross of (c), wherein the progeny comprises the at least one allele of the marker locus,
   thereby identifying and/or selecting a maize plant or plant part having increased yield under non-drought conditions, increased yield stability under drought conditions, and/or increased drought tolerance.

2. The method of claim 1, wherein the plant part in which said at least one marker locus located within said chromosomal interval is detected is regenerated to produce a plant having increased yield under non-drought conditions, increased yield stability under drought conditions, and/or increased drought tolerance.

3. The method of claim 1 wherein a combination of two or more markers associated with increased yield under non-drought conditions, increased yield stability under drought conditions, and/or increased drought tolerance in a maize plant are detected.

4. A method of producing a maize plant having increased yield under non-drought conditions, increased yield stability under drought conditions, and/or increased drought tolerance, comprising:

crossing a first maize plant or maize germplasm with a second maize plant or maize germplasm, wherein said first maize plant or maize germplasm comprises within its genome a marker associated with increased yield under non-drought conditions, increased yield stability under drought conditions, and/or increased drought tolerance in a maize plant, wherein said marker is located within a chromosomal interval on chromosome 5 of the Maize B73 genome version 3 defined by and including base pair (bp) position 164893210 to base pair (bp) position 164900398 (SEQ ID NO: 23), wherein the chromosome interval comprises a haplotype selected from the group consisting of at least one of a C allele corresponding to position 164895193, a G allele corresponding to position 164896921, a G allele corresponding to position 164897496, a G allele corresponding to position 164897515, and a C allele corresponding to position 164897518, wherein the marker has been detected in an isolated nucleic acid; and growing progeny from the cross, wherein the progeny comprises the marker;

thereby producing a plant having increased yield under non-drought conditions, increased yield stability under drought conditions, and/or increased drought tolerance.

5. The method of claim 4 wherein a combination of two or more markers associated with increased yield under non-drought conditions, increased yield stability under drought conditions, and/or increased drought tolerance in a maize plant are detected.

6. A method for producing a hybrid maize plant having increased yield under non-drought conditions, increased yield stability under drought conditions, and/or increased drought tolerance, said method comprising:

identifying a first maize plant comprising a chromosome interval on chromosome 5 defined by and including base pair (bp) position 164893210 to base pair (bp) position 164900398 (SEQ ID NO: 23), wherein the chromosome interval comprises a haplotype selected from the group consisting of at least one of a C allele corresponding to position 164895193, a G allele corresponding to position 164896921, a G allele corresponding to position 164897496, a G allele corresponding to position 164897515, and a C allele corresponding to position 164897518;

crossing the first maize plant and a second maize plant not comprising said haplotype to produce an F1 generation; and selecting one or more members of the F1 generation that comprises said haplotype, whereby a hybrid maize plant having increased yield under non-drought conditions, increased yield stability under drought conditions, and/or increased drought tolerance is produced.

7. The method of claim 1, wherein the chromosome interval comprises a haplotype comprising a G allele corresponding to position 164897496 and at least one additional allele selected from the group consisting of a C allele corresponding to position 164895193, a G allele corresponding to position 164896921, a G allele corresponding to position 164897515, and a C allele corresponding to position 164897518.

8. The method of claim 4, wherein the chromosome interval comprises a haplotype comprising a G allele corresponding to position 164897496 and at least one additional allele selected from the group consisting of a C allele corresponding to position 164895193, a G allele corresponding to position 164896921, a G allele corresponding to position 164897515, and a C allele corresponding to position 164897518.

* * * * *

SEQUENCE LISTING

<160> NUMBER OF SEQ ID NOS: 43

<210> SEQ ID NO 1
<211> LENGTH: 2656
<212> TYPE: DNA
<213> ORGANISM: Zea mays

<400> SEQUENCE: 1

```
gcctatataa agccacccac agccctgcct atcattgcaa gagtttgagc caacacacac      60
agagagagga caactcctca caactctccc ttccctcctg tagggccaa aagggttaga     120 gagtaggaga agtagttccc tagcccaaca caagaaaaac aagctcgatc tcctcatcac     180
cctaatccaa gcaactgctt tgtgtgttgg gaaattcttg tgacccctgt tatattatta     240
tccgtgtagc tactagcttc attccccct ttgtacccat caaatggctg gcatgtctct     300
gcaacacccc tgggcgtttg ctttcggtct actaggtaca tactcacct tcactaatag     360 ctaaacaagc gcccgccgca aagctatgaa ttaagggcag gcatgtttgg tttgctacct     420
attttaccat acttttgtcta acttttctgt ctaaggttat agttcttcaa ttcgaacgat     480
taatcttagc caaagtgtga catggttagc cacgaactaa gcaggccctt aattattgcg     540
catgtatata ttatatattt atcttctat tctgtttaat ttgttttctc tttacatata     600
tatactacta tgtaagtata tattatatgc acaacaagca ggcctccttc gtgcacatat     660
gcatagaatc aatctatacc cttcatagaa gccactttga gatataccct ccaaaacaat     720
cccaaaaaca agacgctcga tcttgcgctc acaatcactt agttttgcac cagattaagc     780
atgcaccact agatttttatg tactgtatta cctctgccat ccatggtcga tcctttagtt     840
tatcctattc atttccgtca tgaactacct gtcgagctag caatcggtcc tttatttaga     900
gtgttcagat aggcatctgt ctttataca acaataaagc ctcacgaatc tttagtcaca     960
aaacaaggca aattagacag gccacggagg tgtaaagtgt cagctctgct tatcacaact    1020
tatctctgct ttatttgggc acacttttgc catacaaatg gctgatcttg gcgcctttt    1080 tttctccttg ctttgcaggt aacgtcatct ccttcatgac cttcctggcc ccgatgtaag    1140
tgacatatat atatatatat attgcttaat taattatcac tgcttcttca gatatatt    1200 catcggttat tttaattaat tatgtggata tgtatgcatc gtataacaga ccgacgttct    1260
accgcatcta caagagcaag tcgacggaag gcttccagtc ggttccctac gtggttgccc    1320
tgttcagcgc catgctgtgg atcttctacg cactgatcaa gtccaacgag accttcctca    1380
tcaccatcaa cgccgccggc tgcgtcatcg agaccatcta cgtcgtcatg tacttcgtct    1440
acgcgcccaa gaaagccaag ctgttcacgg ccaagatcat ggtcctcctc aatgcggcg    1500 tctttggggt catcctcctg ctcacccttc tcctcttcaa gggcagtaag cgcgttgtgc    1560
```

```
tgcttggctg atctgcgtc ggcttctccg tcagtgtctt cgtcgcgcca ctcagcatca    1620
tggtgagccc tgagcacgcg tataaaactg tgccaagatg catggacgac agatcgatca    1680
acccaatcag ttttgatcca tgtgtatcgt ttctaatgca ccgtgtttat atatgtgtgc    1740
agagacgagt gatccagacg aagagcgtgg agtacatgcc cttctccctc tccctctcgc    1800
tcaccctcag cgccgtcgtc tggttcctct acggcctcct catcaaggac aaatacgtcg    1860
cggtaattgt ttcatctaat ctgctgcaac cgccatggta ttggtatctc tcactggtct    1920
ttactgataa actacatacg atctctgtac gtatgcagct ccaaacatc ctgggggttca    1980 ccttcggcgt ggtccagatg gtgctctacg tgttgtacat gaacaagacg ccggtggcgg    2040
cgactgccga gggcaaggat gccggcaagc tttcctcagc tgcagacgag cacgtcctcg    2100
tcaacatcgc caagctcagc ccagccctcc cggagaggag ctccggggtg cacccagtca    2160
cccagatggc gggcgttcct gtcaggagct gcgctgctga agcaaccgcg ccggcgatgc    2220
tgcccaacag ggacgtggtc gacgtcttcg tcagccgaca cagccccgcc gtccacgtgg    2280
catagattct cgatcgatcg cgtgcatggc ccatgcatgc gcccgccaca cgtacgctag    2340 ctttatata ttcgaaggac gacttgctgc tggtcgtgag catatatatg atggagaaaa    2400
tgattaagta gtatatatat aagtaattaa ctgccatgca tggaagctag ctaatggatg    2460
gaggcagagg ccagaacgat gaaggggggaa gctatacata tatgtgtgta attaatatag    2520
atatatgggc tttgtgttca tctttgcagc tatgtattaa tttgcatgga tatctgttat    2580 tccttttttat gtgtaacgtc ttctaataaa atgtaattga acccacacta ctgttgttag    2640
ctaccacaag tttccc                                                   2656

<210> SEQ ID NO 2
<211> LENGTH: 3653
<212> TYPE: DNA
<213> ORGANISM: Zea mays

<400> SEQUENCE: 2
ggctctcttc tccaccggtc ctaccccttaa cctcccaaga tcacaatcct ctgctcctta     60
tatattagcc acaccgctcg ttccctgctg caccgggtga cacacaggca caaagacacc    120
gcccgtacac aggctcgttg gcttggctgc tgtgtgttgc gctcagccat tcagacttga    180
gagctactag ctaactgctc gttgggtgtg ggtgcgctcc cggcctagac cgtggaggaa    240
aggagtccag tccactcact accccctctg ctccgttcgg gttccaggcc agcacagccg    300
agggttccgc acagcgataa gcgcgaagcg gaagagatgg agcatatcgc caggttcttc    360
ttcggagttt ctggtcagta tcaccatgcc attcctgcct ctgctgcatg cctacctgat    420
ggtcttcttc ttgcctcgcc taatctctgt tagatctgtc tccccaggga atgtcattgc    480
gctcttcctc ttcctgtcgc ctgtgtaagt ttttgattcc acgtacctga atccttctgt    540
tcctcactgc ccgcgtccat gctttaaaaa aaaatcgaa acagagaag caatgatata    600 gtacttactt ctactatatg acaaagacta gaacatgggg agaatcagtg tggagagaaa    660
ggctatagca tctttttaggt tcaatccttt ccagcgaaac actgaaattt catacatata    720 taatttttttt ctaaaaaaag caagtagctt ttccccatcc gaaatgcttc ttcttcccaa    780
ccacgccgca ccttttttct tgcgtcttgc ctcagcagcc ttcaggggca gcagcgcagt    840
gcgtgtgttc ctctgacggg tgagaaatct ctttgcagtg tcaccttctg gagggtcatc    900
aggaagcggt cgacggagga cttctccggc gtgccctaca acatgacgct gctcaactgc    960
ctcctatcgg cttggtaacg aaccgctctc tctctctctc tctccctgag agacacggcc    1020
```

```
ttttgatgag cactccacac catttctgtt tctgtctctt cagaaaatta aatcgcatcg    1080
cagatttatg gagtggccgt aaagcagtaa aaccggcgtg gtggtgtagt ttgttttact    1140
tagatttcgg aaatgctgca tggtttgctg gcctgggtga agcaaacgct tggctcctag    1200
cgtagcctct gcccaacccg gcctgtcctg tagatagagt actacccgtg gacccactcg    1260
ctagacgcta gcactgtaag tctgtgacaa cgactgcaat gaaggggggaa aagcttattg    1320 cactgcacca ctgcccgtgg gagcagagcc tacctgttgg cattgccagg acggagatga    1380
cgacctgtgg gcctcgcggc ccttgagccc gcacatgcag cgtcacgttc aagtgttcgt    1440
acctccaaac aaaaaaagtc ttgacgcttt tttttttctt tttggttatt atgatgacgg    1500
acgattctgg tcagggcatc cacataaata tcttaaaagg tattaacgac gtaagtgcaa    1560
aaaaaaagac agtctctagc actaccacgg ttttatccat acaactcacg tacatgaatc    1620
atatcatgag atcttctagt ggaataagat ataaaactta aatatattgg gctatatgaa    1680
agagtttttt agatgtattt agtgcttaaa gaactgaaac gtagtatcta gattgtacat    1740
gtctttatga ctatatggat gagttggtgt cccgtttgat ttttcacgcg cctttgaatc    1800
catgtgaaga tcgatgtgct agctagctag ctcgctcttc atgcgttcgt ctggattttg    1860
tttgaaattc acgcagcata tatgtgtgga atataatctg tatgcacata caggtacggc    1920
ctgccgttcg tgtccccgaa caacatcctg gtgtcgacga tcaacgggac ggggtcggtg    1980
atcgaggcca tctacgtggt gatcttcctc atcttcgcgg tggaccggcg ggccaggctc    2040
agcatgctgg gcctcctggg catcgtcgcc tccatcttca ccaccgtggt gctcgtctcg    2100
ctgctggccc tccacggcaa cgcccgcaag gtcttctgcg gcctcgccgc caccatcttc    2160
tccatctgca tgtacgcctc gccgctctcc atcatggtac gtgagcgatg atgattggtt    2220
gttgctgcct tgctgggtag ctagctccag cgggtcccct tctgggcgtg tacgtgcgtc    2280
cttgctgtca acgtacggca tcagttaaca agctaagcgt gtgcttggtg tgtgcagagg    2340
ctggtgatca agacgaagag cgtggagttc atgccgttcc tgctctccct ggccgtgttc    2400
ctgtgcggca cctcctggtt catctacggc ctcctcggcc gcgacccctt cattattgta    2460
cgcacacggt tctctctcta gtctagatcc tgagccgcac tcaccgcccg gccgtacgca    2520
cgtgctatcc gcgcatgttg tccgattggc actcggaaac cactgtagca gcactgtatc    2580
actagctgtt gggactggac gtaactgcat ctgatctggc cagcacagta cccccgggct    2640
gggcgtcggt tgcccttctcg atgtcccgcc caagcccaac caggcgcaca tgcctgccgc    2700
tgccgcagcc gatgcacggg catgggcgcc ggtagcgtct agcagcgtgg gcgtggccac    2760
ccacaggcag cgcacgccgg tgctagctgc cgatgggccg ccgtgcccat gtccatgcag    2820
ctggattgga cccggcacag gcagaagcaa cagcgcccgc gctctttctt gtcgcaatgc    2880
tagttagcaa actgcacggt gcactccact tcagtacaca ccaacgcgac agactgcgat    2940
gaaatatcta aggccgagtt tttttttttt gcaaatctca tcatgtcgga atgattcatg    3000
cggtccaaac ttcagcacac ccccactgtc gctaaacccg cgctgtctgt gcatgcgtgc    3060
agatcccgaa cgggtgcggg agcttcctgg gcctgatgca gctcatcctg tacgccatct    3120
accggaaaaa caagggcccc gccgcgccgg ccggcaaggg agaggccgcc gccgccgccg    3180
cggaggtgga ggacaccaag aaggtggccg ctgccgtgga gctggccgat gccacgacca    3240
acaaggcagc ggacgccgtc ggcggcgacg gcaaggtcgc cagccaggtg taggcgggca    3300
aggcttattt gctgtctggg actggaggga acatcctaaa cgaggctgcc ttagtttgtc    3360
ggtggagcag attggtgttg gtttctgtgg gcttttacgg ttgttgttac tctcatctcc    3420
```

```
atctctccca ggaggctacc ccaagcatgt agtagcttcc attctgattc tgggacggtg      3480
ttgcacgtta cagtgctctc aagctgtctc tgcaaagtgt gttttttat tccatttccc      3540 tcctgctctt gttctccaac tgcgcttacc tgcccccgat ttctctaaaa aatgtattaa      3600
actatctgag aaattcatcc aactgcgagt actgtgctgt gcgtgagcaa tgc            3653

<210> SEQ ID NO 3
<211> LENGTH: 2911
<212> TYPE: DNA
<213> ORGANISM: Zea mays

<400> SEQUENCE: 3
acacacaaac acatcagcat tcagcaatag ctaatcgagc atcgtcgcct tagctcctct       60
cctctcctct ccgtcgtcgt ggaacttctc tccgccggct gtcatatata taaaggagaa      120
gaagagaaca gcaactctag ctagccggcc ggcctccgtc gtcgccggcg tcgtcgacta      180
gctagctaac tctcgatctc cagttcctgc ccccgcgccc cacgcccggc cgtcgtcgtc      240
agcaatggca ggaggcttct tctccatggc tcacccggcc gtcaccctct ccggcatcgc      300
aggtacgtac gcgccaatga acaacaacg tcgtctcgag ctagatcgat ccatgcatga      360
cgccggccgg gaccggccgg atagataggc ggagatcgac ttgcataatg cttcgcgtgt      420
ttggcctttt cctggtgctt cttttttttt ttaaaaaaaa tcttatggga ccttgatgac      480
atgcttttca tgtggttttc attcattctg ttgccgtact acgttcttct agattttgtt      540
tattccgaca tgacgactgt cttgtccatc cttgtatcat cgatccgtcc tttgcatgca      600
tgcatccacc agtcgtcagc cttccttttt gccgtttgtg ccattgcact gtagagcacg      660
cacgcactct ctagctgtag agaggcgcgg cagtaggcat gcatgcagca gctagtcaca      720
ctggacaacc aactgtcttg tccatcatct atcaacaata cttgcatatc agaatacgta      780
gtatgtagct ttagcatttt ttttttcttca cctatactac tgctagctgc atcttcttga      840
actttctctg atgctccccg cggcccattg agacgacgat gcactctttc tccaattcgt      900
tagctgcgat catggcacag gcctttaatt tgttgctagc tagaacacac atgcatgcat      960
cgccgaggta tagcaacttt tccactcaag aataatggta ataagcagtg cagatcagat     1020
ccacatattg ggcattagat cacgaaatac agttgcaaat agctgctcac aacgtaacgc     1080
actatctaag aatcatttct atatacgtgt atttttgct ggaatggtta tgatcgatcg     1140
gttgggcatg cagcagggaa ggcgtgtgcg tgtgcatgca gctacctagc tttttgccat     1200
atcagcgttt ccttaaccta atcaccacgc ttctctctgt tagtggacgc acacgcattg     1260
tacatatata tgtgtatagt attgtactcc taccacttt actgaaaatg acgacactga     1320
cgcgtagtta ccctcttctc tcttgttct tcgatttgga ttgtgcagga aacatcatct     1380
ccttcctggt gttccttgca ccagtgtaag tagctagcta tagccacctt tcttcgttcc     1440
cttactgtct caatttcaga ccgactcgga ttcatgcgtg aatcgatgga tgatccaaga     1500
ctgacatggc atgcctcttg tacgcaccgt accaaaaaca gggcgacgtt cctgcaggtg     1560
taccggaaga agtcgacggg cgggttcagc tcggtgccgt acgtggtggc gctcttcagc     1620
tcggtgctgt ggatcttcta cgcgctggtg aagaccaact cgaggccgct gctgaccatc     1680
aacgccttcg gctgcggcgt ggaggcggcc tacatagtcc tctacctggc gtacgcgccg     1740
cggcgggcgc gcctgcggac tctgcctac ttcttcctgc tggacgtggc ggccttcgcg     1800
ctcgtcgtcg ccgtcacgct cttcgccgtc cgcgagcccc accgcgtcaa gttcctcggc     1860
agcgtctgcc tcgccttctc catggccgtc ttcgtcgcgc cgctcagcat catcgtcaag     1920
```

| | |
|---|---|
| gtggtcaaga ccaagagcgt cgagttcctg cccatcagcc tctccttctg cctcacgctc | 1980 |
| agcgccgtcg cctggttctg ctacggcctc ttcaccaagg accccttgt catggtaacg | 2040 |
| actgatcaat aatgtaatat atggttaact gatccatata tatatataaa atggtaactg | 2100 |
| aataatgctg gggatgtttc tcgattatat atatctattc agtacccaa cgtcggcggc | 2160 |
| ttcttcttca gctgcgtcca gatgggcctc tacttctggt accgcaagcc ccgcccggcg | 2220 |
| gccaagaaca cgccgtgct gccgacgacc acggacggcg ccaacgcggt gcaggtgcag | 2280 |
| gggcaggtca tcgagctggc gcccaacacg gtggccatcc tgtcggtgag ccccatcccc | 2340 |
| atcgtgggcg tgcacaagat cgaggtggtg gagcagcagc acaaggaggc cgccgtggcc | 2400 |
| gccgagaccc gccggatggc cgccgcaaac ccggacggcg ccatgccgga ggtcatcgag | 2460 |
| atcgtccccg ccgccgccgc ggtgtgaccc aacgccaatc accatgcacc gtacacaccc | 2520 |
| tgctagcttc ttattagcta gctcggatga cgtacgacag tttggtggca agtggctggc | 2580 |
| agctcaagca tgcagatgca ggcatcgtcg tctgctagtt gatcgtttag ttggttaatt | 2640 |
| gttggattat tattgcgtgt ctctctcgtg tgcgtagtct tgtcagttca gttcagttca | 2700 |
| gtgtcgaatc aagtagtagt agctgttgtt tgcattggat ctgacaatgc atgctaataa | 2760 |
| ttatggtggt gtgatggtct tggtcggtac gtgcgtagtc gtctacgtac gccgtgtcaa | 2820 |
| cgtcgtagat ctctacggga agatgataag actgtaacat gcagggcatg catctattta | 2880 |
| tacttaacat attctttgtg tgcttaattt t | 2911 |

```
<210> SEQ ID NO 4
<211> LENGTH: 5438
<212> TYPE: DNA
<213> ORGANISM: Zea mays

<400> SEQUENCE: 4
```

| | |
|---|---|
| ctgagctgac tgtggatctc atccgtatcg tatatacgtc gtcctgtttg gatccaccgc | 60 |
| gttttgctaa ttcccttcga accggccggt ggccttcgtt ctcccaccag gcctgtctgt | 120 |
| ctgctgtatc cgccagagct tccatggatt ccaccctctt catcatcggc gtcataggta | 180 |
| agcttgtgta tcattctgaa ctgctttgtt attattatta gtcttcattc gtccagcttt | 240 |
| ccttatcttc ttcttctaca ttgaaatagg caacatcatc tcagttctcg tcttcatatc | 300 |
| gcctatgtaa gtgtctttct ccatatatat ggtttccctg tcgtcgctgt tgctagctag | 360 |
| cttttctttct gaacaccacc acgggcacca atccatgcat ggatacagca agacgttctg | 420 |
| gaggatcgtg cggggcggga cgacggagga gttcgagccg cgccgtacg tgttgacgct | 480 |
| gctcaacgcg ctgctgtggc tctactacgg cctcaccaag cctgacggct tcctcgtcgc | 540 |
| caccgtcaat ggctttgggg ctgtcatgga ggccatctac gtcgtcctct tcatcgtcta | 600 |
| cgccgccaac catgccacaa gggtgagggg tcggagcagc tggggccagt atatatagtt | 660 |
| cactcacaca atccgttgct taattctgca taattctttc ttcaagcact tgagtcttag | 720 |
| gaattacgga gtatatagtt aaagaaaagc acaaccacca ttcgtttatt aaagaaaagc | 780 |
| atgtgttgcc ttatattata gtttgttcct ttatcgcaat tatgattatg caggttaaga | 840 |
| ccgcgaagct ggcagcagcg ttggacatcg gtggcttcgg agtcgtgttt gcggccacca | 900 |
| cattcgccat cagtgaattt gaattgagaa ttatggtgat aggaatgata tgtgcctgcc | 960 |
| tcaatgtgct catgtacggg tcacccttg cttctatggt aagttttttt tcctcacatg | 1020 |
| catatttata cactattcct ctttttcttc ctttttggt tatttagaa acttaaatcc | 1080 |
| cctctggtat taattcccga gaatttcact taattcccaa gaatcccaaa aaaaattaag | 1140 |

-continued

```
tttctaaact agcccttagt gagacttaat ttatttgttc gccgtaagtc gattttgaga      1200
tgcacatttc tccttaattt tccttttata gctgaccgtg cacggccttg aaacatcacg      1260 atctttcag ttaaatttaa ttagcacggg ctaaattttt acattgcaaa agaaaataaa       1320
ctaatttcac acacacatat atagtatata gctagcaaac tgctaatggg ccagcaaaac      1380
ttatggatga taacattgag caatgaaatt attgtcatgt aacggtaact atattataat      1440
agtgagtttc gatccatgat ctaatatata ccatataata atattgatgc cacttggccc      1500
cacagacaaa gtagagtata gttcaagttt ggagatatat aaatgataat aataataata     1560
aagctgctca agatattttc attctggcga tccatgtctg tccacgatgg atcgacgata      1620
aaatactcgg tgtttattat aatggacagg gcgctttgtg gggcgattat tttatgttgt     1680
gttgtccctt tcatgattat ttattaaata taaggacaga agtccaagca aaacacatgt     1740
gccccaagca atagggatat atagtgacat attgtggaaa tagttatata ttttgggga     1800 gaatcatgtg tcagggatat tgtacaatag aaaaacattt cttagtatgt aggtcctcaa     1860
ctgcccctgt tttttctctt attttagca gatgttcgat ccacttccac aattccactt      1920
gcaggaataa tataataaat atagatatat atggtacata agctgtatgt aaaatccata     1980
taataatatt aatattacat tatataccctc aacgaatcat ttctaaagct tttattaggt    2040
ataataaaaa gtaaatttat attttggtgc ttgtagctag gtgtggccgt gtggggcacg     2100
tgcaagcaac cttactcgtt ccacctccta tcttttgctc cactttgtaa ataatacata     2160
ttacagcgta aaactgtgta gaaagtatga ttttacggct atatacacgg tgtgctacga    2220
ctaaaagtta gggacgacct cacgccgata attggatgac agatttttt cctttgatat      2280 cttcttctc tggcatgcca aatcgaattc ctccctctgc ctttaatttc tatttgttag      2340
gattatatga aactatttcc acaagtatag ttagagactc aaattcagat actagaaatt     2400
aatgatggtt tacaagccat aaataaataa attaaaaata aacatattta gattttaatt     2460
tgaatgaaaa gagaacattg cttcggtttg atgcagatta acttatacag aaatcatata     2520
ttatgtcatg agagacaagc aaagattggt caacttatta ccatttcttg caaaatcaag     2580
tttgccgtat tattattttg tccttttctt ttttaaaaga ttattagctg gttattggtt     2640
ctctgggcag ttaacggggt agagtattcc acagaattaa ataatcacca tgcaaggaac     2700
acgcgttgtc ctctacatac gattctttat ttacttaatt ctacatcaca cattttgtgc    2760
aagaacagta gctattagaa aaaaaatgtg agcatcggtt cacaaccggc tatagtactg     2820
gattatcaac tgatattaga caatcgaaat taaagacctt attttgaag gaccggtgaa      2880 atgaccagaa ggggtgaatt agagccaatc aaatttatt gttaaaaact taaatttaga     2940
ccttatttgt gaaggaccag aagaggtgaa tgagagccaa tcaaatttta ttacaaaaaa    3000
ctaaaattta gcacttaact tcaattgaga tgaagaaatc gttcaaacca gaagcacatc     3060
ggccaaatag taatcttacg atttcaaaat ggtaccccta gatacatttg gttttttgtt    3120
tagaataccg gtattctttg gctaagttca tttggtttat tggttttttgt ttagaatatg    3180 ggtattctaa acaaaaacca aatgaatttt gccaaaagag atggatgtca ataaaagccc     3240
acatatctat ttatagaggt gatggataca tcatatccac ttagccgggg caaaatggat    3300
caactcctag gattttgatc agacgaccac gcgctctaca caaagttgct tcgcctcgac    3360 acacccttg tgatgatgtc atgtgccacc tctgattcct gccgaaaccg ccaccgtcaa     3420
gttttgaggc ccaaactcag caaaaccagc agatgggtgg ttttgaggct caaccacaaa    3480
accaccgcga gtagtgcatc gcatgcgcgt ccccacgtcc tggacacatg tcccattagt    3540
```

| | | | | |
|---|---|---|---|---|
| ccttgaccgc | atcggcgaca | gtgcgacaca | agccactctg | tcatgtcctc gcgctagtgc | 3600 |
| gtgtcctagg | tgtgagccac | cacaacttgt | caaccggctc | ctccgacccc ttggtcaagt | 3660 |
| cctagtgctc | gtctttcatc | actctccgtc | tatcggcata | accctcgtg tgaccttcac | 3720 |
| attcgccatt | gaacaacata | catgtacttc | acacctgcac | accataagcc gagagacatg | 3780 |
| gttgcacaat | acataactca | tactctggtc | agtccaccga | ctacatcaaa atactatccg | 3840 |
| ttgacaatca | cttatcatca | actcgaacca | caagggacaa | atcaacttgt gttcacaatt | 3900 |
| gtttgccata | gagagaaaga | aagcgtactc | cgtgtgttgc | ttgggtttac cgagaagcac | 3960 |
| gtgtgtaaaa | tgggtagcat | actctagtag | tactacgagt | gcacgacgtg actcctacag | 4020 |
| attccaaact | cttggcaaaa | ttaatatcgc | gacatgtcat | catgtccatg ccattacctt | 4080 |
| agctgtattg | acaggccgga | cctgctattt | gtgtcggccg | tacgtgttct tgcggtcctc | 4140 |
| gtcgggtggg | gtttcgctct | ctgaattttc | tgattggttc | catcgatatt ttctgattgg | 4200 |
| ttccatcgaa | agcgaaacca | ggaccgtacg | tggcgccaaa | ttcaaccaga ccacccatcc | 4260 |
| cttcccgggg | tcatgtcaca | tccctgttgc | ttcacgtttt | cttacaaaat tacccgctcc | 4320 |
| gtccgtgaag | caaatataac | tatgatatcc | ctatctgtca | gagtagttta aatttaacta | 4380 |
| aatttataat | aaacaatact | cgctttggtc | ctaaatctag | acacatatat atatatatat | 4440 |
| atatatataa | cacatacatc | aagtattgta | taaattcaca | aaataccact atatgaacgc | 4500 |
| ccttaaattt | taaattaaaa | aattatctaa | gaaaacataa | gcaataatta acccatgcca | 4560 |
| atgcaagttg | aatacttgaa | ttgaaaaaag | ttgattccag | ctcagggaac ctataaccat | 4620 |
| ggcttcgcat | gagttggcga | ttgcctgaac | aggcccatgc | agagcaacta accatagaat | 4680 |
| agaacaatac | gcgatgaaat | tcaccgtacc | ctgcaacgta | atggatgtgt gattagtatc | 4740 |
| accggcacct | catttttacc | cgtcatctcg | ttgtacctac | attttcagaa aacggtgatc | 4800 |
| acgacaaaga | gcgtggagtt | catgccattc | ttcctgtcct | tcttcctctt cctcaacgga | 4860 |
| ggcgtctggg | caacgtacgc | ggtgcttgac | cgcgacatct | tcctcggggt aatgtttaaa | 4920 |
| gcctctctgt | tcttctcgat | cttcttcccc | aacctctgtc | ttttccgcta cccatactaa | 4980 |
| acagaacctc | tcgatcgctc | tctgcatgca | gatccccaat | gggataggct tcgtgcttgg | 5040 |
| caccatccag | ctgatcgtct | acgcgatcta | catgaacagc | aaggcctccc aatgcagcaa | 5100 |
| agaaacagcg | tcctcgcctc | ttctggcctc | cgaccgggga | gaagcatcta gccatgtctg | 5160 |
| atgatgagct | tcgatcagtg | cgcgcgctgg | agtatagcat | agaagtctct tgctgtcaaa | 5220 |
| aacttccaag | accaacggta | cctaccagca | tgcatgcatg | caagaggtta ccaatttta | 5280 |
| ttgtttgaaa | attcatgtaa | acttgtgacc | tccatggatt | gtttcttcct ttggtataag | 5340 |
| cttcgaagat | gttagattgt | tagcacggta | gttttgccag | agaagggtgt tgtcaatata | 5400 |
| atgaagaaat | ggtgaaaatc | catacatttg | attatcga | | 5438 |

<210> SEQ ID NO 5
<211> LENGTH: 3189
<212> TYPE: DNA
<213> ORGANISM: Zea mays

<400> SEQUENCE: 5

| | | | | |
|---|---|---|---|---|
| ctcaggagct | aatgactcac | ctctccgtgc | tcacctcctc | ttcttgaggc ttgagctctc | 60 |
| tcttcctctc | tccccctcagc | tcatctccac | cgtctcccta | tatataggat gctctgccgg | 120 |
| ctccaaggtt | cccaagcgcc | caaggcagcg | gagagagcta | gctccctcct cctcctcagg | 180 |
| tagcgagcga | gcgagctcct | ctgcccctct | gcacacctgg | cctcccctcc tccgctgcag | 240 |

```
gaccgccgtt gacgactgct ccaccagtac tgcgcgcgcc cgcgctgcct acccttacct    300
agccagagcg cggcgcgcga gagggagaac gaccaggagg ggaggagatc gatcgatcga    360
tcgatcgaga tagatggctt tcctcaacat ggagcagcag acctgggcct tcaccttcgg    420
tatcctaggt acatatatac tgtcagtctg tcactcgtag ctactaatta accgcatcaa    480
cggagccgcc ctgccgtctt cgtcctcgtc agtgtttctg cattgttttc cttccttgtc    540
ccaagtcctt tgagacgcac gcatacatga tacatgcatg gcatcatcgt ctcccaagtc    600
ctaggtacag tttcatcacc gcgcgcctct ctcagatatg tgtcgtcgta caggacaaca    660
caacacgtcc tcgtcaatct actagctata tgcgctaata accacctctt cctttccgag    720
ccacggcaca gtatagcctg ccatccgaac gaacggaacc gcccaaaacc caactttttt    780
tgggcctaac taatgcggtg gttagcccaa acaaagaaac cagggcagtc atacatttta    840
catgtagtac ctgcttgacg acgggaacca acacaacggc gcgccgcgag gagagtttgt    900
tccatttcct ccgcctgcag gctagctgca gctaataacc ccggccgccg gatgttctcc    960
ttctcgcatg cttttttttt gggggttct ttctccgcct cctgctcttc gtctgttcta   1020
ccatcgtcga tcacacagca atttgactga ccgcgtctgt ccttccgacc ttgccgtttt   1080
gctttgcagg taacataatc tcgctgatgg tgttcctttc gccgctgtaa gtaactctct   1140
gctttaattt atttaaccta gccgtgaact tttcatattt acgtttacag tatccagtac   1200
catgcataat atactaccaa tatgtttcta tgtatattca gtaaagggaa gcgtccaaaa   1260
tatatactgc catcaggtat gatgagaaca tatatataaa gaacatggca cgcacgcatg   1320
cgtatctcac tgttgaatga atgacgtgcc atcatcgtcc atgctcttct agatccttt   1380
cctttaattt atgcgtggtt ctagatcccc ctatatatat atatatatat atatatatat   1440
atatatatat acgtacacct gaagacaaca tagctagcta ggaaataaac tcgttgggaa   1500
ttgaattgtc gcattaataa cgtcacttta atcagttgcg agccagtacg tgtcactgtt   1560
cggtggttgc gttgcacatg cttttagtat ggaacagcgc acgcaatcta gtaataatta   1620
atctaaaaaa tcacacggta aaaaatattc gttcccgctg atcccgcgca ggccgacgtt   1680
ctaccgcgtg taccgcaaga agtcgacgga ggggttccag tcgacccgt acgtggtgac   1740
gctgttcagc tgcatgctgt ggatcttcta cgcgctgctc aagtccggcg ccgagctgct   1800
ggtgaccatc aacggcgtcg ggtgcgtgat cgaggcggcg tacctggccg cgtacctggt   1860
gtacgcgccc aaggccgcca gggcgctgac ggccaagatg ctgctggggc tcaacgtcgg   1920
cgtcttttgga ctcgccgcgc tcgccaccat ggtggtctcc agccgccgcc tccgcgtgcg   1980
cgtgctcggc tggatctgcg tcagcgtcgc gctcagcgta ttcgccgcgc cgctcagcat   2040
catggcacgt atctaattta atctctctct ctctctctct ctctctctct ctctctctct   2100
ctctgaagag ggatgtgaat tgttggaacc gccattaatt cgctgactgc cctatctaca   2160
tctactttcc tgcagcggca ggtggtccgg accaagagcg tggagttcat gcccatctcg   2220
ctctccttct tcctggtgct gagcgccgtg atctggttcg cgtacggcgc gctgaagagg   2280
gacgtgttcg tggcgttccc caacgtgctg ggcttcgtct tcggcgtcgc gcagatagcg   2340
ctgtacatgg cgtacaggaa caaggagccc gcggcggtga cggtggagga ggcgaagctg   2400
ccggagcacg ccaaggaggt ggtggtggcc gcggcggcgg ccgaggccag ggcgagctgc   2460
ggtgctgagg tgcacccccat cgacatcgac atcgaagcta cgccgacgcc ggtggaggag   2520
gtgcacgagc gcaggtggt cgtggtcgtc gacgtggacg tggagcctgt cacctgcgcc   2580
ggcgccgccg aggcagctgc gggagcaggg gcagatgcgt ccggcgtggc cgacggcggc   2640
```

| | |
|---|---|
| gtccctggac ccatggcgcc gccggagcag ctggcgatca agcccgacat ggccatttcc | 2700 |
| gtggaggcgt aggttggtta aagtgtaata gcagagtgag tcgatatcga tcagtagtag | 2760 |
| atttgtcgag tcaaggaagg ggcctgctgc tgctgctacg cgacagcagc ggccagatgt | 2820 |
| actgcctgca tgcatgcagt ccctcccgtt gactcgaccc gtagaaagg gatgggatgg | 2880 |
| aagtagccgg gtccttgggc gagtagcggc gccttggcac ccacgggcca gccgtactgg | 2940 |
| cctgtgtgat gaaccggcga gagagatgag ataatgtgcg agcgagagag ggttggttgg | 3000 |
| gttgtggtag ttgaagaaga cggctagcta gctgctgctg ctgggctctc tatctgtctc | 3060 |
| tagatctgtg tatgtctgtg taatcgagga ttccctcacc ttgcatgccg cctcccttt | 3120 |
| gtgtccttct agtctgatga ttgttttcat tccatccatg ccggcgtcgc agtaataaaa | 3180 |
| ttttttttgg | 3189 |

<210> SEQ ID NO 6
<211> LENGTH: 801
<212> TYPE: DNA
<213> ORGANISM: Zea mays
<220> FEATURE:
<221> NAME/KEY: misc_feature
<222> LOCATION: (401)..(401)
<223> OTHER INFORMATION: SNP

<400> SEQUENCE: 6

| | |
|---|---|
| wttaytkrtm arcyamrtac kwtctmtgta cgyaygcagc ttccaaacat cctkgggttc | 60 |
| accttcggcg tggtccagat ggtgctctac gtgttgtaca tgaacaagac gccggtggcg | 120 |
| gcgactgccr agggyaagga tgccggcaag ctttcctcag ctgcagacga gcacgtcctc | 180 |
| gtcaacatcr ccaagctcag cccagccctc ccggagagga gctccggggt gyacccagtc | 240 |
| acccagatgg cgggmgttcc ygtyaggagc tgcgctgctg aagcaaccgc gccggckatg | 300 |
| ctgcccaaca gggacgtggt cgacgtcttc gtcasccgac acagcccgc cgtccacgtg | 360 |
| gcatagattc tcgatcgatc gsgtgcatgg cccatgcatg ygcccgcyac acgtacgcta | 420 |
| gmttttatat attcgaagga ckacttgctg ctggtcgtga gcatatatat gatggasraa | 480 |
| atrattaagt agtatatatr taagtaattr actrccatgs atggaagcta gstaatggat | 540 |
| ggaggcagag gycagarcga tgaaggggga agctatacat atatrtgygt aattaatata | 600 |
| gatatatggg mtttgtgtwc wtmtttgcwg ctatgtatta atttgcatgg rtatctgtta | 660 |
| ttccttttta tgtgtaacgt cttctaataa aatgtaattg aaccsacact acyrttgtta | 720 |
| gctaccacaa gtttcscraa aatggcttct rtgtgttcgg gcsggaaagc cctgrcccaa | 780 |
| agttgtcatc cggttcaryc a | 801 |

<210> SEQ ID NO 7
<211> LENGTH: 801
<212> TYPE: DNA
<213> ORGANISM: Zea mays

<400> SEQUENCE: 7

| | |
|---|---|
| gatggtgctc tacgtgttgt acatgaacaa gacgccggtg gcggcgactg ccragggyaa | 60 |
| ggatgccggc aagctttcct cagctgcaga cgagcacgtc ctcgtcaaca tcrccaagct | 120 |
| cagcccagcc ctcccggaga ggagctccgg ggtgyaccca gtcacccaga tggcgggmgt | 180 |
| tccygtyagg agctgcgctg ctgaagcaac cgcgccggck atgctgccca acagggacgt | 240 |
| ggtcgacgtc ttcgtcasccc gacacagccc cgccgtccac gtggcataga ttctcgatcg | 300 |
| atcgsgtgca tggcccatgc atgygcccgc yacacgtacg ctagmtttta tatattcgaa | 360 |

| | |
|---|---|
| ggackacttg ctgctggtcg tgagcatata tatgatggas raaatratta agtagtatat | 420 |
| atrtaagtaa ttractrcca tgsatggaag ctagstaatg gatggaggca gaggycagar | 480 |
| cgatgaaggg ggaagctata catatatrtg ygtaattaat atagatatat gggmtttgtg | 540 |
| twcwtmtttg cwgctatgta ttaatttgca tggrtatctg ttattccttt ttatgtgtaa | 600 |
| cgtcttctaa taaaatgtaa ttgaaccsac actacyrttg ttagctacca caagtttcsc | 660 |
| raaaatggct tctrtgtgtt cgggcsggaa agccctgrcc caaagttgtc atccggttca | 720 |
| rycacactag rtcccrgacr tytataaaag gagccctcaaa ttgctaagyt tcagttttg | 780 |
| actccccacc cctataaatg a | 801 |

<210> SEQ ID NO 8
<211> LENGTH: 801
<212> TYPE: DNA
<213> ORGANISM: Zea mays

<400> SEQUENCE: 8

| | |
|---|---|
| tctgcgtcgg mttctcygtc agtgtcttcg tsgcgccact magcatcatg gtgagcyctg | 60 |
| agcacgcgta taaaactgtg ccaagatgca tggacgacag atygatcarc ccwrtcagtt | 120 |
| ttgatccatg tgtatcrttt ctaatgmrcc gtrtwtatat atgtgtgcag agacgmgtga | 180 |
| tccagacgaa gagcgtggag tacatgcccct tctccctctc cctctcgctc accctcagcg | 240 |
| ccgtcgtctg gttcctctac ggcctcctca tcaaggacaa atacgtcgcg gtaattgttt | 300 |
| catctaatct gctgcarccg ycatggtatt ggtatctctc actkkycwtt aytkrtmarc | 360 |
| yamrtackwt ctmtgtacgy aygcagcttc caaacatcct kgggttcacc ttcggcgtgg | 420 |
| tccagatggt gctctacgtg ttgtacatga acaagacgcc ggtggcggcg actgccragg | 480 |
| gyaaggatgc cggcaagctt tcctcagctg cagacgagca cgtcctcgtc aacatcrcca | 540 |
| agctcagccc agccctcccg gagaggagct ccggggtgya cccagtcacc cagatggcgg | 600 |
| gmgttccygt yaggagctgc gctgctgaag caaccgcgcc ggckatgctg cccaacaggg | 660 |
| acgtggtcga cgtcttcgtc asccgacaca gccccgccgt ccacgtggca tagattctcg | 720 |
| atcgatcgsg tgcatggccc atgcatgygc ccgcyacacg tacgctagmt tttatatatt | 780 |
| cgaaggacka cttgctgctg g | 801 |

<210> SEQ ID NO 9
<211> LENGTH: 801
<212> TYPE: DNA
<213> ORGANISM: Zea mays

<400> SEQUENCE: 9

| | |
|---|---|
| cgggmgttcc ygtyaggagc tgcgctgctg aagcaaccgc gccggckatg ctgcccaaca | 60 |
| gggacgtggt cgacgtcttc gtcasccgac acagccccgc cgtccacgtg gcatagattc | 120 |
| tcgatcgatc gsgtgcatgg cccatgcatg ygcccgcyac acgtacgcta gmttttatat | 180 |
| attcgaagga ckacttgctg ctggtcgtga gcatatatat gatggasraa atrattaagt | 240 |
| agtatatatr taagtaattr actrccatgs atggaagcta gstaatggat ggaggcagag | 300 |
| gycagarcga tgaagggga agctatacat atatrtgygt aattaatata gatatatggg | 360 |
| mtttgtgtwc wtmtttgcwg ctatgtatta atttgcatgg rtatctgtta ttccttttta | 420 |
| tgtgtaacgt cttctaataa aatgtaattg aaccsacact acyrttgtta gctaccacaa | 480 |
| gtttcscraa aatggcttct rtgtgttcgg gcsggaaagc cctgrcccaa agttgtcatc | 540 |

-continued

```
cggttcaryc acactagrtc ccrgacrtyt ataaaaggag cctcaaattg ctaagyttca    600
gtttttgact ccccacccct ataaatgagy gacarcgycc acccaracgc gagtgtggca    660
gcggttaccm gagagcgcga ggcgacgrca gttccccgag agcgaaaggc gacgrcgscc    720
agagactcgc gcgacygcga wgccaagcgc ggyggcggcc tcyagaggca ccayggggcgg   780 ctactcccag atyyggcggc g                                             801
```

<210> SEQ ID NO 10
<211> LENGTH: 501
<212> TYPE: DNA
<213> ORGANISM: Zea mays

<400> SEQUENCE: 10

```
tttcctcagc tgcagacgag cacgtcctcg tcaacatcgc caagctcagc ccagccctcc     60
cggagaggag ctccggggtg cacccagtca cccagatggc gggcgttcct gtcaggagct    120
gcgctgctga agcaaccgcg ccggcgatgc tgcccaacag ggacgtggtc gacgtcttcg    180
tcagccgaca cagccccgcc gtccacgtgg catagattct cgatcgatcg cgtgcatggc    240
ccatgcatgc gcccgccaca cgtacgctag cttttatata ttcgaaggac gacttgctgc    300
tggtcgtgag catatatatg atggagaaaa tgattaagta gtatatatat aagtaattaa    360
ctgccatgca tggaagctag ctaatggatg gaggcagagg ccagaacgat gaaggggggaa   420 gctatacata tatgtgtgta attaatatag atatatgggc tttgtgttca tctttgcagc    480
tatgtattaa tttgcatgga t                                              501
```

<210> SEQ ID NO 11
<211> LENGTH: 801
<212> TYPE: DNA
<213> ORGANISM: Zea mays

<400> SEQUENCE: 11

```
tcgtctggtt cctctacggc ctcctcatca aggacaaata cgtcgcggta attgtttcat     60
ctaatctgct gcarccgyca tggtattggt atctctcact kkycwttayt krtmarcyam    120
rtackwtctm tgtacgyayg cagcttccaa acatcctkgg gttcaccttc ggcgtggtcc    180
agatggtgct ctacgtgttg tacatgaaca agacgccggt ggcggcgact gccragggya    240
aggatgccgg caagctttcc tcagctgcag acgagcacgt cctcgtcaac atcrccaagc    300
tcagcccagc cctcccggag aggagctccg ggtgyaccc agtcacccag atggcgggmg     360
ttccygtyag gagctgcgct gctgaagcaa ccgcgccggc katgctgccc aacagggacg    420
tggtcgacgt cttcgtcasc cgacacagcc ccgccgtcca cgtggcatag attctcgatc    480
gatcgsgtgc atggcccatg catgygcccg cyacacgtac gctagmtttt atatattcga    540
aggackactt gctgctggtc gtgagcatat atatgatgga sraaatratt aagtagtata    600
tatrtaagta attractrcc atgsatggaa gctagstaat ggatggaggc agaggycaga    660
rcgatgaagg gggaagctat acatatatrt gygtaattaa tatagatata tgggmtttgt    720
gtwcwtmttt gcwgctatgt attaatttgc atggrtatct gttattcctt tttatgtgta    780
acgtcttcta ataaaatgta a                                              801
```

<210> SEQ ID NO 12
<211> LENGTH: 801
<212> TYPE: DNA
<213> ORGANISM: Zea mays

<400> SEQUENCE: 12

```
gacgckggca gtgaggaaya gaaggattca ggtrsgtgga atcaaaaact tacacaggcg    60
acaggaagag gaagagcgca atgacattcc ctggggagac agatcyaaca gagattaggc   120
gaggcaagaa gaagaccatc aggtaggcat gmarcagagg caggaatggc atggtgayac   180
tgaccagaaa ctccgaagaa gaacctggcg ataygctcca tctcttccgc ttcgygctta   240
tcgctgtgcg gaaccctcgg ctgtgctgsc ctggaacccg aacggagcag rgggggtagt   300
gastggactg gastcctttc ctccacggtc taggccsgga gcgcacccac acccaacgag   360
cagttagcta gtagctctca agtctgaayr gctgagcsca rcacacagca gccaagccaa   420
cgagcctgtg tacgggcggt gtcttgtgc ctgtgtgtca cccggtgcag cagggaacga    480
gcggtgtggc taatatataa ggagcagagg attgtgatct tgggaggtaa ggggtaggac   540
cggtggagaa gagrrcctgt tcgracggaa gcccatacgt tcttatcttc ttcttagctt   600
gtyagtcaaa gtrtagatgg ccatttggca ctaacacgat gggccggccc aggcayggca   660
cgaaaaagca cggtccaggc acgacccggt ccggttagta tagtgccagt gcctggcacg   720
gcacggctat agtgccgtgc ctgggccact atctcgaccc gtagtgctgg cacgggcacg   780
acacagttac attttttatt t                                             801
```

<210> SEQ ID NO 13
<211> LENGTH: 801
<212> TYPE: DNA
<213> ORGANISM: Zea mays

<400> SEQUENCE: 13

```
gttcctccca gtcccagaca gcaaataagc cttgcccgcc tacacctggc tggcgacctt    60
gccgtcgccg ccgacggcgt ccgcygcstt gttggtcgtg gcrtcggcca gctccacggc   120
agcggccacc ttcttggtgt cctccacctc cgcggcggcg gcggcggcct ctcccttgcc   180
ggccggcgcg gcggggccct tgttttccg gtagatggcg tacaggatga gctgcatcar   240
rcccaggaag ctcccgcacc cgttcggkat ctrcamgcat gcacagacag cgcgggttta   300
gmgacastgg ggstgtrcyg aagtttgsac sgcatgaatc attccgacat gatgagattt   360
gsaraaaaaa aaarctcggc ctwagatatt tcatcgcagt ytgtcgcgtt ggtgtgtact   420
gaagtggagt gcaccgtgca gtttgctary tagcattgcg acaagaaaga gcgcgggcgc   480
tgttgctyct gcctgtgccg ggtccaatcc agctgcatgg acatgggcac ggcggcccat   540
cggcagctag caccggcgtg cgctgcctgt gggtggccac gcccacgctg ctagacgcta   600
ccggcgccca tgcccgtgca tcggcwgcgg cagcggcagg catgtgcgcc tggttgggyt   660
tgggcgggac atcgaaaggg caaccgacgc ccagmccggg ggtactgtgc tggccagaty   720
agatgcagtt acgtccagtc ccaacagcta gtgayacagt rctgctrcag tggtttccga   780
gtgccaawcg gacaacmtgc g                                             801
```

<210> SEQ ID NO 14
<211> LENGTH: 501
<212> TYPE: DNA
<213> ORGANISM: Zea mays

<400> SEQUENCE: 14

```
cttggggtag cctcctggga gagatggaga tgagagtaac aacaaccgta aaagcccaca    60
gaaaccaaca ccaatctgct ccaccgacaa actaaggcag cctcgtttag gatgttcctc   120
ccagtcccag acagcaaata agccttgccc gcctacacct ggctggcgac cttgccgtcg   180
```

```
ccgccgacgg cgtccgctgc cttgttggtc gtggcatcgg ccagctccac ggcagcggcc    240
accttcttgg tgtcctccac ctccgcggcg gcggcggcgg cctctccctt gccggccggc    300
gcggcggggc ccttgttttt ccggtagatg gcgtacagga tgagctgcat caggcccagg    360
aagctcccgc acccgttcgg gatctgcacg catgcacaga cagcgcgggt ttagcgacag    420
tgggggtgtg ctgaagtttg gaccgcatga atcattccga catgatgaga tttgcaaaaa    480
aaaaaaactc ggccttagat a                                              501

<210> SEQ ID NO 15
<211> LENGTH: 501
<212> TYPE: DNA
<213> ORGANISM: Zea mays

<400> SEQUENCE: 15
cctcctggga gagatggaga tgagagtaac aacaaccgta aaagcccaca gaaaccaaca     60
ccaatctgct ccaccgacaa actaaggcag cctcgtttag gatgttcctc ccagtcccag    120
acagcaaata agccttgccc gcctacacct ggctggcgac cttgccgtcg ccgccgacgg    180
cgtccgctgc cttgttggtc gtggcatcgg ccagctccac ggcagcggcc accttcttgg    240
tgtcctccac ctccgcggcg gcggcggcgg cctctccctt gccggccggc gcggcggggc    300
ccttgttttt ccggtagatg gcgtacagga tgagctgcat caggcccagg aagctcccgc    360
acccgttcgg gatctgcacg catgcacaga cagcgcgggt ttagcgacag tgggggtgtg    420
ctgaagtttg gaccgcatga atcattccga catgatgaga tttgcaaaaa aaaaaaactc    480
ggccttagat atttcatcgc a                                              501

<210> SEQ ID NO 16
<211> LENGTH: 501
<212> TYPE: DNA
<213> ORGANISM: Zea mays

<400> SEQUENCE: 16
ccgtaaaagc ccacagaaac caacaccaat ctgctccacc gacaaactaa ggcagcctcg     60
tttaggatgt tcctcccagt cccagacagc aaataagcct tgcccgccta cacctggctg    120
gcgaccttgc cgtcgccgcc gacggcgtcc gctgccttgt tggtcgtggc atcggccagc    180
tccacggcag cggccacctt cttggtgtcc tccacctccg cggcggcggc ggcggcctct    240
cccttgccgg ccggcgcggc ggggcccttg tttttccggt agatggcgta caggatgagc    300
tgcatcaggc ccaggaagct cccgcacccg ttcgggatct gcacgcatgc acagacagcg    360
cgggtttagc gacagtgggg gtgtgctgaa gtttggaccg catgaatcat tccgacatga    420
tgagatttgc aaaaaaaaaa aactcggcct tagatatttc atcgcagtct gtcgcgttgg    480
tgtgtactga agtggagtgc a                                              501

<210> SEQ ID NO 17
<211> LENGTH: 801
<212> TYPE: DNA
<213> ORGANISM: Zea mays

<400> SEQUENCE: 17
atgcaacatt agtttcttga gcagcaatga gagcataatg agctatacta tcaatgtcac     60
gayatcsatg tggcaaaaac aatattactt ctargtctrt cttgagcaat agagtgatta    120
ttgctwacag gaggtayaka agcttaawst gygtgaagat gaaaatcytr tagttgtyaa    180
agtcattatc tamtwtcaag ttsaagyatt rtcttgactt rgtargtgtt ygtggagctt    240
```

```
agcaccctag trgtgtttgg sgaggaaaca attttataga ttaaatcaac attagtttct    300
tgattagtgt aaatatgctt attattatyt tttycttata kttatttgga cygactawak    360
ctagaactgc actcttttga tttgggyatt caagacrggc waaattaagc acacaaagaa    420
tatgttaagt ataaatagat gcatgccctg catgttacag tcttatcatc ttcccgtaga    480
gatctacgac gttgacacgg cgtacgtaga cgactacgya cgtaccgacc aagaccatca    540
caccacyata attattagca tgcattgtca gatccaatgc aaacaamagc tactactact    600
tgattcgaca ctgaastgaa ctgaactgac aagactacgc acacgagaga gacacgcaat    660
aataatccaa caattaacca actaaacgay caactagcag acgacgatgc ctgcatctgc    720
atgcttgagc tgccagccac ttgccaccaa actgtcgtac gtcrtccgag ctrgctaatr    780
agaagctagc agggtgtgta c                                              801

<210> SEQ ID NO 18
<211> LENGTH: 801
<212> TYPE: DNA
<213> ORGANISM: Zea mays

<400> SEQUENCE: 18
tawygttaac tygtrataay tgtraacttg ttataytrga atattttat attwrtatgr      60 ttayygatcg tatttaaaat tmtgmtcrtt aymtgtgyat tttcygtmcc gaacytccaa    120
tattratact gtttccgttt ctaaagttac catwttttat ktmatttccg atataarata    180 traaacrga cacaracaca gttggagcyg tgsaaccrak csgaccwcaa atctacrata    240
ctgcaaagca tgcgagggc ctggtttgtg ttycctagaa gargattgsc tgmactttta    300
cactactaaa acaagcttcy ctygataatc aaakgtatgg attttcacca tttcttcatt    360
rtattgacaa caycettcte tggcmaaact aycgtgctaa yaatctaaca tcttsgaagc    420
ttataccaaa graagaaaca atccatgrag gtcacaagtt tamatrartt ttcaaacaat    480
aaaaattggt aacctsttsc atgcatgcat gcwggtaggt accgttggtc tkggaagttt    540
tygacagcaa gagacttcta tgctatactc cagcgcgcgc actgawygaa gctcatcatc    600
agacatggct agaygcttct cccyggtcgg aggccakaag aggcgaggac gctgtttcyt    660
tgctgcattg ggaggccttg ctgttcatgt agatcgcgta gacgatcagc tggatggtgc    720
caagcacgaa gcctatccca ttggggatct gcaygcagag agcgatcgag aggttctgtt    780
tagtatgggt agcggaaaag a                                              801

<210> SEQ ID NO 19
<211> LENGTH: 501
<212> TYPE: DNA
<213> ORGANISM: Zea mays

<400> SEQUENCE: 19
atcccatccc ttctctacgg gtcgagtcaa cgggagggac tgcatgcatg caggcagtac     60
atctggccgc tgctgtcgcg tagcagcagc agcaggcccc ttccttgact cgacaaatct    120
actactgatc gatatcgact cactctgcta ttacacttta accaacctac gcctccacgg    180
aaatggccat gtcgggcttg atcgccagct gctccggcgg cgccatgggt ccagggacgc    240
cgccgtcggc cacgccggac gcatctgccc ctgctcccgc agctgcctcg gcggcgccgg    300
cgcaggtgac aggctccacg tccacgtcga cgaccacgac cacctgcggc tcgtgcacct    360
cctccaccgg cgtcggcgta gcttcgatgt cgatgtcgat ggggtgcacc tcagcaccgc    420
```

```
agctcgccct ggcctcggcc gccgccgcgg ccaccaccac ctccttggcg tgctccggca        480
gcttcgcctc ctccaccgtc a                                                  501

<210> SEQ ID NO 20
<211> LENGTH: 6509
<212> TYPE: DNA
<213> ORGANISM: Zea mays

<400> SEQUENCE: 20
agctgacgga tggctactgg tcgcagatgt gtgctaggct aggcgtaccc ttaatcggtg         60
ccctggacac tgtctgtgtg atcgttatcc tctccaatgc aaaagacaca ggcgtggtgg        120
tgtgggtcgt tgtttctctt gagaggtact agtaggttgg cgagtcgaac tgtccccggg        180
tccaggcaaa cgcgtgtgta ggagggctac taggagcaga ggcacggccg cgacagggca        240
gggcaccgca ttccttgtgg aacgcatatg ttctgtgggc atgcattcga ccgggcacag        300
atgcgtcacc gtgtccgacc acttttgcca aaggcgagag cgctcgctgg gcacgggatg        360
gctggcaggg atacgcatat gcacgctacg cctacgcagg agatggcgga tgcaaaggcg        420
acaagtgacc tctttcctgc gccgcacgct cacatgcatg cctggcctga gccctgaggc        480
ctgagcatca ctagcccttc accgtcccag acggccagac cagtgcgccg ccgctctcgt        540
tgtcgttgag ctccccctcc aactcccaag cgatagggtg gagtggaacg cgagagcctg        600
cactgttgtc gacgcatcga cactccaggt ccggattgca gtggcgtgcg gtgcacacct        660
tgttgccgac ttgccgggag cgttgaggac ccggacggat cgggggagga cacgcgcaga        720
cgcgccgccc gccgccgcgc tgctgcgtac gcatacgctg cgaccaggac caggggactg        780
gatcggcaag caaaacgctg ggacgtgacg gccgtgaatt gcgccggcgg cgactctcgt        840
cgtcgtcgcc ttcctcgctg actgcctcca gccacgcggc tcctccactc cgttgccacc        900
gccgccgagg cgccggacgc tacaacgttc cacggcgcca ccgatcgtat gcctgcgtaa        960
cgaggatcct cccgtgatcg gtacgtctcg tacgtgctcg gcaggatctg tggaaagcca       1020
tttcgtcagc ggtcagtttg tgccggccat gggatctgtt tgtcccgtga ggcactgagg       1080
cctggtaggg aactagggaa gtggtactgg gtagccacat gcatggcggg cccgcaggcc       1140
tcggcacagc agagacgcga attctgctgc tcagcagctt cgcaagattt ccgttccgtt       1200
gcgtgtgcca agccaccagt gcatcaggat tcaggactcc gactcatgca tgatcggagc       1260
aaacgagtgc tgcagagaca cgtacgcata atgcatgctt gtacacgtcg ccgtacgtac       1320
gcccgcccgt accggaagaa agctgtgtgt agcttgcctg tcttaacgta cgtatttacc       1380
acaggcgcgg gcgcgcggca atggcagttt tcaggcactt tgacttatag atggccaaac       1440
gggccggcac ggcccgaccc ggcacggccc gacggcggca cggcccgcca ggcccggcta       1500
gtgaaccgtg ccgtgtccag atgggccggt ccaggcacgg cccgtgagtc tgttagtcgt       1560
gccgggccgg cccggtggca ctatggccca tctgagtata ttgtagaatt tagcaaaaaa       1620
tgtgtagttg tgagggttcg aactcacaac ctagtgagca agagacttaa acgcatccat       1680
ctaaccagtg caactgcagt tttattgtgt tatatgttga attcttatac ttaatatatg       1740
taaactatta ttttttaaaat aaaaaatgta actgtgtcgt gccgtgcca gcactacggg       1800 tcgagatagt ggcccaggca cggcactata gccgtgccgt gccaggcact ggcactatac       1860
taaccggacc gggtcgtgcc tggaccgtgc ttttcgtgc cgtgcctggg ccggcccatc       1920
gtgttagtgc caaatggcca tctatacttt gactaacaag ctaagaagaa gataagaacg       1980
tatgggcttc cgtccgaaca ggctctcttc tccaccggtc ctaccccttt cctcccaaga       2040
```

| | |
|---|---|
| tcacaatcct ctgctcctta tatattagcc acaccgctcg ttccctgctg caccgggtga | 2100 |
| cacacaggca caaagacacc gcccgtacac aggctcgttg gcttggctgc tgtgtgttgc | 2160 |
| gctcagccat tcagacttga gagctactag ctaactgctc gttgggtgtg ggtgcgctcc | 2220 |
| cggcctagac cgtggaggaa aggagtccag tccactcact accccctctg ctccgttcgg | 2280 |
| gttccaggcc agcacagccg agggttccgc acagcgataa gcgcgaagcg gaagagatgg | 2340 |
| agcatatcgc caggttcttc ttcggagttt ctggtcagta tcaccatgcc attcctgcct | 2400 |
| ctgctgcatg cctacctgat ggtcttcttc ttgcctcgcc taatctctgt tagatctgtc | 2460 |
| tccccaggga atgtcattgc gctcttcctc ttcctgtcgc ctgtgtaagt ttttgattcc | 2520 |
| acgtacctga atccttctgt tcctcactgc ccgcgtccat gctttaaaaa aaaaatcgaa | 2580 |
| aacagagaag caatgatata gtacttactt ctactatatg acaaagacta gaacatgggg | 2640 |
| agaatcagtg tggagagaaa ggctatagca tcttttaggt tcaatccttt ccagcgaaac | 2700 |
| actgaaattt catacatata taatttttt ctaaaaaaag caagtagctt ttccccatcc | 2760 |
| gaaatgcttc ttcttcccaa ccacgccgca cctttttct tgcgtcttgc ctcagcagcc | 2820 |
| ttcaggggca gcagcgcagt gcgtgtgttc ctctgacggg tgagaaatct ctttgcagtg | 2880 |
| tcaccttctg gagggtcatc aggaagcggt cgacggagga cttctccggc gtgccctaca | 2940 |
| acatgacgct gctcaactgc ctcctatcgg cttggtaacg aaccgctctc tctctctctc | 3000 |
| tctccctgag agacacggcc ttttgatgag cactccacac catttctgtt tctgtctctt | 3060 |
| cagaaaatta aatcgcatcg cagatttatg gagtggccgt aaagcagtaa aaccggcgtg | 3120 |
| gtggtgtagt ttgttttact tagatttcgg aaatgctgca tggtttgctg gcctgggtga | 3180 |
| agcaaacgct tggctcctag cgtagcctct gcccaacccg gcctgtcctg tagatagagt | 3240 |
| actcccgtg gacccactcg ctagacgcta gcactgtaag tctgtgacaa cgactgcaat | 3300 |
| gaaggggaa aagcttattg cactgcacca ctgcccgtgg gagcagagcc tacctgttgg | 3360 |
| cattgccagg acgagatga cgacctgtgg gcctcgcggc ccttgagccc gcacatgcag | 3420 |
| cgtcacgttc aagtgttcgt acctccaaac aaaaaaagtc ttgacgcttt ttttttcttt | 3480 |
| tttggttatt atgatgacgg acgattctgg tcagggcatc cacataaata tcttaaaagg | 3540 |
| tattaacgac gtaagtgcaa aaaaaaagac agtctctagc actaccacgg ttttatccat | 3600 |
| acaactcacg tacatgaatc atatcatgag atccttctagt ggaataagat ataaaactta | 3660 |
| aatatattgg gctatatgaa agagtttttt agatgtattt agtgcttaaa gaactgaaac | 3720 |
| gtagtatcta gattgtacat gtctttatga ctatatggat gagttggtgt cccgtttgat | 3780 |
| ttttcacgcg ccttttgaatc catgtgaaga tcgatgtgct agctagctag ctcgctcttc | 3840 |
| atgcgttcgt ctggatttg tttgaaattc acgcagcata tatgtgtgga atataatctg | 3900 |
| tatgcacata caggtacggc ctgccgttcg tgtccccgaa caacatcctg gtgtcgacga | 3960 |
| tcaacgggac ggggtcggtg atcgaggcca tctacgtggt gatcttcctc atcttcgcgg | 4020 |
| tggaccggcg ggccaggctc agcatgctgg gcctcctggg catcgtcgcc tccatcttca | 4080 |
| ccaccgtggt gctcgtctcg ctgctggccc tccacggcaa cgcccgcaag gtcttctgcg | 4140 |
| gcctcgccgc caccatcttc tccatctgca tgtacgcctc gccgctctcc atcatggtac | 4200 |
| gtgagcgatg atgattggtt gttgctgcct tgctgggtag ctagctccag cgggtcccct | 4260 |
| tctgggcgtg tacgtgcgtc cttgctgtca acgtacggca tcagttaaca agctaagcgt | 4320 |
| gtgcttggtg tgtgcagagg ctggtgatca agacgaagag cgtggagttc atgccgttcc | 4380 |
| tgctctccct ggccgtgttc ctgtgcggca cctcctggtt catctacggc ctcctcggcc | 4440 |

```
gcgacccctt cattattgta cgcacacggt tctctctcta gtctagatcc tgagccgcac    4500
tcaccgcccg gccgtacgca cgtgctatcc gcgcatgttg tccgattggc actcggaaac    4560
cactgtagca gcactgtatc actagctgtt gggactggac gtaactgcat ctgatctggc    4620
cagcacagta cccccgggct gggcgtcggt tgcccttcg atgtcccgcc caagcccaac     4680
caggcgcaca tgcctgccgc tgccgcagcc gatgcacggg catgggcgcc ggtagcgtct    4740
agcagcgtgg gcgtggccac ccacaggcag cgcacgccgg tgctagctgc cgatgggccg    4800
ccgtgcccat gtccatgcag ctggattgga cccggcacag gcagaagcaa cagcgcccgc    4860
gctctttctt gtcgcaatgc tagttagcaa actgcacggt gcactccact tcagtacaca    4920
ccaacgcgac agactgcgat gaaatatcta aggccgagtt tttttttttt gcaaatctca    4980
tcatgtcgga atgattcatg cggtccaaac ttcagcacac ccccactgtc gctaaacccg    5040
cgctgtctgt gcatgcgtgc agatcccgaa cgggtgcggg agcttcctgg gcctgatgca    5100
gctcatcctg tacgccatct accgaaaaaa caagggcccc gccgcgccgg ccggcaaggg    5160
agaggccgcc gccgccgccg cggaggtgga ggacaccaag aaggtggccg ctgccgtgga    5220
gctggccgat gccacgacca acaaggcagc ggacgccgtc ggcggcgacg gcaaggtcgc    5280
cagccaggtg taggcgggca aggcttattt gctgtctggg actgggagga acatcctaaa    5340
cgaggctgcc ttagtttgtc ggtggagcag attggtgttg gtttctgtgg gcttttacgg    5400
ttgttgttac tctcatctcc atctctccca ggaggctacc ccaagcatgt agtagcttcc    5460
attctgattc tgggacggtg ttgcacgtta cagtgctctc aagctgtctc tgcaaagtgt    5520
gtttttttat tccatttccc tcctgctctt gttctccaac tgcgcttacc tgccccgat    5580 ttctctaaaa aatgtattaa actatctgag aaattcatcc aactgcgagt actgtgctgt    5640
gcgtgagcaa tgcatctttt gcgtgtacgg tgtgtgtgac acgctgaacc ctgacttatc    5700
acaacaattc tagagtgtgc tctatagcgg cattggagaa attctaagcc taacaataat    5760
tcgtctccct tgtctagcat ggtagactgt tcctggataa atattcatgg atgcaaagcg    5820
gtttgtctag gtgcccgtca atagactatt ttgtgtggcc aattagtttg tttacaggtt    5880
cgtcgtagat aacccaactc acttgtatcc ttgtaaggtc ctgttcggtt tgtacggaat    5940
gatatgctag atatattcct agtcggatcg cttctctagt tcatataaac tttgatttgt    6000
tgaaacgatt tcgagtataa attctaaaca aacgaataaa gcctaaatat ttattcgaat    6060
agagtgaatc tatttcctta accggccaca agttatatcg gtacctcaag attagggtat    6120
ccactcctgc taggttaaaa caggacccg tggctatcct tagtcgcata gtcacatatg     6180
gtctgcccta gctcacagtc taggcccgtc cgacgaggcc gctggcctca ggtggggcc     6240 agcttccacg tgagctctcc ggatccctgg caatggggct ctgtagccgc cacgtgccct    6300
gagaataggg actctttgac atccggggc ggaccctgtg ggacggactc ggacaaccgc     6360
atgtgtcatc cgaacctccg acctaaagag gtctggtgct gctacatgtc tgagacagtg    6420
tcatagggac ccggactccc ctgagcacct tccagacccc tgctaaggtg gttcggagcc    6480
gccatgtgta catgcacttc tagttgttg                                      6509
```

<210> SEQ ID NO 21
<211> LENGTH: 6911
<212> TYPE: DNA
<213> ORGANISM: Zea mays
<220> FEATURE:
<221> NAME/KEY: misc_feature
<222> LOCATION: (6024)..(6123)
<223> OTHER INFORMATION: n is a, c, g, or t

<400> SEQUENCE: 21

```
ccctaggctt ttctccagct ccttcattga atttggctct cctacgtttg ttgcatgatt      60
ccatctctct ccacaggtct ataaaacagt acacttttgt ttttttaac acgatggcac      120
catctgaatc ttcaacctaa tttcgtcctc tccccaccaa actgtacaca acatgcacgt     180
gctgttcatc cttcaagtcg tgggtacctt cttcggcgct agctgcatgc gaactctcta     240
ggcttttctc aagctctttt atttattta ctactataaa gcactcagtt tttaccgtcg      300
tgaaacatgt agttggtgtg tctactcact ctccccaata taataggccg cccaagtat      360
cccacgtgtc acacctccct cttcctctcg ggccccgcag ccaccatcct ttgtctaagg     420
gtttgtccat gaactagacc tttaattatt caagaaaaaa aagaaaagaa gctagttatt     480
cgggaaaaaa ataaaaaaac atttcacata tatatatgta tctcttatac ttattaatgt     540
taattaatat acgttacaat tttattaaat gtagttgata ttgaaggaag ttgtagcatg     600
tttgaaggca cattgagcac taatatttta tcgagtaact gtgtgccgtc ataacacacg     660
ggcactgtat tagtctctac cctttaaatt aagcacaagt ttcatgcgtc atgcgtgcgt     720
tgtacgtcac gtgtaaagcg catagagtag atatgttttt ctcccccgcg tcttgcctaa     780
aaacgaggtt gttatgtcct agctaaatag gacgtgagac acccaaatcc aacacgacac     840
gaagcccaca cacaacataa cgttccggaa tagtatcacc tcgctagcta aaggagaacg     900
agcaactgag tggactataa aaagggact gatcttcttt tcaactaaga tgtttctcat      960
ctttttggct aagataaagt gcaattctac agtttaatat ctgataagtg ggccatatac     1020
ccaccttaa ttttttttgg tgaggtttca cttttatttt aaatttatt ttgtggggag       1080
ggtttaacat caaatacaca cagttttcat taaattgcta gctagttctg ctctccggcg     1140
tttggtgcat tattaagcat gcattattac atctttctcc acgggtctat gtctttctac     1200
aaataaacca cacacacagc caaagttgaa gtaatcctgt ctacttgcga ttggcaggtg     1260
aaaaaaagac acggcacttt atatagccca cttttcacac gcgtcaaatg ccagaaaaaa     1320
gtcctttgag tgcagtgtac atatattatt tttgtttcgg aaaaataaat tattgagctt     1380
gtagttagtt agcagcgcat ttgttgcgta ccaagatctt tgtaggaggt tatatatata     1440
tatatgcata tttcagcaaa ccaatcatgt atatatacaa caactatagc tgtaacacac     1500
tttctgctac ttgtgagaca agtgaaaaac ccatatatac accgtacact tgtttaatt     1560
ttgacatatt tcagacgtta aaaaatatat tatgtatgga ctagtgccat ctcttattaa     1620
tcttaattac catggcatac agtcatctat atattctgag agtggagaaa tatataggag     1680
agaggggcag agaaataaaa gaggtagctt tattagcata tgcacaaatg acttcccctc     1740
gaaatctact gcaaggaaag tgcagattag atacacccat tgtattgtat gccactgtgc     1800
gatcgacctg catgctgtgc tggttggtac acgcatgcat gcatgcatgt accactgcac     1860
accatgcatt attctcttct ctcgccaaca atgccgaact ggacagcacc actgcaatca     1920
acaggccgcg gcctcccaga acggcagaaa gggcagcgcg gccggctata taaatccatg     1980
cccgtgctcg ggtccaaacc acacacaaac acatcagcat tcagcaatag ctaatcgagc     2040
atcgtcgcct tagctcctct cctctcctct cgtcgtcgt ggaacttctc tccgccggct      2100
gtcatatata taaggagaa gaagagaaca gcaactctag ctagccggcc ggcctccgtc      2160
gtcgccggcg tcgtcgacta gctagctaac tctcgatctc cagttcctgc ccccgcgccc     2220
cacgcccggc cgtcgtcgtc agcaatggca ggaggcttct tctccatggc tcacccggcc     2280
gtcacccctct ccggcatcgc aggtacgtac gcgccaatga aacaacaacg tcgtctcgag    2340
```

```
ctagatcgat ccatgcatga cgccggccgg gaccggccgg atagataggc ggagatcgac    2400
ttgcataatg cttcgcgtgt ttggccttt  cctggtgctt cttttttttt ttaaaaaaaa    2460
tcttatggga ccttgatgac atgcttttca tgtggttttc attcattctg ttgccgtact    2520
acgttcttct agattttgtt tattccgaca tgacgactgt cttgtccatc cttgtatcat    2580
cgatccgtcc tttgcatgca tgcatccacc agtcgtcagc cttcctttt  gccgtttgtg    2640 ccattgcact gtagagcacg cacgcactct ctagctgtag agaggcgcgg cagtaggcat    2700
gcatgcagca gctagtcaca ctggacaacc aactgtcttg tccatcatct atcaacaata    2760
cttgcatatc agaatacgta gtatgtagct ttagcatttt ttttttcttca cctatactac    2820 tgctagctgc atcttcttga actttctctg atgctcccg  cggcccattg agacgacgat    2880
gcactctttc tccaattcgt tagctgcgat catggcacag gcctttaatt tgttgctagc    2940
tagaacacac atgcatgcat cgccgaggta tagcaacttt tccactcaag aataatggta    3000
ataagcagtg cagatcagat ccacatattg ggcattagat cacgaaatac agttgcaaat    3060
agctgctcac aacgtaacgc actatctaag aatcatttct atatacgtgt attttttgct    3120
ggaatggtta tgatcgatcg gttgggcatg cagcagggaa ggcgtgtgcg tgtgcatgca    3180
gctacctagc ttttttgccat atcagcgttt ccttaaccta atcaccacgc ttctctctgt    3240
tagtggacgc acacgcattg tacatatata tgtgtatagt attgtactcc taccactttt    3300
actgaaaatg acgacactga cgcgtagtta ccctcttctc tcttgtttct tcgatttgga    3360
ttgtgcagga aacatcatct ccttcctggt gttccttgca ccagtgtaag tagctagcta    3420
tagccacctt tcttcgttcc cttactgtct caatttcaga ccgactcgga ttcatgcgtg    3480
aatcgatgga tgatccaaga ctgacatggc atgcctcttg tacgcaccgt accaaaaaca    3540
gggcgacgtt cctgcaggtg taccggaaga agtcgacggg cgggttcagc tcggtgccgt    3600
acgtggtggc gctcttcagc tcggtgctgt ggatcttcta cgcgctggtg aagaccaact    3660
cgaggccgct gctgaccatc aacgccttcg gctgcggcgt ggaggcggcc tacatagtcc    3720
tctacctggc gtacgcgccg cggcgggcgc gcctgcggac tctggcctac ttcttcctgc    3780
tggacgtggc ggccttcgcg ctcgtcgtcg ccgtcacgct cttcgccgtc cgcgagcccc    3840
accgcgtcaa gttcctcggc agcgtctgcc tcgccttctc catggccgtc ttcgtcgcgc    3900
cgctcagcat catcgtcaag gtggtcaaga ccaagagcgt cgagttcctg cccatcagcc    3960
tctccttctg cctcacgctc agcgccgtcg cctggttctg ctacggcctc ttcaccaagg    4020
acccctttgt catggtaacg actgatcaat aatgtaatat atggttaact gatccatata    4080
tatatataaa atggtaactg aataatgctg gggatgtttc tcgattatat atatctattc    4140
agtaccccaa cgtcggcggc ttcttcttca gctgcgtcca gatgggcctc tacttctggt    4200
accgcaagcc ccgccggcg  gccaagaaca acgccgtgct gccgacgacc acggacggcg    4260
ccaacgcggt gcaggtgcag gggcaggtca tcgagctggc gcccaacacg gtggccatcc    4320
tgtcggtgag ccccatcccc atcgtgggcg tgcacaagat cgaggtggtg gagcagcagc    4380
acaaggaggc cgccgtggcc gccgagaccc gccggatggc cgccgcaaac ccggacggcg    4440
ccatgccgga ggtcatcgag atcgtccccg ccgccgccgc ggtgtgaccc aacgccaatc    4500
accatgcacc gtacacaccc tgctagcttc ttattagcta gctcggatga cgtacgacag    4560
tttggtggca agtggctggc agctcaagca tgcagatgca ggcatcgtcg tctgctagtt    4620
gatcgtttag ttggttaatt gttggattat tattgcgtgt ctctctcgtg tgcgtagtct    4680
tgtcagttca gttcagttca gtgtcgaatc aagtagtagt agctgttgtt tgcattggat    4740
```

```
ctgacaatgc atgctaataa ttatggtggt gtgatggtct tggtcggtac gtgcgtagtc    4800
gtctacgtac gccgtgtcaa cgtcgtagat ctctacggga agatgataag actgtaacat    4860
gcagggcatg catctattta tacttaacat attctttgtg tgcttaattt tgcctgtctt    4920
gaatacccaa atcaaaagag tgcagttcta gatttagtcg gtccaaataa atataagaaa    4980
aagataataa taagcatatt tacactaatc aagaaactaa tgttgattta atctataaaa    5040
ttgtttcctc cccaaacact actagggtgc taagctccac gaacacctac caagtcaaga    5100
caatgcttca acttgatatt agataatgac tttaacaact acaagatttt catcttcaca    5160
cacattaagc ttatgtacct cctgtaagca ataatcactc tattgctcaa gatagactta    5220
gaagtaatat tgttttgcc acatggatgt cgtgacattg atagtatagc tcattatgct    5280
ctcattgctg ctcaagaaac taatgttgca tttgaacctt cttcttattc ggaagccatc    5340
ttaaaagtcg tctagagggg ggtgaatagg caaaacctga aaattataat ctttgaacac    5400
acactttacc cggggttagg gttagaaata aataatgttg aattcggagt gtggaagata    5460
attcttcttg ctattagttg ctcaattaat gcagataaat ttaggagcca actcaaaaca    5520
atatgagcaa gggaacttta gagagaggag aggggagaaa caaattgagt gatgaagatc    5580
aacacaaatg aacacagtga tttgtttccc gaggtttggt tccaagaaac ctactccccg    5640
ttgaggaggc cacaaaggcc gggtatattt caacccttc cctctctcaa tcgatcactt    5700
agaccggtcg agtgcttctt cttaatcaca cgggtcaata agaccccgca gaatcacca    5760
cacaattagg tgtctcttgc taactttaca aagcacttgg aaagattaga gtgagaagaa    5820
gaaagcaacc aatcaacaag agcaacaaaa gaaacacaaa tcaccctctc tcaagtcact    5880
aaacactttt gatcacttga cttgattttg gagcgtggag aggatttgat gttttcattg    5940
tgtatttgga ttgtattctt tgctctagta ttgaatgagt aggttggaaa gcttggatgg    6000
cttgaatggt ggtggttggg gatnnnnnnn nnnnnnnnnn nnnnnnnnnn nnnnnnnnnn    6060
nnnnnnnnnn nnnnnnnnnn nnnnnnnnnn nnnnnnnnnn nnnnnnnnnn nnnnnnnnnn    6120
nnnggcctct tttgcgaggc gcgagatgaa gcggctcaga gccgcaaggc atcccgtgac    6180
tctatgtacg cctttcaagt ccttaacggg ccccatgctg atgatggccg cgatcttctc    6240
tgggttggcc tcgttgcccc gctcggagac gatgaacccc aagagcatgc ctcggggaac    6300
cccgaagaca cacttctcgg gattaagctt cacgcctttc gccttgagac atcggaatgt    6360
cacttcaagg tcggaaagga ggtcggaggc tttcctcgtc ttgactatga tgtcatcgac    6420
gtaggcctcg accgtccggc caatgtgttc gccgaacaca tggttcatgc accgttggta    6480
tgtcgcaccc gcattcctca agccgaacgg catggtgaca tagcagtaca tgccgaaggg    6540
tgtgatgacc aaccactatt ccagccgttg ctgtcgatgg gcacaccaga cagtccggtg    6600
gtgcactgca cactgcacta ttcattgtcc ggtgagtgcc acatcagccg accattgggg    6660
tttggagttg ttgaccgttg aattcttctg tcttcttgtg gcaccggaca gtccggtgcg    6720
atctgacatc ttctgacttc tgacggtcat actattttgc aggcgaccgt tggtgaagtt    6780
gaccattgct gtgttgtctc accggacagt ttggtggcac accggacagt ctgataaatt    6840
ttagtggacg actgctgaga aaacccgaga gcagccagtt cgcgaggtgc tcagccacgg    6900
caacggacag t                                                        6911
```

<210> SEQ ID NO 22
<211> LENGTH: 6656
<212> TYPE: DNA
<213> ORGANISM: Zea mays

<400> SEQUENCE: 22

```
cctatatag tcgactggag agttatacct gtaaatttca tcgagcttat ctaaatctac    60
tttctattgc tatgagtatg cctgtttttc cggtgcttgg ttggcttctc tggtttatca   120
tccgagttat caagtaccta gccgcgtgag aaacgtgtct tcagaaattt ggtaattctt   180
atgcgatata cgtgcacgga tggtatgttg gtgcagtgtt cttcgagatc tcctcgtatc   240
cagtgctccg ttgctgcatt tgactttat ttcgtcagga cgaggcccat cagtacgccc    300
caccggacgt cttattaggg tcctctccca tggcccaagg agtacattta tgccttggcg   360
acccatagga tatctatctc ccacaaaata tatagaacta aaatagggt ttaaggttga    420
gctcaagaat gaatgtcctt tttaaaataa cattatatcg aactacttcg aatcacgact   480
ttcttgataa tgtattatgt tcattggaga aatgtggct ctatatacgc attgtgggca    540
ttatggtcca aagaaaaaa gagagagaaa caacaatttc tatacatcaa gcttgcaagt    600
gatcgtggaa aagggaaact atatagcaaa ggcacataag aatcttctat agcaaagaca   660
cacaataatc tttccatgag tttaatacac catgattata taattata aagatagata     720
gatatattgc aatgatataa caaagcttcg gtttctaatg tgctcattgt agggttaggg   780
agtcacttct atggcgatgg tgcagggtcg atgggagaag tggtggcgcg aggagggccc   840
ttgcatgtat gctcgacatg ggaaatggtg gtgtggggag agggctcgac gagctcacca   900
agaaggtgc tagaagaaga gaagaagaag ggcataacga aggctgaagt tatattgggc    960
acttatcgat tcttgcaaag aaccagtact aaagacctct gaccaagaac tggaaagggg  1020
ccattaatac cagttcttac aaagaaccaa tgctaaagac cttcaggatg gaattgaaaa  1080
agaacctta gtaccgttcg tgtaagaacc aatactaaag agttctttag agagatggca   1140
aactaaacta cgagcgttca ttagagcgat ggtagacaaa acaaagcaag ttacaatctc  1200
tacttgaagc ttattacact aagctcctct ttgttcctaa cgccagctcg gggagcgagg  1260
gttggaggtt ataaagcagg tacattaaca ctagttgaaa acaccaatcg ataataatgt  1320
tatgtcatca aattccagtt aaaaacacca atcggtacta atagaattat attagtacca  1380
attggtgtcg tcaaccgata gtgataagtt aatattagtt ccggttagag acattaatca  1440
gtattaatgc cctagctcta cgaggacgca ttagttaaaa ccggtgctga cgaattgagt  1500
gagtaccgat tttaatgcaa taataggtac taatttgatt taatttactt tagtgcacaa  1560
caatttgtat agtgtacaaa agttcctta ccagagacgg cccttaccac agagtccaaa   1620
gcaggtcgga gatcgagaac cccacgcggt gcacaacaat ttgtagtgta cgactctggc  1680
actgaccgat gtataattga ctaaaaagca tgcacgcaaa gcagctcccg cttttttcga  1740
aaatgtagaa gattatctca atcaattaat gtaacaattt atacactctg gttatatata  1800
tacatggcca gaaaaaatg tcatctatta taaagctgct atatatatac atgcattgaa   1860
aaggatcttt gcgtctatat ataatttcac aaaaaaaagt gttaatatca tatgtgtgtg  1920
attgaagagc cctgagcttg cttgtacacg atgcacaaac acatgtacac caaatcatgc  1980
gtgcatgtgc cacctcgcgt gcctatataa agccacccac agccctgcct atcattgcaa   2040
gagtttgagc caacacacac agagagagga caactcctca caactctccc ttccctcctg  2100
taggggccaa aagggttaga gagtaggaga agtagttccc tagcccaaca caagaaaaac  2160
aagctcgatc tcctcatcac cctaatccaa gcaactgctt tgtgtgttgg gaaattcttg  2220
tgaccctgt tatattatta tccgtgtagc tactagcttc attccccct ttgtacccat    2280
caaatggctg gcatgtctct gcaacacccc tgggcgtttg ctttcggtct actaggtaca  2340
```

```
tactacacct tcactaatag ctaaacaagc gcccgccgca aagctatgaa ttaagggcag    2400
gcatgtttgg tttgctacct attttaccat actttgtcta actttctgt ctaaggttat     2460 agttcttcaa ttcgaacgat taatcttagc caaagtgtga catggttagc cacgaactaa    2520
gcaggccctt aattattgcg catgtatata ttatatattt atctttctat tctgtttaat    2580
ttgttttctc tttacatata tatactacta tgtaagtata tattatatgc acaacaagca    2640
ggcctcctcc gtgcacatat gcatagaatc aatctatacc cttcatagaa gccactttga    2700
gatataccct ccaaaacaat cccaaaaaca agacgctcga tcttgcgctc acaatcactt    2760
agttttgcac cagattaagc atgcaccact agattttatg tactgtatta cctctgccat    2820
ccatggtcga tcctttagtt tatcctattc atttccgtca tgaactacct gtcgagctag    2880
caatcggtcc tttatttaga gtgttcagat aggcatctgt ctttatacaa acaataaagc    2940
ctcacgaatc tttagtcaca aaacaaggca aattagacag gccacggagg tgtaaagtgt    3000
cagctctgct tatcaaact tatctctgct ttatttgggc acacttttgc catacaaatg     3060
gctgatcttg gcgccttttt tttctccttg ctttgcaggt aacgtcatct ccttcatgac    3120
cttcctggcc ccgatgtaag tgacatatat atatatatat attgcttaat taattatcac    3180
tgcttcttca gatatatatt catcggttat tttaattaat tatgtggata tgtatgcatc    3240
gtataacaga ccgacgttct accgcatcta caagagcaag tcgacggaag gcttccagtc    3300
ggttccctac gtggttgccc tgttcagcgc catgctgtgg atcttctacg cactgatcaa    3360
gtccaacgag accttcctca tcaccatcaa cgccgccggc tgcgtcatcg agaccatcta    3420
cgtcgtcatg tacttcgtct acgcgcccaa gaaagccaag ctgttcacgg ccaagatcat    3480
ggtcctcctc aatggcggcg tctttggggt catcctcctg ctcacccttc tcctcttcaa    3540
gggcagtaag cgcgttgtgc tgcttggctg gatctgcgtc ggcttctccg tcagtgtctt    3600
cgtcgcgcca ctcagcatca tggtgagccc tgagcacgcg tataaaactg tgccaagatg    3660
catggacgac agatcgatca acccaatcag ttttgatcca tgtgtatcgt ttctaatgca    3720
ccgtgtttat atatgtgtgc agagacgagt gatccagacg aagagcgtgg agtacatgcc    3780
cttctccctc tccctctcgc tcacccctcag cgccgtcgtc tggttcctct acggcctcct   3840
catcaaggac aaatacgtcg cggtaattgt ttcatctaat ctgctgcaac cgccatggta    3900
ttggtatctc tcactggtct ttactgataa actacatacg atctctgtac gtatgcagct    3960
tccaaacatc ctggggttca ccttcggcgt ggtccagatg gtgctctacg tgttgtacat    4020
gaacaagacg ccggtggcgg cgactgccga gggcaaggat gccggcaagc tttcctcagc    4080
tgcagacgag cacgtcctcg tcaacatcgc caagctcagc ccagccctcc cggagaggag    4140
ctccggggtg cacccagtca cccagatggc gggcgttcct gtcaggagct gcgctgctga    4200
agcaaccgcg ccggcgatgc tgcccaacag ggacgtggtc gacgtcttcg tcagccgaca    4260
cagccccgcc gtccacgtgg catagattct cgatcgatcg cgtgcatggc ccatgcatgc    4320
gcccgccaca cgtacgctag cttttatata ttcgaaggac gacttgctgc tggtcgtgag    4380
catatatatg atggagaaaa tgattaagta gtatatatat aagtaattaa ctgccatgca    4440
tggaagctag ctaatggatg gaggcagagg ccagaacgat gaaggggaa gctatacata     4500 tatgtgtgta attaatatag atatatgggc tttgtgttca tctttgcagc tatgtattaa    4560
tttgcatgga tatctgttat tccttttat gtgtaacgtc ttctaataaa atgtaattga     4620
acccacacta ctgttgttag ctaccacaag tttcccaaaa atggcttctg tgtgttcggg    4680
cgggaaagcc ctggcccaaa gttgtcatcc ggttcaatca cactaggtcc cggacgttta    4740
```

```
taaaaggagc ctcaaattgc taagtttcag tttttgactc cccaccccta taaatgagcg    4800
acaacgccca cccagacgcg agtgtggcag cggttacccg agagcgcgag gcgacggcag    4860
ttccccgaga gcgaaaggcg acggcgccca gagactcgcg cgaccgcgaa gccaagcgcg    4920
gtggcggcct ctagaggcac cacgggcggc tactcccaga tttggcggcg ccgaggtggt    4980
ggctccccga ttcggtggtg cgacggtggt ggctccccga cccggaggag cgatggcggc    5040
atttcttcga tccagcggcg cgacggtggt ggctccttga tccggcggcg cgatggcggc    5100
gattcttcga tccggaggca tgacgacatc ggctcaccga tctagaggcg cagcagcggt    5160
gactccctgg aggcgcgcaa gtggtttgcc ctcggctccg cgggccatgt gacaccctcc    5220
gatccaatgt acctcgggca tcctccggcg acggtatcct ccgatccggc tcaaaattga    5280 tgattttat gatcataaat acaacacata tgaataatca acatctctca cgttggatca    5340
gttttacgat aaaaatgagg atttttacgc taaaagttaa agaattttat gcaaatctag    5400
ggtgcgcacc actgtcatgc atgcatattt tccgcgtgca cagtgaaaaa ggaaacctca    5460
taatttatgg tgtatgtaac tactatgaaa attcaaatcc cttaattatc ttccctaatt    5520
aaatcccaca atcaagtcac gtaatcaaat cccttgatat atggtggctg cgtggacgtg    5580
gaggttgttg gctgggattg aatcaacgtt ttacgctgta tctaacattg ttttatgctc    5640
atatctttat gattttatg ataattaatc taacgtacca gagttgtcaa cgtctctcac    5700
gttggctcgg tacttacagt gaaaactaag gagtttacgc taaacactga agcatttac    5760 actcaaacct agagtgcatc taacaatgta ccacatgcat attttacgtg agcacagaga    5820
aaaaggaaat ttcttgattt attatgtctg tggctaccat aaaaaatcaa atttcctaat    5880
caactcaact aattaaatcc tcctaatcaa ctcccccaat caaatcactt gatttatggt    5940
ggttgcatgg acgcggagac tgttgttggg agtgaatcta catttacaat atattataca    6000
ttatttacgc tcaaacttga gactttttac gctcaaatct gggttgcgcc cacacagtag    6060
tgaaagtcgc ctagagggg gtgaataggg cgaaactgaa atttacaaag ttaatcacaa    6120
ctacaagccg ggttagcgtt agaaatataa tcgagtccgc gagagagggt gcaaaacaaa    6180
tcacaagcaa ataagaagtg tgacacgcg atttgttta ccgaggttcg gttctcgcaa    6240
acctactccc cgttgagaag gccacaaagt tcgggtcttt ttcaacccctt tccctctctc    6300 aaacggtccc tcggaccgag tgagcttctt cttctcaatc gaacgggaac aaaacttccc    6360
cgcaagggcc accacacaat tggtgcctct tgccttggtt acaattgagt tgatcgcaag    6420
aaagaatcaa agaagaaagc aatccaagct caagagctcg aaagaacaca agcaaatctc    6480
tctcactaat cactaaggtg ttgtgtggaa tttagagagg atttgatcac ttgggtgtgt    6540
ctagaattga atgctagagc tcttgtaagt agttgaagtg ggaaaacttg gataacttga    6600
atgtggggtg gttgggggta tttataaccc caaccacaaa ctagccgttt ggtgga       6656
```

<210> SEQ ID NO 23
<211> LENGTH: 7189
<212> TYPE: DNA
<213> ORGANISM: Zea mays
<220> FEATURE:
<221> NAME/KEY: misc_feature
<222> LOCATION: (5977)..(6076)
<223> OTHER INFORMATION: n is a, c, g, or t
<220> FEATURE:
<221> NAME/KEY: misc_feature
<222> LOCATION: (6977)..(7076)
<223> OTHER INFORMATION: n is a, c, g, or t

<400> SEQUENCE: 23

```
ataaaaaatg ttttaacagt tgtttatttg aactcgtagt tgtaatgtaa tcttttttta    60
aaaaaaaaag acttaatcaa gttagagaag catgatttaa tataaaacta aaatttagaa   120
gagcggcctg ctcatagagt tttgtttagt taatacataa acatcattct cttgtatgct   180
atgcatataa agaatatatg tattctaaaa catatatacc aggatcggaa caagcacacg   240
cgcgtacgtc gtagcttctg catggctcta gtaagctcca gcgcgcagcg cgacgacgtc   300
tcttgctgta atgattgata cacatgcttt gtcagtccgt cgttaccagc aaatcatttg   360
taatgataca ctcgctcgct cgctcgcgta gtcgcagcaa attaaaactg ctagcctgc    420
agctagctga tatgcgactg ggaggagtat aattagcgcc accgcatttg tttgcgtacg   480
tttctggctc cggtggacga tccatgcatg attggaagcg gtggatcgat gcgcacgaca   540
cgtacggcag ctagcgggga tcatagcgtc cgcgggaggg agaagccagt gccagcccaa   600
gctggcatgg ctggctcgca tcgcgcatat atacgcaaac gtggcaggtt tcagcttggg   660
caccgtaccg ctagcctagg ctgccgctgg agctggacga cagagccgat tgcaagaagc   720
caggatcaga attagatgga ccctaggcat gcagtttgat tgagcttgga catccatcat   780
atatcatcgt tggaagctat aagctagcta gctagctagc atcacgtacg tgctgctacg   840
tacatttggc tctcgatcga tcagaggccg gccggtgtcg tcgtcgtcgt agactcgtag   900
gtatgaaaat aattgtacgg cggtcagatc atttccgtct cgatcgatcg tccttgggtt   960
gtccgttttt agtttttact actacgtact gtacatgcga gcgtttacct taaaagcatc  1020
gaaacgctcg tcgttagcct gctgcgtcaa gtgcagtgag tacctccact ccgatccagg  1080
cggctgcatc aagcagcaaa tgcaagctag aagggatgcc ccaagcacac tagctagcta  1140
gtactagtcc acaaatacgc agctcacacc ttgccatata tcccggtcat atcatacgtg  1200
taccacccac ccttaccgta tccgtgtatg cgggcggggg tgggtcaccc attaattgcc  1260
ggcgatattt tggcggtaac gtggcgccgc gaaccaggct agcagggagc caggggctag  1320
gcggctagca ccacagacga tctggagcag agcacatgac atgcgacctc gaggagcgcc  1380
ccccacccctg aacccccccac gggacggaac acgtaaagag cacttccatt ccattccgtc  1440
cattccacca gcaggaagaa ggaacgacca catcactgct tcccgttcgt tcgttcggca  1500
cgcagctgcc tgcgcctgcg tgtgtgtgtg cacgacttgc ttgcgaggcc agcactggtg  1560
tgcagtccgt tggccctccc cccgcaaagt tcgtcacgac gctgggatgt gccgtgtctt  1620
ttgtagaaag cgtgagcggg ccgttacgac aactagcagg gcacacaagg gcaagtgcag  1680
gcgaggcgac tcacgtacgt acagttagcg tgtgaccagc tagctgctgc tgcgcctgcg  1740
ccgcatcatc agacgccctg caggaaccgc ggggcttggg ccggacgccg ccgccgccgc  1800
ctctgcctct gctggtggtg gagtttgaca tgtcacgagg cgttacgacg aaacgaaaac  1860
agagccactg agccagtgcg acgcgcaacc acaaaataga tggccggcta ccctctctct  1920
ctttctctcc ccccgcggcg ccaaaaaagc aagcgcgacg cgacaagtcg ttgtgtaatc  1980
atgtagatct aacgggtcca ctcaggagct aatgactcac ctctccgtgc tcacctcctc  2040
ttcttgaggc ttgagctctc tcttcctctc tcccctcagc tcatctccac cgtctcccta  2100
tatataggat gctctgccgg ctccaaggtt cccaagcgcc caaggcagcg gagagagcta  2160
gctccctcct cctcctcagg tagcgagcga gcgagctcct ctgcccctct gcacacctgg  2220
cctcccctttc tccgctgcag gaccgccgtt gacgactgct ccaccagtac tgcgcgcgcc  2280
cgcgctgcct acccttacct agccagagcg cggcgcgcga gagggagaac gaccaggagg  2340
```

```
ggaggagatc gatcgatcga tcgatcgaga tagatggctt tcctcaacat ggagcagcag    2400
acctgggcct tcaccttcgg tatcctaggt acatatatac tgtcagtctg tcactcgtag    2460
ctactaatta accgcatcaa cggagccgcc ctgccgtctt cgtcctcgtc agtgtttctg    2520
cattgttttc cttccttgtc ccaagtcctt tgagacgcac gcatacatga tacatgcatg    2580
gcatcatcgt ctcccaagtc ctaggtacag tttcatcacc gcgcgcctct ctcagatatg    2640
tgtcgtcgta caggacaaca caacacgtcc tcgtcaatct actagctata tgcgctaata    2700
accacctctt cctttccgag ccacggcaca gtatagcctg ccatccgaac gaacggaacc    2760
gcccaaaacc caacttttt tgggcctaac taatgcggtg gttagcccaa acaaagaaac     2820
cagggcagtc atacatttta catgtagtac ctgcttgacg acgggaacca acacaacggc    2880
gcgccgcgag gagagtttgt tccatttcct ccgcctgcag gctagctgca gctaataacc    2940
ccggccgccg gatgttctcc ttctcgcatg cttttttttt gggggttct ttctccgcct     3000 cctgctcttc gtctgttcta ccatcgtcga tcacacagca atttgactga ccgcgtctgt    3060
ccttccgacc ttgccgtttt gctttgcagg taacataatc tcgctgatgg tgttcctttc    3120
gccgctgtaa gtaactctct gctttaattt atttaaccta gccgtgaact tttcatattt    3180
acgtttacag tatccagtac catgcataat atactaccaa tatgtttcta tgtatattca    3240
gtaaagggaa gcgtccaaaa tatatactgc catcaggtat gatgagaaca tatatataaa    3300
gaacatggca cgcacgcatg cgtatctcac tgttgaatga atgacgtgcc atcatcgtcc    3360
atgctcttct agatcctttt cctttaattt atgcgtggtt ctagatcccc ctatatatat    3420 atatatat atatatatat atatatatat acgtacacct gaagacaaca tagctagcta      3480
ggaaataaac tcgttgggaa ttgaattgtc gcattaataa cgtcacttta atcagttgcg    3540
agccagtacg tgtcactgtt cggtggttgc gttgcacatg cttttagtat ggaacagcgc    3600
acgcaatcta gtaataatta atctaaaaaa tcacacggta aaaaatattc gttcccgctg    3660
atcccgcgca ggccgacgtt ctaccgcgtg taccgcaaga agtcgacgga ggggttccag    3720
tcgaccccgt acgtggtgac gctgttcagc tgcatgctgt ggatcttcta cgcgctgctc    3780
aagtccggcg ccgagctgct ggtgaccatc aacggcgtcg ggtgcgtgat cgaggcggcg    3840
tacctggccg cgtacctggt gtacgcgccc aaggccgcca gggcgctgac ggccaagatg    3900
ctgctggggc tcaacgtcgg cgtctttgga ctcgccgcgc tcgccaccat ggtggtctcc    3960
agcgccggcc tccgcgtgcg cgtgctcggc tggatctgcg tcagcgtcgc gctcagcgta    4020
ttcgccgcgc cgctcagcat catggcacgt atctaattta atctctctct ctctctctct    4080
ctctctctct ctctctctct ctctgaagag ggatgtgaat tgttggaacc gccattaatt    4140
cgctgactgc cctatctaca tctactttcc tgcagcggca ggtggtccgg accaagagcg    4200
tggagttcat gcccatctcg ctctccttct tcctggtgct gagcgccgtg atctggttcg    4260 cgtacgcgc gctgaagagg gacgtgttcg tggcgttccc caacgtgctg gcttcgtct     4320 tcggcgtcgc gcagatagcg ctgtacatgg cgtacaggaa caaggagccc gcggcggtga    4380
cggtggagga ggcgaagctg ccggagcacg ccaaggaggt ggtggtggcc gcggcggcgg    4440
ccgaggccag ggcgagctgc ggtgctgagg tgcaccccat cgacatcgac atcgaagcta    4500
cgccgacgcc ggtggaggag gtgcacgagc cgcaggtggt cgtggtcgtc gacgtggacg    4560
tggagcctgt cacctgcgcc ggcgccgcc aggcagctgc gggagcaggg gcagatgcgt     4620
ccggcgtggc cgacgcggc gtccctggac ccatggcgcc gccggagcag ctggcgatca     4680
agcccgacat ggccatttcc gtggaggcgt aggttggtta aagtgtaata gcagagtgag    4740
```

```
tcgatatcga tcagtagtag atttgtcgag tcaaggaagg ggcctgctgc tgctgctacg      4800
cgacagcagc ggccagatgt actgcctgca tgcatgcagt ccctcccgtt gactcgaccc      4860
gtagagaagg gatgggatgg aagtagccgg gtccttgggc gagtagcggc gccttggcac      4920
ccacgggcca gccgtactgg cctgtgtgat gaaccggcga gagagatgag ataatgtgcg      4980
agcgagagag ggttggttgg gttgtggtag ttgaagaaga cggctagcta gctgctgctg      5040
ctgggctctc tatctgtctc tagatctgtg tatgtctgtg taatcgagga ttccctcacc      5100
ttgcatgccg cctccctttt gtgtccttct agtctgatga ttgttttcat tccatccatg      5160
ccggcgtcgc agtaataaaa ttttttggga atggacgggt tcactgccta cctacattgc      5220
cggcgtgagt ccgtgactcc atggcggacc ggtcctcctg cgacgtccgg ccgtgccaaa      5280
ctgcaattgg tccaggcccc gcagaggcag aggcaggtgg tcacgcgcag gcagaggaat      5340
agtacggcgc gcgggcgggg cggacaagtg tgcggcgctg cgcgactcgg caggcaggca      5400
ccggggcagc ggcatatgca cgcacgcgca agcgccccgg gaaagctgga gcccggaggg      5460
acgggccgac gggggtccaa ggcgtccagc caagccaggt gggggtgggg cgagagacgt      5520
gcgcgcgcat ccaagcctgc cttgtcctcc gctgcgttgc acaaggaatt gctactagta      5580
ttcgttcccg tcacgtccac cgccggcgct ggagcgaaga aaccggtacg cttttgcttg      5640
ctcggcgcct ggtctggccg ctgtggcctg cgtgcgcgcg cgcgcatgtg ctgggatgat      5700
gaaacgaaaa tgacctagcc gtgcatggca ggcacgaggg tgtgcgtctc tgcgacacaa      5760
cacgatcgaa cttcaagtcc tcaccggcca cacaccagta tataactttc ccggccattc      5820
atgatatata tatatatata taactcaatt gtcgaatagg tctccatcta gtttaggcaa      5880
caaacataaa aagccatggg tgaacgtgtt aatgccgttg gtacgcggcg cggggaacgt      5940
acgtacgact gcttcactgt caagctgatc atcagcnnnn nnnnnnnnnn nnnnnnnnnn      6000
nnnnnnnnnn nnnnnnnnnn nnnnnnnnnn nnnnnnnnnn nnnnnnnnnn nnnnnnnnnn      6060
nnnnnnnnnn nnnnnntttc cgatttctag agattcgtct ggtaataatt tataatttct      6120
tattcatata attttttacta gcgtatccgt tttttttagag gaacgaactg gaccctaaga      6180
aaaagaagcc agatcgccgg caacagctgc ggctatgaga tgattttaag gaagaaacac      6240
gagtgcgcgg tgcggcagcg tctgatcccg gcccccaacc caagtcgctg tcaagctcct      6300
aacgtgtcct gctgccgtta gttagatccg gcttgttctg ctcagctgat gtggttgctc      6360
ttctccgctg gtccctgttc cctcccatcc gtggccgcat tcgcagtcgc aggcggagcc      6420
ggcctgtgtg gtctgcccct ggcctccatg gattccggct gtccccactg tgatctaccc      6480
tgcacgcccg ttcctccatt caggagcagt gacgggtgtg catgcgtgca tagttttttat      6540
tgtttgttgc tgttgttttt tttccaagta gacttttac tatactagta gtaacattta      6600
taaaagtaat cgataaagtc acgatgtttc ctaggattgg gattttgccc agcatgcatg      6660
catgtagctc tgggggggcct ctcgactagt gctgcgaata tggggtgggg cttttcgggc      6720
cagcatgagc acgtccggaa aatagagtcc aaagcatggc ccggcacgaa ataatatggg      6780
tcaaggctag cactgcccga aggcgggctt gggaatcggt cctcaaattt cacttgttcg      6840
ggaccagcag tccctcgcac agatatggac ccgggctggc cggtccggtc taattagcca      6900
atttattatt tatgaatcta agactgcaac tttatttgta taggatttgc gttgcgttat      6960
gtgggtccaa cagtgannnn nnnnnnnnnn nnnnnnnnnn nnnnnnnnnn nnnnnnnnnn      7020
nnnnnnnnnn nnnnnnnnnn nnnnnnnnnn nnnnnnnnnn nnnnnnnnnn nnnnnncctg      7080
```

```
atgaatcagc ttgattcgtt cgggtgcccg atttgtttcc ataaaaagcg aagccgaccg      7140
ttgtcgaccg ttgcagatct ggcgcaccgg acagtccggt gcacaccgg                  7189

<210> SEQ ID NO 24
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: n is a C or a G

<400> SEQUENCE: 24
gcgttgatgg tcagcagcgg cctcgagttg gtcttcacca gcgcgtagaa gatccacagc       60
accgagctga agagcgccac cacgtacggc accgagctga acccgcccgt cgacttcttc      120
cggtacacct gcaggaacgt cgccctgttt ttggtacggt gcgtacaaga ggcatgccat      180
gtcagtcttg gatcatccat cgattcacgc atgaatccga gtcggtctga aattgagaca      240
gtaagggaac gaagaaaggt ggctatagct agctacttac actggtgcaa ggaacaccag      300
gaaggagatg atgtttcctg cacaatccaa atcgaagaaa caagagagaa gagggtaact      360
acgcgtcagt gtcgtcattt tcagtaaaag tggtaggagt acaatactat acacatatat      420
atgtacaatg cgtgtgcgtc cactaacaga gagaagcgtg gtgattaggt taaggaaacg      480
ctgatatggc aaaaagctag ntagctgcat gcacacgcac acgccttccc tgctgcatgc      540
ccaaccgatc gatcataacc attccagcaa aaatacacg tatatagaaa tgattcttag      600
atagtgcgtt acgttgtgag cagctatttg caactgtatt tcgtgatcta atgcccaata      660
tgtggatctg atctgcactg cttattacca ttattcttga gtggaaaagt tgctatacct      720
cggcgatgca tgcatgtgtg ttctagctag caacaaatta aaggcctgtg ccatgatcgc      780
agctaacgaa ttggagaaag agtgcatcgt cgtctcaatg ggccgcgggg agcatcagag      840
aaagttcaag aagatgcagc tagcagtagt ataggtgaag aaaaaaaaat gctaaagcta      900
catactacgt attctgatat gcaagtattg ttgatagatg atggacaaga cagttggttg      960
tccagtgtga ctagctgctg catgcatgcc tactgccgcg c                         1001

<210> SEQ ID NO 25
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: n is a C or G

<400> SEQUENCE: 25
attattagca tgcattgtca gatccaatgc aaacaacagc tactactact tgattcgaca       60
ctgaactgaa ctgaactgac aagactacgc acacgagaga gacacgcaat aataatccaa      120
caattaacca actaaacgat caactagcag acgacgatgc ctgcatctgc atgcttgagc      180
tgccagccac ttgccaccaa actgtcgtac gtcatccgag ctagctaata agaagctagc      240
agggtgtgta cggtgcatgg tgattggcgt tgggtcacac cgcggcggcg gcgggacga      300 tctcgatgac ctccggcatg gcgccgtccg ggtttgcggc ggccatccgg cgggtctcgg      360
cggccacggc ggcctccttg tgctgctgct ccaccacctc gatcttgtgc acgcccacga      420
tggggatggg gctcaccgac aggatggcca ccgtgttggg cgccagctcg atgacctgcc      480
cctgcacctg caccgcgttg ncgccgtccg tggtcgtcgg cagcacggcg ttgttcttgg      540
```

```
ccgccgggcg gggcttgcgg taccagaagt agaggcccat ctggacgcag ctgaagaaga      600
agccgccgac gttggggtac tgaatagata tatataatcg agaaacatcc ccagcattat      660
tcagttacca ttttatatat atatatggat cagttaacca tatattacat tattgatcag      720
tcgttaccat gacaaagggg tccttggtga agaggccgta gcagaaccag gcgacggcgc      780
tgagcgtgag gcagaaggag aggctgatgg gcaggaactc gacgctcttg gtcttgacca      840
ccttgacgat gatgctgagc ggcgcgacga agacggccat ggagaaggcg aggcagacgc      900
tgccgaggaa cttgacgcgg tggggctcgc ggacggcgaa gagcgtgacg gcgacgacga      960
gcgcgaaggc cgccacgtcc agcaggaaga agtaggccag a                        1001
```

<210> SEQ ID NO 26
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: n is a T or G

<400> SEQUENCE: 26

```
ccacttgcca ccaaactgtc gtacgtcatc cgagctagct aataagaagc tagcagggtg       60
tgtacggtgc atggtgattg gcgttgggtc acaccgcggc ggcggcgggg acgatctcga      120
tgacctccgg catggcgccg tccgggtttg cggcggccat ccggcgggtc tcggcggcca      180
cggcggcctc cttgtgctgc tgctccacca cctcgatctt gtgcacgccc acgatgggga      240
tggggctcac cgacaggatg ccaccgtgt tgggcgccag ctcgatgacc tgcccctgca      300
cctgcaccgc gttggcgccg tccgtggtcg tcggcagcac ggcgttgttc ttggccgccg      360 ggcgggctt gcgtaccag aagtagaggc ccatctggac gcagctgaag aagaagccgc       420
cgacgttggg gtactgaata gatatatata atcgagaaac atccccagca ttattcagtt      480 accatttttat atatatatat ngatcagtta accatatatt acattattga tcagtcgtta     540
ccatgacaaa ggggtccttg gtgaagaggc cgtagcagaa ccaggcgacg gcgctgagcg     600
tgaggcagaa ggagaggctg atgggcagga actcgacgct cttggtcttg accaccttga     660
cgatgatgct gagcggcgcg acgaagacgg ccatggaaga ggcgaggcag acgctgccga     720
ggaacttgac gcgtgggc tcgcggacgg cgaagagcgt gacggcgacg acgagcgcga      780
aggccgccac gtccagcagg aagaagtagg ccagagtccg caggcgcgcc cgccgcggcg     840
cgtacgccag gtagaggact atgtaggccg cctccacgcc gcagccgaag gcgttgatgg     900
tcagcagcgg cctcgagttg gtcttcacca gcgcgtagaa gatccacagc accgagctga     960
agagcgccac cacgtacggc accgagctga acccgcccgt c                        1001
```

<210> SEQ ID NO 27
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: n is a G or A

<400> SEQUENCE: 27

```
tgttgataga tgatggacaa gacagttggt tgtccagtgt gactagctgc tgcatgcatg       60
cctactgccg cgcctctcta cagctagaga gtgcgtgcgt gctctacagt gcaatggcac      120
aaacggcaaa aaggaaggct gacgactggt ggatgcatgc atgcaaagga cggatcgatg      180
```

```
atacaaggat ggacaagaca gtcgtcatgt cggaataaac aaaatctaga agaacgtagt    240
acggcaacag aatgaatgaa aaccacatga aaagcatgtc atcaaggtcc cataagattt    300
tttttaaaaa aaaaagaag caccaggaaa aggccaaaca cgcgaagcat tatgcaagtc     360
gatctccgcc tatctatccg gccggtcccg gccggcgtca tgcatggatc gatctagctc    420
gagacgacgt tgttgtttca ttggcgcgta cgtacctgcg atgccggaga gggtgacggc    480
cgggtgagcc atggagaaga ngcctcctgc cattgctgac gacgacgcc gggcgtgggg     540 cgcgggggca ggaactggag atcgagagtt agctagctag tcgacgacgc cggcgacgac    600
ggaggccggc cggctagcta gagttgctgt tctcttcttc tcctttatat atatgacagc    660
cggcggagag aagttccacg acgacggaga ggagaggaga ggagctaagg cgacgatgct    720
cgattagcta ttgctgaatg ctgatgtgtt tgtgtgtggt ttggacccga gcacgggcat    780
ggatttatat agccggccgc gctgccottt ctgccgttct gggaggccgc ggcctgttga    840
ttgcagtggt gctgtccagt tcggcattgt tggcgagaga agagaataat gcatggtgtg    900
cagtggtaca tgcatgcatg catgcgtgta ccaaccagca cagcatgcag gtcgatcgca    960
cagtggcata caatacaatg ggtgtatcta atctgcactt t                      1001
```

<210> SEQ ID NO 28
<211> LENGTH: 1001
<212> TYPE: DNA
<213> ORGANISM: Zea mays

<400> SEQUENCE: 28

```
cggccgggcg tggggcgcgg gggcaggaac tggagatcga gagttagcta gctagtcgac     60
gacgccggcg acgacggagg ccggccggct agctagagtt gctgttctct tcttctcctt    120
tatatatatg acagccggcg gagagaagtt ccacgacgac ggagaggaga ggagaggagc    180
taaggcgacg atgctcgatt agctattgct gaatgctgat gtgtttgtgt gtggtttgga    240
cccgagcacg gcatggatt tatatagccg gccgcgctgc cctttctgcc gttctgggag     300
gccgcggcct gttgattgca gtggtgctgt ccagttcggc attgttggcg agagaagaga    360
ataatgcatg gtgtgcagtg gtacatgcat gcatgcatgc gtgtaccaac cagcacagca    420
tgcaggtcga tcgcacagtg gcatacaata caatgggtgt atctaatctg cactttcctt    480
gcagtagatt tcgagggaa gtcatttgtg catatgctaa taaagctacc tcttttattt     540
ctctgcccct ctcctata tatttctcca ctctcagaat atatagatga ctgtatgcca     600
tggtaattaa gattaataag agatggcact agtccataca taatatattt tttaacgtct    660
gaaatatgtc aaaaattaaa caagtgtacg gtgtatatat gggttttca cttgtctcac    720 aagtagcaga aagtgtgtta cagctatagt tgttgtatat atacatgatt ggtttgctga    780
aatatgcata tatatatata taacctccta caaagatctt ggtacgcaac aaatgcgctg    840
ctaactaact acaagctcaa taatttattt ttccgaaaca aaaataatat atgtacactg    900
cactcaaagg acttttttct ggcatttgac gcgtgtgaaa agtgggctat ataaagtgcc    960
gtgtcttttt ttcacctgcc aatcgcaagt agacaggatt a                      1001
```

<210> SEQ ID NO 29
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: r is a A or G

<400> SEQUENCE: 29

```
gagagcgcga ggcgacggca gttccccgag agcgaaaggc gacggcgccc agagactcgc    60
gcgaccgcga agccaagcgc ggtggcggcc tctagaggca ccacgggcgg ctactcccag   120
atttggcggc gccgaggtgg tggctccccg attcggtggt gcgacggtgg tggctccccg   180
acccggagga gcgatggcgg catttcttcg atccagcggc gcgacggtgg tggctccttg   240
atccggcggc gcgatggcgg cgattcttcg atccggaggc atgacgacat cggctcaccg   300
atctagaggc gcagcagcgg tgactccctg gaggcgcgca agtggtttgc cctcggctcc   360
gcgggccatg tgacaccctc cgatccaatg tacctcgggc atcctccggc gacggtatcc   420
tccgatccgg ctcaaaattg atgattttta tgatcataaa tacaacacat atgaataatc   480
aacatctctc acgttggatc rgttttacga taaaaatgag gatttttacg ctaaaagtta   540
aagaatttta tgcaaatcta gggtgcgcac cactgtcatg catgcatatt ttccgcgtgc   600
acagtgaaaa aggaaacctc ataatttatg gtgtatgtaa ctactatgaa aattcaaatc   660
ccttaattat cttccctaat taaatcccac aatcaagtca cgtaatcaaa tcccttgata   720
tatggtggct gcgtggacgt ggaggttgtt ggctgggatt gaatcaacgt tttacgctgt   780
atctaacatt gttttatgct catatcttta tgatttttat gataattaat ctaacgtacc   840
agagttgtca acgtctctca cgttggctcg gtacttacag tgaaaactaa ggagtttacg   900
ctaaacactg aagcatttta cactcaaacc tagagtgcat ctaacaatgt accacatgca   960
tattttacgt gagcacagag aaaaaggaaa tttcttgatt t                      1001
```

<210> SEQ ID NO 30
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: y is a C or T

<400> SEQUENCE: 30

```
aaaaatggct tctgtgtgtt cgggcgggaa agccctggcc caaagttgtc atccggttca    60
atcacactag gtcccggacg tttataaaag gagcctcaaa ttgctaagtt tcagttttttg   120
actccccacc cctataaatg agcgacaacg cccacccaga cgcgagtgtg gcagcggtta   180
cccgagagcg cgaggcgacg gcagttcccc gagagcgaaa ggcgacggcg cccagagact   240
cgcgcgaccg cgaagccaag cgcggtggcg gcctctagag gcaccacggg cggctactcc   300
cagatttggc ggcgccgagg tggtggctcc ccgattcggt ggtgcgacgg tggtggctcc   360
ccgacccgga ggagcgatgg cggcatttct tcgatccagc ggcgcgacgg tggtggctcc   420
ttgatccggc ggcgcgatgg cggcgattct tcgatccgga ggcatgacga catcggctca   480
ccgatctaga ggcgcagcag yggtgactcc ctggaggcgc gcaagtggtt tgccctcggc   540
tccgcgggcc atgtgacacc ctccgatcca atgtacctcg gcatcctcc ggcgacggta   600
tcctccgatc cggctcaaaa ttgatgattt ttatgatcat aaatacaaca catatgaata   660
atcaacatct ctcacgttgg atcagtttta cgataaaaat gaggattttt acgctaaaag   720
ttaaagaatt ttatgcaaat ctagggtgcg caccactgtc atgcatgcat attttccgcg   780
tgcacagtga aaaggaaac ctcataattt atggtgtatg taactactat gaaaattcaa   840
atcccttaat tatcttccct aattaaatcc cacaatcaag tcacgtaatc aaatcccttg   900
```

```
atatatggtg gctgcgtgga cgtggaggtt gttggctggg attgaatcaa cgttttacgc    960
tgtatctaac attgttttat gctcatatct ttatgatttt t                      1001
```

<210> SEQ ID NO 31
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: m is a C or A

<400> SEQUENCE: 31

```
tcgatcaacc caatcagttt tgatccatgt gtatcgtttc taatgcaccg tgtttatata     60
tgtgtgcaga gacgagtgat ccagacgaag agcgtggagt acatgccctt ctccctctcc    120
ctctcgctca ccctcagcgc cgtcgtctgg ttcctctacg gcctcctcat caaggacaaa    180
tacgtcgcgg taattgtttc atctaatctg ctgcaaccgc catggtattg gtatctctca    240 ctggtctttta ctgataaact acatacgatc tctgtacgta tgcagcttcc aaacatcctg   300
gggttcacct tcggcgtggt ccagatggtg ctctacgtgt tgtacatgaa caagacgccg    360
gtggcggcga ctgccgaggg caaggatgcc ggcaagcttt cctcagctgc agacgagcac    420
gtcctcgtca acatcgccaa gctcagccca gccctcccgg agaggagctc cggggtgcac    480
ccagtcaccc agatggcggg mgttcctgtc aggagctgcg ctgctgaagc aaccgcgccg    540
gcgatgctgc ccaacaggga cgtggtcgac gtcttcgtca gccgacacag ccccgccgtc    600
cacgtggcat agattctcga tcgatcgcgt gcatggccca tgcatgcgcc cgccacacgt    660
acgctagctt ttatatattc gaaggacgac ttgctgctgg tcgtgagcat atatatgatg    720
gagaaaatga ttaagtagta tatatataag taattaactg ccatgcatgg aagctagcta    780
atggatggag gcagaggcca gaacgatgaa gggggaagct atacatatat gtgtgtaatt    840
aatatagata tatgggcttt gtgttcatct ttgcagctat gtattaattt gcatggatat    900
ctgttattcc tttttatgtg taacgtcttc taataaaatg taattgaacc cacactactg    960
ttgttagcta ccacaagttt cccaaaaatg gcttctgtgt g                      1001
```

<210> SEQ ID NO 32
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: k is a G or T

<400> SEQUENCE: 32

```
atgcaccgtg tttatatatg tgtgcagaga cgagtgatcc agacgaagag cgtggagtac     60
atgcccttct ccctctccct ctcgctcacc ctcagcgccg tcgtctggtt cctctacgc    120 ctcctcatca aggacaaata cgtcgcggta attgtttcat ctaatctgct gcaaccgcca    180
tggtattggt atctctcact ggtctttact gataaactac atacgatctc tgtacgtatg    240
cagcttccaa acatcctggg gttcaccttc ggcgtggtcc agatggtgct ctacgtgttg    300
tacatgaaca agacgccggt ggcggcgact gccgagggca aggatgccgg caagctttcc    360
tcagctgcag acgagcacgt cctcgtcaac atcgccaagc tcagcccagc cctcccggag    420
aggagctccg gggtgcaccc agtcacccag atggcgggcg ttcctgtcag gagctgcgct    480
gctgaagcaa ccgcgccggc katgctgccc aacagggacg tggtcgacgt cttcgtcagc    540
```

```
cgacacagcc ccgccgtcca cgtggcatag attctcgatc gatcgcgtgc atggcccatg      600
catgcgcccg ccacacgtac gctagctttt atatattcga aggacgactt gctgctggtc      660
gtgagcatat atatgatgga gaaaatgatt aagtagtata tatataagta attaactgcc      720
atgcatggaa gctagctaat ggatggaggc agaggccaga acgatgaagg gggaagctat      780
acatatatgt gtgtaattaa tatagatata tgggctttgt gttcatcttt gcagctatgt      840
attaatttgc atggatatct gttattcctt tttatgtgta acgtcttcta ataaaatgta      900
attgaaccca cactactgtt gttagctacc acaagtttcc caaaaatggc ttctgtgtgt      960
tcgggcggga aagccctggc ccaaagttgt catccggttc a                        1001
```

<210> SEQ ID NO 33
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: r is a G or A

<400> SEQUENCE: 33

```
ctctacgtgt tgtacatgaa caagacgccg gtggcggcga ctgccgaggg caaggatgcc       60
ggcaagcttt cctcagctgc agacgagcac gtcctcgtca acatcgccaa gctcagccca      120
gccctcccgg agaggagctc cggggtgcac ccagtcaccc agatggcggg cgttcctgtc      180
aggagctgcg ctgctgaagc aaccgcgccg gcgatgctgc caacaggga cgtggtcgac       240 gtcttcgtca gccgacacag ccccgccgtc cacgtggcat agattctcga tcgatcgcgt      300
gcatggccca tgcatgcgcc cgccacacgt acgctagctt ttatatattc gaaggacgac      360
ttgctgctgg tcgtgagcat atatatgatg gagaaaatga ttaagtagta tatatataag      420
taattaactg ccatgcatgg aagctagcta atggatggag gcagaggcca gaacgatgaa      480
gggggaagct atacatatat rtgtgtaatt aatatagata tatgggcttt gtgttcatct      540
ttgcagctat gtattaattt gcatggatat ctgttattcc ttttatgtg taacgtcttc       600 taataaaatg taattgaacc cacactactg ttgttagcta ccacaagttt cccaaaaatg      660
gcttctgtgt gttcgggcgg gaaagccctg gcccaaagtt gtcatccggt tcaatcacac      720
taggtcccgg acgtttataa aaggagcctc aaattgctaa gtttcagttt ttgactcccc      780 accctataa atgagcgaca acgcccaccc agacgcgagt gtggcagcgg ttacccgaga       840
gcgcgaggcg acggcagttc cccgagagcg aaaggcgacg gcgcccagag actcgcgcga      900
ccgcgaagcc aagcgcggtg gcggcctcta gaggcaccac gggcggctac tcccagattt      960
ggcggcgccg aggtggtggc tccccgattc ggtggtgcga c                        1001
```

<210> SEQ ID NO 34
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: n is a C or T

<400> SEQUENCE: 34

```
cgtttcatca tcccagcaca tgcgcgcgcg cgcacgcagg ccacagcggc cagaccaggc       60
gccgagcaag caaagcgta ccggtttctt cgctccagcg ccggcggtgg acgtgacggg      120
aacgaatact agtagcaatt ccttgtgcaa cgcagcggag gacaaggcag gcttggatgc      180
```

```
gcgcgcacgt ctctcgcccc accccacct ggcttggctg gacgcctgga cccccgtcg      240 gcccgtccct ccgggctcca gctttccggg ggcgcttgcg cgtgcgtgca tatgccgctg      300
ccccggtgcc tgcctgccga gtcgcgcagc gccgcacact tgtccgcccc gcccgcgcgc      360
cgtactattc ctctgcctgc gcgtgaccac ctgcctctgc ctctgcgggg cctggaccaa      420
ttgcagtttg gcacggccgg acgtcgcagg aggaccggtc cgccatggag tcacggactc      480
acgccggcaa tgtaggtagg nagtgaaccc gtccattcca aaaaatttt attactgcga      540 cgccggcatg gatggaatga aaacaatcat cagactagaa ggacacaaaa gggaggcggc      600
atgcaaggtg agggaatcct cgattacaca gacatacaca gatctagaga cagatagaga      660
gcccagcagc agcagctagc tagccgtctt cttcaactac cacaacccaa ccaaccctct      720
ctcgctcgca cattatctca tctctctcgc cggttcatca cacaggccag tacgctggc      780 ccgtgggtgc caaggcgccg ctactcgccc aaggacccgg ctacttccat cccatccctt      840
ctctacgggt cgagtcaacg ggagggactc catgcatgca ggcagtacat ctggccgctg      900
ctgtcgcgta gcagcagcag caggccccctt ccttgactcg acaaatctac tactgatcga      960
tatcgactca ctctgctatt acactttaac caacctacgc c                         1001
```

<210> SEQ ID NO 35
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: n is a G or C

<400> SEQUENCE: 35

```
cacgcggagg ccggcgctgg agaccaccat ggtggcgagc gcggcgagtc caaagacgcc       60
gacgttgagc cccagcagca tcttggccgt cagcgccctg gcggccttgg gcgcgtacac      120
caggtacgcg gccaggtacg ccgcctcgat cacgcacccg acgccgttga tggtcaccag      180
cagctcggcg ccggacttga gcagcgcgta aagatccac agcatgcagc tgaacagcgt      240
caccacgtac ggggtcgact ggaacccctc cgtcgacttc ttgcggtaca cgcggtagaa      300
cgtcggcctg cgcgggatca gcgggaacga atatttttta ccgtgtgatt ttttagatta      360
attattacta gattgcgtgc gctgttccat actaaaagca tgtgcaacgc aaccaccgaa      420
cagtgacacg tactggctcg caactgatta aagtgacgtt attaatgcga caattcaatt      480
cccaacgagt ttatttccta nctagctatg ttgtcttcag gtgtacgtat atatatatat      540
atatatatat atatatatat atatataggg ggatctagaa ccacgcataa attaaaggaa      600
aaggatctag aagagcatgg acgatgatgg cacgtcattc attcaacagt gagatacgca      660
tgcgtgcgtg ccatgttctt tatatatatg ttctcatcat acctgatggc agtatatatt      720
ttggacgctt ccctttactg aatatacata gaaacatatt ggtagtatat tatgcatggt      780
actggatact gtaaacgtaa atatgaaaag ttcacggcta ggttaaataa attaaagcag      840
agagttactt acagcggcga aaggaacacc atcagcgaga ttatgttacc tgcaaagcaa      900
aacggcaagg tcggaaggac agacgcggtc agtcaaattg ctgtgtgatc gacgatggta      960
gaacagacga agagcaggag gcggagaaag aacccccccaa a                        1001
```

<210> SEQ ID NO 36
<211> LENGTH: 1001
<212> TYPE: DNA
<213> ORGANISM: Zea mays

```
<220> FEATURE:
<221> NAME/KEY: misc_feature
<222> LOCATION: (501)..(501)
<223> OTHER INFORMATION: n is a G or T

<400> SEQUENCE: 36
tagaaccacg cataaattaa aggaaaagga tctagaagag catggacgat gatggcacgt      60
cattcattca acagtgagat acgcatgcgt gcgtgccatg ttctttatat atatgttctc     120
atcatacctg atggcagtat atattttgga cgcttccctt tactgaatat acatagaaac     180
atattggtag tatattatgc atggtactgg atactgtaaa cgtaaatatg aaaagttcac     240
ggctaggtta aataaattaa agcagagagt tacttacagc ggcgaaagga acaccatcag     300
cgagattatg ttacctgcaa agcaaaacgg caaggtcgga aggacagacg cggtcagtca     360
aattgctgtg tgatcgacga tggtagaaca gacgaagagc aggaggcgga gaaagaaccc     420
cccaaaaaaa aagcatgcga aaggagaac atccggcggc cggggttatt agctgcagct     480
agcctgcagg cggaggaaat ngaacaaact ctcctcgcgg cgcgccgttg tgttggttcc     540
cgtcgtcaag caggtactac atgtaaaatg tatgactgcc ctggtttctt tgtttgggct     600
aaccaccgca ttagttaggc ccaaaaaaag ttgggttttg ggcggttccg ttcgttcgga     660
tggcaggcta tactgtgccg tggctcggaa aggaagaggt ggttattagc gcatatagct     720
agtagattga cgaggacgtg ttgtgttgtc ctgtacgacg acacatatct gagagaggcg     780
cgcggtgatg aaactgtacc taggacttgg gagacgatga tgccatgcat gtatcatgta     840
tgcgtgcgtc tcaaaggact tgggacaagg aaggaaaaca atgcagaaac actgacgagg     900
acgaagacgg cagggcggct ccgttgatgc ggttaattag tagctacgag tgacagactg     960
acagtatata tgtacctagg ataccgaagg tgaaggccca g                        1001

<210> SEQ ID NO 37
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: n is a G or a C

<400> SEQUENCE: 37
aaggaaaagg atctagaaga gcatggacga tgatggcacg tcattcattc aacagtgaga      60
tacgcatgcg tgcgtgccat gttctttata tatatgttct catcatacct gatggcagta     120
tatattttgg acgcttccct ttactgaata tacatagaaa catattggta gtatattatg     180
catggtactg gatactgtaa acgtaaatat gaaaagttca cggctaggtt aaataaatta     240
aagcagagag ttacttacag cggcgaaagg aacaccatca gcgagattat gttacctgca     300
aagcaaaacg gcaaggtcgg aaggacagac gcggtcagtc aaattgctgt gtgatcgacg     360
atggtagaac agacgaagag caggaggcgg agaaagaacc cccaaaaaaa aaagcatgcg     420
agaaggagaa catccggcgg ccggggttat tagctgcagc tagcctgcag gcggaggaaa     480
tggaacaaac tctcctcgcg ncgcgccgtt gtgttggttc ccgtcgtcaa gcaggtacta     540
catgtaaaat gtatgactgc cctggtttct ttgtttgggc taaccaccgc attagttagg     600
cccaaaaaaa gttgggtttt ggcggttcc gttcgttcgg atggcaggct atactgtgcc     660
gtggctcgga aaggaagagg tggttattag cgcatatagc tagtagattg acgaggacgt     720
gttgtgttgt cctgtacgac gacacatatc tgagagaggc gcgcggtgat gaaactgtac     780
```

| | |
|---|---|
| ctaggacttg ggagacgatg atgccatgca tgtatcatgt atgcgtgcgt ctcaaaggac | 840 |
| ttgggacaag gaaggaaaac aatgcagaaa cactgacgag gacgaagacg gcagggcggc | 900 |
| tccgttgatg cggttaatta gtagctacga gtgacagact gacagtatat atgtacctag | 960 |
| gataccgaag gtgaaggccc aggtctgctg ctccatgttg a | 1001 |

<210> SEQ ID NO 38
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: n is a C or a T

<400> SEQUENCE: 38

| | |
|---|---|
| gaaaaggatc tagaagagca tggacgatga tggcacgtca ttcattcaac agtgagatac | 60 |
| gcatgcgtgc gtgccatgtt ctttatatat atgttctcat catacctgat ggcagtatat | 120 |
| attttggacg cttcccttta ctgaatatac atagaaacat attggtagta tattatgcat | 180 |
| ggtactggat actgtaaacg taaatatgaa aagttcacgg ctaggttaaa taaattaaag | 240 |
| cagagagtta cttacagcgg cgaaaggaac accatcagcg agattatgtt acctgcaaag | 300 |
| caaaacggca aggtcggaag gacagacgcg gtcagtcaaa ttgctgtgtg atcgacgatg | 360 |
| gtagaacaga cgaagagcag gaggcggaga agaaccccc caaaaaaaaa gcatgcgaga | 420 |
| aggagaacat ccggcggccg gggttattag ctgcagctag cctgcaggcg gaggaaatgg | 480 |
| aacaaactct cctcgcggcg ngccgttgtg ttggttcccg tcgtcaagca ggtactacat | 540 |
| gtaaaatgta tgactgccct ggtttctttg tttgggctaa ccaccgcatt agttaggccc | 600 |
| aaaaaaagtt gggttttggg cggttccgtt cgttcggatg gcaggctata ctgtgccgtg | 660 |
| gctcggaaag gaagaggtgg ttattagcgc atatagctag tagattgacg aggacgtgtt | 720 |
| gtgttgtcct gtacgacgac acatatctga gagaggcgcg cggtgatgaa actgtaccta | 780 |
| ggacttggga gacgatgatg ccatgcatgt atcatgtatg cgtgcgtctc aaaggacttg | 840 |
| ggacaaggaa ggaaaacaat gcagaaacac tgacgaggac gaagacgcga gggcggctcc | 900 |
| gttgatgcgg ttaattagta gctacgagtg acagactgac agtatatatg tacctaggat | 960 |
| accgaaggtg aaggcccagg tctgctgctc catgttgagg a | 1001 |

<210> SEQ ID NO 39
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: n is a G or a A

<400> SEQUENCE: 39

| | |
|---|---|
| cttaacgcag gtggcgccca ttatgccaga ggcttacgtc aggttccacc ggagggctta | 60 |
| cgtcatgcgc cacgggacat gtggcatcaa caggtcatca ccttagcggg gagcaacaac | 120 |
| tagaagtgca tgtacacatg gcggctccga accaccttag caggggtctg gaaggtgctc | 180 |
| aggggagtcc gggtccctat gacactgtct cagacatgta gcagcaccag acctcttag | 240 |
| gtcgggaggtt cggatgacac atgcggttgt ccgagtccgt cccacagggt ccgccccgg | 300 |
| atgtcaaaga gtccctattc tcagggcacg tggcggctac agagccccat gccagggat | 360 |

```
ccggagagct cacgtggaag ctggccccca cctgaggcca gcggcctcgt cggacgggcc      420
tagactgtga gctagggcag accatatgtg actatgcgac taaggatagc cacggggtcc      480
tgttttaacc tagcaggagt ngataccta atcttgaggt accgatataa cttgtggccg       540
gttaaggaaa tagattcact ctattcgaat aaatatttag gctttattcg tttgtttaga      600
atttatactc gaaatcgttt caacaaatca aagtttatat gaactagaga agcgatccga      660
ctaggaatat atctagcata tcattccgta caaaccgaac aggaccttac aaggatacaa      720
gtgagttggg ttatctacga cgaacctgta aacaaactaa ttggccacac aaaatagtct      780
attgacgggc acctagacaa accgctttgc atccatgaat atttatccag gaacagtcta     840
ccatgctaga caagggagac gaattattgt taggcttaga atttctccaa tgccgctata      900
gagcacactc tagaattgtt gtgataagtc agggttcagc gtgtcacaca caccgtacac      960
gcaaaagatg cattgctcac gcacagcaca gtactcgcag t                        1001

<210> SEQ ID NO 40
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: n is a T or a C

<400> SEQUENCE: 40
atttccgaaa tctaagtaaa acaaactaca ccaccacgcc ggttttactg ctttacggcc      60
actccataaa tctgcgatgc gatttaattt tctgaagaga cagaaacaga atggtgtgg      120 agtgctcatc aaaaggccgt gtctctcagg gagagagaga gagagagagc ggttcgttac     180
caagccgata ggaggcagtt gagcagcgtc atgttgtagg gcacgccgga gaagtcctcc     240
gtcgaccgct tcctgatgac cctccagaag gtgacactgc aaagagattt ctcacccgtc     300
agaggaacac acgcactgcg ctgctgcccc tgaaggctgc tgaggcaaga cgcaagaaaa     360
aaggtgcggc gtggttggga agaagaagca tttcggatgg ggaaaagcta cttgcttttt     420
ttagaaaaaa attatatatg tatgaaattt cagtgtttcg ctggaaagga ttgaacctaa     480
aagatgctat agcctttctc nccacactga ttctccccat gttctagtct ttgtcatata    540
gtagaagtaa gtactatatc attgcttctc tgttttcgat ttttttttta aagcatggac    600
gcgggcagtg aggaacagaa ggattcaggt acgtggaatc aaaaacttac acaggcgaca    660
ggaagaggaa gagcgcaatg acattccctg gggagacaga tctaacagag attaggcgag    720
gcaagaagaa gaccatcagg taggcatgca gcagaggcag gaatggcatg gtgatactga    780
ccagaaactc cgaagaagaa cctggcgata tgctccatct cttccgcttc gcgcttatcg    840
ctgtgcggaa ccctcggctg tgctggcctg gaacccgaac ggagcagagg gggtagtgag    900
tggactggac tcctttcctc cacggtctag gccgggagcg cacccacacc caacgagcag    960
ttagctagta gctctcaagt ctgaatggct gagcgcaaca c                        1001

<210> SEQ ID NO 41
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: n is a G or a A
```

<400> SEQUENCE: 41

```
ttgctaaaag taacctgtcg gaggtaagct ccagctaggt ggcggatagc acccgctcta      60
atcctaagat gaggagggag catgaggtta gcctatagag agataaacac aagaacaaac     120
aagaatttag agtagttcgg gccgccgaag cgtaataccc tactccacta tgagttgtac     180
tgctgatagc ttgagaaagc ttacgtctaa tggagtcttt gcgtgaatgc ctatgagtcg     240
tcctggcctg aacaacttta ggttgctctg ctctctaccg agtgtgccct ctcttttata     300
gcctaaggga ggggttttac atggtgtctg agccctaaca agtgggacca gaaaaacaag     360
tgggaccaga aaaacaaaga gatcgctgag taagagcgaa gctggtggac cgagatcttc     420
tccgtctagt cttatcttct acccagtctt gttggcatgt ggacaaaggc tacgacgtag     480
gttgcggcgt ggtgagcgta nggagaatac gaacggtgtc gtcgcgtccc ccccgcatgt     540
tccctctcgc cttggtaaag agtaggtgag cgtagggaga atatcttggt ccaaggctta     600
atatgattga tagaatattc ataaaaacaa ggtgcatcat tttttcgaaa gcctgtctcg     660
aaagaacctc tagattaagc gtgcttggcc aagagtaatc ttaggatggg tgatcgatca     720
ggaagtcttc tcgggtgcgc atgagtgagg acaaagtgca cacaaaagac tcatgttggt     780
ctatgtggat ggtctatgat tctagagggc tgctaggagt aagtaccgcg ggtccgagag     840
tggacgggtg ttacaacgac gcattgagtt aatggtcttg cctcgataac gcgtgggttt     900
ctgatgcggt ataggccttg caggctgcgc acgcctcctg catttaatgc ggggtgcacg     960
tcacctatta cttggtgtga atggacacgc actctgccca c                       1001
```

<210> SEQ ID NO 42
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: n is a G or a T

<400> SEQUENCE: 42

```
ggtctatgat tctagagggc tgctaggagt aagtaccgcg ggtccgagag tggacgggtg      60
ttacaacgac gcattgagtt aatggtcttg cctcgataac gcgtgggttt ctgatgcggt     120
ataggccttg caggctgcgc acgcctcctg catttaatgc ggggtgcacg tcacctatta     180
cttggtgtga atggacacgc actctgccca cacttaacgc aggtggcgcc cattatgcca     240
gaggcttacg tcaggttcca ccggagggct tacgtcatgc gccacgggac atgtggcatc     300
aacaggtcat caccttagcg gggagcaaca actagaagtg catgtacaca tggcggctcc     360
gaaccacctt agcagggggtc tggaaggtgc tcagggggagt ccgggtccct atgacactgt     420
ctcagacatg tagcagcacc agacctcttt aggtcggagg ttcggatgac acatgcggtt     480
gtccgagtcc gtcccacagg ntccgccccc ggatgtcaaa gagtccctat tctcagggca     540
cgtggcggct acagagcccc attgccaggg atccggagag ctcacgtgga agctggcccc     600
cacctgaggc cagcggcctc gtcggacggg cctagactgt gagctagggc agaccatatg     660
tgactatgcg actaaggata gccacggggt cctgttttaa cctagcagga gtggataccc     720
taatcttgag gtaccgatat aacttgtggc cggttaagga aatagattca ctctattcga     780
ataaatattt aggctttatt cgtttgttta gaatttatac tcgaaatcgt ttcaacaaat     840
caaagtttat atgaactaga gaagcgatcc gactaggaat atatctagca tatcattccg     900
```

```
tacaaaccga acaggacctt acaaggatac aagtgagttg ggttatctac gacgaacctg    960
taaacaaact aattggccac acaaaatagt ctattgacgg g                       1001

<210> SEQ ID NO 43
<211> LENGTH: 1001
<212> TYPE: DNA
<213> ORGANISM: Zea mays
<220> FEATURE:
<221> NAME/KEY: misc_feature
<222> LOCATION: (500)..(500)
<223> OTHER INFORMATION: n is a, c, g, or t

<400> SEQUENCE: 43
tacggccact ccataaatct gcgatgcgat ttaattttct gaagagacag aaacagaaat     60
ggtgtggagt gctcatcaaa aggccgtgtc tctcagggag agagagagag agagagcggt    120
tcgttaccaa gccgatagga ggcagttgag cagcgtcatg ttgtagggca cgccggagaa    180
gtcctccgtc gaccgcttcc tgatgaccct ccagaaggtg acactgcaaa gagatttctc    240
acccgtcaga ggaacacacg cactgcgctg ctgcccctga aggctgctga ggcaagacgc    300
aagaaaaaag gtgcggcgtg gttgggaaga agaagcattt cggatgggga aaagctactt    360
gcttttttta gaaaaaaatt atatatgtat gaaatttcag tgtttcgctg gaaaggattg    420
aacctaaaag atgctatagc ctttctctcc acactgattc tccccatgtt ctagtctttg    480
tcatatagta gaagtaagtn ctatatcatt gcttctctgt tttcgatttt ttttttaaag    540
catggacgcg ggcagtgagg aacagaagga ttcaggtacg tggaatcaaa aacttacaca    600
ggcgacagga agaggaagag cgcaatgaca ttccctgggg agacagatct aacagagatt    660
aggcgaggca agaagaagac catcaggtag gcatgcagca gaggcaggaa tggcatggtg    720
atactgacca gaaactccga agaagaacct ggcgatatgc tccatctctt ccgcttcgcg    780
cttatcgctg tgcggaaccc tcggctgtgc tggcctggaa cccgaacgga gcagagggg     840 tagtgagtgg actggactcc tttcctccac ggtctaggcc gggagcgcac ccacacccaa    900
cgagcagtta gctagtagct ctcaagtctg aatggctgag cgcaacacac agcagccaag    960
ccaacgagcc tgtgtacggg cggtgtcttt gtgcctgtgt g                      1001
```